(12) United States Patent
Barth et al.

(10) Patent No.: US 7,019,147 B1
(45) Date of Patent: Mar. 28, 2006

(54) BENZIMIDAZOLE DERIVATIVES USEFUL AS ANTIPROLIFERATIVE AGENTS

(75) Inventors: Wayne E. Barth, East Lyme, CT (US); Michael J. Luzzio, Noank, CT (US); Joseph P. Lyssikatos, Superior, CO (US)

(73) Assignee: Pfizer Inc., New York, NY (US)

( * ) Notice: Subject to any disclaimer, the term of this patent is extended or adjusted under 35 U.S.C. 154(b) by 424 days.

(21) Appl. No.: 10/148,335

(22) PCT Filed: Nov. 10, 2000

(86) PCT No.: PCT/IB00/01636

§ 371 (c)(1),
(2), (4) Date: Dec. 10, 2002

(87) PCT Pub. No.: WO01/40217

PCT Pub. Date: Jun. 7, 2001

Related U.S. Application Data

(60) Provisional application No. 60/168,217, filed on Nov. 30, 1999.

(51) Int. Cl.
*C07D 27/02* (2006.01)
*C07D 401/00* (2006.01)
*C07D 215/20* (2006.01)
*A61K 31/47* (2006.01)
*A01N 43/50* (2006.01)

(52) U.S. Cl. .................... 548/125; 546/167; 546/170; 514/277; 514/311; 514/385; 514/396

(58) Field of Classification Search ............... 548/125; 546/167, 170; 514/277, 311, 385, 396
See application file for complete search history.

(56) References Cited

U.S. PATENT DOCUMENTS 5,523,408 A * 6/1996 Batt et al. .................... 546/167
5,578,609 A * 11/1996 Batt et al. .................... 514/314

FOREIGN PATENT DOCUMENTS

WO  9220642  11/1992
WO  9916755  4/2000

OTHER PUBLICATIONS

Palmer, et al., Structure-Activity Relationships for 1-Phenylbenzimidazoles as Selective ATP Site Inhibitors of the Platelet-Derived Growth Factor Receptor; J. Med. Chem., (1998); vol. 41, pp. 5457-5465.
Palmer, et al., Structure-Activity Relationships for 5-Substituted 1-Phenylbenzimidazoles as Selective Inhibitors of the Platelet-Derived Growth Factor Receptor, J. Med. Chem., (1999); vol. 42, pp. 2373-2382.

* cited by examiner

*Primary Examiner*—Richard Raymond
*Assistant Examiner*—Paul V. Ward
(74) *Attorney, Agent, or Firm*—Steve Zelson; David L. Kershner

(57) ABSTRACT

The invention relates to compounds of formula (1) and to pharmaceutically acceptable salts, prodrugs and solvates thereof, wherein $R^1$, $R^7$, $R^8$, $R^9$, $R^{10}$, and $R^{11}$ are as defined herein. The invention also relates to methods of treating abnormal cell growth, such as cancer, in mammals by administering the compounds of formula 1 and to pharmaceutical compositions for treating such disorders which contain the compounds of formula (1). The invention also relates to methods of preparing the compounds of formula (1).

20 Claims, No Drawings

BENZIMIDAZOLE DERIVATIVES USEFUL AS ANTIPROLIFERATIVE AGENTS

This application claims the benefit of and is the National Stage application under 35 U.S.C. §371(c) of International Application No. PCT/IB0001636, filed Nov. 10, 2000, published in English on Jun. 7, 2001 as International Publication Number WO 200140217, which claims the benefit of U.S. Provisional Application Ser. No. 60/68,217, filed Nov. 30, 1999, the contents of the aforementioned patent applications are hereby incorporated by reference in their entirety.

BACKGROUND OF THE INVENTION

This invention relates to novel benzimidazole derivatives that are useful in the treatment of abnormal cell growth, such as cancer, in mammals. This invention also relates to a method of using such compounds in the treatment of abnormal cell growth in mammals, especially humans, and to pharmaceutical compositions containing such compounds.

It is known that a cell may become cancerous by virtue of the transformation of a portion of its DNA into an oncogene (i.e., a gene which, on activation, leads to the formation of malignant tumor cells). Many oncogenes encode proteins that are aberrant tyrosine kinases capable of causing cell transformation. Alternatively, the overexpression of a normal proto-oncogenic tyrosine kinase may also result in proliferative disorders, sometimes resulting in a malignant phenotype.

Receptor tyrosine kinases are enzymes which span the cell membrane and possess an extracellular binding domain for growth factors such as epidermal growth factor, a transmembrane domain, and an intracellular portion which functions as a kinase to phosphorylate specific tyrosine residues in proteins and hence to influence cell proliferation. Other receptor tyrosine kinases include c-erbB-2, c-met, tie-2, PDGFr, FGFr, and VEGFR. It is known that such kinases are frequently aberrantly expressed in common human cancers such as breast cancer, gastrointestinal cancer such as colon, rectal or stomach cancer, leukemia, and ovarian, bronchial or pancreatic cancer. It has also been shown that epidermal growth factor receptor (EGFR), which possesses tyrosine kinase activity, is mutated andor overexpressed in many human cancers such as brain, lung, squamous cell, bladder, gastric, breast, head and neck, oesophageal, gynecological and thyroid tumors.

Accordingly, it has been recognized that inhibitors of receptor tyrosine kinases are useful as selective inhibitors of the growth of mammalian cancer cells. For example, erbstatin, a tyrosine kinase inhibitor, selectively attenuates the growth in athymic nude mice of a transplanted human mammary carcinoma that expresses epidermal growth factor receptor tyrosine kinase (EGFR) but is without effect on the growth of another carcinoma that does not express the EGF receptor. Thus, the compounds of the present invention, which are selective inhibitors of certain receptor tyrosine kinases, in particular PDGFr, are useful in the treatment of abnormal cell growth, in particular cancer, in mammals.

Various other compounds, such as styrene derivatives, have also been shown to possess tyrosine kinase inhibitory properties. More recently, five European patent publications, namely EP 0 566 226 A1 (published Oct. 20, 1993), EP 0 602 851 A1 (published Jun. 22, (1994), EP 0 635 507 A1 (published Jan. 25, 1995), EP 0 635 498 A1 (published Jan. 25, 1995), and EP 0 520 722 A1 (published Dec. 30, 1992), refer to certain bicyclic derivatives, in particular quinazoline derivatives, as possessing anti-cancer properties that result from their tyrosine kinase-inhibitory properties. Also, World Patent Application WO 92/20642 (published Nov. 26, 1992), refers to certain bis-mono and bicyclic aryl and heteroaryl compounds as tyrosine kinase inhibitors that are useful in inhibiting abnormal cell proliferation. World Patent Applications WO96/16960 (published Jun. 6, 1996), WO 96/09294 (published Mar. 6, 1996), WO 97/30034 (published Aug. 21, 1997). WO 98/102434 (published Jan. 22, 1998). WO 98/02437 (published Jan. 22, 1998), and WO 98/02438 (published Jan. 22, 1998), also refer to substituted bicyclic heteroaromatic derivatives as tyrosine kinase Inhibitors that are useful for the same purpose. Also see WO 99/16755, J. Med. Chem. 1998, 41, 5457–5465 and J. Med. Chem. 1999, 42, 2373–2382.

SUMMARY OF THE INVENTION

The present invention relates to compounds of the formula 1

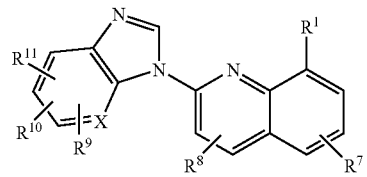

and to pharmaceutically acceptable salts, prodrugs and solvates thereof, wherein:

X is CH or N;

$R^1$ is selected from —$(CR^4R^5)_tC(O)OR^3$, —$(CR^4R^5)_tC(O)NR^3R^4$, —$(CR^4R^5)_tOR^3$, —$(CR^4R^5)_tC(O)(C_3-C_{10}$ cycloalkyl), —$(CR^4R^5)_tC(O)(C_6-C_{10}$ aryl), —$(CR^4R^5)_tC(O)$(4 to 10 membered heterocylic), —$(CR_4R^5)_t(C_3-C_{10}$ cycloalkyl), —$(CR^4R^5)_t(C_3-C_{10}$ aryl), and —$(CR^4R^5)_t$(4 to 10 membered heterocylic), wherein each t is independently an integer from 0 to 5; said cycloalkyl, aryl and heterocyclic $R^1$ moieties are optionally fused to a benzene ring, a $C_5-C_8$ cycloalkyl group, or a 4 to 10 membered heterocyclic group; the —$(CR^4R^5)_t$— moieties of the foregoing $R^1$ groups optionally include a carbon—carbon double or triple bond where t is an integer between 2 and 5: the foregoing $R^1$ groups are each optionally substituted by 1 or 2 groups independently selected from —$NR^3R^4$, —$OR^3$, $C_1-C_{10}$ alkyl, $C_2-C_{10}$ alkenyl, and $C_2-C_{10}$ alkynyl, wherein said alkyl, alkenyl and alkynyl groups are substituted by 1 or 2 groups independently selected from —$NR^3R^4$ and —$OR^3$; and the foregoing $R^1$ groups are optionally substituted by 1 to 3 $R^2$ groups;

each $R^2$ is independently selected from H, $C_1-C_{10}$ alkyl, $C_2-C_{10}$ alkenyl, $C_2-C_{10}$ alkynyl, $C_3-C_{10}$, cycloalkyl, oxo, halo, cyano, nitro, trifluoromethyl, difluoromethoxy, trifluoromethoxy, azido, —$OR^3$, —$C(O)R^3$, —$C(O)OR^3$, —$NR^4C(O)OR^6$, —$OC(O)R^3$, —$NR^4SO_2R^6$, —$SO_2NR^3R^4$, —$NR_4(CR^4R^5)_m(C_6-C_{10}$ aryl), —$O(CR^4R^5)_m$(4 to 10 membered heterocycle), —$NR^4(CR^4R^5)_m$(4 to 10 membered heterocycle), —$(CR^4R^5)_m$(4 to 10 membered heterocyclic), and —$(CR_4R^5)_m(C_3-C_{10}$ cycloalkyl) wherein each m is independently an integer from 0 to 4; said alkyl, alkenyl and alkynyl groups optionally contain 1 or 2 hetero moieties selected from O, —$S(O)_j$— wherein j is an integer from 0 to 2, and —$N(R^3)$— with the proviso that two O atoms, two S atoms, or an O and S atom are not attached directly to each other, and the proviso that an O atom, a S atom or a N atom are not attached directly to a triple bond or a non-aromatic double bond; said cycloalkyl, aryl and heterocyclic $R^2$ groups are optionally fused to a $C_6$–$C_{10}$ aryl group, a $C_5$–$C_8$ cycloalkyl group, or a 4 to 10 membered heterocyclic group; and said alkyl, cycloalkyl, aryl and heterocyclic $R^2$ groups are optionally substituted by 1 to 5 substituents independently selected from oxo (=O), halo, cyano, nitro, trifluoromethyl, difluoromethoxy, trifluoromethoxy, azido, —$NR^4SO_2R^6$, —$SO_2NR^3R^4$, —$C(O)R^3$, —$C(O)OR^3$, —$OC(O)R^3$, —$NR^4C(O)OR^6$, —$NR^4C(O)R^3$; —$C(O)NR^3R^4$, —$NR^3R^4$, —$OR^3$, $C_1$–$C_{10}$ alkyl, —$(CR^4R^5)_m(C_6$–$C_{10}$ aryl), and —$(CR^4R^5)_m$(4 to 10 membered heterocyclic), wherein each m is independently an integer ranging from 0 to 4;

each $R^3$ is independently selected from H, $C_1$–$C_{10}$alkyl, —$(CR_4R^5)_m(C_6$–$C_{10}$ aryl), and —$(CR^4R^5)_m$(4 to 10 membered heterocyclic), wherein each m is independently an integer from 0 to 4; said alkyl group optionally includes 1 or 2 hetero moieties selected from O, —$S(O)_j$— wherein j is an integer ranging from 0 to 2, and —$N(R^4)$— with the proviso that two O atoms, two S atoms, or an O and S atom are not attached directly to each other; said cycloalkyl, aryl and heterocyclic $R^3$ groups are optionally fused to a $C_6$–$C_{10}$ aryl group, a $C_5$, —$C_8$ cycloalkyl group, or a 4 to 10 membered heterocyclic group; and the foregoing $R^3$ substituents, except H, are optionally substituted by 1 to 5 substituents independently selected from oxo, halo, cyano, nitro, trifluoromethyl, difluoromethoxy, trifluoromethoxy, azido, —$C(O)R^4$, —$C(O)OR^4$, —$OC(O)R^4$, —$NR^4C(O)R^5$, —$C(O)NR^4R^5$, —$NR^4R^5$, hydroxy, $C_1$–$C_6$ alkyl, and $C_1$–$C_6$ alkoxy;

each $R^4$ and $R^5$ is independently H or $C_1$–$C_6$ alkyl;

or, where $R^4$ and $R^5$ are attached to the same carbon or nitrogen atom, $R^4$ and $R^5$ together with said carbon or nitrogen may be taken together to form a 4 to 10 membered ring which may be carbocyclic or heterocyclic;

each $R^6$ is selected from the substituents provided in the definition of $R^3$ except $R^6$ is not H;

each $R^7$, $R^8$, $R^9$, $R^{10}$ and $R^{11}$ is independently selected from the group of subsituents provided in the definition of $R^2$.

In a specific embodiment of the present invention $R^1$ is $C_6$–$C_{10}$ aryl or 4 to 10 membered heterocyclic wherein the foregoing $R^1$ groups are each substituted by 1 or 2 groups independently selected from —$NR^3R^4$, —$OR^3$ and $C_1$–$C_3$ alkyl, wherein said alkyl groups are substituted by 1 or 2 groups independently selected from —$NR^3R^4$ and —$OR^3$; and the foregoing $R^1$ groups are optionally substituted by 1 to 3 $R^2$ groups;

each $R^2$ is independently selected from H, $C_1$–$C_{10}$ alkyl, $C_3$–$C_{10}$ cycloalkyl, oxo(=O), —$OR^3$, —$C(O)R^3$, —$C(O)OR^3$, —$NR^4C(O)R^3$, —$C(O)NR^3R^4$, —$NR^3R^4$, —$NR^4SO_2R^6$, —$SO_2NR^3R^4$, —$(CR^4R^5)_m$(4 to 10 membered heterocyclic), and $(CR_4R^5)_m$($C_3$–$C_{10}$ cycloalkyl); and said alkyl groups optionally contain 1 or 2 hetero moieties selected from O; —$S(O)_j$— wherein j is an integer from 0 to 2, and —$N(R^3)$— with the proviso that two O atoms, two S atoms; or an O and S atom are not attached directly to each other; and said alkyl and cycloalkyl $R^2$ groups are optionally substituted by 1 to 5 substituents independently selected from oxo, cyano, trifluoromethyl, trifluoromethoxy, —$NR^4SO_2R^6$, —$SO_2NR^3R^4$, —$C(O)$ $OR^3$, —$NR^4C(O)OR^6$, —$NR^4C(O)R^3$, —$C(O)NR^3R^4$, —$NR^3R^4$, —$OR^3$, and $C_1$–$C_{10}$ alkyl, wherein each m is independently an integer ranging from 0 to 4.

In another specific embodiment of the present invention, $R^1$ is piperidinyl, piperzinyl, or phenyl, wherein said $R^1$ groups are substituted by —$NR^3R^4$, oxo (=O), —$OR^3$ and $C_1$–$C_3$ alkyl, wherein said alkyl groups are substituted by 1 or 2 groups independently selected from —$NR^3R^4$ and —$OR^3$; and the foregoing $R^1$ groups are optionally substituted by 1 to 3 $R^2$ groups. In a more specific embodiment, said $R^1$ groups are substituted by —$NR^3R^4$, oxo (=O), $OR^3$, or $C_1$–$C_3$ alkyl, wherein said alkyl group are substituted by —$NR^3R^4$.

In another specific embodiment of the present invention, $R^1$ is phenyl substituted by pyrrolidin-1-yl which pyrrolidin-1-yl is optionally substituted by 1 to 3 substituents independently selected from oxo, cyano, trifluoromethyl, trifluoromethoxy, —$NR^4SO_2R^6$, —$SO_2NR^3R^4$, —$C(O)R^3$, —$C(O)OR^3$, —$NR^4C(O)OR^6$, —$NR^4C(O)R^3$, —$C(O)NR^3R^4$, —$NR^3R^4$, —$OR^3$, and $C_1$–$C_{10}$ alkyl; and $R^{11}$ is —$OR^3$. More specifically, $R^1$ is 4-pyrrolidin-1-ylmethyl-phenyl optionally subtituted by 1 to 3 substituents independently selected from oxo, cyano, trifluoromethyl, trifluoromethoxy, —$NR^4SO_2R^6$, —$SO_2NR^3R^4$, —$C(O)R^3$, —$C(O)OR^3$, —$NR^4C(O)OR^6$, —$NR^4C(O)R^3$, —$C(O)NR^3R^4$, —$NR^3R^4$, —$OR^3$, and $C_1$–$C_{10}$ alkyl; and $R^{11}$ is —$OR^3$. More specifically, $R^{11}$ is connected at the 5 position of the benzimidazole moiety of the compound of formula 1 and is 2-methoxyethoxy.

In another specific embodiment of the present invention, $R^1$ is pyrrolidin-1-yl or piperidin-1-yl, said $R^1$ being optionally substituted by 1 to 3 substituents independently selected from oxo, cyano, trifluoromethyl, trifluoromethoxy, —$NR^4SO_2R^6$, —$SO_2NR^3R^4$, —$C(O)R^3$, —$C(O)OR^3$, —$NR^4C(O)OR^6$, —$NR^4C(O)R^3$, —$C(O)NR^3R^4$, —$NR^3R^4$, —$OR^3$, and $C_1$–$C_{10}$ alkyl. More specifically, $R^1$ is pyrrolidin-1-yl or piperidin-1-yl substituted by —$NR^3R^4$ and optionally substituted by 1 or 2 substituents independently selected from oxo, cyano, trifluoromethyl, trifluoromethoxy, —$NR^4SO_2R^6$, —$SO_2NR^3R^4$, —$C(O)R^3$, —$C(O)OR^3$, —$NR^4C(O)OR^6$, —$NR$ $C(O)R^3$, —$C(O)NR^3R^4$, —$NR^3R^4$, —$OR^3$, and $C_1$–$C_{10}$ alkyl; and $R^{11}$ is —$OR^3$. More specifically, $R^{11}$ is connected at the 5 position of the benzimidazole moiety of the compound of formula 1 and is —$OR^3$ and $R^9$ and $R^{10}$ are both H. More specifically, $R^{11}$ is connected at the 5 position of the benzimidazole moiety of the compound of formula 1 and is 2-methoxyethoxy and $R^9$ and $R^{10}$ are both H.

Preferred compounds include those selected from the group consisting of:

[1-[2-(5-Methoxy-benzoimidazol-1-yl)-quinolin-8-yl]-piperidin-4-ylamine;

1-[8-(4-Amino-piperidin-1-yl)-quinolin-2-yl]-1H-benzoimidazol-5-ol;

1-{2-[5-(Pyridin-2-ylmethoxy)-benzoimidazol-1-yl]-quinolin-8-yl)-piperidin-4-ylamine;

{1-[2-(5-Methoxy-benzoimidazol-1-yl)-quinolin-8-yl]-piperidin-4-yl}-dimethyl-amine;

{4-[2-(5-Methoxy-benzoimidazol-1-yl)-quinolin-8-yl]-benzyl}-methyl-amine;

{4-[2-(5-Methoxy-benzoimidazol-1-yl)-quinolin-8-yl]-benzyl}-dimethyl-amine;

Cyclopropyl-{4-[2-(5-methoxy-benzoimidazol-1-yl)-quinolin-8-yl]-benzyl}-amine;

tert-Butyl-{4-[2-(5-methoxy-benzoimidazol-1-yl)-quinolin-8-yl]-benzyl}-amine;

4-[2-(5-Methoxy-benzoimidazol-1-yl)-quinolin-8-yl]-benzylamine;
1-[2-(5-Ethoxy-benzoimidazol-1-yl)-quinolin-8-yl]-piperidin-4-ylamine;
{1-[2-(5-Ethoxy-benzoimidazol-1-yl)-quinolin-8-yl]-piperidin-4-yl}-dimethylamine;
1-[2-(5-Trifluoromethoxy-benzoimidazol-1-yl)-quinolin-8-yl]-piperidin-4-ylamine;
{4-[2-(5-Ethoxy-benzoimidazol-1-yl)-quinolin-8-yl]-benzyl}-methyl-amine;
Cyclopropyl-{4-[2-(5-ethoxy-benzoimidazol-1-yl)-quinolin-8-yl]-benzyl}-amine;
tert-Butyl-{4-[2-(5-ethoxy-benzoimidazol-1-yl)-quinolin-8-yl]-benzyl}-amine;
{4-[2-(5-Ethoxy-benzoimidazol-1-yl)-quinolin-8-yl]-benzyl}-dimethyl-amine;
1-[2-(5-Methoxy-benzoimidazol-1-yl)-quinolin-8-yl]-piperidin-4-one;
1-[2-(5-Ethoxy-benzoimidazol-1-yl)-quinolin-8-yl]-piperidin-4-one;
1-[2-(5-Ethoxy-benzoimidazol-1-yl)-quinolin-8-yl]-piperidin-4-ol;
tert-Butyl-{1-[2-(5-ethoxy-benzoimidazol-1-yl)-quinolin-8-yl]-piperidin-4-yl}amine;
{1-[2-(5-Methoxy-benzoimidazol-1-yl]quinolin-8-yl]-piperidin-4-yl}-methyl-amine;
2-(5-Methoxy-benzoimidazol-1-yl)-8-(1-oxa-6-aza-spiro[2.5]oct-6-yl]-quinoline;
4-Dimethylaminomethyl-1-[2-(5-methoxy-benzoimidazol-1-yl)-quinolin-8-yl]-piperidin-4-ol;
1-[2-(5-Methoxy-benzoimidazol-1-yl)-quinolin-8-yl]4-methylaminomethyl-piperidin-4-ol;
4-Aminomethyl-1-[2-(5-methoxy-benzoimidazol-1-yl-quinolin-8-yl]-piperidin-4-ol;
1-[2-(5-Methoxy-benzoimidazol-1-yl)-quinolin-8-yl]-pyrrolidin-3-ylamine;
1-(2-Benzoimidazol-1-yl-quinolin-8-yl)-piperidin-4-ylamine;
1-(2-imidazo[4,5-b]pyridin-3-yl-quinolin-8-yl)-piperidin-4-ylamine;
1-{2-[5-(4-Methoxy-phenyl)-benzoimidazol-1-yl]-quinolin-8-yl}-piperidin-4-ylamine;
1-[2-(5-Cyclopropylmethoxy-benzoimidazol-1-yl]-quinolin-8-yl]-piperidin-4-ylamine;
1-{2-[5-(3-Dimethylamino-propoxy)-benzoimidazol-1-yl]-quinolin-8-yl}-piperidin-4-ylamine;
1-{2-[5-(3-Amino-propoxy)-benzoimidazol-1-yl]-quinolin-8-yl}-piperidin-4-ylamine;
1-{2-[5-(2-Dimethylamino-ethoxy)-benzoimidazol-1-yl]-quinolin-8-yl}-piperidin-4-ylamine;
1-{2-[5-(Pyridin-4-ylmethoxy)-benzoimidazol-1-yl]-quinolin-8-yl}-piperidin-4-ylamine;
1-[2-(5-Benzyloxy-benzoimidazol-1-yl)-quinolin-8-yl]-piperidin-4-ylamine;
1-{2-[5-(Pyridin-3-ylmethoxy)-benzoimidazol-1-yl]-quinolin-8-yl}-piperidin-4-ylamine;
1-2-[5-(2-Methoxy-ethoxy)-benzoimidazol-1-yl]-quinolin-8-yl)-piperidin-4-ylamine;
1-[2-(5-Methoxy-benzoimidazol-1-yl)-quinolin-8-yl]-piperidine-4-carboxylic acid ethyl ester;
1-[2-(5-Methoxy-benzoimidazol-1-yl)-quinolin-8-yl]-piperidine-4-carboxylic acid;
4-Dimethylaminomethyl-1-[2-(5-methoxy-benzoimidazol-1-yl)-quinolin-8-yl]-piperidin-4-ol;
N-{1-[2-(5-Methoxy-benzoimidazol-1-yl)-quinolin-8-yl]-piperidin-4-yl}-acetamide;
N-{1-[2-(5-Cyclopropylmethoxy-benzoimidazol-1-yl)-quinolin-8-yl]-piperidin-4-yl}acetamide;
1-{2-[5-(2-Methoxy-ethoxy)-benzoimidazol-1-yl]-quinolin-8-yl}-piperidin-4-ol;
{1-[2-(5-Methoxy-benzoimidazol-1-yl)-quinolin-8-yl]-piperidin-4-yl}-urea;
4-Aminomethyl-1-{2-[5-(pyridin-2-ylmethoxy)-benzoimidazol-1-yl]-quinolin-8-yl}piperidin-4-ol;
Cyclopropyl-(1-2-[5-(2-methoxy-ethoxy]-benzoimidazol-1-yl]-quinolin-8-yl)-piperidin-4-yl-dimethyl-amine;
(1-{2-[5-(2-Methoxy-ethoxy)-benzoimidazol-1-yl]-quinolin-8-yl}piperidin-4-yl)-dimethyl-amine;
1-2-[5-(2-Methoxy-ethoxy)-benzoimidazol-1-yl]-quinolin-8-yl}piperidin-4-yl)-methylamine;
(1-{2-[5-(3-Dimethylamino-propoxy)-benzoimidazol-1-yl]-quinolin-8-yl)-piperidin-4-yl)-dimethyl-amine;
{1-[2-(5-Cyclopropylmethoxy-benzoimidazol-1-yl)-quinolin-8-yl]-piperidin-4-yl}-methylamine;
{1-[2-(5-Cyclopropylmethoxy-benzoimidazol-1-yl]quinolin-8-yl]-piperidin-4-yl}-dimethyl-amine;
2-Amino-N-(1-{2-[5-(2-methoxy-ethoxy)-benzoimidazol-1-yl]-quinolin-8-yl}-piperidin-4-yl)-acetamide;
—(S)-2-Amino-N-(1-{2-[5-(2-methoxy-ethoxy)-benzoimidazol-1-yl]-quinolin-8-yl}piperidin-4-yl)-propionamide;
—(R)-2-Amino-N-(1-2-[5-(2-methoxy-ethoxy)-benzoimidazol-1-yl]-quinolin-8-yl}piperidin-4-yl)-propionamide;
2-Amino-N-(1-{2-[5-(2-methoxy-ethoxy)-benzoimidazol-1-yl]-quinolin-8-yl}-piperidin-4-yl)-isobutyramide;
1-(1-{2-[5-(2-Methoxy-ethoxy)-benzoimidazol-1-yl]-quinolin-8-yl}piperidin-4-ylamino) 2-methyl-propan-2-ol;
(1-{2-[5-(2-Methoxy-ethoxy)-benzoimidazol-1-yl]-quinolin-8-yl}-piperidin-4-yl)-pyridin-2-ylmethyl-amine;
(1-2-[5-(2-Methoxy-ethoxy)-benzoimidazol-1-yl]-quinolin-8-yl}-piperidin-4-yl)-pyridin-3-ylmethyl-amine;
4-2-[5-(2-Methoxy-ethoxy)-benzoimidazol-1-yl]-quinolin-8-yl}phenol;
[2-(4-2-[5-(2-Methoxy-ethoxy)-benzoimidazol-1-yl]-quinolin-8-yl}-phenoxy)-ethyl]dimethyl-amine;
2-[5-(2-Methoxy-ethoxy)-benzoimidazol-1-yl]-8-piperazin-1-yl-quinoline;
[2-(4-{2-[5-(2-Methoxy-ethoxy)-benzoimidazol-1-yl]-quinolin-8-yl}-piperazin-1-yl)ethyl]-dimethyl-amine;
2-[5-(2-Methoxy-ethoxy)-benzoimidazol-1-yl]-8-(4-pyridin-2-ylmethyl-piperazin-1-yl]quinoline;
2-[5-(2-Methoxy-ethoxy)-benzoimidazol-1-yl]-8-(4-pyridin-3-ylmethyl-piperazin-1-yl)quinoline;
2-Amino-1-(4-{2-[5-(2-methoxy-ethoxy)-benzoimidazol-1-yl]-quinolin-8-yl}-piperazin-1-yl)-2-methyl-propan-1-one;
(S)-2-Amino-1-(4-2-[5-(2-methoxy-ethoxy)-benzoimidazol-1-yl]-quinolin-8-yl}piperazin-1-yl)-propan-1-one;
(S)-2-Amino-1-(4-{2-[5-(2-methoxy-ethoxy)-benzoimidazol-1-yl]-quinolin-8-yl}piperazin-1-yl)-propan-1-one;
2-Amino-1-(4-2-[5-(2-methoxy-ethoxy)-benzoimidazol-1-yl]-quinolin-8-yl}-piperazin-1 yl)-ethanone;
(1-Amino-cyclopropyl)-(4-{2-[5-(2-methoxy-ethoxy]benzoimidazol-1-yl)-quinolin-8-yl}piperazin-1-yl)-methanone;
2-(4-{2-[5-(2-Methoxy-ethoxy)-benzoimidazol-1-yl]-quinolin-8-yl)-piperazin-1-yl]ethylamine;
(R-2-Amino-3-(4-{2-[5-(2-methoxy-ethoxy)-benzoimidazol-1-yl]-quinolin-8-yl}piperazin-1-yl)-propan-1-ol;
3-{2-[5-(2-Methoxy-ethoxy)-benzoimidazol-1-yl]-quinolin-8-yl}-3-aza-bicyclo[3.1.0]hex-6-ylamine;
(S)-1-2-[5-(2-Methoxy-ethoxy)-benzoimidazol-1-yl]-quinolin-8-yl}-pyrrolidin-3-ylamine;

(R)-1-(2-[5-(2-Methoxy-ethoxy)-benzoimidazol-1-yl]-quinolin-8-yl]-pyrrolidin-3-ylamine;
2-[5-(2-Methoxy-ethoxy)-benzoimidazol-1-yl]-8-pyridin-3-yl-quinoline;
2-[5-(2-Methoxy-ethoxy)-benzoimidazol-1-yl]-8-(6-methoxy-pyridin-3-yl)-quinoline;
4-{2-[5-(2-Methoxy-ethoxy)-benzoimidazol-1-yl]-quinolin-8-yl}-benzoic acid methyl ester;
1-2-[5-(2-Methoxy-ethoxy)-benzoimidazol-1-yl]-quinolin-8-yl}-4-methyl-piperidin-4-ylamine;
1-[2-(6,7-Dihydro-5,8-dioxa-1,3-diaza-cyclopenta[b]naphthalen-1-yl)-quinolin-8-yl]piperidin-4-ylamine;
2-{1-[8-(4-Amino-piperidin-1-yl)-quinolin-2-yl]-1H-benzoimidazol-5-yloxy}-ethanol;
4-Cyclopropylaminomethyl-1-2-[5-(2-methoxy-ethoxy)-benzoimidazol-1-yl]-quinolin-8-yl}-piperidin-4-ol;
1-[8-(4-Amino-piperidin-1-yl)-quinolin-2-yl]-1H-benzoimidazole-5-sulfonic acid dimethylamide;
1-[2-(6-Methoxy-benzoimidazol-1-yl)-quinolin-8-yl]-piperidin-4-ylamine;
1-[2-(5,6-Dimethoxy-benzoimidazol-1-yl)-quinolin-8-yl]-piperidin-4-ylamine;
2-Dimethylamino-1-(4-2-[5-(2-methoxy-ethoxy)-benzoimidazol-1-yl]-quinolin-8-yl}piperazin-1-yl)-ethanone;
1-[2-(5-Benzyloxy-benzoimidazol-1-yl)-quinolin-8-yl]-4-methyl-piperidin-4-ol;
(4-2-[5-(2-Methoxy-ethoxy)-benzoimidazol-1-yl]-quinolin-8-yl]-benzyl)-dimethyl-amine;
(4-{2-[5-(2-Methoxy-ethoxy)-benzoimidazol-1-yl]-quinolin-8-yl}-benzyl]methyl-amine;
2-[5-(2-Methoxy-ethoxy)-benzoimidazol-1-yl]-8-(4-morpholin-4-ylmethyl-phenyl)quinoline;
2-(4-{2-[5-(2-Methoxy-ethoxy)-benzoimidazol-1-yl]-quinolin-8-yl)-benzylamino)-ethanol;
4-2-[5-(2-Methoxy-ethoxy)-benzoimidazol-1-yl]-quinolin-8-yl}benzylamine;
2-[5-(2-Methoxy-ethoxy)-benzoimidazol-1-yl]-8-(4-pyrrolidin-1-ylm thyl-phenyl)-quinoline;
2-[5-(2-Methoxy-ethoxy)-benzoimidazol-1-yl]-8-(4-pyrrolidin-1-ylmethyl-phenyl)quinoline;
2-[5-(2-Methoxy-ethoxy)-benzoimidazol-1-yl]-8-(4-pyrrolidin-1-ylmethyl-phenyl)quinoline;
1-(4-{2-[5-(2-Methoxy-ethoxy)-benzoimidazol-1-yl]-quinolin-8-yl}-benzyl)-cis-pyrrolidine-3,4-diol;
R,R-(1-(4-2-[5-(2-Methoxy-ethoxy)-benzoimidazol-1-yl]-quinolin-8-yl}-benzyl)-trans-pyrrolidine-3,4-diol);
1-(4-{2-[5-(2-Methoxy-ethoxy)-benzoimidazol-1-yl]-quinolin-8-yl}-benzyl)-pyrrolidin-3-ol;
R-(1-(4-2-[5-(2-Methoxy-ethoxy)-benzoimidazol-1-yl]-quinolin-8-yl}-benzyl)-pyrrolidin-3-ol);
S-(1-(4-2-[5-(2-Methoxy-ethoxy)-benzoimidazol-1-yl]-quinolin-8-yl)-benzyl]pyrrolidin-3-ol);
1-(4-{2-[5-(2-Methoxy-ethoxy)-benzoimidazol-yl]quinolin-8-yl}-benzyl)-azetidin-3-ol;
2-[5-(2-Methoxy-ethoxy)-benzoimidazol-1-yl]-8-[4-(4-methyl-piperazin-1-ylmethyl) phenyl]-quinoline;
4-(4-{2-[5-(2-Methoxy-ethoxy)-benzoimidazol-1-yl-quinolin-8-yl)-benzyl)-piperazine-1carboxylic acid tert-butyl ester;
[1-(4-(2-[5-(2-Methoxy-ethoxy)-benzoimidazol-1-yl]-quinolin-8-yl}-benzyl)-piperidin-4-yl]-carbamic acid tert-butyl ester;
1-(4-{2-[5-(2-Methoxy-ethoxy)-benzoimidazol-1-yl]-quinolin-8-yl}-benzyl)-piperidin-4-ylamine;
(1-{2-[5-(2-Methoxy-ethoxy]benzoimidazol-1-yl]-quinolin-8-yl}-piperidin-4-yl)-methanol;
(1-{2-[5-(2-Methoxy-ethoxy)-benzoimidazol-1-yl]-quinolin-8-yl}piperidin-4-ylmethyl)-methyl-amine;
2-[5-(2-Methoxy-ethoxy)-benzoimidazol-1-yl]-8-[4-(4-methyl-piperazin-1-ylmethyl)-piperidin-1-yl]-quinoline;
(1-{2-[5-(2-Methoxy-ethoxy)-benzoimidazol-1-yl]-quinolin-8-yl)-piperidin-4-ylmethyl)-dimethyl-amine;
1-(1-2-[5-(2-Methoxy-ethoxy)-benzoimidazol-1-yl]-quinolin-8-yl)-piperidin-4-ylmethyl)-pyrrolidin-3-ol;
C-(1-{2-[5-(2-Methoxy-ethoxy)-benzoimidazol-1-yl]-quinolin-8-yl}-piperidin-4-yl)-methylamine;
1-{2-[5-(2-Dimethylamino-ethoxy)-benzoimidazol-1-yl]-quinolin-8-yl}4-methyl-piperidin-4-ol;
1-2-[5-(2-Dimethylamino-ethoxy]benzoimidazol-1-yl]-quinolin-8-yl}-piperidin-4-ol;
S,S-(1-(4-[(2-[5-(2-Methoxy-ethoxy]benzoimidazol-1-yl]-quinolin-8-yl]-benzyl)-trans-pyrrolidine-3,4-diol);
4-{2-[5-(3-Amino-propoxy)-benzoimidazol-1-yl]-quinolin-8-yl}-phenol;
4-{2-[5-(3-Dimethylamino-propoxy)-benzoimidazol-1-yl]-quinolin-8-yl}-phenol;
1-[2-(5-Phenyl-benzoimidazol-1-yl)-quinolin-8-yl]-piperidin-4-ylamine;
[2-(5-Pyridin-4-yl-benzoimidazol-1-yl)-quinolin-8-yl]-piperidin-4-ylamine;
1-2-[5-(3-Methoxy-phenyl)-benzoimidazol-1-yl]-quinolin-8-yl}-piperidin-4-ylamine;
1-[2-(5-Pyridin-3-yl-benzoimidazol-1-yl)-quinolin-8-yl]-piperidin-4-ylamine;
1-{2-[5-(6-Methoxy-pyridin-3-yl)-benzoimidazol-1-yl]-quinolin-8-yl}-piperidin-4-ylamine;
1-2-[5-(4-Aminomethyl-phenyl)-benzoimidazol-1-yl]-quinolin-8-yl}-piperidin-4-ylamine;
4-{1-[8-(4-Amino-piperidin-1-yl)-quinolin-2-yl]-1H-benzoimidazol-5-yl}-benzoic acid methyl ester;
4-{1-[8-(4-Amino-piperidin-1-yl)-quinolin-2-yl]-1H-benzoimidazol-5-yl}-phenol;
2-(5-Methoxy-benzoimidazol-1-yl)-quinoline-8-carboxylic acid methyl ester;
2-[5-(2-Methoxy-ethoxy)-benzoimidazol-1-yl]-quinoline-8-carboxylic acid methyl ester;
2-(5-Methoxy-benzoimidazol-1-yl)-quinoline-8-carboxylic acid (2-dimethylamino-ethyl)-amide;
2-(5-Cyclopropylmethoxy-benzoimidazol-1-yl)-quinoline-8-carboxylic acid methyl ester;
[2-(5-Cyclopropylmethoxy-benzoimidazol-1-yl)-quinolin-8-yl]-pyrrolidin-1-yl-methanone;
[2-(5-Cyclopropylmethoxy-benzoimidazol-1-yl)-quinolin-8-yl]-morpholin-4-yl-methanone;
[2-(5-Cyclopropylmethoxy-benzoimidazol-1-yl)-quinolin-8-yl]-piperidin-1-yl-methanone;
(3-Amino-pyrrolidin-1-yl)-[2-(5-cyclopropylmethoxy-benzoimidazol-1-yl)-quinolin-8-yl]-methanone;
8-Allyloxy-2-(5-methoxy-benzoimidazol-1-yl)-quinoline;
{2-[2-(5-Methoxy-benzoimidazol-1-yl)-quinolin-8-yloxy]-ethyl}-methyl-amine;
{2-[2-(5-Methoxy-benzoimidazol-1-yl)-quinolin-8-yloxy]-ethyl}-dimethyl-amine;
2-[2-(5-Methoxy-benzoimidazol-1-yl)-quinolin-8-yloxy]-ethylamine;
1-[[2-[5-(3-Morpholinoethoxy)-1H-benzimidazol-1-yl]-quinolin-8-yl]]-piperidin-4-ylamine trihydrochloride;
1-[[2-[5-(3-Morpholinoethoxy)-1H-benzimidazol-1-yl]-quinolin-8-yl]]-piperidin-4-ylamine trihydrochloride;
5-{2-[5-(2-Methoxy-ethoxy)-benzoimidazol-1-yl]-quinolin-8-yl}-[1,3,4]oxadiazol-2-ylamine;
Ethyl 1-[8-(4-aminopiperidin-1-yl)-quinolin-2-yl]-benzimidazole-5-carboxylate;

1-[8-(4-Aminopiperidin-1-yl)-quinolin-2-yl]-benzimidazole-5-carboxylic acid;
N-(4-Morpholino)ethyl-1-[8-(4-aminopiperidin-1-yl)-quinolin-2-yl]-benzimidazole-5-carboxamide;
4-1-[8-(4-Amino-piperidin-1-yl)-quinolin-2-yl]-1H-benzoimidazol-5-yl}-benzaldehyde;
1-2-[5-(4-Methylaminomethyl-phenyl)-benzoimidazol-1-yl]-quinolin-8-yl}-piperidin-4-ylamine;
1-2-[5-(4-Dimethylaminomethyl-phenyl)-benzoimidazol-1-yl]-quinolin-8-yl}-piperidin-4-ylamine;
1-(2-5-[2-(2-Methyl-imidazol-1-yl)-ethoxy]-benzoimidazol-1-yl}-quinolin-8-yl)-piperidin-4-ylamine and
1-2-[5-(2-[1,2,4]Triazol-1-yl-ethoxy)-benzoimidazol-1-yl]-quinolin-8-yl}-piperidin-4-ylamine,
and the pharmaceutically acceptable salts, prodrugs and solvates of the foregoing compounds.

In accordance with the present invention, preferred compounds include those selected from the group consisting of:
1-[2-(5-Methoxy-benzoimidazol-1-yl)-quinolin-8-yl]-piperidin-4-ylamine;
1-[8-(4-Amino-piperidin-1-yl)-quinolin-2-yl]-1H-benzoimidazol-5-ol;
1-{2-[5-Pyridin-2-ylmethoxy)-benzoimidazol-1-yl]-quinolin-8-yl}-piperidin-4-ylamine;
{1-[2-(5-Methoxy-benzoimidazol-1-yl)-quinolin-8-yl]-piperidin-4-yl}-dimethyl-amine;
{4-[2-(5-Methoxy-benzoimidazol-1-yl]quinolin-8-yl]-benzyl}-methyl-amine;
{4-[2-(5-Methoxy-benzoimidazol-1-yl)-quinolin-8-yl]-benzyl}-dimethyl-amine;
1-[2-(5-Ethoxy-benzoimidazol-1-yl)-quinolin-8-yl]-piperidin-4-ylamine;
(1-[2-(5-Ethoxy-benzoimidazol-1-yl)-quinolin-8-yl]-piperidin-4-yl}-dimethylamine;
(4-[2-(5-Ethoxy-benzoimidazol-1-yl)-quinolin-8-yl]-benzyl}-methyl-amine;
{4-[2-(5-Ethoxy-benzoimidazol-1-yl)-quinolin-8-yl]-benzyl}-dim ethyl-amine;
{1-[2-(5-Methoxy-benzoimidazol-1-yl)-quinolin-8-yl]-piperidin-4-yl}-methyl-amine;
4-Dimethylaminomethyl-1-[2-(5-methoxy-benzoimidazol-1-yl)-quinolin-8-yl]-piperidin-4-ol;
1-[2-(5-Methoxy-benzoimidazol-1-yl)-quinolin-8-yl]4-methylaminomethyl-piperidin-4-ol;
4-Aminomethyl-1-[2-(5-methoxy-benzoimidazol-1-yl)-quinolin-8-yl]-piperidin-4-ol;
1-{2-[5-(4-Methoxy-phenyl)-benzoimidazol-1-yl]-quinolin-8-yl}-piperidin-4-ylamine;
1-[2-(5-Cyclopropylmethoxy-benzoimidazol-1-yl)-quinolin-8-yl]-piperidin-4-ylamine;
1-{2-[5-(3-Dimethylamino-propoxy)-benzoimidazol-1-yl]-quinolin-8-yl}-piperidin-4-ylamine;
1-(2-[5-(3-Amino-propoxy)-benzoimidazol-1-yl]-quinolin-8-yl}-piperidin-4-ylamine;
1-{2-[5-(2-Dimethylamino-ethoxy)-benzoimidazol-1-yl]-quinolin-8-yl}-piperidin-4-ylamine;
1-{2-[5-(Pyridin-4-ylmethoxy)-benzoimidazol-1-yl]-quinolin-8-yl}-piperidin-4-ylamine;
1-[2-(5-Benzyloxy-benzoimidazol-1-yl)-quinolin-8-yl]-piperidin-4-ylamine;
1-{2-[5-(Pyridin-3-ylmethoxy)-benzoimidazol-1-yl]-quinolin-8-yl}-piperidin-4-ylamine;
1-{2-[5-(2-Methoxy-ethoxy)-benzoimidazol-1-yl]-quinolin-8-yl}-piperidin-4-ylamine;
4-Dimethylaminomethyl-1-[2-(5-methoxy-benzoimidazol-1-yl]quinolin-8-yl]-piperidin-4-ol;
4-Aminomethyl-1-[2-[5-(pyridin-2-ylmethoxy)-benzoimidazol-1-yl]-quinolin-8-yl}piperidin-4-ol;
1-2-[5-(2-Methoxy-ethoxy]benzoimidazol-1-yl-quinolin-8-yl}-piperidin-4-yl)-dimethyl-amine;
1-2-[5-(2-Methoxy-ethoxy)-benzoimidazol-1-yl]-quinolin-8-yl}-piperidin-4-yl)-methyl-amine;
(1-{2-[5-(3-Dimethylamino-propoxy)-benzoimidazol-1-yl]-quinolin-8-yl}-piperidin-4-yl) dimethyl-amine;
{1-[2-(5-Cyclopropylmethoxy-benzoimidazol-1-yl]quinolin-8-yl]-piperidin-4-yl]methyl-amine;
{1-[2-(5-Cyclopropylmethoxy-benzoimidazol-1-yl)-quinolin-8-yl]-piperidin-4-yl}-dimethyl-amine;
1-(2-[5-(2-Methoxy-ethoxy)-benzoimidazol-1-yl]-quinolin-8-yl}-piperidin-4-yl)-pyridin-2-ylmethyl-amine;
(1-{2-[5-(2-Methoxy-ethoxy)-benzoimidazol-1-yl]-quinolin-8-yl}-piperidin-4-yl)-pyridin-3-ylmethyl-amine;
4-2-[5-(2-Methoxy-ethoxy)-benzoimidazol-1-yl]-quinolin-8-yl}-phenol;
[2-(4-{2-[5-(2-Methoxy-ethoxy)-benzoimidazol-1-yl]-quinolin-8-yl}-phenoxy)-ethyl]15 dimethyl-amine;
2-[5-(2-Methoxy-ethoxy)-benzoimidazol-1-yl]-8-piperazin-1-yl-quinoline;
[2-(4-{2-[5-(2-Methoxy-ethoxy)-benzoimidazol-1-yl]-quinolin-8-yl)-piperazin-1-yl)-ethyl]-dimethyl-amine;
2-Amino-1-(4-{2-[5-(2-methoxy-ethoxy)-benzoimidazol-1-yl]-quinolin-8-yl}-piperazin-1-yl)-2-methyl-propan-1-one;
(S)-2-Amino-1-(4-{2-[5-(2-methoxy-ethoxy)-benzoimidazol-1-yl]-quinolin-8-yl)-piperazin-1-yl)-propan-1-one;
(S)-2-Amino-1-(4-{2-[5-(2-methoxy-ethoxy)-benzoimidazol-1-yl]-quinolin-8-yl)-piperazin-1-yl)-propan-1-one;
2-Amino-1-(4-{2-[5-(2-methoxy-ethoxy)-benzoimidazol-1-yl]-quinolin-8-yl}-piperazin-1-yl)-ethanone;
2-(4-2-[5-(2-Methoxy-ethoxy)-benzoimidazol-1-yl]-quinolin-8-yl}piperazin-1-yl)-ethylamine;
3-{2-[5-(2-Methoxy-ethoxy)-benzoimidazol-1-yl]-quinolin-8-yl)-3-aza-bicyclo[3.1.0]hex-6-ylamine;
1-{2-[5-(2-Methoxy-ethoxy)-benzoimidazol-1-yl]-quinolin-8-yl)₄-methyl-piperidin-4-ylamine;
2-(1-[8-(4-Amino-piperidin-1-yl)-quinolin-2-yl]-1H-benzoimidazol-5-yloxy}-ethanol;
1-[2-(5,6-Dimethoxy-benzoimidazol-1-yl)-quinolin-8-yl]-piperidin-4-ylamine;
1-[2-(6,7-Dihydro-5,8-dioxa-1,3-diaza-cyclopenta[b]naphthalen-1-yl)-quinolin-8-yl]-piperidin-4-ylamine;
(4-2-[5-(2-Methoxy-ethoxy)-benzoimidazol-1-yl]-quinolin-8-yl}-b nzyl)-dimethyl-amine;
(4-{2-[5-(2-Methoxy-ethoxy)-benzoimidazol-1-yl]-quinolin-8-yl}-benzyl)-methyl-amine;
2-(4-{2-[5-(2-Methoxy-ethoxy)-benzoimidazol-1-yl]-quinolin-8-yl)-benzylamino)—ethanol;
4-(2-[5-(2-Methoxy-ethoxy)-benzoimidazol-1-yl]-quinolin-8-yl}-benzylamine;
2-[5-(2-Methoxy-ethoxy)-benzoimidazol-1-yl]-8-(4-pyrrolidin-1-ylmethyl-phenyl)-quinoline;
2-[5-(2-Methoxy-ethoxy)-benzoimidazol-1-yl]-8-(4-pyrrolidin-1-ylmethyl-phenyl)-quinoline;
2-[5-(2-Methoxy-ethoxy)-benzoimidazol-1-yl]-8-(4-pyrrolidin-1-ylmethyl-phenyl)-quinoline;
1-(4-{2-[5-(2-Methoxy-ethoxy]benzoimidazol-1-yl)-quinolin-8-yl}-benzyl)-cis-pyrrolidine-3,4-diol;
R,R-(1-(4-{2-[5-(2-Methoxy-ethoxy)-benzoimidazol-1-yl]-quinolin-8-yl}-benzyl)-trans-pyrrolidine-3,4-diol);
1-(4-{2-[5-(2-Methoxy-ethoxy)-benzoimidazol-1-yl]-quinolin-8-yl}-benzyl]pyrrolidin-3-ol;
R-(1-(4-{2-[5-(2-Methoxy-ethoxy)-benzoimidazol-1-yl]-quinolin-8-yl)-benzyl)-pyrrolidin-3-ol);

S-(1-(4-{2-[5-(2-Methoxy-ethoxy)-benzoimidazol-1-yl]-quinolin-8-yl}-benzyl)-pyrrolidin-3-ol);
1-(4-{2-[5-(2-Methoxy-ethoxy)-benzoimidazol-1-yl]-quinolin-8-yl}-benzyl)-azetidin-3-ol 2-[5-(2-Methoxy-ethoxy)-benzoimidazol-1-yl]-8-[4-(4-methyl-piperazin-1-ylmethyl)-phenyl]-quinoline;
1-(4-{2-[5-(2-Methoxy-ethoxy)-benzoimidazol-1-yl]-quinolin-8-yl)-benzyl)-piperidin-4-ylamine;
(1-2-[5-(2-Methoxy-ethoxy)-benzoimidazol-1-yl]-quinolin-8-yl}-piperidin-4-yl)-methanol;
(1-2-[5-(2-Methoxy-ethoxy)-benzoimidazol-1-yl]-quinolin-8-yl)-piperidin-4-ylmethyl)-methyl-amine;
2-[5-(2-Methoxy-ethoxy)-benzoimidazol-1-yl]-8-[4-(4-methyl-piperazin-1-ylmethyl)-piperidin-1-yl]-quinoline;
(1-2-[5-(2-Methoxy-ethoxy)-benzoimidazol-1-yl]-quinolin-8-yl}-piperidin-4-ylmethyl)-dimethyl-amine;
C-(1-(2-[5(2-Methoxy-ethoxy)-benzoimidazol-1-yl]-quinolin-8-yl}pip ridin-4-yl)-methylamine;
S,S-(1-(4-{2-[5-(2-Methoxy-ethoxy)-benzoimidazol-1-yl]-quinolin-8-yl}-benzyl)-trans-pyrrolidine-3,4-diol);
4-2-[5-(3-Dimethylamino-propoxy)-benzoimidazol-1-yl]-quinolin-8-yl}-phenol;
1-[2-(5-Phenyl-benzoimidazol-1-yl]quinolin-8-yl]-piperidin-4-ylamine;
1-[2-(5-Pyridin-4-yl-benzoimidazol-1-yl)-quinolin-8-yl]-piperidin-4-ylamine;
1-{2-[5-(3-Methoxy-phenyl)-benzoimidazol-1-yl]-quinolin-8-yl}-piperidin-4-ylamine;
1-[2-(5-Pyridin-3-yl-benzoimidazol-1-yl)-quinolin-8-yl]-piperidin-4-ylamine;
1-2-[5-(6-Methoxy-pyridin-3-yl)-benzoimidazol-1-yl]-quinolin-8-yl}-piperidin-4-ylamine;
1-{2-[5-(4-Aminomethyl-phenyl)-benzoimidazol-1-yl]-quinolin-8-yl}-piperidin-4-ylamine;
4-{1-[8-(4-Amino-piperidin-1-yl)-quinolin-2-yl]-1H-benzoimidazol-5-yl}-benzoic acid
methyl ester;
4-{1-[8-(4-Amino-piperidin-1-yl]quinolin-2-yl]-1H-benzoimidazol-5-yl}-phenol;
1-[[2-[5-(3-Morpholinoethoxy)-1H-benzimidazol-1-yl]-quinolin-8-yl]]-piperidin-4-ylamine trihydrochloride;
Ethyl 1-[8-(4-aminopiperidin-1-yl)-quinolin-2-yl]-benzimidazole-5-carboxylate;
N-(4-Morpholino)ethyl-1-[8-(4-aminopiperidin-1-yl)-quinolin-2-yl]-benzimidazole-5-carboxamide;
1-2-[5-(4-Methylaminomethyl-phenyl)-benzoimidazol-1-yl]-quinolin-8-yl}-piperidin-4-ylamine;
1-{2-[5-(4-Dimethylaminomethyl-phenyl)-benzoimidazol-1-yl]-quinolin-8-yl}-piperidin-4-ylamine;
1-(2-{5-[2-(2-Methyl-imidazol-1-yl)-ethoxy]-benzoimidazol-1-yl}-quinolin-8-yl)-piperidin-4-ylamine and
1-{2-[5-(2-[1,2,4]Triazol-1-yl-ethoxy)-benzoimidazol-1-yl]-quinolin-8-yl}-piperidin-4-ylamine, and the pharmaceutically acceptable salts, prodrugs and solvates of the foregoing compounds.

The invention also relates to a pharmaceutical composition for the treatment of a hyperproliferative disorder in a mammal which comprises a therapeutically effective amount of a compound of formula 1, or a pharmaceutically acceptable salt, prodrug or hydrate thereof, and a pharmaceutically acceptable carrier. In one embodiment, said pharmaceutical composition is for the treatment of cancer such as brain, lung, squamous cell, bladder, gastric, pancreatic, breast, head, neck, renal, kidney, ovarian, prostate, colorectal, oesophageal, testicular, gynecological or thyroid cancer. In another embodiment, said pharmaceutical composition is for the treatment of a non-cancerous hyperproliferative disorder such as benign hyperplasia of the skin (e.g., psoriasis), restenosis, or prostate (e.g., benign prostatic hypertropy (BPH)).

The invention also relates to a pharmaceutical composition for the treatment of pancreatitis or kidney disease (including proliferative glomerulonephritis and diabetes-induced renal disease) in a mammal which comprises a therapeutically effective amount of a compound of formula 1, or a pharmaceutically acceptable salt, prodrug or hydrate thereof, and a pharmaceutically acceptable carrier.

The invention also relates to a pharmaceutical composition for the prevention of blastocyte implantation in a mammal that comprises a therapeutically effective amount of a compound of formula 1, or a pharmaceutically acceptable salt, prodrug or hydrate thereof, and a pharmaceutically acceptable carrier.

The invention also relates to a pharmaceutical composition for treating a disease related to vasculogenesis or angiogenesis in a mammal which comprises a therapeutically effective amount of a compound of formula 1, or a pharmaceutically acceptable salt, prodrug or hydrate thereof, and a pharmaceutically acceptable carrier. In one embodiment, said pharmaceutical composition is for treating a disease selected from the group consisting of tumor angiogenesis, chronic inflammatory disease such as rheumatoid arthritis, atherosclerosis, skin diseases such as psoriasis, excema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

The invention also relates to a method of treating a hyperproliferative disorder in a mammal that comprises administering to said mammal a therapeutically effective amount of the compound of formula 1, or a pharmaceutically acceptable salt, prodrug or hydrate thereof. In one embodiment, said method relates to the treatment of cancer such as brain, squamous cell, bladder, gastric, pancreatic, breast, head, neck, oesophageal, prostate, colorectal, lung, renal, kidney, ovarian, testicular, gynecological or thyroid cancer. In another embodiment, said method relates to the treatment of a non-cancerous hyperproliferative disorder such as benign hyperplasia of the skin (e.g., psoriasis), restenosis or prostate (e.g., benign prostatic hypertropy (BPH)).

The invention also relates to a method for the treatment of a hyperproliferative disorder in a mammal which comprises administering to said mammal a therapeutically effective amount of a compound of formula 1, or a pharmaceutically acceptable salt, prodrug or hydrate thereof, in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens.

The invention also relates to a method of treating pancreatitis or kidney disease in a mammal which comprises administering to said mammal a therapeutically effective amount of a compound of formula 1, or a pharmaceutically acceptable salt, prodrug or hydrate thereof.

The invention also relates to a method of preventing blastocyte implantation in a mammal which comprises administering to said mammal a therapeutically effective amount of a compound of formula 1, or a pharmaceutically acceptable salt, prodrug or hydrate thereof.

The invention also relates to a method of treating diseases related to vasculogenesis or angiogenesis in a mammal which comprises administering to said mammal an effective amount of a compound of formula 1, or a pharmaceutically acceptable salt, prodrug or hydrate thereof. In one embodiment, said method is for treating a disease selected from the group consisting of tumor angiogenesis, chronic inflammatory disease such as rheumatoid arthritis, atherosclerosis, skin diseases such as psoriasis, excema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

Patients that can be treated with a compounds of formula 1, and the pharmaceutically acceptable salts, prodrugs and hydrates of said compounds, according to the methods of this invention include, for example, patients that have been diagnosed as having psoriasis, restenosis, atherosclerosis, BPH, lung cancer, bone cancer, CMML, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, testicular, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphonas, cancer of the bladder, cancer of the kidney or ureter (e.g., renal cell carcinoma, carcinoma of the renal pelvis), or neoplasms of the central nervous system (e.g., primary CNS lymphona, spinal axis tumors, brain stem gliomas or pituitary adenomas).

This invention also relates to a pharmaceutical composition for inhibiting abnormal cell growth in a mammal which comprises an amount of a compound of formula 1, or a pharmaceutically acceptable salt or solvate or prodrug thereof, in combination with an amount of a chemotherapeutic, wherein the amounts of the compound, salt, solvate, or prodrug, and of the chemotherapeutic are together effective in inhibiting abnormal cell growth. Many chemotherapeutics are presently known in the art. In one embodiment, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, e.g. anti-androgens.

This invention further relates to a method for inhibiting abnormal cell growth in a mammal or treating a hyperproliferative disorder which method comprises administering to the mammal an amount of a compound of formula 1, or a pharmaceutically acceptable salt or solvate or prodrug thereof, in combination with radiation therapy, wherein the amount of the compound, salt, solvate or prodrug is in combination with the radiation therapy effective in inhibiting abnormal cell growth or treating the hyperproliferative disorder in the mammal. Techniques for administering radiation therapy are known in the art, and these techniques can be used in the combination therapy described herein. The administration of the compound of the invention in this combination therapy can be determined as described herein.

It is believed that the compounds of formula 1 can render abnormal cells more sensitive to treatment with radiation for purposes of killing and/or inhibiting the growth of such cells. Accordingly, this invention further relates to a method for sensitizing abnormal cells in a mammal to treatment with radiation which comprises administering to the mammal an amount of a compound of formula 1 or pharmaceutically acceptable salt, prodrug or solvate thereof, which amount is effective in sensitizing abnormal cells to treatment with radiation. The amount of the compound, salt, or solvate in this method can be determined according to the means for ascertaining effective amounts of such compounds described herein.

This invention also relates to a method of and to a pharmaceutical composition for inhibiting abnormal cell growth in a mammal which comprises an amount of a compound of formula 1, a pharmaceutically acceptable salt or solvate thereof, a prodrug thereof, or an isotopically-labelled derivative thereof, and an amount of one or more substances selected from anti-angiogenesis agents, signal transduction inhibitors, and antiproliferative agents.

Anti-angiogenesis agents, such as MMP-2 (matrix-metalloprotienase 2) inhibitors, MMP-9 (matrix-metalloprotienase 9) inhibitors, and COX-II (cyclooxygenase II) inhibitors, can be used in conjunction with a compound of formula 1 and pharmaceutical compositions described herein. Examples of useful COX-II inhibitors include CELEBREX™ (alecoxib), valdecoxib, and rofecoxib. Examples of useful matrix metalloproteinase inhibitors are described in WO 9633172 (published Oct. 24, 1996), WO 9627583 (published March 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 9834918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published July 13, 1994), European Patent Publication 931,788 (published Jul. 28, 1999), WO 90/05719 (published May 331, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

Some specific examples of MMP inhibitors useful in the present invention are AG-3340, RO 32-3555, RS 13-0830, and the compounds recited in the following list:

3-[[4-(4-fluoro-phenoxy)-benzenesulfonyl]-(1-hydroxycarbamoyl-cyclopentyl)-amino]propionic acid;

3-exo-3-[4-(4-fluoro-phenoxy)-benzenesulfonylamino]-8-oxa-bicyclo[3.2.1]octane-3-carboxylic acid hydroxyamide;

(2R, 3R) 1-[4-(2-chloro-4-fluoro-benzyloxy)-benzenesulfonyl]-3-hydroxy-3-methyl-piperidine-2-carboxylic acid hydroxyamide;

4-[4-(4-fluoro-phenoxy)-benzenesulfonylamino]-tetrahydro-pyran-4-carboxylic acid hydroxyamide;

3-[[4-(4-fluoro-phenoxy)-benzenesulfonyl]-(1-hydroxycarbamoyl-cyclobutyl)-amino]-propionic acid;

4-[4-(4-chloro-phenoxy)-benzenesulfonylamino]-tetrahydro-pyran-4-carboxylic acid hydroxyamide;

(R) 3-[4-(4-chloro-phenoxy)-benzenesulfonylamino]-tetrahydro-pyran-3-carboxylic acid hydroxyamide;

(2R, 3R) 1-[4-(4-fluoro-2-methyl-benzyloxy)-benzenesulfonyl]-3-hydroxy-3-methyl-piperidine-2-carboxylic acid hydroxyamide;

3-[[4-(4-fluoro-phenoxy]benzenesulfonyl]-(1-hydroxycarbamoyl-1-methyl-ethyl)-amino]-propionic acid;

3-[[4-(4-fluoro-phenoxy)-benzenesulfonyl]-(4-hydroxycarbamoyl-tetrahydro-pyran-4-yl)-amino]-propionic acid;

3-exo-3-[4-(4-chloro-phenoxy)-benzenesulfonylamino]-8-oxa-bicyclo[3.2.1]octane-3-carboxylic acid hydroxyamide;

3-endo-3-[4-(4-fluoro-phenoxy)-benzenesulfonylamino]-8-oxa-bicyclo[3.2.1]octane-3-carboxylic acid hydroxyamide; and (R) 3-[4-(4-fluoro-phenoxy)-benzenesulfonylamino]-tetrahydro-furan-3-carboxylic acid hydroxyamide;

and pharmaceutically acceptable salts and solvates of said compounds.

Other anti-angiogenesis agents, including other COX-II inhibitors and other MMP inhibitors, can also be used in the present invention.

A compound of formula 1, can also be used with signal transduction inhibitors, such as agents that can inhibit EGFR (epidermal growth factor receptor) responses, such as EGFR antibodies, EGF antibodies, and molecules that are EGFR inhibitors; VEGF (vascular endothelial growth factor) inhibitors, such as VEGF receptors and molecules that can inhibit VEGF; and erbB2 receptor inhibitors, such as organic molecules or antibodies that bind to the erbB2 receptor, for example, HERCEPTIN™ (Genentech, Inc. of South San Francisco, Calif., USA).

EGFR inhibitors are described in, for example in WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998), and such substances can be used in the present invention as described herein. EGFR-inhibiting agents include, but are not limited to, the monoclonal antibodies C225, anti-EGFR 22Mab (ImClone Systems Incorporated of New York, N.Y., USA), and ABX-EGF (Abgenix antibody) the compounds ZD-1839 (AstraZeneca), BIBX-1382 (Boehringer Ingelheim), MDX-447 (Medarex Inc. of Annandale, N.J., USA), and OLX-103 (Merck & Co. of Whitehouse Station, N.J., USA), VRCTC-310 (Ventech Research) and EGF fusion toxin (Seragen Inc. of Hopkinton, Massachusettes). These and other EGFR-inhibiting agents can be used in the present invention.

VEGF inhibitors, for example SU-5416 and SU-6668 (Sugen Inc. of South San Francisco, Calif., USA), can also be combined with the compound of the present invention. VEGF inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are incorporated herein in their entireties by reference. Other examples of some specific VEGF inhibitors useful in the present invention are IM862 (Cytran Inc. of Kirkland, Wash., USA); IMC-1C11 Imclone antibody, anti-VEGF monoclonal antibody of Genentech, Inc. of South San Francisco, Calif.; and angiozyme, a synthetic ribozyme from Ribozyme (Boulder, Colo.) and Chiron (Emeryville, Calif.). These and other VEGF inhibitors can be used in the present invention as described herein.

ErbB2 receptor inhibitors, such as GW-282974 (Glaxo Wellcome pic), and the monoclonal antibodies AR-209 (Aronex Pharmaceuticals Inc. of The Woodlands, Tex., USA) and 2B-1 (Chiron), can furthermore be combined with the compound of the invention, for example those indicated in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), which are all hereby incorporated herein in their entireties by reference. ErbB2 receptor inhibitors useful in the present invention are also described in U.S. Provisional Application No. 60/117,341, filed Jan. 27, 1999, and in U.S. Provisional Application No. 60/117,346, filed Jan. 27, 1999, both of which are incorporated in their entireties herein by reference. The erbB2 receptor inhibitor compounds and substance described in the aforementioned PCT applications, U.S. patents, and U.S. provisional applications, as well as other compounds and substances that inhibit the erbB2 receptor, can be used with the compound of the present invention in accordance with the present invention.

The compound of the invention can also be used with other agents useful in treating abnormal cell growth or cancer, including, but not limited to, agents capable of enhancing antitumor immune responses, such as CTLA4 (cytotoxic lymphocite antigen 4) antibodies, and other agents capable of blocking CTLA4; and anti-proliferative agents such as farnesyl protein transferase inhibitors, and αv β3 inhibitors, such as the αv β3 antibody Vitaxin, and αvβ5 inhibitors and the like. Specific CTLA4 antibodies that can be used in the present invention include those described in U.S. Provisional Application 60/113,647 (filed Dec. 23, 1998) which is incorporated by reference in its entirety, however other CTLA4 antibodies can be used in the present invention.

The compounds of formula 1 and their pharmaceutically acceptable salts, prodrugs and solvates can each independently also furthermore be used in a palliative neo-adjuvant/adjuvant therapy in alleviating the symptoms associated with the diseases recited herein as well as the symptoms associated with abnormal cell growth. Such therapy can be a monotherapy or can be in a combination with chemotherapy and/or immunotherapy.

The invention also relates to a method of preparing a compound of the formula 1

The terms "abnormal cell growth" and "hyperproliferative disorder" are used interchangeably in this application.

"Abnormal cell growth", as used herein, unless otherwise indicated, refers to cell growth that is independent of normal regulatory mechanisms (e.g., loss of contact inhibition). This includes the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (4) any tumors that proliferate by receptor tyrosine kinases; (5) any tumors that proliferate by aberrant serine/threonine kinase activation; and (6) benign and malignant cells of other proliferative diseases in which aberrant serine/threonine kinase activation occurs.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above.

The term "Me" means methyl, "Et" means ethyl, and "Ac" means acetyl.

The term "halo", as used herein, unless otherwise indicated, means fluoro, chloro, bromo or iodo. Preferred halo groups are fluoro, chloro and bromo.

The term "alkyl", as used herein, unless otherwise indicated, includes saturated monovalent hydrocarbon radicals having straight, branched, or cyclic moieties (including fused and bridged bicyclic and spirocyclic moieties), or a combination of the foregoing moieties. For an alkyl group to have cyclic moieties, the group must have at least three carbon atoms.

The term "cycloalkyl", as used herein, unless otherwise indicated, includes cyclic alkyl moieties wherein alkyl is as defined above. The use of the term "cycloalkyl" shall not be construed as limiting the term "alkyl" to non-cyclic moieties.

The term "alkenyl", as used herein, unless otherwise indicated, includes alkyl moieties having at least one carbon—carbon double bond wherein alkyl is as defined above and including E and Z isomers of said alkenyl moiety.

The term "alkynyl", as used herein, unless otherwise indicated, includes alkyl moieties having at least one carbon—carbon triple bond wherein alkyl is as defined above.

The term "alkoxy", as used herein, unless otherwise indicated, includes O-alkyl groups wherein alkyl is as defined above.

The term "aryl", as used herein, unless otherwise indicated, includes an organic radical derived from an aromatic hydrocarbon by removal of one hydrogen, such as phenyl or naphthyl.

The term "4 to 10 membered heterocyclic", as used herein, unless otherwise indicated, includes aromatic and non-aromatic heterocyclic groups containing one to four heteroatoms each selected from O, S and N, wherein each heterocyclic group has from 4–10 atoms in its ring system, and with the proviso that the ring of said group does not contain two adjacent O or S atoms. Non-aromatic heterocyclic groups include groups having only 4 atoms in their ring system, but aromatic heterocyclic groups must have at least 5 atoms in their ring system. The heterocyclic groups include benzo-fused ring systems. An example of a 4 membered heterocyclic group is azetidinyl (derived from azetidine). An example of a 5 membered heterocyclic group is thiazolyl and an example of a 10 membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyclo[3.1.0]hexanyl, 3-azabicyclo[4.1.0]heptanyl, azabicyclo[2.2.2]hexanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Spiro moieties are also included within the scope of this definition including 1-oxa-6-aza-spiro[2.5]oct-6-yl. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached). An example of a heterocyclic group wherein 2 ring carbon atoms are substituted with oxo (=O) moieties is 1,1-dioxo-thiomorpholinyl.

The phrase "pharmaceutically acceptable salt(s)", as used herein, unless otherwise indicated, includes salts of acidic or basic groups which may be present in the compounds of formula 1. The compounds of formula 1 that are basic in nature are capable of forming a wide variety of salts with various inorganic and organic acids. The acids that may be used to prepare pharmaceutically acceptable acid addition salts of such basic compounds of formula 1 are those that form non-toxic acid addition salts, i.e., salts containing pharmacologically acceptable anions, such as the acetate, benzenesulfonate, benzoate, bicarbonate, bisulfate, bitartrate, borate, bromide, calcium edetate, camsylate, carbonate, chloride, clavulanate, citrate, dihydrochloride, edetate, dislyate, estolate, esylate, ethylsuccinate, fumarate, gluceptate, gluconate, glutamate, glycollylarsanilate, hexylresorcinate, hydrabamine, hydrobromide, hydrochloride, iodide, isothionate, lactate, lactobionate, laurate, malate, maleate, mandelate, mesylate, methylsulfate, mucate, napsylate, nitrate, oleate, oxalate, pamoate (embonate), palmitate, pantothenate, phospate/diphosphate, polygalacturonate, salicylate, stearate, subacetate, succinate, tannate, tartrate, teoclate, tosylate, triethiodode, and valerate salts. Since a single compound of the present invention may include more than one acidic or basic moieties, the compounds of the present invention may include mono, di or tri-salts in a single compound.

Those compounds of the present invention that are acidic in nature are capable of forming base salts with various pharmacologically acceptable cations. Examples of such salts include the alkali metal or alkaline earth metal salts and, particularly, the calcium, magnesium, sodium and potassium salts of the compounds of the present invention.

In the compounds of formula 1, where terms such as $(CR^4R^5)_m$ or $(CR^4R^5)_t$ are used, $R^4$ and $R^5$ may vary with each iteration of m or t above 1. For instance, where m or t is 2, the terms $(CR^4R^5)_m$ or $(CR^4R^5)_t$ may equal —CH$_2$CH$_2$—, or —CH(CH$_3$)C(CH$_2$CH$_3$)(CH$_2$CH$_2$CH$_3$)—, or any number of similar moieties falling within the scope of the definitions of $R^4$ and $R^5$.

Certain compounds of formula 1 may have asymmetric centers and therefore exist in different enantiomeric forms. All optical isomers and stereoisomers of the compounds of formula 1, and mixtures thereof, are considered to be within the scope of the invention. With respect to the compounds of formula 1, the invention includes the use of a racemate, one or more enantiomeric forms, one or more diastereomeric forms, or mixtures thereof. The compounds of formula 1 may also exist as tautomers. This invention relates to the use of all such tautomers and mixtures thereof.

The subject invention also includes isotopically-labelled compounds, which are identical to those recited in formula 1, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes ar particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of formula 1 of this invention and prodrugs thereof can generally be prepared by carrying out the procedures disclosed in the Schemes and/or in the Examples and Preparations below, by substituting a readily available isotopically labelled reagent for a non-isotopically labelled reagent.

This invention also encompasses pharmaceutical compositions containing and methods of treating proliferative disorders, or abnormal cell growth, by administering prodrugs of compounds of the formula 1. Compounds of formula 1 having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of formula 1. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in *Advanced Drug Delivery Reviews,* 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. Free amines can also be derivatized as amides, sulfonamides or phosphonamides. All of these prodrug moieties may incorporate groups including but not limited to ether, amine and carboxylic acid functionalities.

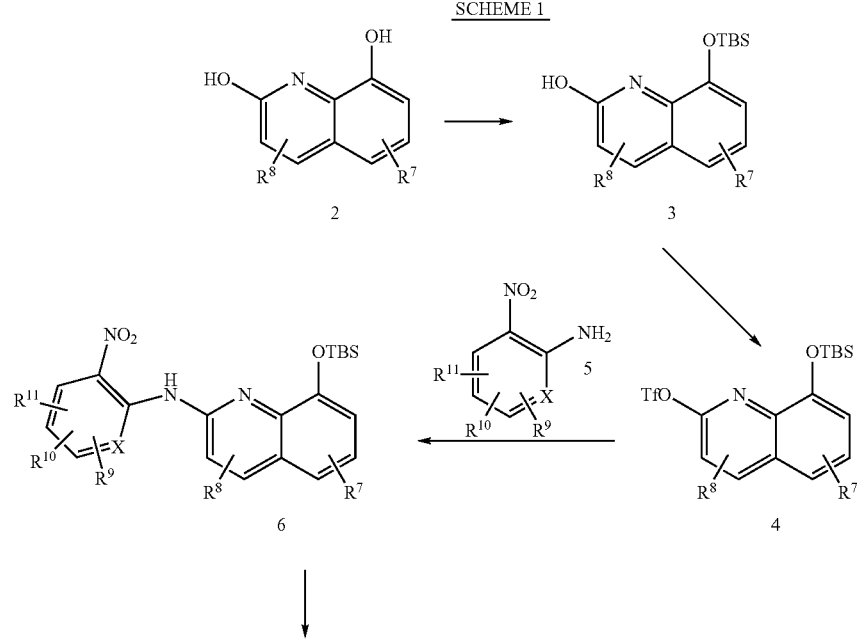

-continued
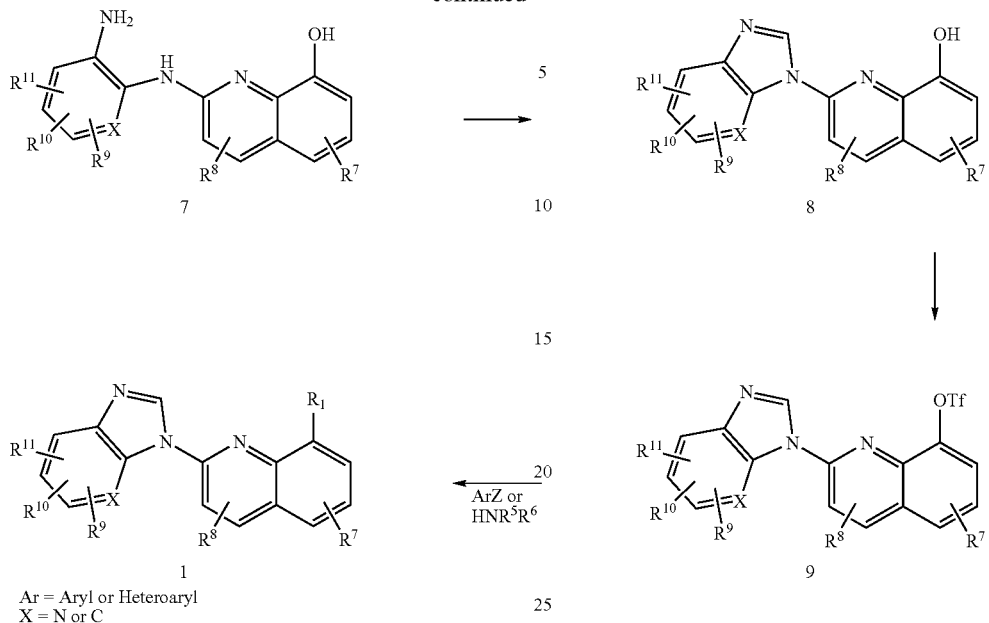
Ar = Aryl or Heteroaryl
X = N or C
SCHEME 1A
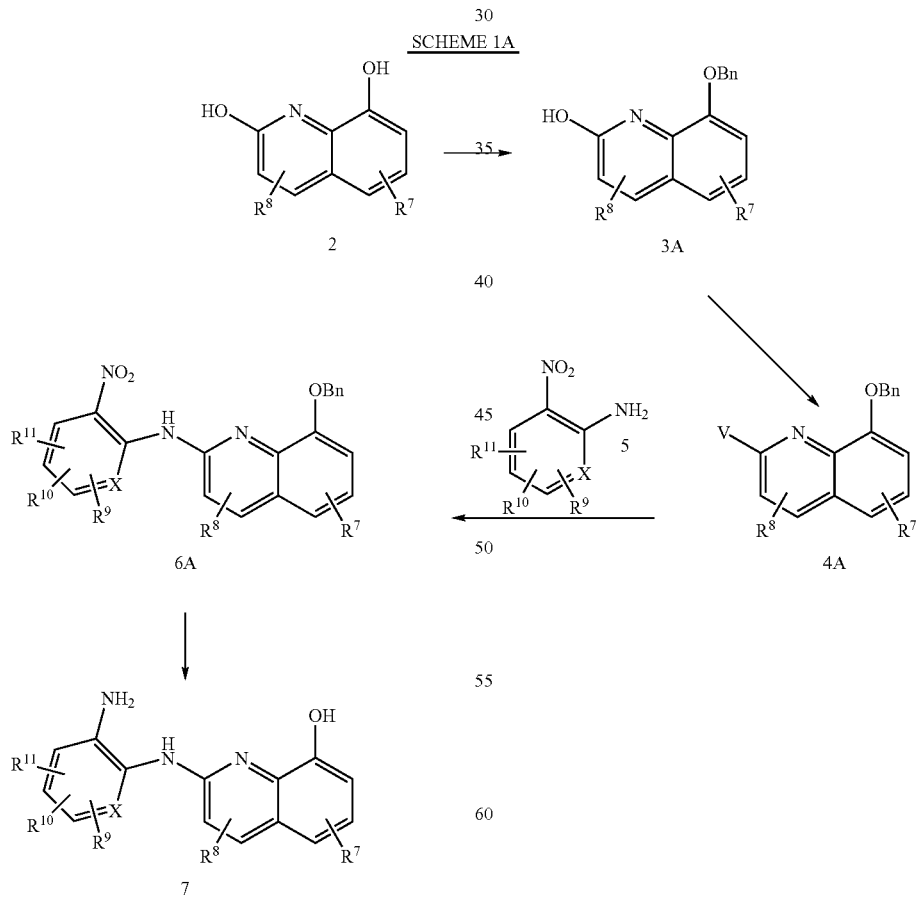
X = N or C
V = Cl, Br, OTf SCHEME 1B
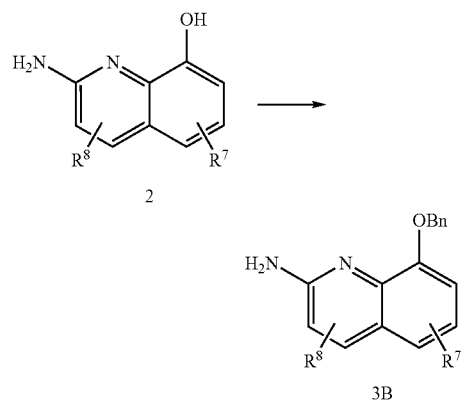
X = N or C
SCHEME 3
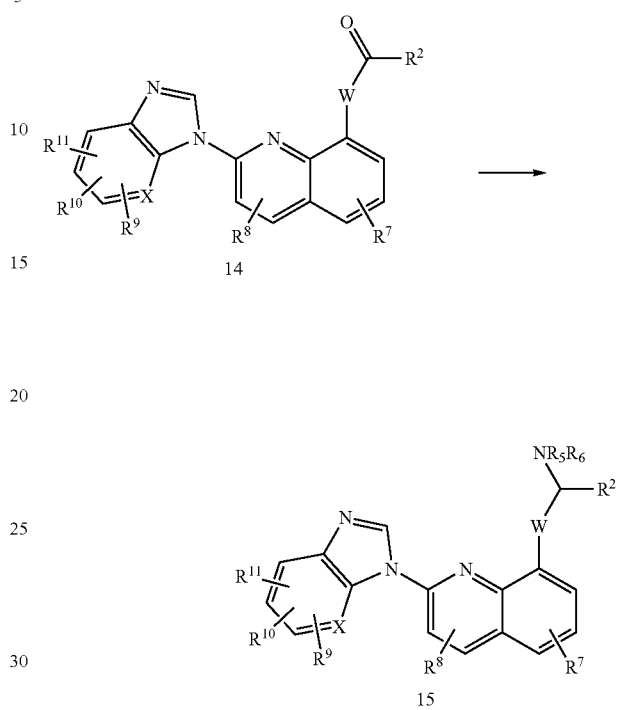
W = aryl or heterocycle
X = C or N
SCHEME 2
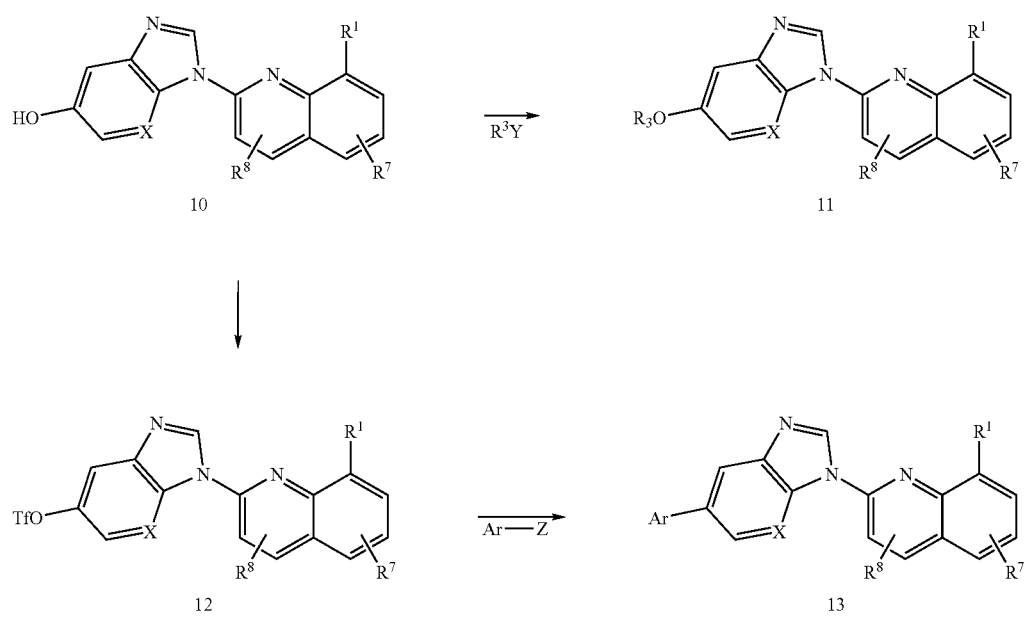
Ar = Aryl or Heteroaryl
X = N, C SCHEME 4
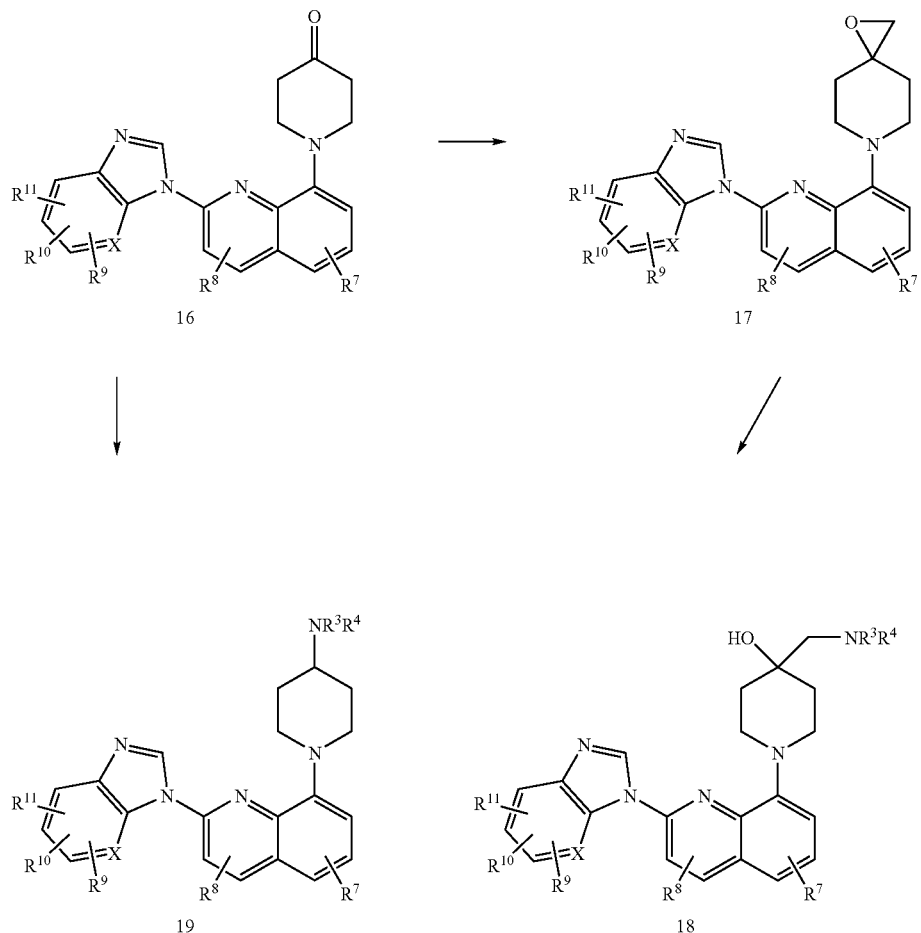
X = C or N
SCHEME 5
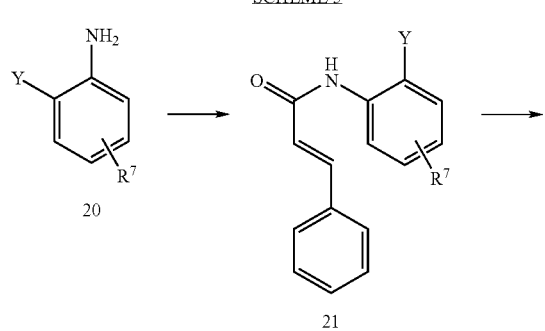
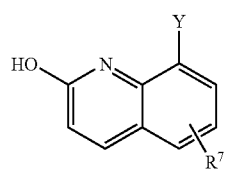
Y = Cl or Br
-continued
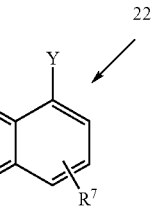

SCHEME 6
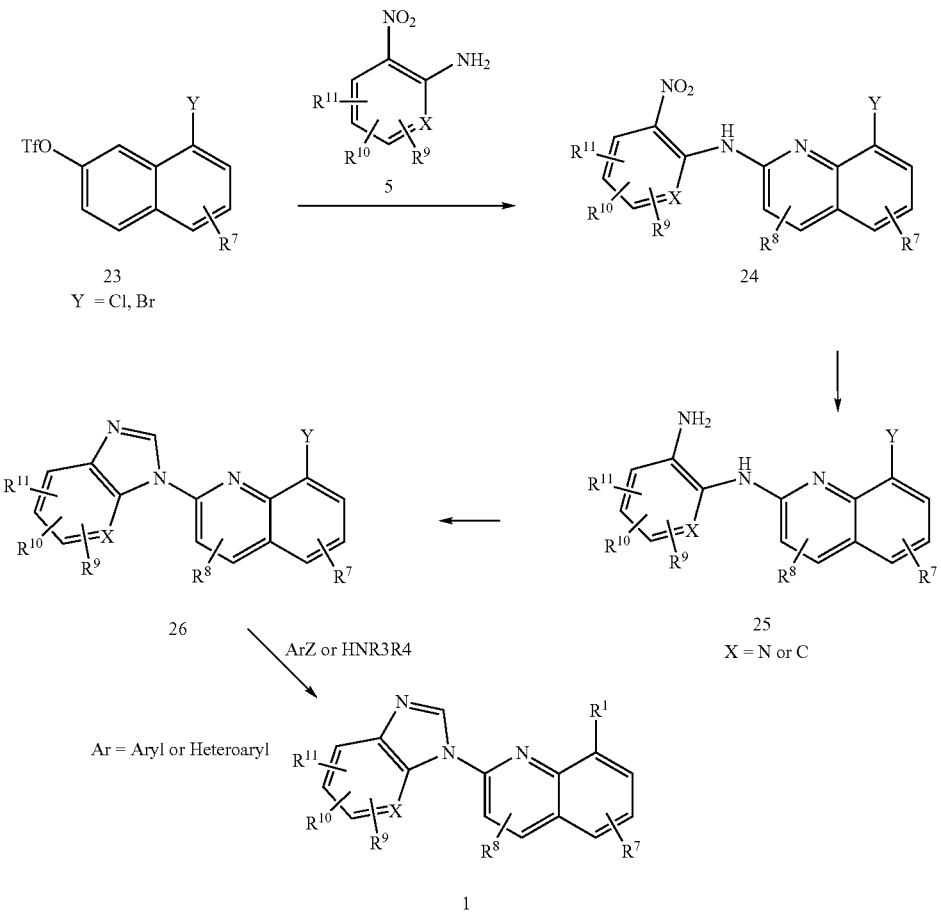
SCHEME 7
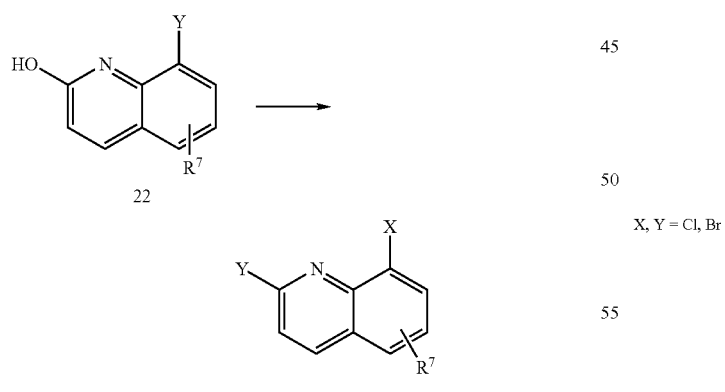
X, Y = Cl, Br
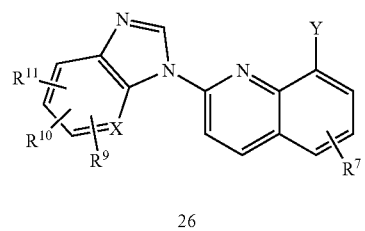
SCHEME 8
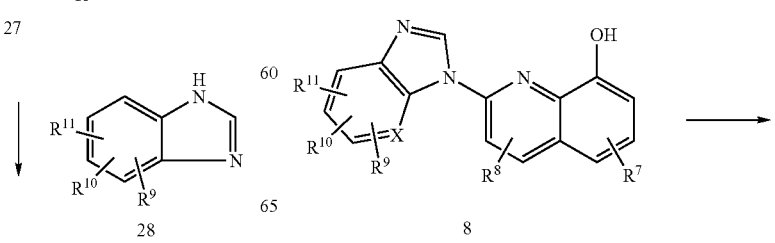

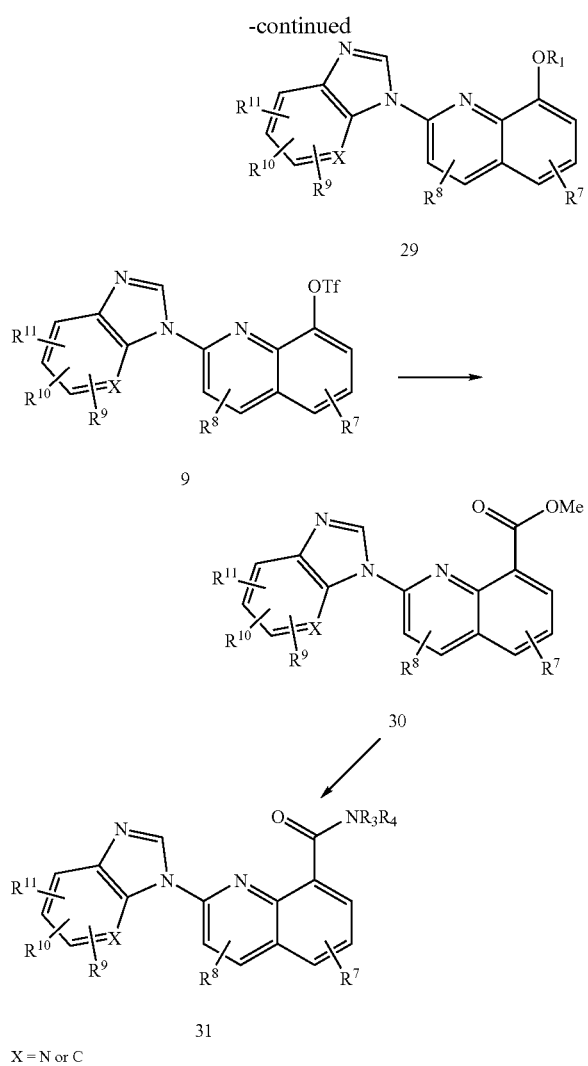

X = N or C

DETAILED DESCRIPTION OF THE INVENTION

General synthetic methods which may be referred to for preparing the compounds of the present invention are provided in U.S. Pat. No. 5,990,146 (issued Nov. 23, 1999) (Warner-Lambert Co.) and PCT published application number WO 99/16755 (published Apr. 8, 1999)(Merck & Co.). The foregoing patent and patent application are incorporated herein by reference in their entirety.

Scheme 1 illustrates the synthesis of compounds of formula 1. In step 1, the diol of formula 2 is reacted with a trialkylsilyl chloride or trialkylsilyl trifluoromethanesulphonate (such as tert-butyldimethylsilyl) with a suitable organic base, such as imidazole or pyridine, in an organic solvent, such as dichloromethane (DCM) at temperature ranging from −78° C. to 45° C., preferably at ambient temperature, for 1 to 12 hours to give compound of formula 3. In step 2, compound of formula 3 is reacted with a triflating reagent and base, such as N-phenyl-bis(trifluoromethane sulfonimide) and sodium hydride or trifluoromethane sulfonic anhydrid and 2,6-dimethylpyridine, in an anhydrous organic solvent such as tetrahydrofuran (THF) or DCM at a temperature ranging from −78° C. to ambient temperature, preferably at ambient temperature, for 1 to 12 hours to give compound of formula 4.

In step 3, compound of formula 4 is reacted with the amine of formula 5, preferably X=C, with a palladium catalyst such as, tris(dibenzylideneacetone)dipalladium (0) or palladium(II) acetate and a base such as, cesium carbonate or sodium tert-butoxide, preferably cesium carbonate, and a palladium ligand such as 2,2'-bis(diphenylposphino)-1,1'-binapthyl (BINAP) or 1,2-bis(diphenylphosphio)ethane (DIPHOS), in a solvent such as 1,4-dioxane or toluene, preferably toluene, at a temperature ranging from ambient temperature to between 80–105° C., preferably at 105° C. for 1 to 48 hours. In step 4, the resulting compound of formula 6 is reduced under palladium catalysis, using either 10% palladium on carbon or 20% palladium hydroxide on carbon, with a hydrogen source, such as hydrazine, ammonium formate, or formic acid in an organic solvent such as ethanol or methanol with or without a cosolvent solvent such as THF, at a temperature ranging from ambient temperature to reflux for 1 to 24 hours to give compound of the formula 7.

In step 5, compound of the formula 7 is reacted with formamidine acetate or formic acid in an organic solvent such as 2-methoxyethanol, 1-butanol, ethanol, or formic acid, preferably ethanol, at a temperature ranging from ambient temperature to reflux, preferably at reflux, for 1 to 48 hours to give compound of formula 8. In step 6, compound of formula 8 is reacted with a triflating reagent and base, such as N-phenyl-bis(trifluoromethanesulfonimide) and sodium hydride or triethylamine in an anhydrous organic solvent such as THF, with or without a co-solvent such as dimethylformamide (DMF), at a temperature ranging from −78° C. to ambient temperature, preferably at ambient temperature, for 1 to 24 hours to give compound of formula 9.

In step 7, for $R^1$ groups that include an aryl or heteroaryl group (where Ar=aryl or heteroaryl), compound of formula 9 is reacted under palladium catalysis, such as with tetrakis (triphenylphosphine)palladium (0), with the appropriate organoborane (where $Z=B(OH)_2$ or $B(Alkyl)_2$), organostannane (where $Z=Sn(alkyl)_3$) or organozinc (where $Z=Zn$ (Halogen)). When $Z=B(OH)_2$, a base such as potassium phosphate is used in a solvent such as 1,4-dioxane or 1,2-dimethoxyethane at a temperature ranging from ambient temperature to reflux, preferably at reflux, for 1 to 48 hours to give compound of the formula 1. When $Z=B(alkyl)_2$, a base such as sodium carbonate with or without lithium chloride is used in a solvent system including ethanol and water with or without toluene at a temperature ranging from ambient temperature to reflux, preferably around 90° C., for 1 to 48 hours to give compound of the formula 1. When $Z=Sn(alkyl)_3$, with or without a base such as potassium phosphate, in a suitable organic solvent such as toluene or 1,4-dioxane and at a temperature ranging from ambient temperature to reflux, preferably between 80–100° C., for 1 to 48 hours to give compound of the formula 1. When $Z=Zn(Halogen)$, a suitable organic solvent such as THF, 1,4-dioxane or 1,2-dimethoxyethane is uased at a temperature ranging from −78° C. to reflux, preferably between 20–45° C., for 1 to 48 hours to give compound of the formula 1. For $R^1$ with an $NR^5R^6$ moiety, compound of the formula 9 is reacted with an amine $HNR^5R^6$ using a palladium catalyst such as tris(dibenzylideneacetone)dipalladium (0) or palladium acetate and a base such as, cesium carbonate or sodium tert-butoxide, preferably cesium carbonate, and a palladium ligand such as 2,2'-bis(diphenylposphino)-

1,1'-binapthyl (BINAP) or 1,2-bis(diphenylphosphio)ethane (DIPHOS) in a solvent such as 1,4-dioxane, toluene, and xylenes preferably toluene, at a temperature ranging from ambient temperature to reflux, preferably at reflux for 1 to 48 hours to give compound of formula 1. Compounds of formula 1 may have protecting groups, such as $R^{11}$, $R^{10}$ or $R^9$=OMe, that can be removed by standard conditions as discussed in "Protective Groups for Organic Synthesis". For example, $R^{11}$, $R^{10}$ or $R^9$=OMe can be transformed to $R^{11}$, $R^{10}$ or $R^9$=OH by treating with borontribromide in an organic solvent such as DCM at a temperature ranging from −78° C. to 45° C., preferably at ambient temperature for 1 to 24 hours.

Scheme 1A illustrates an alternative synthesis of compounds of formula 7. In step 1, the diol of formula 2 is reacted with benzyl chloride or benzyl bromide, preferably benzyl bromide, with a suitable base, such as potassium carbonate, sodium carbonate or cesium carbonate, in an organic solvent, such as DMF at temperature ranging from −78° C. to 100° C., preferably between 60–80° C. for 3 to 24 hours to give compound of formula 3A. In step 2, compound of formula 3A is reacted with a triflating reagent and base, such as N-phenyl-bis(trifluoromethanesulfonimide) and sodium hydride or trifluoromethanesulfonic anhydride and 2,6-dimethylpyridine, in an anhydrous organic solvent such as tetrahydrofuran (THF) or DCM at a temperature ranging from −78° C. to ambient temperature, preferably at ambient temperature, for 1 to 12 hours to give compound of formula 4A (where V=OTf. Alternatively, compound of the formula 3A is reacted with a chlorinating reagent, such as phophorus oxychloride, thionyl chloride or oxallyl chloride, in an organic solvent such as DCM, 1,2-dichloroethane(DCE) or chloroform at a temperature ranging from ambient temperature to reflux, preferably at reflux, to give compound of the formula 4A (where V=Cl). Alternatively, compound of the formula 3A is reacted with a brominating reagent, such as phophorus oxybromide, in an organic solvent such as DCM, 1,2-dichlroethane (DCE) or chloroform at a temperature ranging from ambient temperature to reflux, preferably at reflux, to give compound of the formula 4A (where V=Br).

In step 3, compound of formula 4A is reacted with the amine of formula 5, preferably X=C, with a palladium catalyst such as, tris(dibenzylideneacetone)dipalladium (0) or palladium(II) acetate and a base such as, cesium carbonate or sodium tert-butoxide, preferably cesium carbonate, and a palladium ligand such as 2,2'-bis(diphenylposphino)-1,1'-binapthyl (BINAP) or 1,2-bis(diphenylphosphio)ethane (DIPHOS), in a solvent such as 1,4-dioxane or toluene, preferably toluene, at a temperature ranging from ambient temperature to 105° C., preferably between 80–105° C. for 1 to 48 hours. In step 4, the resulting compound of formula 6A is reduced under palladium catalysis, using either 10% palladium on carbon or 20% palladium hydroxide on carbon, with a hydrogen source, such as ammonium formate, triethylammonium formate or formic acid, preferably ammonium formate triethylammonium formate, in an organic solvent such as ethanol (EtOH) or methanol (MeOH) with or without a co-solvent solvent such as THF, at a temperature ranging from ambient temperature to reflux, preferably between 75° C. and at reflux, for 1 to 24 hours to give compound of the formula 7.

Scheme 1B illustrates an alternative synthesis of compounds of formula 6A. In step 1, the aminoquinoline of formula 2B is reacted with benzyl chloride or benzyl bromide, preferably benzyl bromide, with a suitable base, such as sodium hydride or potassium hydride, in an organic solvent, such as DMF, THF or 1,2-dimethoxyethane, at temperature ranging from −78° C. to 65° C., preferably between 0–25° C., for 1 to 24 hours to give compound of formula 3B. In step 2, compound of formula 3B is reacted with bromoaromatic compound of formula 5A with a palladium catalyst such as, tris(dibenzylideneacetone)dipalladium (0) or palladium(II) acetate, preferably tris(dibenzylideneacetone)dipalladium (0), and a base such as, cesium carbonate or sodium tert-butoxide, preferably sodium tert-butoxide, and a palladium ligand such as 2,2'-bis(diphenylposphino)-1,1'-binapthyl (BINAP) or 1,2-bis(diphenylphosphio)ethane (DIPHOS), preferably 2,2'-bis(diphenylposphino)-1,1'-binapthyl (BINAP), in a solvent such as 1,4-dioxane or toluene, at a temperature ranging from ambient temperature to 105° C., preferably between 80–105° C. for 1 to 48 hours to give compound of the formula 6A.

Scheme 2 illustrates the synthesis of compounds of formula 11. In step 1, compound of the formula 10 is reacted under standard alkylation conditions by treating with an electrophile $R^3Y$, where Y can be mesylate, tosylate, bromo, iodo and chloro, preferably bromo or iodo, and a base such as sodium hydride, potassium hydride, sodium carbonate, potassium carbonate or cesium carbonate, preferably cesium carbonate in an organic solvent such as DMF or THF, preferably DMF, for 1 to 48 hours at a temperature ranging from −78° C. to 85° C. Compounds of the type formula 11 can also be obtained by starting with the appropriate amine compound of the formula 5 in step 3 of scheme 1 or step 2 of scheme 1A. Alternatively, compounds of the type formula 11 can also be obtained by starting with the appropriate bromoaromatic compound of the formula 5A in step 2 of scheme 1B.

Scheme 2 also illustrates the synthesis of compounds of formula 13 (wherein Ar is an aryl or heteroaryl group). In step 2, compound of the formula 10 is reacted with a triflating reagent and base, such as N-phenyl-bis(trifluoromethanesulfonimide) and sodium hydride or trifluoromethanesulfonic anhydride and pyridine, in an anhydrous organic solvent such as THF, with or without a co-solvent such as DMF, at a temperature ranging from −78° C. to ambient temperature, preferably at ambient temperature, for 1 to 24 hours to give compound of formula 12. In step 2, compound of formula 12 is reacted under palladium catalysis, such as with tetrakis(triphenylphosphine)palladium (0), with the appropriate organoborane (where $Z=B(OH)_2$ or $B(Alkyl)_2$), organostannane (where $Z=Sn(alkyl)_3$) or organozinc (where Z=Zn(Halogen)). When $Z=B(OH)_2$, a base such as potassium phosphate is used in a solvent such as 1,4-dioxane or 1,2-dimethoxyethane at a temperature ranging from ambient temperature to reflux, preferably at reflux, for 1 to 48 hours to give compound of the formula 13. When $Z=B(alkyl)_2$, a base such as sodium carbonate with or without lithium chloride is used in a solvent system including ethanol and water with or without toluene at a temperature ranging from ambient temperature to reflux, preferably around 90° C., for 1 to 48 hours to give compound of the formula 13. When $Z=Sn(alkyl)_3$, with or without a base such as potassium phosphate, in a suitable organic solvent such as toluene or 1,4-dioxane and at a temperature ranging from ambient temperature to reflux, preferably between 80–100° C., for 1 to 48 hours to give compound of the formula 13. When Z=Zn(Halogen), a suitable organic solvent such as THF, 1,4-dioxane or 1,2-dimethoxyethane is uased at a temperature ranging from −78° C. to reflux, preferably between 20–45° C., for 1 to 48 hours to give compound of the formula 13. Compounds of formula 13 may have protecting groups, such as $R^{11}$, $R^{10}$ or $R^9$—OMe, that can be removed by standard conditions as discussed in "Protective Groups for Organic Synthesis". For example, $R^{11}$, $R^{10}$ or $R^9$—OMe can be transformed to $R^{11}$, $R^{10}$ or $R^9$—OH by treating with borontribromide in an organic solvent such as DCM at a temperature ranging from −78° C. to 45° C., preferably at ambient temperature for 1 to 24 hours. Compounds of the type formula 13 can also be obtained by starting with the appropriate amine compound of the formula 5 in step 3 of scheme 1 or step 2 of scheme 1A. Alternatively, compounds of the type formula 11 can also be obtained by starting with the appropriate bromoaromatic compound of the formula 5A in step 2 of scheme 1 B.

Scheme 3 illustrates the synthesis of compounds of formula 15 (where W=aryl, or heterocycle). In step 1, compound of formula 14 is reacted with an amine $HNR^3R^4$ and reducing agent, such as sodium cyanoborohydride or sodium triacetoxyborohydride, and acetic acid in an organic solvent, such as methanol or ethanol, and with or without a cosolvent such as 1,2-dichloroethane, at a temperature ranging from 0° C. to 80° C., preferably at ambient temperature, for 1 to 24 hours. Compounds of formula 15 may have protecting groups, such as $R^{11}$, $R^{10}$ or $R^9$—OMe, that can be removed by standard conditions as discussed in "Protective Groups for Organic Synthesis". For example, $R^{11}$, $R^{10}$ or $R^9$=OMe can be transformed to $R^{11}$, $R^{10}$ or $R^9$=OH by treating with borontribromide in an organic solvent such as DCM at a temperature ranging from −78° C. to 45° C., preferably at ambient temperature for 1 to 24 hours. Compounds of the type formula 15 can also be obtained by starting with the appropriate ArZ or amine $NR^5R^6$ in step 7 of scheme 1.

Scheme 4 illustrates the synthesis of compounds of formula 18. In step 1, compound of formula 16 is reacted with trimethylsulfonium iodide and a base, such as sodium hydride, in an organic solvent, such as dimethylsulfoxide (DMSO) or THF, at a temperature ranging from −78° C. to 65° C., preferably at ambient temperature, for 1 to 24 hours. The resulting compound of formula 17 is reacted in step 2 with an amine $NR^3R^4$ in a solvent such as THF, methanol, ethanol, water, DMF, DMSO or any combination thereof at a temperature ranging from 0° C. to 100° C., preferably at 65° C. in a sealed tube, for 1 to 48 hours to give compound of formula 18. Compounds of formula 18 may have protecting groups, such as $R^{11}$, $R^{10}$ or $R^9$—OMe, that can be removed by standard conditions as discussed in Protective Groups for Organic Synthesis". For example, $R^{11}$, $R^{10}$ or $R^9$—OMe can be transformed to $R^{11}$, $R^{10}$ or $R^9$—OH by treating with borontribromide in an organic solvent such as DCM at a temperature ranging from −78° C. to 45° C., preferably at ambient temperature for 1 to 24 hours. Compounds of the type formula 18 can also be obtained by starting with the appropriate amine $NR^6R^6$ in step 7 of scheme 1.

Scheme 4 also illustrates the synthesis of compound of formula 19. In step 1, compound of formula 16 is reacted with an amine $HNR^3R^4$ and reducing agent, such as sodium cyanoborohydride or sodium triacetoxyborohydride, and acetic acid in an organic solvent, such as methanol, ethanol and with or without a co-solvent such as 1,2-dichloroethane (DCE), at a temperature ranging from 0° C. to 80° C., preferably at ambient temperature, for 1 to 24 hours. Compounds of formula 19 may have protecting groups, such as $R^{11}$, $R^{10}$ or $R^9$—OMe, that can be removed by standard conditions as discussed in Protective Groups for Organic Synthesis". For example, $R^{11}$, $R^{10}$ or $R^9$—OMe can be transformed to $R^{11}$, $R^{10}$ or $R^9$—OH by treating with borontribromide in an organic solvent such as DCM at a tempera-ture ranging from −78° C. to 45° C., preferably at ambient temperature for 1 to 24 hours. Compound of the type formula 19 can also be obtained by starting with the appropriate amine $NR^5R^6$ in step 7 of scheme 1.

Scheme 5 and 6 illustrate an alternative synthetic scheme for compound of formula 1. In step 1, bromoaniline 20 is acylated with cinnamyl chloride in an organic solvent, such as DCM or THF, preferably DCM, in the presence of an organic base, such as pyridine or triethylamine, preferably pyridine, at a temperature ranging from −78° C. to 40° C., preferably between 0° C. and 25° C., for 1 to 24 hours to give compound of formula 21. In step 2, compound of formula 21 is reacted with a strong Lewis acid, such as aluminum trichloride, in an organic solvent, such as chlorobenzene, at a temperature ranging from 25° C. to 120° C., preferably between 90 ° C. and 120° C., for 1 to 24 hours to give compound of formula 22. In step 3, compound of formula 22 is reacted with a triflating reagent and base, such as N-phenyl-bis(trifluoromethanesulfonimide) and sodium hydride or trifluoromethanesulfonic anhydride and 2,6-dimethylpyridine, in an anhydrous organic solvent such as THF or DCM at a temperature ranging from −78° C. to ambient temperature, preferably at ambient temperature, for 1 to 24 hours to give compound of formula 23.

In scheme 6, compound of formula 23, in step 1, is reacted with an amine of formula 5, preferably X=C, with a palladium catalyst such as, tris(dibenzylideneacetone)dipalladium (0) or palladium(II) acetate and a base such as, cesium carbonate or sodium tert-butoxide, preferably cesium carbonate, and a palladium ligand such as 2,2'-bis (diphenylposphino)-1,1-binapthyl (BINAP) or 1,2-bis (diphenylphosphio)ethane (DIPHOS), in a solvent such as 1,2-dioxane or toluene, preferably toluene, at a temperature ranging from ambient temperature to 105° C., preferably between 80° C.–105° C. for 1 to 48 hours. In step 2, the resulting compound of formula 24 is reduced with iron powder and ammonium chloride in an organic solvent, such as ethanol or methanol, with or without a co-solvent solvent, such as water, at a temperature ranging from ambient temperature to reflux, preferably at reflux, for 1 to 24 hours to give compound of the formula 25.

In step 3, compound of the formula 25 is reacted with formamidine acetate or formic acid in an organic solvent such as 2-methoxyethanol, 1-butanol, ethanol, or formic acid, preferably ethanol, at a temperature ranging from ambient temperature to reflux, preferably at reflux, for 1 to 48 hours to give compound of formula 26. In step 4, for $R^1$ groups that include an aryl or heteroaryl group (where Ar=aryl or heteroaryl), compound of formula 26 is reacted under palladium catalysis, such as with tetrakis(triphenylphosphine)palladium (0), with the appropriate organoborane (where Z=B(OH)$_2$ or B(Alkyl)$_2$), organostannane (where Z=Sn(alkyl)$_3$) or organozinc (where Z=Zn(Halogen)). When Z=B(OH)$_2$, a base such as potassium phosphate is used in a solvent such as 1,4-dioxane or 1,2-dimethoxyethane at a temperature ranging from ambient temperature to reflux, preferably at reflux, for 1 to 48 hours to give compound of the formula 1. When Z=B(alkyl)$_2$, a base such as sodium carbonate with or without lithium chloride is used in a solvent system including ethanol and water with or without toluene at a temperature ranging from ambient temperature to reflux, preferably around 90° C., for 1 to 48 hours to give compound of the formula 1. When Z=Sn(alkyl)$_3$, with or without a base such as potassium phosphate, in a suitable organic solvent such as toluene or 1,4-dioxane and at a temperature ranging from ambient temperature to reflux, preferably between 80–100° C., for 1 to 48 hours to give compound of the formula 1. When Z=Zn(Halogen), a suitable organic solvent such as THF, 1,4-dioxane or 1,2-dimethoxyethane is uased at a temperature ranging from −78° C. to reflux, preferably between 20–45° C., for 1 to 48 hours to give compound of the formula 1. For $R^1$ with an $NR^5R^6$ moiety, compound of the formula 26 is reacted with an amine $HNR^5R^6$ using a palladium catalyst such as tris(dibenzylideneacetone)dipalladium (0) or palladium acetate and a base such as, cesium carbonate or sodium tert-butoxide, preferably cesium carbonate, and a palladium ligand such as 2,2'-bis(diphenylposphino)-1,1'-binapthyl (BINAP) or 1,2-bis(diphenylphosphio)ethane (DIPHOS) in a solvent such as 1,4-dioxane, toluene, and xylenes, preferably toluene when Y=Br and preferably xylenes when Y=Cl, at a temperature ranging from ambient temperature to reflux, preferably at reflux for 1 to 72 hours to give compound of formula 1. Compounds of formula 1 may have protecting groups, such as $R^{11}$, $R^{10}$ or $R^9$=OMe, that can be removed by standard conditions as discussed in Protective Groups for Organic Synthesis". For example, $R^{11}$, $R^{10}$ or $R^9$=OMe can be transformed to $R^{11}$, $R^{10}$ or $R^9$=OH by treating with borontribromide in an organic solvent such as DCM at a temperature ranging from −78° C. to 45° C., preferably at ambient temperature for 1 to 24 hours.

Alternatively, compound of formula 26 can be prepared from compounds of formula 22 in a two step sequence as outlined in scheme 7. In step 1, compound of formula 22, where X=Cl, is reacted with either phosphorous oxychloride, thionyl chloride or oxallyl chloride, preferably oxallyl chloride, with or without an organic solvent, such as chloroform or DCE, preferably DCE, at a temperature ranging from ambient temperature to reflux, preferably at reflux, for 1 to 24 hours to give compound of the formula 27. Where X=Br, compound of formula 22 is reacted with phosphorous oxybromide with an organic solvent, such as chloroform or DCE, preferably chloroform, at a temperature ranging from ambient temperature to reflux, preferably at reflux, for 1 to 24 hours to give compound of the formula 27. In step 2, compound of formula 27, where X=Br or Cl, is reacted with a compound of formula 28 in an organic solvent, such as DMF or 1-methyl-2-pyrrolidinone, with or without a base, such as sodium hydride or sodium bis(trimethylsilyl)amide, at a temperature ranging from ambient temperature to 150° C., preferably at 60–85° C. when using a base and 150° C. when not, for 1 to 24 hours to give compound of the formula 26.

In step 1 of scheme 8, compound of the formula 8 is reacted with an electrophile RY, where Y is a mesylate, tosylate, bromide, chloride or iodide, and a base, such as sodium hydride, potassium hydride, potassium carbonate, sodium carbonate or cesium carbonate, in a solvent, such as DMF, THF, DMSO or 1,2-dimethoxyethane, at a temperature ranging from −78° C. to 65° C., to give compound of the the formula 29. Compounds of formula 29 may have protecting groups, such as $R^{11}$, $R^{10}$ or $R^9$=OMe, that can be removed by standard conditions as discussed in "Protective Groups for Organic Synthesis". For example, $R^{11}$, $R^{10}$ or $R^9$=OMe can be transformed to $R^{11}$, $R^{10}$ or $R^9$=OH by treating with borontribromide in an organic solvent such as DCM at a temperature ranging from −78° C. to 45° C., preferably at ambient temperature for 1 to 24 hours.

Also outlined in scheme 1 in step 1, compound of the formula 9 is reacted with carbon monoxide, at a pressure range of atmospheric to 50 psi, preferably 50 psi, in the presence of an organic base, such as triethylamine, under palladium catalysis, such as palladium acetate, with a ligand, such as 1,3-bis(diphenylphosphino)propane, in a solvent, such as DMF, in the presence of methanol to give compound of the formula 30. In step 2, compound of the formula 30 is reacted with a preformed complex of an amine $HNR^3R^4$ (or its hydrochloride salt) with trimethylaluminum in a solvent such as DCM or DCE at a temperature range of 0° C. to reflux to give compound of the formula 31. Compounds of formula 31 may have protecting groups, such as $R^{11}$, $R^{10}$ or $R^9$=OMe, that can be removed by standard conditions as discussed in "Protective Groups for Organic Synthesis". For example, $R^{11}$, $R^{10}$ or $R^9$=OMe can be transformed to $R^{11}$, $R^{10}$ or $R^9$=OH by treating with borontribromide in an organic solvent such as DCM at a temperature ranging from −78° C. to 45° C., preferably at ambient temperature for 1 to 24 hours.

The compounds of the present invention may have asymmetric carbon atoms. Diasteromeric mixtures can be separated into their individual diastereomers on the basis of their physical chemical differences by methods known to those skilled in the art, for example, by chromatography or fractional crystallization. Enantiomers can be separated by converting the enantiomeric mixtures into a diastereomric mixture by reaction with an appropriate optically active compound (e.g., alcohol), separating the diastereomers and converting (e.g., hydrolyzing) the individual diastereomers to the corresponding pure enantiomers. All such isomers, including diastereomeric mixtures and pure enantiomers are considered as part of the invention.

The compounds of formulas 1, 13, 15, 18, 19, 29, 31 that are basic in nature are capable of forming a wide variety of different salts with various inorganic and organic acids. Although such salts must be pharmaceutically acceptable for administration to animals, it is often desirable in practice to initially isolate the compound of formula 1, 13, 15, 18, 19, 29, 31 from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of formula 1, 13, 15, 18, 19, 29, 31 that are acidic in nature are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of formula 1, 13, 15, 18, 19, 29, 31. Such non-toxic base salts include those derived from such pharmacologically acceptable cations as sodium, potassium calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product. Since a single compound of the present invention may include more than one acidic or basic moieties, the compounds of the present invention may include mono, di or tri-salts in a single compound.

The activity of the compounds of formula 1, 13, 15, 18, 19, 29, 31 may be determined by the following procedure.

| General PGT Kinase ELISA Method |  |
| --- | --- |
| The following reagent and stock solutions are used: | |
| adenosine triphosphat (ATP) | Sigma, cat. #A-2383 |
| bovine serum albumin (BSA) | Sigma, cat. #A-3294 |
| Dulbecco's PBS (dPBS) | Gibco-BRL, cat. #14190-136 |
| MaxiSorp plates | Nunc, cat. #439454 |
| $MgCl_2$ | Sigma, cat. #M-1028 |
| Poly-Glu-Tyr (PGT) | Sigma, cat. #P-0275 |
| TMB Micowell Substrate | Kirkegaard & Perry, cat. #50-76-05 |
| Tween 20 | Sigma, cat. #P-1379 |
| HRP-PY54 antibody | OSI Pharmaceuticals, Inc. |

Phosphorylation Buffer (PB): 50 mM HEPES, pH 7.3, 125 mM NaCl, 24 mM $MgCl_2$; Wash Buffer (WB): dPBS + 0.1% Tween 20 (polyoxyethylene sorbitan); and Blocking Buffer: 3% BSA, 0.05% Tween 20 in dPBS.

Assay Procedure:

(a) For plate coating, fill Nunc MaxiSorp plate with 100 μl per well of Poly-Glu-Tyr (PGT) diluted in dPBS (various concentrations). The plate is the incubated overnight at 37° C. The supernatant PGT is then disgarded, and the plates are washed 3× with Wash Buffer.

(b) The PDGF enzyme is then diluted in PB to an appropriate concentration, and 25 μl of this stock solution is added per well.

(c) ATP is then diluted (from 20 mM stock) to an appropriate concentration (0.5 nM–2 uM) with PB. The phosphorylation reaction is commenced by addition of 25 μl ATP solution to each well of the assay plate. Incubation is continued for about 10 minutes, with shaking at room temperature.

(d) The reaction is stopped by aspirating off the reaction mixture. The plate is then washed 4× with WB.

(e) The HRP-PY54 antibody is diluted to an appropriate concentration in blocking buffer. 50 μl of this solution is then added per well, followed by incubation for 25–35 minutes at room temperature. The antibody-containing solution is aspirated away and the plate is again washed 4× with WB.

(f) The extent of reaction is determined by measurement of light absorbance at 450 nm. First, color is developed by addition of TMB solution, 50 μl per well, and the reaction is permitted to run until wells with positive signals achieve about 0.6–1.2 $OD_{450}$ units. Color development is then stopped by addition of 50 μl per well of 0.09 M $H_2SO_4$. The background controls are wells without PGT, but with all other components included. As aforementioned, preferred signal is generally in the range of 0.6–1.2 OD units, with esentially no background.

The in vitro activity of the compounds of the present invention in inhibiting the PDGF β receptor may be determined by the following procedure.

Inhibition of tyrosine kinase activity may be measured using a recombinant enzyme in an assay that measures the ability of compounds to inhibit the phosphorylation of the exogenous substrate, polyGluTyr (PGT, Sigma™, 4:1). The cytoplasmic domain of the human PDGFβ receptor (amino acids 559–1106) (Ishikawa, F., et al. Nature 338: 557–562, 1989) is expressed in Sf9 insect cells as a glutathione S-transferase (GST)-fusion protein using the baculovirus expression system. The protein is then purified from the lysates of these cells using glutathione agarose affinity columns.

The enzyme assay is performed in 96-well plates that are coated with the PGT substrate (0.625 μg PGT per well). Test compounds are diluted in dimethylsulfoxide (DMSO), and then added to the PGT plates so that the final concentration of DMSO in the assay is 1.6% (v/v). The recombinant enzyme is diluted in phosphorylation buffer (50 mM Hepes, pH 7.3, 125 mM NaCl, 24 mM $MgCl_2$). The reaction is initiated by the addition of ATP to a final concentration of 10 μM. After a 10 minute incubation at room temperature with shaking, the reaction is aspirated, and the plates are washed with wash buffer (PBS-containing 0.1% Tween-20): The amount of phosphorylated PGT is quantitated by incubation with a horseradish peroxidase(HRP)-conjugated PY-54 antibody (Transduction Labs), developing with TMB peroxidase (TMB is 3,3',5,5'-tetramethylbenzidine), and detection on a BioRad™ Microplate reader at 450 nM. Inhibition of the kinase enzymatic activity by the test compound is detected as a reduced absorbance, and the concentration of the compound that is required to inhibit the signal by 50% (under the circumstances of the assay) is reported as the IC 50 value for the test compound.

To measure the ability of the compounds to inhibit PDGFRβ tyrosine kinase activity for the full length protein that exists in a cellular context, the porcine aortic endothelial (PAE) cells transfected with the human PDGFRβ (Westermark, Bengt, et. al., PNAS 87, pp128–132, 1990) may be used. Cells are plated and allowed to attach to 96-well dishes in the same media (Ham's F12) with 10% FBS (fetal bovine serum) for 6–8 hours. The cells are washed, re-fed with serum depleted media, and allowed to incubate over night. Immediately prior to dosing with compound, the cells are re-fed with the serum depleted media. Test compounds, dissolved in DMSO, are diluted into the media (final DMSO concentration 0.5% (v/v)). At the end of a 10 minutes incubation, PDGF-BB (100 ng/ml final) is added to the media for an 8 minute incubation. The cells are washed with Hepes buffered saline solution (HBSS) and lysed in 50 ul of HNTG buffer (20 mM Hepes, pH 7.5, 150 mM NaCl, 0.2% Triton™ X-100, 10% glycerol, plus 0.2 mM PMSF (phenymethylsulfonyl fluoride), 1 μg/ml pepstatin, 1 μg/ml leupeptin, 1 μg/ml aprotonin, 2 mM sodium pyrophosphate, 2 mM sodium orthovanadate) and then diluted with 50 ul of HG dilution buffer (20 mM Hepes, pH 7.5, 10% glycerol, 0.2 mM PMSF (phenymethylsulfonyl fluoride), 1 μg/ml pepstatin, 1 μm/l leupeptin, 1 μg/ml aprotonin, 2 mM sodium pyrophosphate, 2 mM sodium orthovanadate). The extent of phosphorylation of PDGFRβ is measured using an ELISA assay. The 96-well Protein A coated plates are blocked with Superblock (Pierce) and coated with 0.5 μg per well anti-PDGFRβ P20 antibody (Santa Cruz, catalog number SC-339).

Any unbound antibody is washed off the plates prior to addition of the cell lysate. After a 2 hour room temperature incubation of the lysates (50 ul) with the PDGFRβ antibody, the PDGFRβ associated phosphotyrosine is quantitated by development with the HRP-conjugated PY-54 antibody and TMB, as described above. The ability of the compounds to inhibit the PDGF-BB stimulated autophosphorylation reaction by 50% under the conditions used, relative to PDGF-BB-stimulated controls, is reported as the $IC_{50}$ value for the test compound. The compounds of the present invention, including the examples recited below, generally have $IC_{50}$ values using the foregoing procedure falling within the following range: 1–1000 nM.

Assay for Inhibition Activity Toward the KDR/VEGF Receptor

The in vitro activity of the compounds of the present invention in inhibiting the KDR/VEGF receptor may be determined by the following procedure.

The ability of the compounds of the present invention to inhibit tyrosine kinase activity may be measured using a recombinant enzyme in an assay that measures the ability of compounds to inhibit the phosphorylation of the exogenous substrate, polyGluTyr (PGT, Sigma™, 4:1). The kinase domain of the human KDR/VEGF receptor (amino acids 805–1350) is expressed in Sf9 insect cells as a glutathione S-transferase (GST)-fusion protein using the baculovirus expression system. The protein is purified from the lysates of these cells using glutathione agarose affinity columns. The enzyme assay is performed in 96-well plates that are coated with the PGT substrate (0.625 μg PGT per well). Test compounds are diluted in dimethylsulfoxide (DMSO), and then added to the PGT plates so that the final concentration of DMSO in the assay is 1.6% (v/v). The recombinant enzyme is diluted in phosphorylation buffer (50 mM Hepes, pH 7.3, 125 mM NaCl, 24 mM $MgCl_2$). The reaction is initiated by the addition of ATP to a final concentration of 10 μM. After a 30 minute incubation at room temperature with shaking, the reaction is aspirated, and the plates are washed with wash buffer (PBS-containing 0.1% Tween-20). The amount of phosphorylated PGT is quantitated by incubation with a HRP-conjugated (HRP is horseradish peroxidase) PY-54 antibody (Transduction Labs), developed with TMB peroxidase (TMB is 3,3',5,5'-tetramethylbenzidine), and the reaction is quantitated on a BioRad™ Microplate reader at 450 nM. Inhibition of the kinase enzymatic activity by the test compound is detected as a reduced absorbance, and the concentration of the compound that is required to inhibit the signal by 50% is reported as the $IC_{50}$ value for the test compound.

To measure the ability of the compounds to inhibit KDR tyrosine kinase activity for the full length protein that exists in a cellular context, the porcine aortic endothelial (PAE) cells transfected with the human KDR (Waltenberger et al., J. Biol. Chem. 269:26988, 1994) may be used. Cells are plated and allowed to attach to 96-well dishes in the same media (Ham's F12) with 10% FBS (fetal bovine serum). The cells are then washed, re-fed with serum depleted media that contains 0.1% (v/v) bovine serum albumin (BSA), and allowed to incubate for 24 hours. Immediately prior to dosing with compound, the cells are re-fed with the serum depleted media (without BSA). Test compounds, dissolved in DMSO, are diluted into the media (final DMSO concentration 0.5% (v/v)). At the end of a 2 hour incubation, $VEGF_{165}$ (50 ng/ml final) is added to the media for an 8 minute incubation. The cells are washed and lysed in HNTG buffer (20 mM Hepes, pH 7.5, 150 mM NaCl, 0.2% Triton™ X-100, 10% glycerol, 0.2 mM PMSF (phenymethylsulfonyl fluoride), 1 μg/ml pepstatin, 1 μg/ml leupeptin, 1 μg/ml aprotonin, 2 mM sodium pyrophosphate, 2 mM sodium orthovanadate). The extent of phosphorylation of KDR is measured using an ELISA assay. The 96-well plates are coated with 1 μg per well of goat anti-rabbit antibody. Unbound antibody is washed off the plate and remaining sites are blocked with Superblock buffer (Pierce) prior to addition of the anti-flk-1 C-20 antibody (0.5 μg per plate, Santa Cruz). Any unbound antibody is washed off the plates prior to addition of the cell lysate. After a 2 hour incubation of the lysates with the flk-1 antibody, the KDR associated phosphotyrosine is quantitated by development with the HRP-conjugated PY-54 antibody and TMB, as described above. The ability of the compounds to inhibit the VEGF-stimulated autophosphorylation reaction by 50%, relative to VEGF-stimulated controls is reported as the $IC_{50}$ value for the test compound.

Administration of the compounds of the present invention (hereinafter the "active compound(s)") can be effected by any method that enables delivery of the compounds to the site of action. These methods include oral routes, intraduodenal routes, parenteral injection (including intravenous, subcutaneous, intramuscular, intravascular or infusion), topical, and rectal administration.

The amount of the active compound administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to about 7 g/day, preferably about 0.2 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

The active compound may be applied as a sole therapy or may involve one or more other anti-tumour substances, for example those selected from, for example, mitotic inhibitors, for example vinblastine; alkylating agents, for example cis-platin, carboplatin and cyclophosphamide; anti-metabolites, for example 5-fluorouracil, cytosine arabinoside and hydroxyurea, or, for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid; growth factor inhibitors; cell cycle inhibitors; intercalating antibiotics, for example adriamycin and bleomycin; enzymes, for example interferon; and anti-hormones, for example anti-estrogens such as Nolvadex™ (tamoxifen) or, for example anti-androgens such as Casodex™ (4'-cyano-3-(4-fluorophenylsulphonyl)-2-hydroxy-2-methyl-3'-(trifluoromethyl)propionanilide). Such conjoint treatment may be achieved by way of the simultaneous, sequential or separate dosing of the individual components of the treatment.

The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefor, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, *Remington's Pharmaceutical Sciences*, Mack Publishing Company, Easter, Pa., 15th Edition (1975).

The examples and preparations provided below further illustrate and exemplify the compounds of the present invention and methods of preparing such compounds. It is to be understood that the scope of the present invention is not limited in any way by the scope of the following examples and preparations. In the following examples molecules with a single chiral center, unless otherwise noted, exist as a racemic mixture. Those molecules with two or more chiral-centers, unless otherwise noted, exist as a racemic mixture of diastereomers. Single enantiomers/diastereomers may be obtained by methods known to those skilled in the art.

Where HPLC chromatography is referred to in the preparations and examples below, the general conditions used, unless otherwise indicated, are as follows. The column used is a ZORBAX™RXC 18 column (manufactured by Hewlett Packard) of 150 mm distance and 4.6 mm interior diameter. The samples are run on a Hewlett Packard-1100 system. A gradient solvent method is used running 100 percent ammonium acetate/acetic acid buffer (0.2 M) to 100 percent acetonitrile over 10 minutes. The system then proceeds on a wash cycle with 100 percent acetonitrile for 1.5 minutes and then 100 percent buffer solution for 3 minutes. The flow rate over this period is a constant 3 ml/minute. In the following examples and preparations, "Et" means ethyl, "Ac" means acetyl, "Me" means methyl, and "Bu" means butyl.

EXPERIMENTAL EXAMPLES

Example 1

Synthesis of 1-[2-(5-Methoxy-benzoimidazol-1-yl)-quinolin-8-yl]-piperidin-4-ylamine

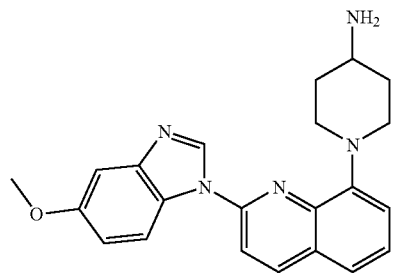

Example 1A

Trifluoro-methanesulfonic acid 8-(tert-butyl-dimethyl-silanyloxy) quinolin-2-yl ester 2,8-Quinolinediol (20.0 g, 124 mMol) was suspended in 500 mL of dichloromethane (DCM) under an atmosphere of dry nitrogen ($N_2$). To this solution was added imidazole (20.3 g, 298 mMol) followed by tert-butyldimethylsilyl chloride (20.6 g, 137 mMol) and 4-dimethylaminopyridine (1.50 g, 12.4 mMol). The reaction mixture was stirred overnight at ambient temperature after which time it was partitioned between DCM and 1% aqueous sodium bisulfate ($NaHSO_4$). The DCM layer was saved and washed two more times with 1% aqueous $NaHSO_4$, then aqueous saturated sodium bicarbonate ($NaHCO_3$) and finally brine. The DCM layer was dried over sodium sulfate ($Na_2SO_4$), filtered and concentrated under vacuum to give crude product (40 g) as a white solid. The solid was dissolved in 500 mL of anhydrous tetrahydrofuran (THF) under an atmosphere of dry $N_2$. To this solution was added N-phenyl-bis(trifluoromethanesulfonimide) (48.7 g, 136 mMol) and the solution was cooled to 0° C. To this solution was slowly added (3.2 g, 136 mMol) sodium hydride (60% in oil). After the addition was complete, the reaction mixture was warmed to ambient temperature. An additional 1.00 g sodium hydride (60% in oil) was added after one hour and stirred for an additional 30 minutes. The mixture was concentrated under vacuum and taken up in DCM. Water (1.0 mL) was slowly added dropwise to quench any unreacted sodium hydride and then the reaction mixture was extracted twice from 0.1N aqueous sodium hydroxide (NaOH) and then washed with brine. The DCM layer was dried over $Na_2SO_4$, filtered and concentrated under vacuum to give 57 g of the crude triflate 1A as a yellow oil.

Example 1B ([8-(tert-Butyl-dimethyl-silanyloxy)-quinolin-2-yl]-(4-methoxy-2-nitro-phenyl)-amine Trifluoro-methanesulfonic acid 8-(tert-butyl-dimethyl-silanyloxy) quinolin-2-yl ester 1A (9.81 g, 24.1 mMol) and 4-methoxy-2-nitroaniline (4.86 g, 28.9 mMol) were dissolved in 100 mL of dioxane under an atmosphere of dry $N_2$. To this solution was added (11.0 g, 33.7 mMol) cesium carbonate (Cs$_2$CO$_3$), (900 mg, 1.45 mMol) racemic-2,2'-bis(diphenylposphinol)-1,1'-binapthyl (BINAP) and tris(dibenzylideneacetone)dipalladium (0) (883 mg, 0.964 mMol) and the reaction mixture was heated to 100° C. and reacted at this temperature for 4 hours. The mixture was then cooled to ambient temperature, concentrated under vacuum, treated with DCM, filtered and concentrated under vacuum to give a red solid. The solid was chromatographed on flash silica gel eluting with hexanes/DCM (3:1) to give 7.25 g of the title compound 1B as a red solid.

Example 1C

N$^1$-[8-(tert-Butyl-dimethyl-silanyloxy)-quinolin-2-yl]-4-methoxy-benzene-1,2-diamine ([8-(tert-Butyl-dimethyl-silanyloxy)-quinolin-2-yl]-(4-methoxy-2-nitro-phenyl)-amine 1B (21.9 g, 51.3 mMol) was dissolved in a solution of 200 mL ethanol (EtOH) and 70 mL of THF under an atmosphere of dry N$_2$. To this solution was added 10% palladium on carbon (2.18 g) followed by the dropwise addition of 10 mL of anhydrous hydrazine. The reaction mixture was stirred at ambient temperature for 2 hours after which time it was filtered through Celite™ and the Celite™ was washed with DCM. The combined filtrates were concentrated under vacuum and the resulting residue was partitioned between DCM and aqueous saturated NaHCO$_3$. The DCM layer was then washed again with saturated NaHCO$_3$ and then brine, dried over Na$_2$SO$_4$, filtered and concentrated under vacuum to give 18.3 g of a tan solid as the title compound 1C.

Example 1D 2-(5-Methoxy-benzoimidazol-1-yl)-quinolin-8-ol

N$^1$-[8-(tert-Butyl-dimethyl-silanyloxy)-quinolin-2-yl]-4-methoxy-benzene-1,2-diamine 1C (18.3 g, 46.1 mMol) was dissolved in 40 mL of 2-methoxyethanol under an atmosphere of dry N$_2$. To this solution was added formamidine acetate (5.28 g, 50.7 mMol) and the reaction mixture was heated to 125° C. and reacted at this temperature for 1.5 hours. The solvent was removed under vacuum and the resulting solid was triturated with ethyl ether (Et$_2$O), dried under vacuum to give 13.3 g of a pink solid as the title compound 1D.

Example 1E

Trifluoro-methanesulfonic acid 2-(5-methoxy-benzoimidazol-1-yl]quinolin-8-yl ester 2-(5-Methoxy-benzoimidazol-1-yl)-quinolin-8-ol 1D (13.9 g, 47.8 mMol) was dissolved in 100 mL of anhydrous THF under an atmosphere of dry N$_2$. To this solution was added N-phenyl-bis(trifluoromethanesulfonimide)(20.3 g, 47.8 mMol) and then the solution was subsequently cooled to 0° C. To this solution was slowly added (1.31 g, 54.9 mMol) sodium hydride (60% in oil). After the addition was complete the reaction mixture was warmed to ambient temperature. After 30 minutes, 500 mg more of sodium hydride (60% in oil) was added followed by 3.50 g of N-phenyl-bis(trifluoromethanesulfonimide) and the reaction mixture was stirred at ambient temperature for 1 hour. The solvent was then removed under vacuum and the resulting residue was taken up in DCM. To this solution was slowly added 1.0 mL of water to decompose any unreacted sodium hydride. The mixture was subsequently partitioned between DCM and 0.1 N aqueous NaOH. The DCM layer was then washed again with 0.1 N aqueous NaOH, followed by brine and then dried over magnesium sulfate (MgSO$_4$), filtered and concentrated under vacuum to give 20.7 g of a pink solid as the crude title compound 1E.

Example 1F

{1-[2-(5-Methoxy-benzoimidazol-1-yl)-quinolin-8-yl]-piperidin-4-yl}-carbamic acid tert-butyl ester Trifluoro-methanesulfonic acid 2-(5-methoxy-benzoimidazol-1-yl)-quinolin-8-yl ester 1E (15.0 g, 35.4 mMol) and piperidin-4-yl-carbamic acid tert-butyl ester (14.2 g, 70.9 mMol) were dissolved in 200 mL of dioxane under an atmosphere of dry N$_2$. To this solution was added Cs$_2$CO$_3$, (16.2 g, 49.6 mMol), racemic-BINAP (1.28 g, 2.12 mMol) and tris(dibenzylideneacetone)dipalladium (0) (1.29 g, 1.41 mMol) and the reaction mixture was heated to 100° C. and reacted at this temperature overnight. The mixture was then cooled to ambient temperature, filtered, and concentrated under vacuum to give an orange foam. The foam was chromatographed on flash silica gel eluting with a gradient from ethyl acetate (EtOAc)DCM (1:5) to EtOAc/DCM (7:3) give 12.3 g of the title compound 1F as a slightly yellow solid.

Example 1G

{1-[2-(5-Methoxy-benzoimidazol-1-yl)-quinolin-8-yl]-piperidin-4-ylamine

{1-[2-(5-Methoxy-benzoimidazol-1-yl)-quinolin-8-yl]-piperidin-4-yl}carbamic acid tert-butyl ester 1F (8.40 g, 17.7 mMol) was dissolved in 50 mL of trifluoroacetic acid (TFA) under an atmosphere of dry N$_2$. The reaction mixture was stirred at ambient temperature for 15 minutes after which time it was concentrated under vacuum to give a yellow oil. The oil was partitioned between DCM and 0.1N aqueous NaOH. The DCM layer was washed again with 0.1N aqueous NaOH. The DCM layer was dried over Na$_2$SO$_4$, filtered and concentrated to give 5.85 g of the title compound 1 as a yellow solid.

C.I. m/z 374 [M+1]; $^1$H NMR (CDCl$_3$) δ 8.66 (s, 1H), 8.37 (d, J=8.9 Hz, 1H), 8.30 (d, J=8.7 Hz, 1H), 7.68 (d, J=8.9 Hz, 1H), 7.47 (m, 2H), 7.35 (d, J=2.3 Hz, 1H), 7.25 (m, 1H), 7.06 (dd, J=2.5, 8.9 Hz, 1H), 3.91 (s, 3H), 3.88 (m, 2H), 2.90 (m, 3H), 2.05 (m, 2H), 1.83 (m, 2H), 1.50 (brs, 2H).

Example 2

1-[8-(4-Amino-piperidin-1-yl)-quinolin-2-yl]-1H-benzoimidazol-5-ol

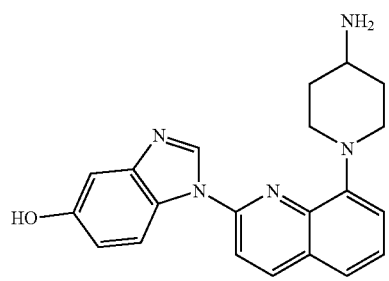

1-[2-(5-Methoxy-benzoimidazol-1-yl)-quinolin-8-yl]-piperidin-4-ylamine 1 (500 mg, 1.10 mMol) was dissolved in 10 mL of DCM under an atmosphere of dry $N_2$. To this solution was added boron tribromide (300 µL, 3.30 mMol) and the mixture was stirred overnight at ambient temperature. Then an additional 200 µL of borontribromide was added and the mixture was stirred for two hours. The reaction mixture was then poured over crushed ice and the pH of the resulting solution was adjusted to 9 with the careful addition of sodium carbonate ($Na_2CO_3$). The slurry was filtered and the solid was washed with water followed by $Et_2O$ and then dried under vacuum to give the title compound 2 as a yellow solid.

C.I. m/z 360 [M+1]; $^1$H NMR (DMSO) δ 9.07 (s, 1H), 8.76 (d, J=8.9 Hz, 1H), 8.48 (d, J=8.9 Hz, 1H), 8.10 (d, J=8.9 Hz, 1H), 7.56 (d, J=7.4 Hz, 1H), 7.45 (m, 1H), 7.26 (d, J=7.4 Hz, 1H), 7.01 (d, J=2.2 Hz, 1H), 6.95 (dd, J=2.2, 8.9 Hz, 1H), 3.72 (m, 2H), 2.76 (m, 3H), 1.88 (m, 2H), 1.65 (m, 2H).

Example 3

1-{2-[5-(Pyridin-2-ylmethoxy)-benzoimidazol-1-yl]-quinolin-8-yl}-piperidin-4-ylamine

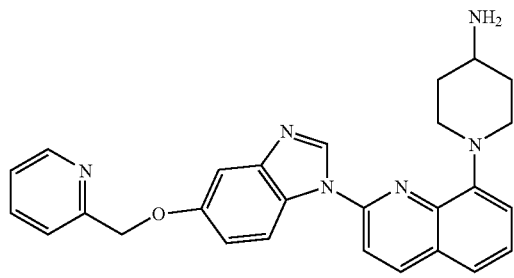

Example 3A

{1-[2-(5-Hydroxy-benzoimidazol-1-yl)-quinolin-8-yl]-piperidin-4-yl}-carbamic acid tert-butyl ester 1-[8-(4-Amino-piperidin-1-yl)-quinolin-2-yl]-1H-benzoimidazol-5-ol 2 (460 mg, 1.30 mMol) was dissolved in 5 mL of anhydrous DMF under an atmosphere of dry $N_2$. To this solution was added di-tert-butyldicarbonate (279 mg, 1.30 mMol) and the reaction mixture was stirred at ambient temperature overnight. The reaction mixture was then concentrated under vacuum and partitioned between DCM and aqueous saturated $NaHCO_3$. The DCM layer was dried over $Na_2SO_4$, filtered and concentrated under vacuum to give a yellow solid. The solid was chromatographed on flash silica gel eluting with EtOAc to give 273 mg of the title compound 3A as a yellow solid.

Example 3B (1-{2-[5-(Pyridin-2-ylmethoxy)-benzoimidazol-1-yl]-quinolin-8-yl}-piperidin-4-yl)-carbamic acid tert-butyl ester {1-[2-(5-Hydroxy-benzoimidazol-1-yl)-quinolin-8-yl]-piperidin-4-yl}-carbamic acid tert-butyl ester 3A (73 mg, 0.16 mMol) was dissolved in 1 mL of anhydrous DMF under an atmosphere of dry $N_2$. To this solution was added (37 mg, 0.17 mMol) potassium bis(trimethyl)silylamide (95%) followed by 2-picolyl chloride (25 µL, 0.17 mMol). The reaction mixture was stirred overnight at ambient temperature after which time the reaction mixture was concentrated under vacuum and then partitioned between DCM and aqueous saturated $NaHCO_3$. The DCM layer was dried over $Na_2SO_4$, filtered and concentrated under vacuum to give a yellow gel. The gel was chromatographed on flash silica gel eluting with a gradient from DCM to DCM/MeOH (98:2) to give 55 mg of the title compound 3B.

Example 3C

1-{2-[5-(Pyridin-2-ylmethoxy)-benzoimidazol-1-yl]-quinolin-8-yl}piperidin-4-ylamine (1-{-2-[5-(Pyridin-2-ylmethoxy)-benzoimidazol-1-yl]-quinolin-8-yl}piperidin-4-yl)-carbamic acid tert-butyl ester 3B (55 mg, 0.094 mMol) was dissolved in 1 mL of TFA under an atmosphere of dry $N_2$ and stirred for 15 minutes at ambient temperature. The reaction mixture was then concentrated under vacuum to give an oil which was subsequently partitioned between 0.1 N aqueous NaOH and DCM. The DCM layer was dried over $Na_2SO_4$, filtered and concentrated under vacuum to give 38.9 mg of a yellow film as the title compound 3.

C.I. m/z 451 [M+1]; $^1$H NMR (CDCl$_3$) δ 8.64 (s, 1H), 8.60 (m, 1H), 8.42 (dd, J=1.5, 8.9 Hz, 1 H), 8.27 (d, J=8.9 Hz, 1H), 7.64–7.72 (m, 2H), 7.57 (d, J=7.9 Hz, 1H), 7.45 (m, 2H), 7.40 (d, J=2.5 Hz, 1H), 7.18–7.25 (m, 3H), 5.29 (s, 2H), 3.87 (m, 2H), 2.92 (m, 3H), 2.04 (m, 2 H), 1.80 (m, 2H), 1.60 (brs, 2H).

Example 4

{1-[2-(5-Methoxy-benzoimidazol-1-yl)-quinolin-8-yl]-piperidin-4-yl}-dimethyl-amine

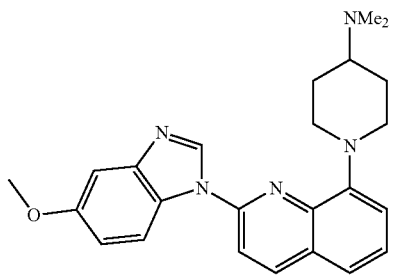

1-[2-(5-Methoxy-benzoimidazol-1-yl)-quinolin-8-yl]-piperidin-4-ylamine 1 (160 mg, 0.43 mMol) was dissolved in 2 mL of chloroform under an atmosphere of dry $N_2$. To this solution was added 50 µL of 37% aqueous formaldehyde and 100 µL formic acid and the reaction mixture was subsequently heated to 65° C. and reacted at this temperature for 4 hours. The reaction mixture was then partitioned between DCM and 0.1 N aqueous NaOH. The DCM layer was dried over $Na_2SO_4$, filtered and concentrated under vacuum to give an orange solid as the title compound 4.

C.I. m/z 402 [M+1]; $^1$H NMR (CDCl$_3$) δ 8.65 (s, 1H), 8.42 (d, J=8.9 Hz, 1H), 8.28 (d, J=8.7 Hz, 1H), 7.66 (d, J=8.9 Hz, 1H), 7.45 (m, 2H), 7.33 (d, J=2.5 Hz, 1H), 7.25 (m, 1H), 7.05 (dd, J=2.5, 8.9 Hz, 1H), 4.00 (m, 2H), 3.89 (s, 3H), 2.80 (m, 2H), 2.38 (m, 1H), 2.37 (s, 6H), 1.99 (m, 4H).

Example 5

{4-[2-(5-Methoxy-benzoimidazol-1-yl)-quinolin-8-yl]-benzyl)-methyl-amine

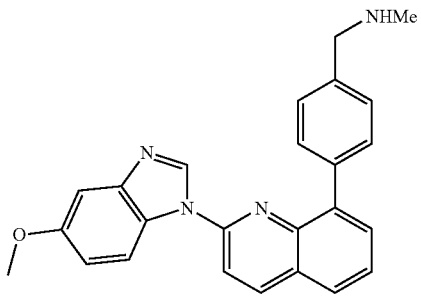

Example 5A

4-[2-(5-Methoxy-benzoimidazol-1-yl)-quinolin-8-yl]-benzaldehyde

Trifluoro-methanesulfonic acid 2-(5-methoxy-benzoimidazol-1-yl)-quinolin-8-yl ester 1E (265 mg, 0.630 mMol) was dissolved in 3 mL of dioxane under an atmosphere of dry $N_2$. To this solution was added 4-formylbenzene boronic acid (145 mg, 0.940 mMol), potassium phosphate (267 mg, 1.26 mMol) and tetrakis(triphenylphosphine)palladium (0) (36 mg, 0.032 mMol). The reaction mixture was heated to 105° C. and reacted at this temperature overnight. The reaction mixture was then cooled to ambient temperature, concentrated under vacuum and partitioned between DCM and aqueous saturated $NaHCO_3$. The DCM layer was then washed with brine, dried over $Na_2SO_4$, filtered and concentrated under vacuum to give a yellow solid as the title compound 5A which was pushed on without further purification.

Example 5B

{4-[2-(5-Methoxy-benzoimidazol-1-yl)-quinolin-8-yl]-benzyl}-methyl-amine

4-[2-(5-Methoxy-benzoimidazol-1-yl)-quinolin-8-yl]-benzaldehyde 5A (120 mg, 0.32 mMol) was dissolved in 2 mL of methanol under an atmosphere of dry $N_2$. To this solution was added 800 μL of a solution of 2.0 M methylamine in methanol and then acetic acid (AcOH) was added dropwise until the pH of the solution was ~5. To this solution was added (42 mg, 0.64 mMol) sodium cyanoborohydride ($NaCNBH_3$) and the reaction mixture was stirred at ambient temperature overnight. The reaction mixture was then concentrated under vacuum and subsequently partitioned between DCM and 0.1 N aqueous NaOH. The DCM layer was washed again with 0.1 N aqueous NaOH, then dried over $MgSO_4$, filtered and concentrated under vacuum to give 220 mg of a green residue. The residue was chromatographed on flash silica gel eluting with a gradient DCM/MeOH (595) to DCM/MeOH (15/85) to DCM/MeOH/$NH_4OH$ (1584.50.5) to give 50 mg of a white solid of the title compound 5.

C.I. m/z 395 [M+1]; 1H NMR ($CDCl_3$) δ 8.55 (s, 1H), 8.29 (d, J=8.9 Hz, 1H), 7.92 (d, J=8.9 Hz, 1H), 7.79 (d, J=8.1 Hz, 1H), 7.74 (m, 1H), 7.63 (m, 3H), 7.56 (m, 1H), 7.44 (d, J=8.1 Hz, 2H), 7.23 (d, J=2.3 Hz, 1' H), 6.73 (dd, J=2.3, 8.9, 1. H), 3.88 (s, 2H), 3.83 (s, 3H), 2.53 (s, 3H), 2.43 (brs, 1H).

Example 6

{4-[2-(5-Methoxy-benzoimidazol-1-yl)-quinolin-8-yl]-benzyl}-dimethyl-amine

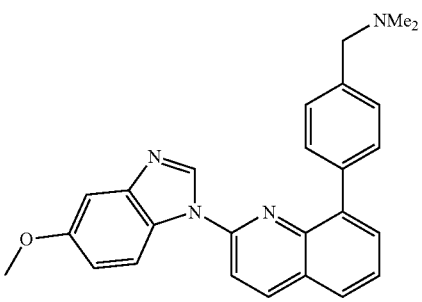

The same procedure that used for Example 5 was followed with the exception that 2.0 M dimethylamine in methanol was used in the place of 2.0 M methylamine in methanol in Example 5B to give the title compound 6 as a white solid.

C.I. m/z 409 [M+1]; $^1$H NMR ($CDCl_3$) δ 8.56 (s, 1H), 8.29 (d, J=8.7 Hz, 1H), 7.98 (d, J=9.1 Hz, 1H), 7.79 (d, J=8.1 Hz, 1H), 7.76 (m, 1H), 7.63 (m, 3H), 7.56 (m, 1H), 7.45 (d, J=7.9 Hz, 2H), 7.25 (d, J=2.3 Hz, 1H), 6.74 (dd, J=2.3, 8.9, 1H), 3.84 (s, 3H), 3.57 (s, 2H), 2.35 (s, 6H).

Example 7

Cyclopropyl-{4-[2-(5-methoxy-benzoimidazol-1-yl)-quinolin-8-yl]-benzyl}-amine

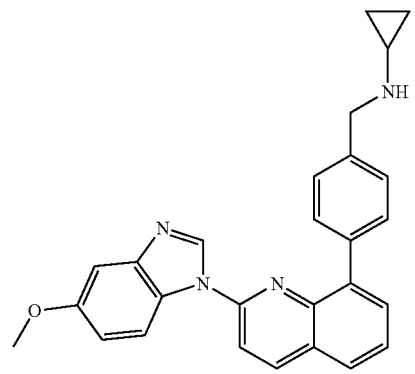

4-[2-(5-Methoxy-benzoimidazol-1-yl)-quinolin-8-yl]-benzaldehyde 5A (50 mg, 0.13 mMol) was dissolved in 500 μL of dichloroethane (DCE) under an atmosphere of dry $N_2$. To this solution was added 80 μL of AcOH, cyclopropylamine (50 μL, 0.65 mMol) and (42 mg, 0.20 mMol) sodium triacetoxyborohydride ($NaHB(OAc)_3$). The reaction mixture was stirred at ambient temperature for 2 hours after which time an additional 20 μL of cyclopropylamine and 20 mg of $NaHB(OAc)_3$ were added and the resulting mixture was stirred overnight. The reaction mixture was then partitioned between aqueous 0.1 N NaOH and DCM. The DCM layer washed again with aqueous 0.1 N NaOH and then dried over Na$_2$SO$_4$, filtered and concentrated under vacuum to give a 60 mg of the title compound 7 as a yellow solid.

C.I. m/z 421 [M+1]; $^1$H NMR (CDCl$_3$) δ 8.58 (s, 1H), 8.33 (d, J=8.7 Hz, 1H), 7.96 (d, J=9.1 Hz, 1H), 7.83 (d, J=7.7 Hz, 1H), 7.77 (d, J=7.3 Hz, 1H), 7.64 (m, 3H), 7.59 (m, 1H), 7.45 (d, J=7.9 Hz, 2H), 7.25 (m, 1H), 6.75 (dd, J=2.3, 8.9, 1H), 3.97 (s, 2H), 3.86 (s, 3H), 2.26 (m, 1H), 1.95 (brs, 1H), 0.49 (m, 4H).

Example 8 tert-Butyl-4-[2-(5-methoxy-benzoimidazol-1-yl]quinolin-8-yl]-benzyl}-amine

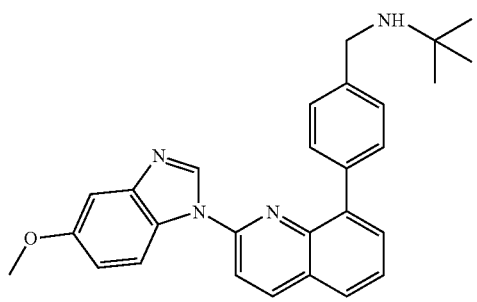

The same procedure that used for Example 7 was followed with the exception that tert-butylamine was used in the place of cyclopropylamine to give the title compound 8 as a yellow solid.

C.I. m/z 437 [M+1]; $^1$H NMR (CDCl$_3$) δ 8.59 (s, 1H), 8.33 (d, J=8.9 Hz, 1H), 7.95 (d, J=8.9 Hz, 1H), 7.82 (m, 1H), 7.77 (m, 1H), 7.65 (m, 3H), 7.58 (m, 1H), 7.49 (d, J=8.1 Hz, 2H), 7.26 (d, J=2.3 Hz, 1H), 6.79 (dd, J=2.3, 8.9, 1H), 3.86 (s, 5H), 1.24 (s, 9H).

Example 9

4-[2-(5-Methoxy-benzoimidazol-1-yl)-quinolin-8-yl]-benzylamine

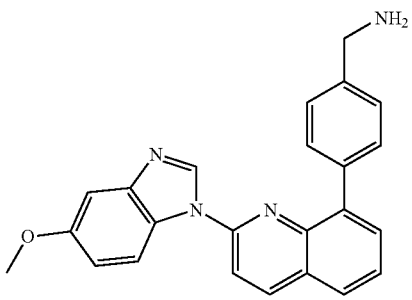

The same procedure that used for Example 5 was followed with the exception that ammonium acetate was used in the place of 2.0 M methylamine in methanol in Example 5B to give a yellow solid. The solid was chromatographed on flash silica gel eluting with a gradient from DCM/MeOH (5/95) to DCM/MeOH (15/85) to DCM/MeOH/NH$_4$OH (15/94.5/0.5) to give the title compound 9 as a white solid.

C.I. m/z 381 [M+1]; $^1$H NMR (CDCl$_3$) δ 8.59 (s, 1H), 8.35 (d. J=8.9 Hz, 1H), 7.94 (d, J=8.92 Hz, 1H), 7.84 (m, 1H), 7.78 (dd, J=1.5, 7.3 Hz, 1H), 7.66 (m, 3H), 7.60 (m, 1H), 7.46 (d, J=8.1 Hz, 2H), 7.26 (d, J=2.5 Hz, 1H), 6.76 (dd, J=2.5, 8.9, 1H), 4.00 (s, 2H), 3.85 (s, 3H), 1.78 (brs, 2H).

Example 10

1-[2-(5-Ethoxy-benzoimidazol-1-yl)-quinolin-8-yl]-piperidin-4-ylamine

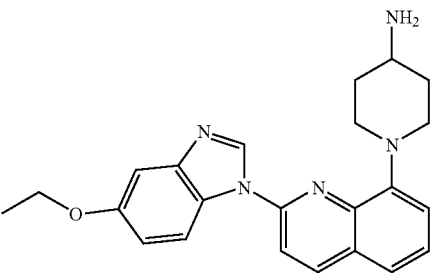

The same procedure that used for Example 1 was followed with the exception that 4-ethoxy-2-nitroaniline was used in the place of that 4-methoxy-2-nitroaniline in example 1B to give the title compound 10 as a yellow solid.

C.I. m/z 388 [M+1]; $^1$H NMR (CDCl$_3$) δ 8.63 (s, 1H), 8.36 (d, J=8.9 Hz, 1H), 8.26 (d, J=8.7 Hz, 1H), 7.64 (d, J=8.7 Hz, 1H), 7.44 (m, 2H), 7.32 (d, J=2.5 Hz, 1H), 7.25 (m, 1H), 7.05 (dd, J=2.5, 8.9 Hz, 1H), 4.10 (q, J=7.0 Hz, 2H), 3.86 (m, 2H), 2.90 (m, 3H), 2.04 (m, 2H), 1.79 (m, 2H), 1.45 (t, J=7.0 Hz, 3H).

Example 11

{1-[2-(5-Ethoxy-benzoimidazol-1-yl)-quinolin-8-yl]-piperidin-4-yl)-dimethyl-amine

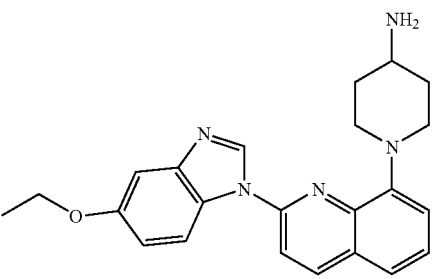

The same procedure that used in Example 4 was followed with the exception 1-[2-(5-ethoxy-benzoimidazol-1-yl)-quinolin-8-yl]-piperidin-4-ylamine 10 was used in the place of 1-[2-(5-methoxy-benzoimidazol-1-yl]quinolin-8-yl]-piperidin-4-ylamine 1 to give the title compound 11 as a yellow solid.

C.I. m/z 416 [M+1]; $^1$H NMR (CDCl$_3$) 8.65 (s, 1H), 8.39 (d, J=8.9 Hz, 1H), 8.28 (d, J=8.7 Hz, 1H), 7.66 (d, J=8.7 Hz,

1H), 7.45 (m, 2H), 7.32 (d, J=2.5 Hz, 1H), 7.24 (m, 1H), 7.05 (dd, J=2.5, 8.9 Hz, 1H), 4.10 (q, J=7.0 Hz, 2H), 4.00 (m, 2H), 2.80 (m, 2H), 2.40 (m, 1H), 2.38 (s, 6H), 2.00 (m, 4H), 1.46 (t, J=7.0 Hz, 3H).

Example 12

1-[2-(5-Trifluoromethoxy-benzoimidazol-1-yl)-quinolin-8-yl]-piperidin-4-ylamine

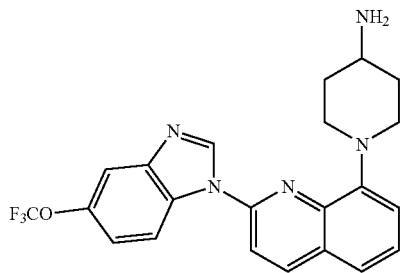

The same procedure that used in Example 1 was followed with the exception that 2-nitro-4-(trifluoromethoxy)aniline was used in the place of 4-methoxy-2-nitroaniline in example 1B to give the title compound 12 as a yellow solid.

C.I. m/z 428 [M+1]; $^1$H NMR (CDCl$_3$) δ 8.74 (s, 1H), 8.50 (d, J=8.9 Hz, 1H), 8.33 (d, J=8.7 Hz, 1H), 7.74 (d, J=1.0 Hz, 1H), 7.67 (d, J=8.7 Hz, 1H), 7.47 (m, 2H), 7.32 (m, 1H), 7.25 (m, 1H), 3.87 (m, 2H), 2.90 (m, 3H), 2.05 (m, 2H), 1.77 (m, 2H), 1.71 (brs, 2H).

Example 13

{4-[2-(5-Ethoxy-benzoimidazol-1-yl)-quinolin-8-yl]-benzyl}-methyl-amine

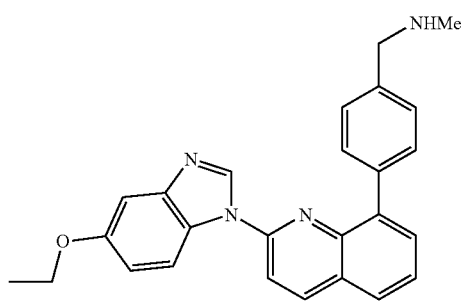

The same procedure that used for Example 5 was followed with the exception that 4-ethoxy-2-nitroaniline was used in the place of 4-methoxy-2-nitroaniline in example 1B to give the title compound 13 as a tan solid.

C.I. m/z 409 [M+1]; $^1$H NMR(CDCl$_3$) δ8.54 (s, 1H), 8.26 (d, J=8.7 Hz, 1H), 7.92 (d, J=9.1 Hz, 1H), 7.77 (d, J=8.1 Hz, 1H), 7.72 (d, J=7.1 Hz, 1H), 7.62 (m, 3H), 7.54 (m, 1H), 7.52 (d, J=8.1 Hz, 2H), 7.21 (d, J=2.5 Hz, 1H), 6.73 (dd, J=2.5, 8.9 Hz, 1H), 4.04 (q, J=7.0 Hz, 2H), 3.91 (s, 2H), 2.97 (brs, 1H), 2.55 (s, 3H), 1.41 (t, J=7.0 Hz, 3H).

Example 14

Cyclopropyl-{4-[2-(5-ethoxy-benzoimidazol-1-yl)-quinolin-8-yl]-benzyl}-amine

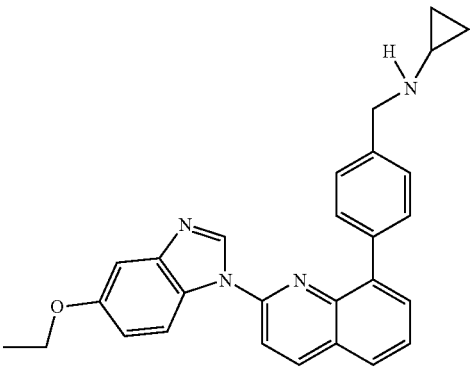

The same procedure that used for Example 7 was followed with the exception that 4-ethoxy-2-nitroaniline was used in the place of 4-methoxy-2-nitroaniline in example 1B to give the title compound 14 as a yellow solid.

C.I. m/z 435 [M+1]; $^1$H NMR (CDCl$_3$) δ 8.57 (s, 1H), 8.32 (d, J=8.7 Hz, 1H), 7.94 (d, J=8.9 Hz, 1H), 7.83 (m, 1H), 7.77 (m, 1H), 7.65 (m, 3H), 7.58 (m, 1H), 7.45 (d, J=8.1 Hz, 2H), 7.25 (m, 1H), 6.76 (dd, J=2.5, 9.1, 1H), 4.06 (q, J=7.0 Hz, 2H), 3.97 (s, 2H), 2.28 (m, 1H), 1.93 (brs, 1H), 1.44 (t, J=7.0 Hz, 3H), 0.48 (m, 4H).

Example 15 tert-Butyl-{4-[2-(5-ethoxy-benzoimidazol-1-yl)-quinolin-8-yl]-benzyl}-amine

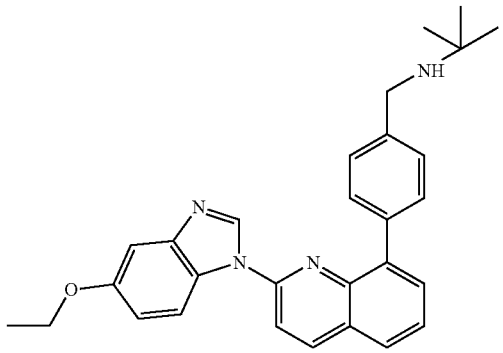

The same procedure that used for Example 8 was followed with the exception that 4-ethoxy-2-nitroaniline was used in the place of 4-methoxy-2-nitroaniline in example 1B to give the titlecompound 15 as a yellow solid.

C.I. m/z 451 [M+1]; $^1$H NMR (CDCl$_3$) δ 8.55 (s, 1H), 8.33 (d, J=8.7 Hz, 1H), 7.92 (d, J=10.1 Hz, 1H), 7.79 (dd, J=1.3, 8.1 Hz, 1H), 7.71 (d, J=7.1 Hz, 1H), 7.65 (m, 3H), 7.55 (m, 1H), 7.48 (d, J=8.1 Hz, 2H), 7.23 (d, J=2.5 Hz, 1H), 6.78 (dd, J=2.5, 8.9, 1H), 4.06 (q, J=7.0 Hz, 2H), 3.89 (s, 2H), 1.43 (t, J=7.0 Hz, 3H), 1.28 (s, 9H).

Example 16

{4-[2-(5-Ethoxy-benzoimidazol-1-yl)-quinolin-8-yl]-benzyl}-dimethyl-amine

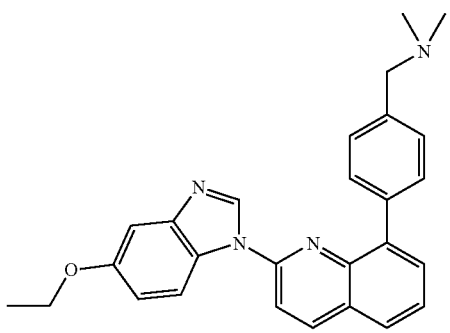

The same procedure that used for Example 6 was followed with the exception that 4-ethoxy-2-nitroaniline was used in the place of 4-methoxy-2-nitroaniline in example 1B to give the title compound 16 as a yellow solid.

C.I. m/z 423 [M+1]; $^1$H NMR (CDCl$_3$) δ 8.57 (s, 1H), 8.31 (d, J=8.7 Hz, 1H), 7.96 (d, J=8.9 Hz, 1H), 7.80 (m, 1H), 7.75 (m, 1H), 7.64 (m, 3H), 7.56 (m, 1H), 7.42 (d, J=7.9 Hz, 2H), 7.20 (d, J=2.4 Hz, 1H), 6.73 (dd, J=2.4, 8.9 Hz, 1H), 4.06 (q, J=7.0 Hz, 2H), 3.55 (s, 2H), −2.31 (s, 6H), 1.41 (t, J=7.0 Hz, 3H).

Example 17

1-[2-(5-Methoxy-benzoimidazol-1-yl]-quinolin-8-yl]-piperidin-4-one

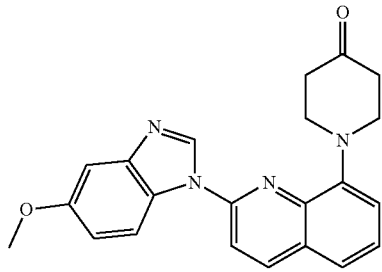

The same procedure that used for Example 1 was followed with the exception that 4-piperdone was used in the place of piperidin-4-yl-carbamic acid tert-butyl ester in example 1F to give the title compound 17 as a white solid.

C.I. m/z 373 [M+]; $^1$H NMR (CDCl$_3$) δ 8.67 (s, 1H), 8.35 (m, 2H), 7.72 (d, J=8.9 Hz, 1H), 7.55 (dd, J=1.3, 8.2, 1H), 7.50 (m, 1H), 7.36 (d, J=2.5 Hz, 1H), 7.28 (m, 1H), 7.04 (dd, J=2.5, 8.9 Hz, 1H), 3.90 (s, 3H), 3.71 (m, 4H), 2.79 (m, 4H).

Example 18

1-[2-(5-Ethoxy-benzoimidazol-1-yl)-quinolin-8-yl]-piperidin-4-one

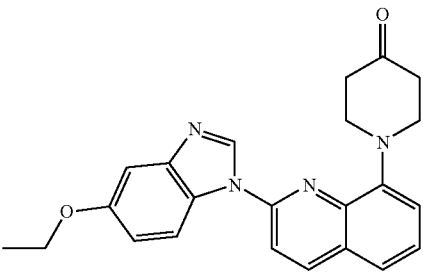

The same procedure that was used for example, 17 was followed except that 4-ethoxy-2-nitroaniline was used in the place of 4-methoxy-2-nitroaniline in example 1B to give the title compound 18 as a white solid.

C.I. m/z 387 [M+]; $^1$H NMR (CDCl$_3$) δ 8.57 (s, 1H), 8.30 (m, 2H), 7.65 (d, J=8.7 Hz, 1H), 7.50 (dd, J=1.3, 8.1, 1H), 7.44 (m, 1H), 7.30 (d, J=2.3 Hz, 1H), 7.23 (m, 1H), 6.99 (dd, J=2.5, 8.9 Hz, 1H), 4.07 (q, J=7.0 Hz, 2H), 3.65 (m, 4H), 2.74 (m, 4H), 1.42 (t, J=7.0 Hz, 3H).

Example 19

1-[2-(5-Ethoxy-benzoimidazol-1-yl)-quinolin-8-yl]-piperidin-4-ol

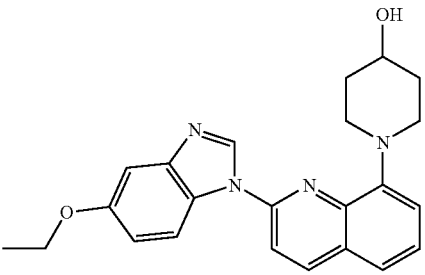

1-[2-(5-Ethoxy-benzoimidazol-1-yl)-quinolin-8-yl]-piperidin-4-one 18 (140 mg, 0.36 mMol) was dissolved in 1.5 mL of methanol under an atmosphere of dry N$_2$. To this solution was added sodium borohydride (NaBH$_4$) (14 mg, 0.36 mMol) and the solution was stirred at ambient temperature overnight. The reaction mixture was then concentrated under vacuum and partitioned between DCM and saturated aqueous NaHCO$_3$. The DCM layer was then washed with brine, dried over Na$_2$SO$_4$, filtered and concentrated under vacuum to give a green foam. The foam was chromatographed on flash silica gel eluting with a gradient from MeOH/DCM (1/99) to MeOH/DCM (496) to give the title compound 19 as a yellow foam.

C.I. m/z 389 [M+]; $^1$H NMR (CDCl$_3$) δ 8.65 (s, 1H), 8.39 (d, J=8.9 Hz, 1H), 8.30 (d, J=8.7 Hz, 1H), 7.68 (d, J=8.9 Hz, 1H), 7.47 (m, 2H), 7.33 (d, J=2.3 Hz, 1H), 7.25 (m, 1H), 7.07 (dd, J=2.5, 8.9 Hz, 1H), 4.13 (q, J=7.0 Hz, 2H), 3.97 (m, 1H), 3.75 (m, 2H), 3.10 (m, 2H), 2.10 (m, 2H), 1.96 (m, 2H), 1.46 (t, J=7.0 Hz, 3H).

Example 20

Cyclopropyl-(1-[2-(5-ethoxy-benzoimidazol-1-yl)-quinolin-8-yl]-piperidin-4-yl)-amine

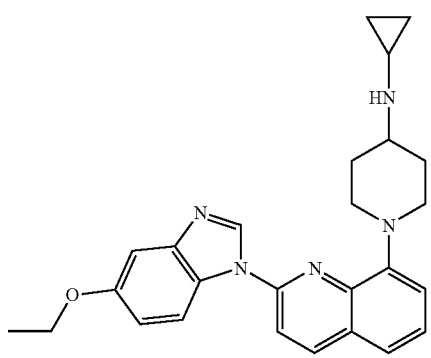

1-[2-(5-Ethoxy-benzoimidazol-1-yl)quinolin-8-yl]-piperidin-4-one 18 (130 mg, 0.340 mMol) was dissolved in 1.5 mL of DCE under an atmosphere of dry N₂. To this solution was added cyclopropyl amine (110 μL, 1.70 mMol) and 200 μL of AcOH and the solution was stirred for 10 minutes. To this solution was added NaHB(OAc)₃ (107 mg, 0.50 mMol) and the solution was stirred at ambient temperature for 5 hours. The reaction mixture was then partitioned between DCM and aqueous 0.1 N NaOH. The DCM layer was again washed with aqueous 0.1 N NaOH, dried over Na₂SO₄, filtered and concentrated under vacuum to give 150 mg of a green foam. The foam was chromatographed on flash silica gel eluting with a gradient from MeOH/DCM (299) to MeOH/DCM (496) to give the title compound 20 as a yellow solid.

C.I. m/z 428 [M+1]; ¹H NMR (CDCl₃) δ 8.64 (s, 1H), 8.38 (d, J=9.1 Hz, 1H), 8.28 (d, J=8.7 Hz, 1H), 7.66 (d, J=8.7 Hz, 1H), 7.45 (m, 2H), 7.32 (d, J=2.5 Hz, 1H), 7.25 (m, 1H), 7.07 (dd, J=2.5, 9.1 Hz, 1H), 4.13 (q, J=7.0 Hz, 2H), 3.91 (m, 2H), 2.90 (m, 3H), 2.25 (m, 1H), 2.16 (m, 2H), 1.83 (m, 2H), 1.46 (t, J=7.0 Hz, 3H), 0.43 (m, 2H), 0.42 (m, 2H).

Example 21 tert-Butyl-1-[2-(5-ethoxy-benzoimidazol-1-yl)-quinolin-8-yl]-piperidin-4-yl}-amine

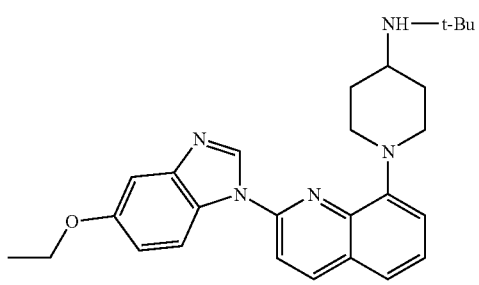

The same procedure that was used for example 20 was followed except tert-butylamine was used in the place of cyclopropylamine to give the title compound 21 as a yellow solid.

C.I. m/z 444 [M+1]; ¹H NMR (CDCl₃) δ8.65 (s, 1H), 8.35 (d, J=8.9 Hz, 1H), 8.28 (d, J=8.9 Hz, 1H), 7.67 (d, J=8.7 Hz, 1H), 7.45 (m, 2H), 7.32 (d, J=2.5 Hz, 1H), 7.24 (m, 1H), 7.08 (dd, J=2.5, 8.91 Hz, 1H), 4.13 (q, J=7.0 Hz, 2H), 3.90 (m, 2H), 2.91 (m, 2H), 2.79 (m, 1H), 2.00 (m, 2H), 1.88 (m, 2H), 1.47 (t, J=7.0 Hz, 3H), 1.17 (s, 9H).

Example 22

{1-[2-(5-Methoxy-benzoimidazol-1-yl)-quinolin-8-yl]-piperidin-4-yl}-methyl-amine

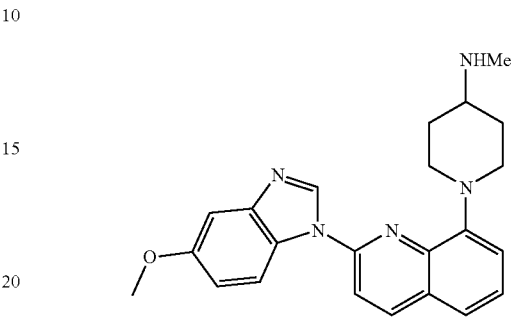

1-[2-(5-Methoxy-benzoimidazol-1-yl)-quinolin-8-yl]-piperidin-4-one 17 (200 mg, 0.540 mMol) was dissolved in 2 mL of MeOH under an atmosphere of dry N₂. To this solution was added 1.34 mL of a 2.0 M solution of methylamine in methanol and AcOH was then added until the pH-5. To this solution was added 95% NaCNBH₃ (93 mg, 0.540mMol) and the reaction mixture was stirred at ambient temperature for 4 hours. The reaction mixture was then concentrated under vacuum and subsequently partitioned between DCM and aqueous 0.1 N NaOH. The DCM layer was then washed again with aqueous 0.1 N NaOH, dried over Na₂SO₄, filtered and concentrated under vacuum to give a green foam. The foam was chromatographed on flash silica gel eluting with a gradient from MeOH/DCM (595) to MeOH/DCM (1090) to MeOH/DCM/NH₄OH (10891) give the title compound 22 as a green solid.

C.I. m/z 388 [M+1]; ¹H NMR (CDCl₃) δ 8.65 (s, 1H), 8.38 (d, J=8.9 Hz, 1H), 8.29 (d, J=8.7 Hz, 1H), 7.67 (d, J=8.7 Hz, 1H), 7.46 (m, 2H), 7.33 (d, J=2.3 Hz, 1H), 7.25 (m, 1H), 7.08 (dd, J=2.5, 8.9 Hz, 1H), 3.93 (m, 2H), 3.89 (s, 3H), 2.90 (m, 2H), 2.62 (m, 1H), 2.51 (s, 3H), 2.14 (m, 2H), 1.82 (m, 2H), 1.75 (brs, 1H).

Example 23

2-(5-Methoxy-benzoimidazol-1-yl)-8-(1-oxa-6-aza-spiro[2.5]oct-6-yl)-quinoline

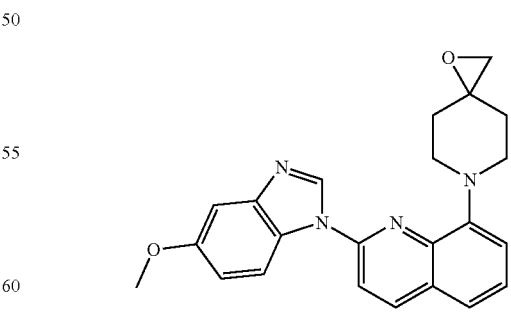

Trimethyl sulfonium iodide (326 mg, 1.60 mMol) was dissolved in 6 mL of anhydrous dimethylsulfoxide (DMSO) under an atmosphere of dry N₂. To this solution was added (67.7 mg, 1.7 mMol) sodium hydride (60% in oil) and the reaction mixture was stirred for 10 minutes at ambient temperature. To this solution was added a solution of 1-[2-

(5-Methoxy-benzoimidazol-1-yl)-quinolin-8-yl]-piperidin-4-one 17 (450 mg, 1.21 mMol) in 4 mL of anhydrous DMSO and the reaction mixture was subsequently stirred overnight at ambient temperature. The reaction mixture was then partitioned between EtOAc and water. The EtOAc layer was washed with 3 more times with water and then with brine. The EtOAc layer was dried over Na$_2$SO$_4$, filtered and concentrated under vacuum to give a yellow foam as the title compound 23.

C.I. m/z 387 [M+1]; $^1$H NMR (CDCl$_3$) δ 8.64 (s, 1H), 8.39 (d, J=8.9 Hz, 1H), 8.31 (d, J=8.9 Hz, 1H), 7.68 (d, J=8.7 Hz, 1H), 7.48 (m, 2H), 7.34 (d, J=2.3 Hz, 1H), 7.29 (m, 1H), 7.06 (dd, J=2.5, 8.9 Hz, 1H), 3.90 (s, 3H), 3.68 (m, 2H), 3.41 (m, 2H), 2.78 (s, 2H), 2.32 (m, 2H), 1.75 (m, 2H).

Example 24

4-Dimethylaminomethyl-1-[2-(5-methoxy-benzoimidazol-1-yl)-quinolin-8-]-piperidin-4-ol

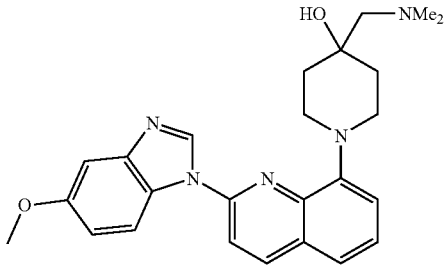

2-(5-Methoxy-benzoimidazol-1-yl)-8-(1-oxa-6-aza-spiro[2.5]oct-6-yl)-quinoline 23 (250 mg, 0.647 mMol) and 2 mL of 2.0 M dimethylamine in THF were suspended in 2 mL of methanol in a pressure vial. The vial was capped, heated to 65° C. and reacted at this temperature for 2 hours. The reaction mixture was concentrated under vacuum to give a yellow solid. The solid was chromatographed on flash silica gel eluting with a gradient from MeOH/DCM (1090) to MeOH/DCM/NH$_4$OH (10891) give 160 mg of the title compound 24 as a yellow solid.

C.I. m/z 432 [M+1]; $^1$H NMR (CDCl$_3$) δ 8.64 (s, 1H), 8.39 (d, J=8.9 Hz, 1H), 8.29 (d, J=8.7 Hz, 1H), 7.66 (d, J=8.7 Hz, 1H), 7.46 (m, 2H), 7.33 (d, J=2.5 Hz, 1H), 7.30 (m, 1H), 7.01 (dd, J=2.5, 8.9 Hz, 1H), 3.89 (s, 3H), 3.68 (m, 2H), 3.24 (m, 2H), 2.42 (s, 8H), 2.00 (m, 2H), 1.90 (brs, 1H), 1.79 (m, 2H).

Example 25

20-1-[2-(5-Methoxy-benzoimidazol-1-yl)-quinolin-8-yl]-4-methylaminomethyl-piperidin-4-ol

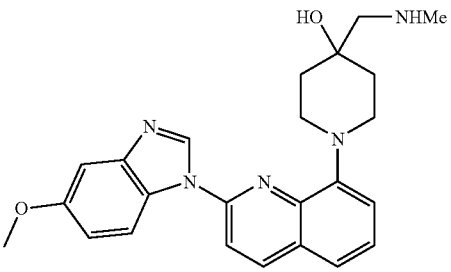

The same procedure that was used in example 24 was followed except that 2.0 M methylamine in methanol was used in the place of 2.0 M dimethylamine in THF to give the title compound 25

C.I. m/z 418 [M+1]; $^1$H NMR (CDCl$_3$) δ 8.65 (s, 1H), 8.32 (m, 2H), 7.67 (d, J=8.7 Hz, 1H), 7.46 (m, 2H), 7.33 (d, J=2.3 Hz, 1H), 7.29 (m, 1H), 7.02 (dd, J=2.5, 8.9 Hz, 1H), 3.90 (s, 3H), 3.70 (m, 2H), 3.23 (m, 2H), 2.65 (s, 2H), 2.54 (s, 3H), 2.04 (m, 2H), 1.79 (m, 2H).

Example 26

4-Aminomethyl-1-[2-(5-methoxy-benzoimidazol-1-yl)-quinolin-8-yl]-piperidin-4-ol

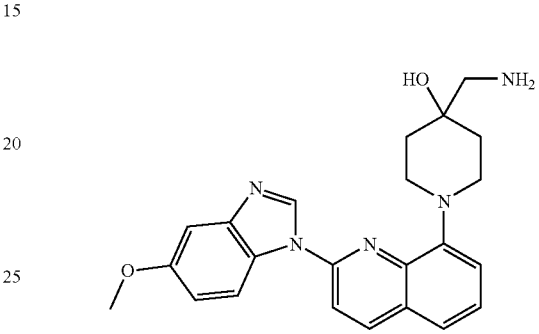

The same procedure that was used in example 24 was followed except that ammonium hydroxide was used in the place of 2.0 M dimethylamine in THF and the solvent was THF rather than methanol to give the title compound 26.

C.I. m/z 404 [M+]; $^1$H NMR (CDCl$_3$) δ 8.65 (s, 1H), 8.30 (m, 2H), 7.66 (d, J=8.9 Hz, 1H), 7.47 (m, 2H), 7.33 (d, J=2.5 Hz, 1H), 7.29 (m, 1H), 7.01 (dd, J=2.3, 8.9 Hz, 1H), 3.89 (s, 3H), 3.71 (m, 2H), 3.23 (m, 2H), 2.78 (s, 2H), 1.96 (m, 2H), 1.79 (m, 2H).

Example 27

1-[2-(5-Methoxy-benzoimidazol-1-yl]quinolin-8-yl]-pyrrolidin-3-ylamine

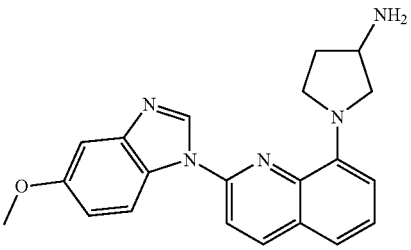

The same procedure that was used in example 1 was followed except that (+/−)3-(t-butoxycarbonylamino)-pyrrolidine was used in the place on the piperidin-4-yl-carbamic acid tert-butyl ester in example 1F to give the title compound 27 as a yellow solid.

C.I. m/z 360 [M+]$^1$H NMR (CDCl$_3$) δ 8.61 (s, 1H), 8.23 (d, J=8.7 Hz, 1H), 7.83 (d, J=8.9 Hz, 1H), 7.59 (d, J=8.7 Hz, 1H), 7.40 (m, 1H), 7.33 (d, J=2.3 Hz, 1H), 7.19 (d, J=8.5 Hz, 1H), 7.00 (dd, J=2.5, 8.9 Hz, 1H), 6.83 (d, J=7.9 Hz, 1H), 4.00 (m, 1H), 3.90 (m, 1H), 3.88 (s, 3H), 3.75 (m, 2H), 3.56 (m, 1H), 2.24 (m, 1H), 1.92 (brs, 2H), 1.82 (m, 1H).

Example 28

1-(2-Benzoimidazol-1-yl-quinolin-8-yl)-piperidin-4-ylamine

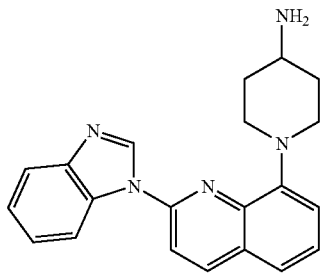

Example 28A

8-Benzyloxy-quinolin-2-ylamine

2-Amino-8-hydroxyquinoline (20.0 g, 122 mMol) was dissolved in 50 mL of anhydrous DMF under an atmosphere of dry $N_2$. The reaction mixture was cooled to 0° C. after which time (4.89 g, 122 mMol) sodium hydride (60% in oil) was slowly added and the reaction mixture was stirred for 30 minutes. To this solution was added benzyl bromide (14.5 mL, 122 mMol) and the reaction mixture was subsequently warmed to ambient temperature and stirred overnight. The reaction mixture was then filtered and the resulting solid was washed with $Et_2O$ and then dried under vacuum to give 29.4 g of the title compound 28A as a white solid.

Example 28B (8-Benzyloxy-quinolin-2-yl(2-nitro-phenyl)-amine

8-Benzyloxy-quinolin-2-ylamine 28A (3.50 g, 14.0 mMol) and 1-bromo-2-nitrobenzene (3.20 g, 15.4 mMol) were dissolved in 70 mL of dioxane under an atmosphere of dry $N_2$. To this solution was added $Cs_2CO_3$ (18.3 g, 56.0 mMol), racemic-BINAP (1.00 g, 1.68 mMol) and (513 mg, 0.560 mMol) tris(dibenzylideneacetone)dipalladium (0). The reaction mixture was heated to 100° C. and reacted at this temperature overnight. The mixture was then cooled to ambient temperature, concentrated under vacuum, treated with DCM, filtered and concentrated under vacuum to give a red solid. The solid was chromatographed on flash silica gel eluting with DCM to give 5.16 g of the title compound 28B as an orange solid.

Example 28C 2-(2-Amino-phenylamino)-quinolin-8-ol (8-Benzyloxy-quinolin-2-yl)-(2-nitro-phenyl)-amine 28B (5.16 μg, 13.9 mMol) was suspended in 60 mL of EtOH under an atmosphere of dry $N_2$. To this solution was added ammonium formate (17.5 g, 278 mMol) and 550 mg of 20% palladium hydroxide on carbon. The reaction mixture was heated to 78° C. and stirred at this temperature for 2 hours after which time it was cooled to ambient temperature and filtered through Celite". The Celite™ was washed with ethanol, the filtrates were combined and concentrated under vacuum to give the title compound 28C which was subsequently carried on crude to the next step:

Example 28D 1-(2-Benzoimidazol-1-yl-quinolin-8-yl)-piperidin-4-ylamine

The same procedure that was used in example 1 except that compound 2-(2-aminophenylamino)-quinolin-8-ol 28C was used in the place of 2-(5-methoxy-benzoimidazol-1-yl]quinolin-8-ol 1D in example 1E to give the title compound 28.

C.I. m/z 344 [M+1]; $^1$H NMR (CDCl$_3$) δ 8.71 (s, 1H), 8.43 (m, 1H), 8.31 (d, J=8.9 Hz, 1H), 7.89 (m, 1H), 7.71 (d, J=8.7 Hz, 1H), 7.36–7.49 (m, 4H), 7.24 (m, 1H), 3.89 (m, 2H), 2.90 (m, 3H), 2.04 (m, 2H), 1.82 (m, 2H), 1.28 (brs, 2H).

Example 29

1-(2-Imidazo[4,5-b]pyridin-3-yl-quinolin-8-yl)-piperidin-4-ylamine

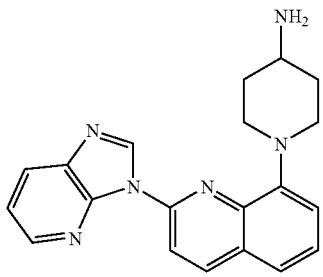

The same procedure that was used in example 28 that 2-chloro-3-nitropyridine was used in the place of 1-bromo-2-nitrobenzene in example 28B to give the title compound 29.

C.I. m/z 345 [M+1]; $^1$H NMR (CDCl$_3$) δ 9.36 (s, 1H), 9.00 (d, J=8.9 Hz, 1H), 8.49 (dd, J=1.4, 4.7 Hz, 1H), 8.34 (d, J=8.9 Hz, 1H), 8.15 (dd, J=1.4, 8.1, 1H), 7.45 (m, 2H), 7.33 (dd, J=4.8, 8.1 Hz, 1H), 7.17 (dd, J=1.7, 7.1 1H), 3.93 (m, 2H), 2.98 (m, 1H), 2.91 (m, 2H), 2.12 (m, 2H), 1.98 (brs, 2H), 1.88 (m, 2H).

Example 30

1-{2-[5-(4-Methoxy-phenyl)-benzoimidazol-1-yl]-quinolin-8-yl}-piperidin-4-ylamine

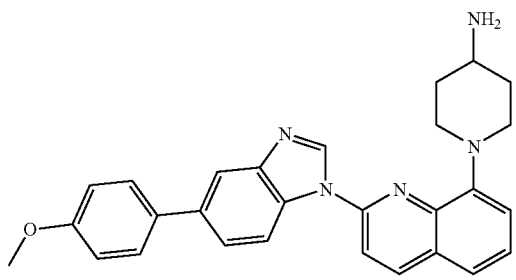

Example 30A

4'-Methoxy-3-nitro-biphenyl-4-ylamine

To a solution of 30 mL of water and 40 mL of dioxane were added 4-methoxyphenylboronic acid (1.69 g, 11.1 mMol), 4-bromo-2-nitroaniline (2.18 g, 10.0 mMol), tetrakis(triphenylphosphine)palladium (0) (580 mg, 0.502 mMol) and $Na_2CO_3$ (6.00 g, 56.6 mMol) under an atmosphere of dry $N_2$. The reaction mixture was subsequently heated to 80° C. and stirred at this temperature overnight. The reaction mixture was then partitioned between DCM and water. The DCM layer was then washed with brine, dried over $Na_2SO_4$, filtered and concentrated under vacuum. The resulting residue was chromatographed on flash silica gel eluting with a gradient starting from DCM/hexanes (1:1) to DCM to give 2.38 g of the title compound 30A.

Example 30B

1-{2-[5-(4-Methoxy-phenyl)-benzoimidazol-1-yl]-quinolin-8-yl}-piperidin-4-ylamine The same procedure that was used in example 1 was followed except that 4'-methoxy-3-nitro-biphenyl-4-ylamine was used in the place of 4-methoxy-2-nitroaniline in example 1B to give the title compound 30.

C.I. m/z 450 [M+1]; $^1$H NMR (CDCl$_3$) δ 8.71 (s, 1H), 8.43 (d, J=8.7 Hz, 1H), 8.28 (d, J=8.7 Hz, 1H), 8.01 (d, J=1.5 Hz, 1H), 7.67 (d, J=8.7 Hz, 1H), 7.62 (m, 3H), 7.45 (m, 2H), 7.35 (dd, J=1.3, 5.8 Hz, 1H), 6.99 (dd, J=2.1, 6.9 Hz, 2H), 3.98 (m, 2H), 3.83 (s, 3H), 2.88 (m, 3H), 2.04 (m, 2H), 1.83 (m, 2H), 1.77 (brs, 2H).

Example 31

(4-{2-[5-(4-Methoxy-phenyl)-benzoimidazol-1-yl]-quinolin-8-yl}-benzyl)-methyl-amine

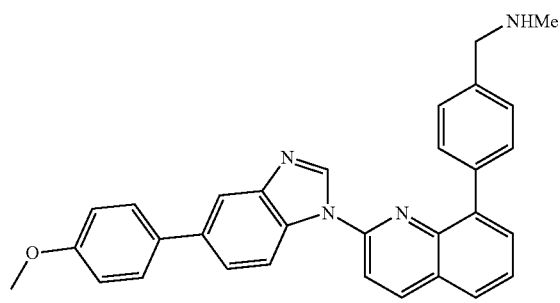

The same procedure that was used for example 5 was followed except that compound 4-methoxy-3-nitro-biphenyl-4-ylamine was used in the place of 4-methoxy-2-nitroaniline in example 1B to give the title compound 31.

C.I. m/z 471 [M+1]; $^1$H NMR (CDCl$_3$) δ 8.60 (s, 1H), 8.27 (d, J=8.9 Hz, 1H), 8.02 (d, J=8.7 Hz, 1H), 7.91 (d, J=1.5 Hz, 1H), 7.76 (m, 2H), 7.64 (m, 3H), 7.47–7.57 (m, 5H), 7.31 (dd, J=1.7, 8.5 Hz, 1H), 6.96 (m, 2H), 3.91 (s, 2H), 3.82 (s, 3H), 2.87 (brs, 1H), 2.55 (s, 3H).

Example 32

1-[2-(5-Cyclopropylmethoxy-benzoimidazol-1-yl]quinolin-8-yl]-piperidin-4-ylamine

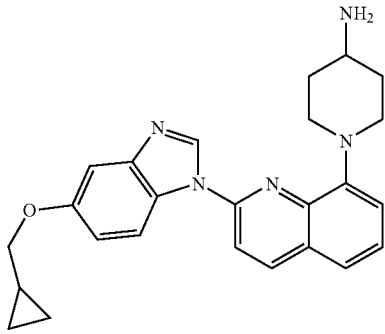

{1-[2-(5-Hydroxy-benzoimidazol-1-yl)-quinolin-8-yl]-piperidin-4-yl}-carbamic acid tert-butyl ester 3A (200 mg, 0.435 mMol) was dissolved in 1.5 mL of anhydrous DMF under an atmosphere of dry $N_2$. To this solution was added $Cs_2CO_3$ (170 mg, 0.520 mMol) followed by cyclopropyl methane bromide (46 µL, 0.48 mMol). The reaction mixture was subsequently heated to 65° C. and stirred at this temperature for 4 hours. The reaction mixture was then cooled to ambient temperature and partitioned between EtOAc and water. The EtOAc layer was washed 4 more times with water and then with brine. The EtOAc was then dried over $Na_2SO_4$, filtered and concentrated under vacuum and the resulting green oil was chromatographed on flash silica gel eluting with MeOH/DCM (2:98) to give the a green oil. The oil was dissolved in 1.5 mL of TFA under an atmosphere of dry $N_2$. The reaction mixture was stirred at ambient temperature for 10 minutes after which time it was concentrated under vacuum and the resulting residue was partitioned between DCM and aqueous 0.1 N NaOH. The DCM layer was then washed with basic brine (pH 10), dried over $Na_2SO_4$, filtered and concentrated under vacuum to give 118 mg of the title compound as a yellow solid 32.

C.I. m/z 414 [M+1]; $^1$H NMR (CDCl$_3$) δ 8.63 (s, 1H), 8.37 (d, J=8.9 Hz, 1H), 8.27 (d, J=8.7 Hz, 1H), 7.65 (d, J=8.7 Hz, 1H), 7.44 (m, 2H), 7.30 (d, J=2.5 Hz, 1H), 7.24 (m, 1H), 7.09 (dd, J=2.5, 8.9 Hz, 1H), 3.87 (m, 4H), 2.87 (m, 3H), 2.03 (m, 2H), 1.81 (m, 2H), 1.56 (brs, 2H), 1.32 (m, 1H), 0.66 (m, 2H), 0.39 (m, 2H).

Example 33

1-{2-[5-(2-Methoxy-ethoxy)-benzoimidazol-1-yl]-quinolin-8-yl}-piperidin-4-ylamine

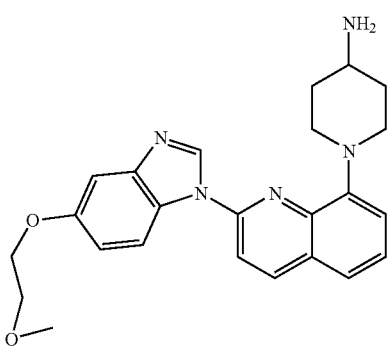

The same procedure that was used for example 1 was followed except that trifluoromethanesulfonic acid 2-[5-(2-methoxy-ethoxy)-benzoimidazol-1-yl]-quinolin-8-yl ester 77E was used in the place of trifluoro-methanesulfonic acid 2-(5-methoxy-benzoimidazol-1-yl)-quinolin-8-yl ester 1E in example 1F to give the title compound 33.

C.I. m/z 418 [M+1]; $^1$H NMR (CDCl$_3$) δ 8.65 (s, 1H), 8.40 (d, J=8.7 Hz, 1H), 8.29 (d, J=8.7 Hz, 1H), 7.67 (d, J=8.7 Hz, 1H), 7.45 (m, 2H), 7.35 (d, J=2.5 Hz, 1H), 7.25 (m, 1H), 7.13 (dd, J=2.5, 8.7 Hz, 1H), 4.22 (m, 2H), 3.88 (m, 2H), 3.81 (m, 2H), 3.48 (s, 3H), 2.89 (m, 3H), 2.05 (m, 2H), 1.82 (m, 2H), 1.57 (brs, 2H).

Example 33A

1-{2-[5-(2-Methoxy-ethoxy)-benzoimidazol-1-yl]-quinolin-8-yl}-piperidin-4-ylamine p-toluenesulphonate salt

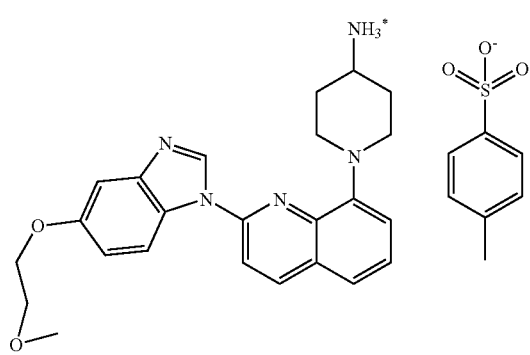

1-{2-[5-(2-Methoxy-ethoxy)-benzoimidazol-1-yl]-quinolin-8-yl}-piperidin-4-ylamine 33 (15.13 g, 36.2 mMol) was dissolved in 93 mL of EtOH and the reaction was heated to reflux under an atmosphere of dry N$_2$. To this solution was added p-toluenesulphonic acid mono hydrate (6.89 g, 36.2 mMol) which was then stirred at reflux overnight. The reaction mixture was then cooled to ambient temperature and filtered. The filtercake was washed with EtOH, dried under vacuum to give 18.46 g of the title compound 33A as an off-white solid.

$^1$H NMR (CD$_3$OD) δ 8.93 (s, 1H), 8.57 (d, J=9.1 Hz, 1H), 8.40 (d, J=8.7 Hz, 1H), 7.89 (d, J=8.7 Hz, 1H), 7.68 (d, J=6.2 Hz, 2H), 7.58 (m, 1H), 7.49 (m, 1H), 7.33 (dd, J=1.2, 7.9 Hz, 1H), 7.25 (d, J=2.5 Hz, 1H), 7.17 (m, 3H), 4.18 (m, 2H), 3.93 (m, 2H), 3.77 (m, 2H), 3.43 (s, 3H), 3.30 (m, 1H), 2.86 (m, 2H), 2.31 (s, 3H), 2.16 (m, 2H), 2.06 (m, 2H).

Example 34

1-{2-[5-(Pyridin-3-ylmethoxy)-benzoimidazol-1-yl]-quinolin-8-yl}piperidin-4-ylamine

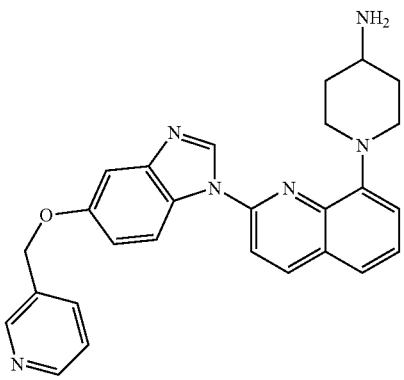

The same procedure that was used for example 32 was followed except 3-picolyl chloride hydrochloride was used in the place of cyclopropyl methane bromide in example 32 and the equivalents of Cs$_2$CO$_3$ was doubled to give the title compound 34.

C.I. m/z 451 [M+1]; $^1$H NMR (CDCl$_3$) δ 8.73 (d, J=2.3 Hz, 1H), 8.65 (s, 1H), 8.58 (dd, J=1.4, 5.0 Hz, 1H), 8.42 (d, J=8.9 Hz, 1H), 8.29 (d, J=8.7 Hz, 1H), 7.82 (m, 1H), 7.66 (d, J=8.7 Hz, 1H), 7.46 (m, 2H), 7.41 (d, J=2.5 Hz, 1H), 7.31 (m, 1H), 7.26 (m, 1H), 7.13 (m, 1H), 5.17 (s, 2H), 3.88 (m, 2H), 2.91 (m, 3H), 2.03 (m, 2H), 1:80 (m, 2H), 1.61 (brs, 2H).

Example 35

1-[2-(5-Benzyloxy-benzoimidazol-1-yl)-quinolin-8-yl]-piperidin-4-ylamine

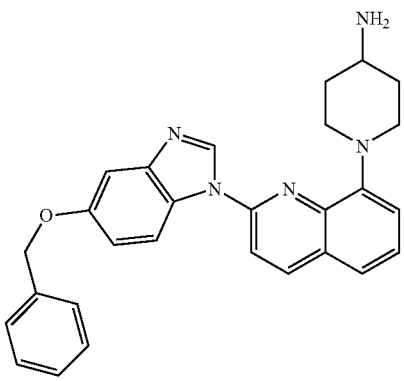

The same procedure that was used for example 32 was followed except benzyl bromide was used in the place of cyclopropyl methane bromide to give the title compound 35.

C.I. m/z 450[M+1]; $^1$H NMR (CDCl$_3$) δ 8.65 (s, 1H), 8.42 (d, J=8.9 Hz, 1H), 8.30 (d, J=8.7, Hz, 1H), 7.67 (d, J=8.7 Hz, 1H), 7.37–7.51 (m 7H), 7.33 (d, J=7.3 Hz, 1H), 7.26 (m,

1H), 7.18 (dd, J=2.5, 8.9 Hz, 1H), 5.16 (s, 2H), 3.88 (m, 2H), 2.90 (m, 3H), 2.04 (m, 2H), 1.81 (m, 2H), 1.40 (brs, 2H).

Example 36

1-{2-[5-(Pyridin-4-ylmethoxy)-benzoimidazol-1-yl]-quinolin-8-yl}-piperidin-4-ylamine

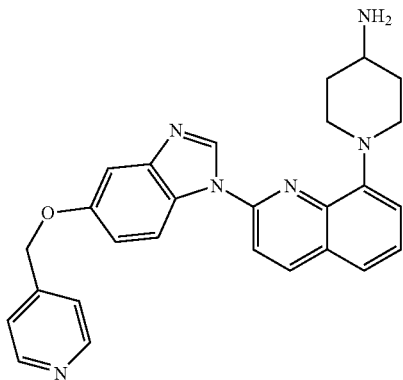

The same procedure that was used for example 32 was followed except the hydrochloride salt of 4-picolyl chloride was used in the place of cyclopropyl methane bromide and the number of equivalents of $Cs_2CO_3$ was doubled to give the title compound 36.

C.I. m/z 451[M+1]; $^1$H NMR (CDCl$_3$) δ 8.65 (s, 1H), 8.63 (m, 2H), 8.44 (d, J=9.1 Hz, 1H), 8.31 (d, J=8.9 Hz, 1H), 7.68 (d, J=8.7 Hz, 1H), 7.47 (m, 2H), 7.41 (d, J=6.0 Hz, 2H), 7.37 (d, J=2.3 Hz, 1H), 7.26 (m, 1H), 7.16 (dd, J=2.3, 9.1 Hz, 1H), 5.19 (s, 2H), 3.90 (m, 2H), 2.90 (m, 3H), 2.05 (m, 2H), 1.80 (m, 2H), 1.55 (brs, 2H).

Example 37

1-{2-[5-(2-Dimethylamino-ethoxy)-benzoimidazol-1-yl]-quinolin-8-yl)-piperidin-4-ylamine

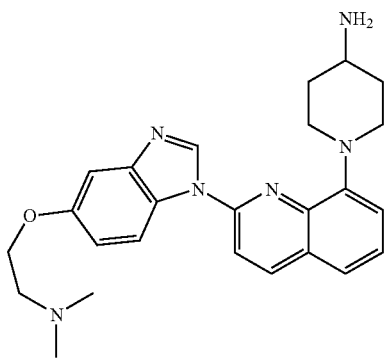

The same procedure that was used for example 32 was followed except that the hydrochloride salt of 2-dimethylamino ethyl chloride was used in the place of cyclopropyl methane bromide and the number of equivalents of $Cs_2CO_3$ was doubled to give the title compound 37.

C.I. m/z 431 [M+1]; $^1$H NMR (CDCl$_3$) δ 8.61 (s, 1H), 8.45 (d, J=8.9 Hz, 1H), 8.27 (d, J=8.7 Hz, 1H), 7.62 (d, J=8.7 Hz, 1H), 7.44 (m, 2H), 7.31 (m, 1H), 7.24 (m, 1H), 7.12 (m, 1H), 4.12 (m, 2H), 3.72–3.88 (m, 4H), 2.90 (m, 3H), 1.78–2.10 (m, 12H).

Example 38

1-2-[5-(3-Amino-propoxy)-benzoimidazol-1-yl]-quinolin-8-yl}-piperidin-4-ylamine

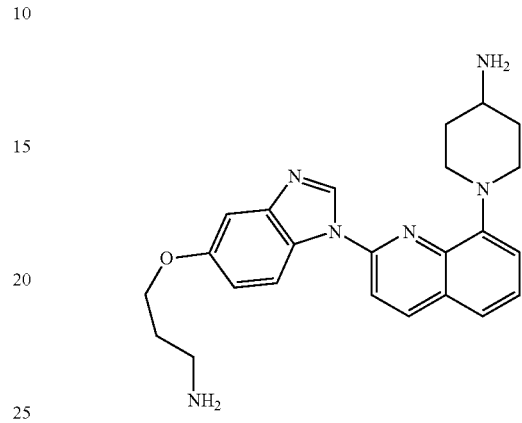

Example 38A

[1-(2-{5-[3-(1,3-Dioxo-1,3-dihydro-isoindol-2-yl)-propoxy]-benzoimidazol-1-yl}-quinolin-8-yl]-piperidin-4-yl]-carbamic acid tert-butyl ester The same procedure that was used for example 32 was followed except N-(3-bromopropyl)-pthalimide was used in the place of cyclopropyl methane bromide and, the tert-butyl carbamate ester intermediate was not subjected to TFA mediated cleavage, to give the title compound 38A as a yellow solid.

Example 38B (1-{2-[5-(3-Amino-propoxy)-benzoimidazol-1-yl]-quinolin-8-yl}-piperidin-4-yl)-carbamic acid tert-butyl ester

[1-(2-{5-[3-(1,3-Dioxo-1,3-dihydro-isoindol-2-yl)-propoxy]-benzoimidazol-1-yl}-quinolin-8-yl)-piperidin-4-yl]-carbamic acid tert-butyl ester 38A (200 mg, 0.31 mMol) was dissolved in 1 mL of EtOH under an atmosphere of dry $N_2$. To this solution was added 50 μL of hydrazine and the resulting solution was stirred at ambient temperature for 3 hours. The reaction mixture was then filtered, concentrated under vacuum and purified via silica gel chromatography eluting with DCM/MeOH/NH$_4$OH (89101) to give 120 mg of the title compound 38B as a yellow film.

Example 38C

1-{2-[5-(3-Amino-propoxy)-benzoimidazol-1-yl]-quinolin-8-yl}-piperidin-4-ylamine (1-{2-[5-(3-Amino-propoxy)-benzoimidazol-1-yl]-quinolin-8-yl}-piperidin-4-yl)-carbamic acid tert-butyl ester 38B (175 mg, 0.42 mMol) was dissolved in a solution of 0.5 mL of TFA and 0.5 mL of DCM under an atmosphere of dry $N_2$ and was stirred at ambient temperature for 1 hour. The reaction mixture was then concentrated under vacuum and subsequently partitioned between DCM and aqueous 1 N NaOH. The DCM layer was then dried over MgSO₄, filtered and concentrated to give the title compound 38 as a light green solid.

C.I. m/z 417 [M+1]; ¹H NMR (CDCl₃) δ 8.63 (s, 1H), 8.36 (d, J=8.7 Hz, 1H), 8.26 (d, J=8.7 Hz, 1H), 7.64 (d, J=8.7 Hz, 1H), 7.44 (m, 2H), 7.31 (d, J=2.5 Hz, 1H), 7.23 (m, 1H), 7.04 (m, 1H), 4.12 (t, J=6.2 Hz, 2H), 3.87 (m, 2H), 2.89 (m, 3H), 2.03 (m, 2H), 1.94 (m, 2H), 1.77 (m, 2H), 1.54 (brs, 4H).

Example 39

1-{2-[5-(3-Dimethylamino-propoxy)-benzoimidazol-1-yl]-quinolin-8-yl}-piperidin-4-ylamine

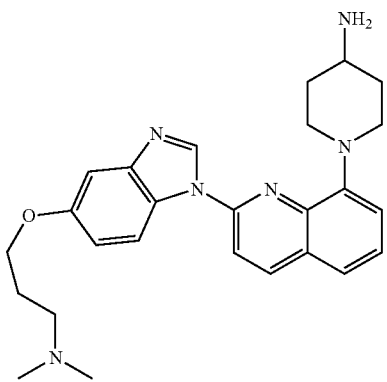

(1-{2-[5-(3-Amino-propoxy)-benzoimidazol-1-yl]-quinolin-8-yl}piperidin-4-yl)-carbamic acid tert-butyl ester 38B (120 mg, 0.288 mMol) was dissolved in a cooled (0C) solution of 1 mL of acetonitrile (ACN) and 0.5 mL of formaldehyde (37% wt in water) under an atmosphere of dry N₂. To this solution was added NaCNBH₃ (72 mg, 1.2 mMol) and the solution was stirred for 30 minutes after which time 200 μL of AcOH was added. The reaction mixture was subsequently warmed to ambient temperature and stirred overnight. The reaction mixture was then concentrated under vacuum and partitioned between aqueous 0.1 N NaOH and DCM. The aqueous layer was washed 3 more times with DCM. The DCM extracts were combined, dried over Na₂SO₄, filtered and concentrated under vacuum to give a green film. The film was purified using flash silica gel chromatography eluting with DCM/MeOH/NH₄OH (89.9100.1) to give 70 mg of the tert-butylcarbonyl protected product. This residue was dissolved in a solution of 1 mL of TFA and 1 mL of DCM under an atmosphere of dry N₂. The reaction mixture was stirred for 1 hour after which time it was concentrated under vacuum, partitioned bewteen DCM and aqueous 1 N NaOH. The aqueous layer was washed 2 more times with DCM. The DCM extracts were combined and dried over Na₂SO₄, filtered and concentrated under vacuum to give a yellow film. The film was purified using flash silica gel chromatography eluting with DCM/MeOH/NH₄OH (84.9150.1) to give 30 mg of the title compound 39 as a yellow film.

C.I. m/z 445 [M+1]; ¹H NMR (CD₃OD) δ 8.87 (s, 1H), 8.58 (d, J=8.8 Hz, 1H), 8.31 (dd, J=2.0, 8.7 Hz, 1H), 7.80 (dd J=2.0, 8.7 Hz, 1H), 7.48 (m, 1H), 7.43 (m, 1H), 7.25 (m, 1H), 7.17 (d, J=2.1 Hz, 1H), 7.10 (m, 1H), 4.02 (m, 2H), 3.78 (m, 2H), 2.71–2.84 (m, 3H), 2.53 (m, 2H), 2.27 (s, 6H), 2.03 (m, 2H), 1.99 (m, 4H), 1.79 (m, 2H).

Example 40

1-[2-(5-Methoxy-benzoimidazol-1-yl]quinolin-8-yl]-piperidine-4-carboxylic acid ethyl ester

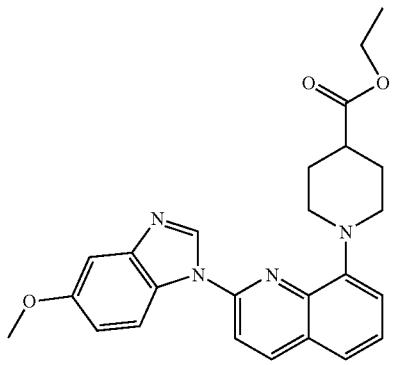

The same procedure that was used in example 1 was followed except that ethyl isonipecotate was used in the place on the piperidin-4-yl-carbamic acid tert-butyl ester in example 1F to give the title compound 40 as a yellow solid.

C.I. m/z 431 [M+1]; ¹H NMR (CDCl₃) δ 8.64 (s, 1H), 8.40 (d, J=8.9 Hz, 1H), 8.28 (d, J=8.9 Hz, 1H), 7.66 (d, J=8.7 Hz, 1H), 7.44 (m, 2H), 7.33 (m, 1H), 7.23 (m, 1H), 7.08 (dd, J=2.5, 8.9 Hz, 1H), 4.18 (q, J=7.5, 2H), 3.89 (s, 3H), 3.85 (m, 2H), 2.90 (m, 2H), 2.52 (m, 1H), 2.14 (m, 4H), 1.29 (t, J=7.5 Hz, 3H).

Example 41

1-[2-(5-Methoxy-benzoimidazol-1-yl)-quinolin-8-yl]-piperidine-4-carboxylic acid

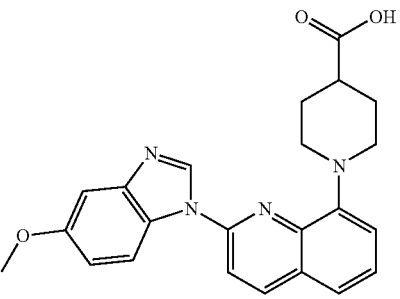

1-[2-(5-Methoxy-benzoimidazol-1-yl)-quinolin-8-yl]-piperidine-4-carboxylic acid ethyl ester 40 (28 mg, 0.065 mMol) was dissolved in 1 mL of ethanol (EtOH). To this solution was added 1 mL of 1 N aqueous NaOH and the mixture was subsequently heated to 60° C. and reacted at this temperature overnight. The reaction mixture was then cooled to ambient temperature and partitioned between 10% aqueous citric acid and ethyl acetate. The organic layer was washed again with 10% aqueous citric acid then three more times with water. The ethyl acetate layer was dried over Na₂SO₄, filtered and concentrated to give 7 mg of the title compound 41 as a yellow solid.

C.I. m/z 403 [M+1]; $^1$H NMR (CD$_3$OD) δ 8.94 (s, 1H), 8.73 (d, J=9.2 Hz, 1H), 8.40 (d, J=8.9 Hz, 1H), 7.90 (d, J=8.9 Hz, 1H), 7.55 (m, 1H), 7.47 (m, 1H), 7.31 (m, 1H), 7.23 (d, J=2.3 Hz, 1H), 7.07 (dd, J=2.4, 9.0 Hz, 1H), 3.87 (s, 3H), 3.79 (m, 2H), 2.85 (m, 2H), 2.50 (m, 1H), 2.08 (m, 4H).

Example 42

4-Dimethylaminomethyl-1-[2-(5-methoxy-benzoimidazol-1-yl)-quinolin-8-yl]-piperidin-4-ol

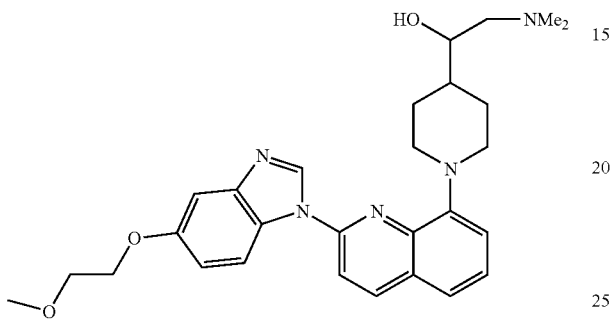

Example 42A 5-(2-Methoxy-ethoxy)-2-nitro-phenylamine

4-Amino-3-nitrophenol (58.53 g, 379.7 mMol) was dissolved in 600 mL of anhydrous DMF under an atmosphere of dry N$_2$ and the solution was mechanically stirred. The reaction mixture was then cooled to 0° C. and to this mixture was added CS$_2$CO$_3$ (177.4 g, 455.7 mMol), sodium iodide (5.7 g, 37.9 mMol) and 2-bromoethyl methyl ether (39.3 mL, 417.7 mMol). After stirring for 15 minutes, the reaction mixture was then warmed up to ambient temperature and then stirred overnight. The reaction mixture is then poured into 6 L of water. The precipitate was collected via suction filtration. The wet precipitate was taken up in toluene and then concentrated under vacuum to remove the water. Finally, the solid was recrystallized from 2-propanol to give 57.93 g of 5-(2-Methoxy-ethoxy)-2-nitro-phenylamine 42A as an orange solid. A second crop of 12.5 g of compound 42A was also obtained.

Example 42B

4-Dimethylaminomethyl-1-[2-(5-methoxy-benzoimidazol-1-yl)-quinolin-8-yl]-piperidin-4-ol The same procedure that was used in example 24 was followed except that 5-(2-Methoxyethoxy)$_2$-nitro-phenylamine 42A was used in the place of 4-methoxy-2-nitroaniline in example 1B to give the title compound 42 as a yellow solid.
C.I. m/z 476 [M+1; $^1$H NMR (CD$_3$OD) δ 8.85 (s, 1H), 8.55 (d, J=9.1 Hz, 1H), 8.29 (d, J=8.7 Hz, 1H), 7.76 (d, J=8.7 Hz, 1H), 7.43 (m, 2H), 7.27 (d, J=7.5 Hz, 1H), 7.21 (d, J=2.5 Hz, 1H), 7.00 (dd, J=2.5, 9.0 Hz, 1H), 4.13 (m, 2H), 3.77 (m, 2H), 3.44 (s, 3H), 3.32 (m, 2H), 3.16 (m, 2H), 2.42 (s, 2H), 2.38 (s, 6H), 1.97 (m, 2H), 1.75 (m, 2H).

Example 43

N-{1-[2-(5-Methoxy-benzoimidazol-1-yl)-quinolin-8-yl]-piperidin-4-yl}-acetamide

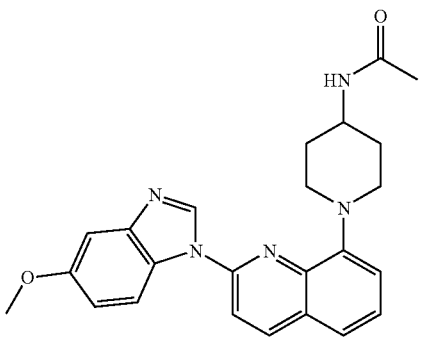

1-[2-(5-Methoxy-benzoimidazol-1-yl]quinolin-8-yl]-piperidin-4-ylamine 1 (100 mg, 0.268 mMol) and sodium cyanate (35 mg, 0.536 mMol) were dissolved in 1 mL of AcOH under an atmosphere of dry N$_2$. The reaction mixture was stirred overnight at ambient temperature. The reaction mixture was then concentrated under vacuum and partitioned between DCM and saturated aqueous NaHCO$_3$. The organic layer was dried over Na$_2$SO$_4$, filtered and concentrated to a yellow foam which was chromatographed on flash silica gel eluting with MeOH/NH$_4$OH/DCM (2/0.2/97.8) to give the title compound 43.
C.I. m/z 416 [M+1]; $^1$H NMR (CDCl$_3$) δ 8.63 (s, 1H), 8.30 (m, 2H), 7.66 (d, J=8.7 Hz, 1H), 7.43 (m, 2H), 7.33 (d, J=2.5 Hz, 1H), 7.23 (dd, J=1.7, 7.1 Hz, 1H), 7.03 (dd, J=2.5, 9.0 Hz, 1H), 5.64 (brd, J=8.3 Hz, 1H), 4.03 (m, 1H), 3.89 (s, 3H), 3.84 (m, 2H), 2.93 (m, 2H), 2.16 (m, 2H), 2.02 (s, 3H), 1.88 (m, 2H).

Example 44

N-{1-[2-(5-Cyclopropylmethoxy-benzoimidazol-1-yl)-quinolin-8-yl]-piperidin-4-yl}-acetamide

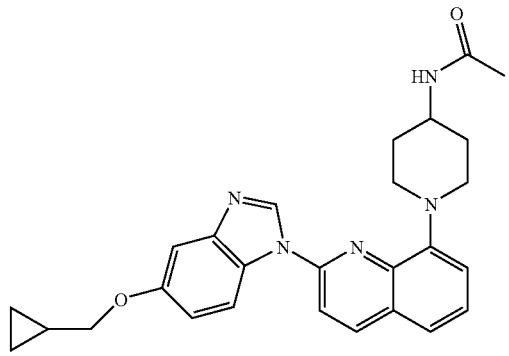

The procedure used in example 43 was followed except that 1-[2-(5-cyclopropylmethoxy-benzoimidazol-1-yl)-quinolin-8-yl]-piperidin-4-ylamine 32 was used in the place of 1-[2-(5-methoxy-benzoimidazol-1-yl)-quinolin-8-yl]-piperidin-4-ylamine 1 to give the title compound 44 as a yellow solid.

C.I. m/z 456 [M+1]; $^1$H NMR (CDCl$_3$) δ8.61 (s, 1H), 8.33 (d, J=8.7 Hz, 1H), 8.28 (d, J=8.7Hz, 1H), 7.65 (d, J=8.7 Hz, 1H), 7.45 (m, 2H), 7.28 (d, J=2.1 Hz, 1H), 7.22 (m, 1H), 7.07 (dd, J=1.5, 8.7 Hz, 1H), 5.63 (brd, J=8.3 Hz, 1H), 4.03 (m, 1H), 3.88 (d, J=7.0 Hz, 2H), 3.85 (m, 2H), 2.92 (m, 2H), 2.14 (m, 2H), 2.04 (s, 3H), 1.88 (m, 2H), 1.33 (m, 1H), 0.67 (m, 2H), 0.38 (m, 2H).

Example 45

1-{2-[5-(2-Methoxy-ethoxy)-benzoimidazol-1-yl]-quinolin-8-yl}-piperidin-4-ol

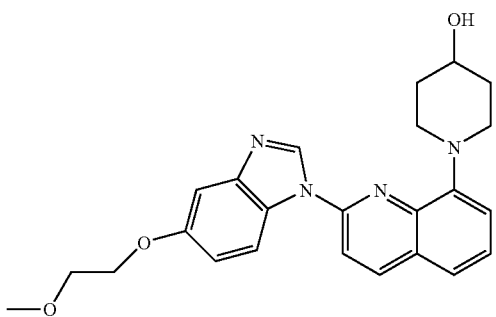

The same procedure that was used for example 19 was followed except that 5-(2-methoxyethoxy)-2-nitro-phenylamine 42A was used in the place of was used in the place of 4-methoxy-2-nitroaniline nitroaniline in example 1B to give the title compound 45 as a yellow solid.

C.I. m/z 419 [M+1]; $^1$H NMR (CDCl$_3$) δ 8.62 (s, 1H), 8.39 (d, J=9.1 Hz, 1H), 8.24 (d, J=8.7 Hz, 1H), 7.62 (d, J=8.7 Hz, 1H), 7.43 (m, 2H), 7.31 (d, J=2.1 Hz, 1H), 7.23 (m, 1H), 7.10 (m, 1H), 4.17 (m, 2H), 3.93 (m, 1H), 3.77 (m, 2H), 3.71 (m, 2H), 3.44 (s, 3H), 3.04 (m, 2H), 2.47 (brd, J=3.3 Hz, 1H), 2.14 (m, 2H), 1.97 (m, 2H).

Example 46

{1-[2-(5-Methoxy-benzoimidazol-1-yl)quinolin-8-yl]-piperidin-4-yl}-urea

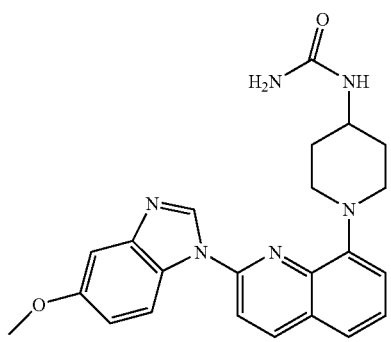

1-[2-(5-Methoxy-benzoimidazol-1-yl]-quinolin-8-yl]-piperidin-4-ylamine 1 (150 mg, 0.402 mMol) and 1,1'-carbonyldiimidazole (78 mg, 0.48 mMol) were dissolved in 1 mL of anhydrous THF under an atmosphere of dry N$_2$. The reaction mixture was stirred for 2 hours at ambient temperature. 1.0 mL of concentrated ammonium hydroxide (NH$_4$OH) was then added to the reaction mixture that was then stirred overnight. The reaction mixture was then partitioned between DCM and water. The DCM layer was dried over Na$_2$SO$_4$, filtered and concentrated under vacuum. The residue was chromatographed over flash silica gel eluting with MeOH/DCM (595) to give 15 mg of the title compound 46 as a white solid.

C.I. m/z 417 [M+1]; $^1$H NMR (CD$_3$OD) δ 8.89 (s, 1H), 8.59 (d, J=8.9 Hz, 1H), 8.36 (J=8.9 Hz, 2H), 7.85 (d, J=8.7 Hz, 1H), 7.74 (brs, 1H), 7.53 (d, J=8.1 Hz, 1H), 7.45 (m, 1H), 7.30 (d, J=7.5 Hz, 1H), 7.23 (m, 1H), 7.05 (m, 1H), 3.86 (s, 3H), 3.73 (m, 2H), 3.66 (m, 1H), 2.87 (m, 2H), 2.08 (m, 2H), 1.83 (m, 2H).

Example 47

4-Aminomethyl-1-{2-[5-(pyridin-2-ylmethoxy)-benzoimidazol-1-yl]-quinolin-8-yl}piperidin-4-ol

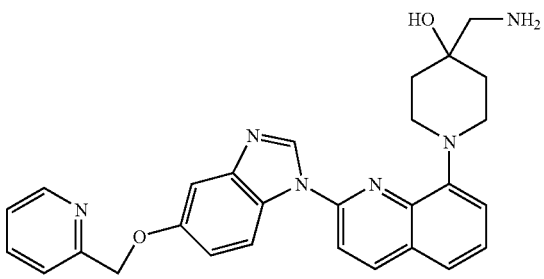

Example 47A

2-Nitro-4-(pyridin-2-ylmethoxy)-phenylamine

4-Amino-3-nitrophenol (5.00 g, 32.4 mMol), Cs$_2$CO$_3$ (22.8 g, 70 mMol), sodium iodide (476 mg, 3.20 mMol) and 2-picolyl chloride hydrochloride (11.2 g, 35 mMol) were added to 20 mL of anhydrous DMF under an atmosphere of dry N$_2$. The reaction mixture was stirred overnight at ambient temperature. The reaction mixture is then poured into water. The precipitate was collected via suction filtration. The precipitate was partitioned between DCM and 1.0 N aqueous NaOH. The organic layer was washed 2 more times with 1 N aqueous NaOH to remove any unreacted phenol. The organic layer was then washed with brine, dried over Na$_2$SO$_4$, filtered and concentrated under vacuum to give 7.7 g of a dark red solid. The solid was chromatographed on flash silica gel eluting with EtOAc/DCM (2080) to give 3.7 g of the title compound 47A as an orange solid.

Example 47B

4-Aminomethyl-1{-2-[5-(pyridin-2-ylmethoxy)-benzoimidazol-1-yl]-quinolin-8-yl)-piperidin-4-ol The same procedure that was used in example 26 was followed except that 2-nitro-4-(pyridin-2-ylmethoxy]phenylamine 47A was used in the place of 4-methoxy-2-nitroaniline in example 1B to give the title compound 47.

C.I. m/z 481 [M+1]; $^1$H NMR (CDCl$_3$) δ 8.64 (s, 1H), 8.60 (dd, J=0.8, 5.0 Hz, 1H), 8.31 (d, J 9.1+Hz, 1, H), 8.27 (d, J=8.7 Hz, 1H), 7.68 (m, 1H), 7.63 (d, J=9.1 Hz, 1-H), 7.55 (d, J=7.9 Hz, 1H), 7.44 (m, 2H), 7.38 (d, J=2.1 Hz, 1H), 7.27 (m, 1H), 7.24 (m, 1H), 7.12 (m, 1H), 5.27 (s, 2H), 3.67 (m, 2H), 3.22 (m, 2H), 2.78 (s, 2H), 2.40 (brs, 3H), 1.96 (m, 2H), 1.81 (m, 2H).

Example 48

Cyclopropyl-(1-{2-[5-(2-methoxy-ethoxy)-benzoimidazol-1-yl]-quinolin-8-yl}piperidin-4-yl)amine

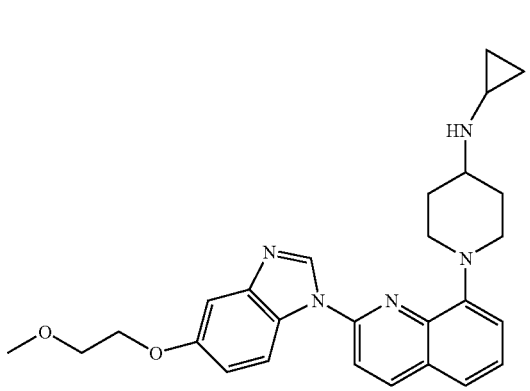

The same procedure that was used in example 20 was followed except that 5-(2-methoxy-ethoxy)-2-nitro-phenylamine 42A was used in the place of 4-methoxy-2-nitroaniline in example 1B to give the title compound 48 as a yellow solid.

C.I. m/z 458 [M+1]; $^1$H NMR (CDCl$_3$) δ 8.65 (s, 1H), 8.40 (d, J=8.7 Hz, 1H), 8.28 (d, J=8.7 Hz, 1H), 7.66 (d, J=8.7 Hz, 1H), 7.45 (m, 2H), 7.35 (d, J=2.5 Hz, 1H), 7.25 (m, 1H), 7.15 (m, 1H), 4.22 (m, 2H), 3.82 (m, 2H), 3.80 (m, 2H), 3.47 (s, 3H), 2.88 (m, 3H), 2.27 (m, 1H), 2.18 (m, 2H), 1.85 (m, 2H), 0.50 (m, 2H), 0.47 (m, 2H).

Example 49

(1-{2-[5-(2-Methoxy-ethoxy)-benzoimidazol-1-yl]-quinolin-8-yl}-piperidin-4-yl)-dimethyl-amine

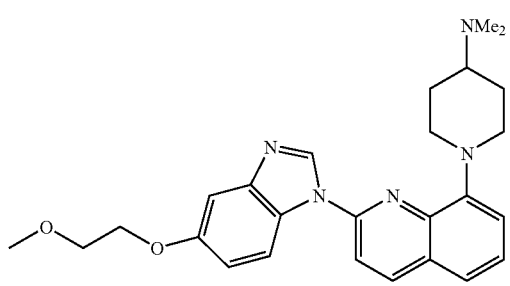

The same procedure that was used in example 4 was followed except that 5-(2-methoxyethoxy)-2-nitro-phenylamine 42A was used in the place of 4-methoxy-2-nitroaniline in example 1B to give the title compound 49.

C.I. m/z 446 [M+1]; $^1$H NMR (CDCl$_3$) δ 8.59 (s, 1H), 8.35 (d, J=8.7 Hz, 1H), 8.18 (d, J=8.7 Hz, 1H), 7.57 (d, J=8.7 Hz, 1H), 7.38 (m, 2H), 7.28 (d, J=2.5 Hz, 1H), 7.15 (d, J=2.5, 6.2 Hz, 1H), 7.06 (m, 1H), 4.18 (m, 2H), 3.94 (m, 2H), 3.75 (m, 2H), 3.42 (s, 3H), 2.72 (m, 2H), 2.40 (m, 1H), 2.34 (s, 6H), 1.95 (m, 4H).

Example 50

(1-{2-[5-(2-Methoxy-ethoxy)-benzoimidazol-1-yl]-quinolin-8-yl}-piperidin-4-yl)-methyl-amine.

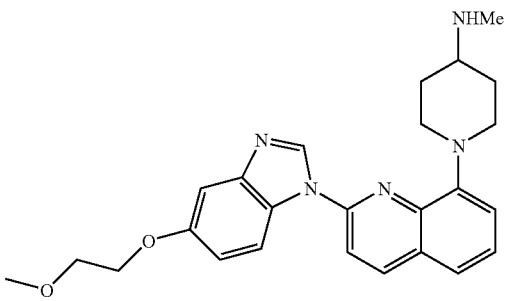

The same procedure that was used in example 22 was followed except that 5-(2-methoxyethoxy)-2-nitro-phenylamine 42A was used in the place of 4-methoxy-2-nitroaniline in example 1B to give the title compound 50.

C.I. m/z 432 [M+1]; $^1$H NMR (CDCl$_3$) δ 8.62 (s, 1H), 8.37 (d, 1=9.1 Hz, 1H), 8.23 (d, J=8.7 Hz, 1H), 7.61 (d, J=8.7 Hz, 1H), 7.42 (m, 2H), 7.31 (d, J=2.1 Hz, 1H), 7.20 (d, J=3.0, 5.8 Hz, 1H), 7.11 (dd, J=2.5, 9.1 Hz, 1H), 4.18 (m, 2H), 3.88 (m, 2H), 3.76 (m, 2H), 3.45 (s, 3H), 2.85 (m, 2H), 2.59 (m, 1H), 2.47 (s, 3H), 2.18 (brs, 1H), 2.11 (m, 2H), 1.75 (m, 2H).

Example 51

(1-2-[5-(3-Dimethylamino-propoxy)-benzoimidazol-1-yl]-quinolin-8-yl}-piperidin-4-yl)-dimethylamine

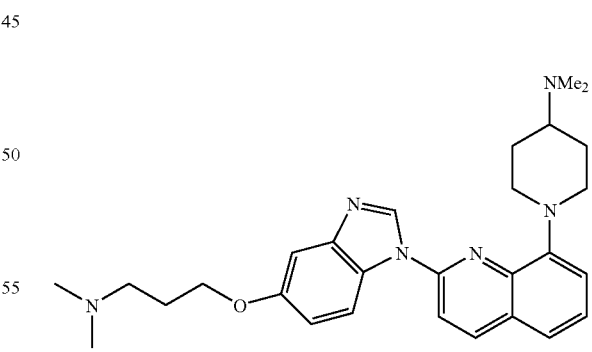

The same procedure that was used in example 4 was followed except that 1[-2-[5-(3-dimethylamino-propoxy)-benzoimidazol-1-yl]-quinolin-8-yl}piperidin-4-ylamine 39 was used in the place of 1-[2-(5-methoxy-benzoimidazol-1-yl)-quinolin-8-yl]-piperidin-4-ylamine 1 to give the title compound 51.

C.I. m/z 473 [M+1]; $^1$H NMR (CD$_3$OD) δ 8.87 (s, 1H), 8.61 (d, J=9.1 Hz, 1H), 8.31 (d, J=8.7 Hz, 1H), 7.78 (d, J=8.7 Hz, 1H), 7.48 (d, J=6.4 Hz, 1H), 7.42 (m, 1H), 7.21 (m, 2H), 7.05 (m, 1H), 4.05 (m, 2H), 3.82 (m, 2H), 3.19 (m, 1H), 2.65 (m, 5H), 2.40 (m, 1H), 2.34 (s, 6H), 1.95 (m, 4H).

Example 52

{1-[2-(5-Cyclopropylmethoxy-benzoimidazol-1-yl)-quinolin-8-yl]-piperidin-4-yl}-methyl-amine

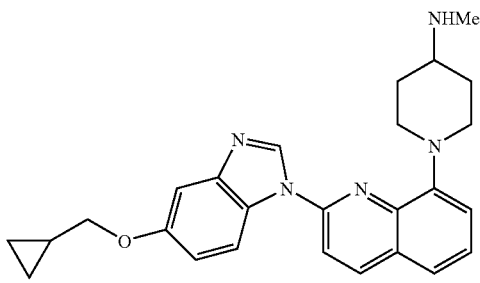

Example 52A

4-Cyclopropylmethoxy-2-nitro-phenylamine

4-Amino-3-nitrophenol (13.3 g, 84.8 mMol), Cs$_2$CO$_3$ (33.2 g, 102 mMol) and cyclopropylmethyl bromide (9.1 mL, 93.3 mMol) were added to 30 mL of anhydrous DMF under an atmosphere of dry N$_2$. The reaction mixture was stirred overnight at ambient temperature. The reaction mixture is then poured into water. The precipitate was collected via suction filtration. The precipitate was partitioned between DCM and 1.0 N aqueous NaOH. The organic layer was washed 2 more times with 1 N aqueous NaOH to remove any unreacted phenol. The organic layer was then washed with brine, dried over Na$_2$SO$_4$, filtered and concentrated under vacuum to give 18.6 g of the title compound 52A as an orange solid.

Example 52B

{-[2-(5-Cyclopropylmethoxy-benzoimidazol-1-yl)-quinolin-8-yl]-piperidin-4-yl}methyl-amine The same procedure that was used in example 22 was followed except that 4-cyclopropylmethoxy-2-nitro-phenylamine 52A was used in the place of 4-methoxy-2-nitroaniline in example 1B to give the title compound 52.

C.I. m/z 428 [M+1]; $^1$H NMR (CDCl$_3$) δ 8.63 (s, 1H), 8.38 (d, J=9.1 Hz, 1H), 8.28 (d, J=8.7 Hz, 1H), 7.65 (d, J=8.7 Hz, 1H), 7.46 (m, 2H), 7.30 (d, J=2.5 Hz, 1H), 7.24 (m, 1H), 7.06 (m, 1H), 3.89 (m, 4H), 2.90 (m, 2H), 2.71 (m, 1H), 2.55 (s, 3H), 2.16 (m, 2H), 2.00 (brs, 1H), 1.89 (m, 2H), 1.30 (m, 1H), 0.64 (m, 2H), 0.38 (m, 2H).

Example 53

{1-[2-(5-Cyclopropylmethoxy-benzoimidazol-1-yl)-quinolin-8-yl]-piperidin-4-yl}-dimethyl-amine

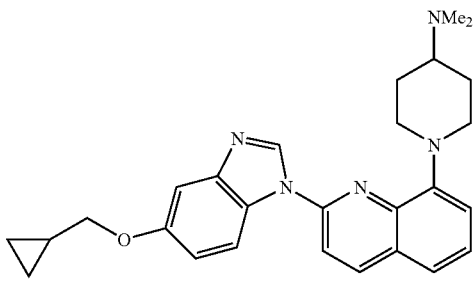

The same procedure that was used in example 4 was followed except that {1-[2-(5-cyclopropylmethoxy-benzoimidazol-1-yl)-quinolin-8-yl]-piperidin-4-yl]methyl-amine 52 was used in the place of 1-[2-(5-methoxy-benzoimidazol-1-yl)-quinolin-8-yl]-piperidin-4-ylamine 1 to give the title compound 53:

C.I. m/z 442 [M+1]; $^1$H NMR (CDCl$_3$) δ 8.65 (s, 1H), 8.38 (d, J=9.0 Hz, 1H), 8.30 (d, J=9.0 Hz, 1H), 7.69 (d, J=8.7 Hz, 1H), 7.48 (m, 2H), 7.31 (d, J=2.3 Hz, 1H), 7.24 (m, 1H), 7.09 (d, J=2.3, 9.0 Hz, 1H), 4.03 (m, 2H), 3.89 (d, J=6.8 Hz, 2H), 2.83 (m, 2H), 2.55 (m, 1H), 2.44 (s, 6H), 2.06 (m, 4H), 1.30 (m, 1H), 0.68 (m, 2H), 0.39 (m, 2H).

Example 54

2-Amino-N-(1-{2-[5-(2-methoxy-ethoxy)-benzoimidazol-1-yl]-quinolin-8-yl}-piperidin-4-yl)acetamide

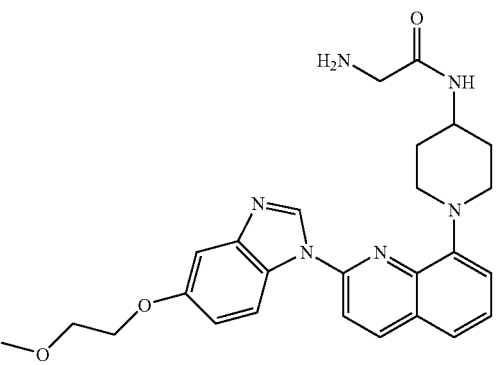

N-(tert-butoxycarbonyl)glycine (105 mg, 0.600 mMol) was dissolved in 3 mL of DCM under an atmosphere of dry N$_2$. To this mixture was added 1,1'-carbonyldiimidazole (100 mg, 0.61 mMol) and the reaction mixture was stirred at ambient temperature for 30 minutes. To this solution was then added 4-dimethylaminopyridine (8.0 mg, 0.065 mMol)

and 1-{2-[5-(2-methoxy-ethoxy)-benzoimidazol-1-yl]-quinolin-8-yl}-piperidin-4-ylamine 33 (170 mg, 0.408 mMol). The reaction mixture was subsequently stirred overnight at ambient temperature. The reaction mixture was then partitioned between DCM and saturated aqueous NaHCO$_3$. The organic layer was saved and washed again with saturated aqueous NaHCO$_3$, dried over Na$_2$SO$_4$, filtered and concentrated under vacuum to give a yellow foam. The residue was chromatographed on flash silica gel eluting with MeOH/DCM (397) to give 182 mg of a yellow residue. The residue was dissolved in 0.5 ml of TFA and stirred at ambient temperature for 30 minutes under an atmosphere of dry N$_2$. The reaction mixture was subsequently concentrated under vacuum and then partitioned between 0.1 N aqueous NaOH. The organic layer was saved and washed again with 0.1 N aqueous NaOH, dried over Na$_2$SO$_4$, filtered and concentrated under vacuum to give a yellow foam. The foam was chromatographed on flash silica gel eluting with MeOH/DCM (595) to give 75 mg of the title compound as 54 a yellow solid.

C.I. m/z 475 [M+1]; $^1$H NMR (CDCl$_3$) δ 8.62 (s, 1H), 8.31 (d, J=8.7 Hz, 1H), 8.27 (d, J=8.7 Hz, 1H), 7.64 (d, J=8.7 Hz, 1H), 7.44 (m, 2H), 7.38 (brd, J=7.9 Hz, 1H), 7.32 (d, J=2.1 Hz, 1H), 7.22 (m, 1H), 7.06 (d, J=2.5, 9.2 Hz, 1H), 4.20 (m, 2H), 4.02 (m, 1H), 3.86 (m, 2H), 3.78 (m, 2H), 3.46 (s, 3H), 3.37 (s, 2H), 2.94 (m, 2H), 2.13 (m, 2H), 1.90 (m, 2H), 1.74 (brs, 2H).

Example 55

-(S)-2-Amino-N-(1-2-[5-(2-methoxy-ethoxy)-benzoimidazol-1-yl]-quinolin-8-yl}-piperidin-4-yl)propionamide

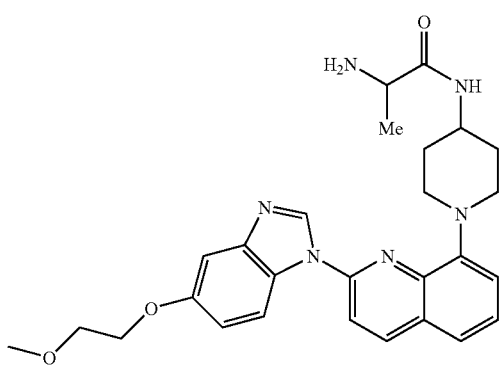

The same procedure that was used in example 54 was followed except that N-(tert-butoxycarbonyl)-L-alanine was used in the place of N-(tert-butoxycarbonyl)glycine to give the title compound 55 as a yellow solid.

C.I. m/z 489 [M+1]; $^1$H NMR (CDCl$_3$) δ 8.61 (s, 1H), 8.27 (d, J=8.7 Hz, 1H), 8.25 (d, J=9.1 Hz, 1H), 7.63 (d, J=8.7 Hz, 1H), 7.42 (m, 3H), 7.30 (d, J=2.5 Hz, 1H), 7.22 (dd, J=2.1, 8.7 Hz, 1H), 7.07 (d, J=2.5, 8.7 Hz, 1H), 4.17 (m, 2H), 3.95 (m, 1H), 3.85 (m, 2H), 3.77 (m, 2H), 3.50 (m, 1H), 3.43 (s, 3H), 2.91 (m, 2H), 2.10 (m, 2H), 1.85 (m, 4H), 1.34 (d, J=6.7 Hz, 3H).

Example 56

-(R)-2-Amino-N-(1-{2-[5-(2-methoxy-ethoxy)-benzoimidazol-1-yl]-quinolin-8-yl}-piperidin-4-yl)-4-yl)-propionamide

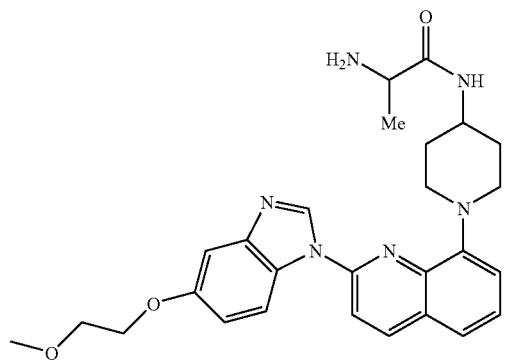

The same procedure that was used in example 54 was followed except that N-(tert-butoxycarbonyl)-D-alanine was used in the place of N-(tert-butoxycarbonyl)glycine to give the title compound 56 as a yellow solid.

C.I. m/z 489 [M+1]; $^1$H NMR (CDCl$_3$) δ 8.63 (s, 1H), 8.26 (m, 2H), 7.65 (d, J=8.7 Hz, 1H), 7.44 (m, 2H), 7.38 (brd, J=8.7 Hz, 1H), 7.33 (d, J=2.5 Hz, 1H), 7.22 (dd, J=2.1, 7.0 Hz, 1H), 7.10 (d, J=2.5, 8.7 Hz, 1H), 4.20 (m, 2H), 3.99 (m, 1H), 3.86 (m, 2H), 3.79 (m, 2H), 3.50 (m, 1H), 3.46 (s, 3H), 2.96 (m, 2H), 2.12 (m, 2H), 1.88 (m, 2H), 1.52 (brs, 2H), 1.35 (d, J=7.1 Hz, 3H).

Example 57

2-Amino-N-(1-{2-[5-(2-methoxy-ethoxy)-benzoimidazol-1-yl]-quinolin-8-yl}-piperidin-4-yl isobutyramide

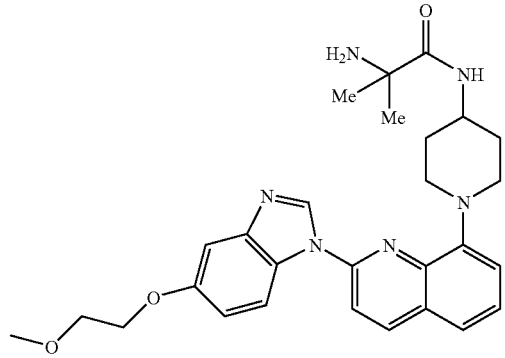

N-(tert-butoxycarbonyl)glycine (73 mg, 0.36 mMol) and 1-(3-dimethylaminopropyl)-3-ethylcarbodiimide hydrochloride (69 mg, 0.36 mMol) were dissolved in 1 mL of anhydrous DMF under an atmosphere of dry N$_2$ and stirred at ambient temperature for 30 minutes. Triethylamine (167 μL, 1.24 mMol) and 1-{-2-[5-(2-methoxy-ethoxy)-benzoimidazol-1-yl]quinolin-8-yl)-piperidin-4-ylamine 33 (146 mg, 0.35 mMol) were then added to the reaction mixture which was subsequently stirred overnight. The reaction mixture was then partitioned between DCM and saturated aqueous NaHCO₃. The organic layer was saved and washed two more times with saturated aqueous NaHCO₃, dried over Na₂SO₄, filtered and concentrated under vacuum to give a yellow oil. The residue was chromatographed on flash silica gel eluting with a gradient of DCM to MeOH/DCM (298) to give 30 mg of a yellow residue. The residue was dissolved in 0.25 ml of TFA and stirred at ambient temperature for 30 minutes under an atmosphere of dry N₂. The reaction mixture was subsequently concentrated under vacuum and then partitioned between 0.1 N aqueous NaOH. The organic layer was saved and washed again with 0.1 N aqueous NaOH, dried over Na₂SO₄, filtered and concentrated under vacuum to give the title compound 57 as a yellow residue.

C.I. m/z 503 [M+1]; ¹H NMR (CDCl₃) δ 8.70 (s, 1H), 8.29 (d, J=8.7 Hz, 1H), 8.21 (d, J=9.1 Hz, 1H), 7.66 (m, 2H), 7.44 (m, 2H), 7.25 (d, J=2.5 Hz, 1H), 7.21 (dd, J=2.6, 9.1 Hz, 1H), 7.12 (m, 1H), 4.19 (m, 2H), 3.95 (m, 1H), 3.88 (m, 2H), 3.79 (m, 2H), 3.46 (s, 3H), 2.93 (m, 2H), 2.09 (m, 2H), 1.90 (m, 2H), 1.49 (s, 6H).

Example 58

1-(1-{2-[5-(2-Methoxy-ethoxy)-benzoimidazol-1-yl]-quinolin-8-yl}-piperidin-4-ylamino)-2-methyl-propan-2-ol

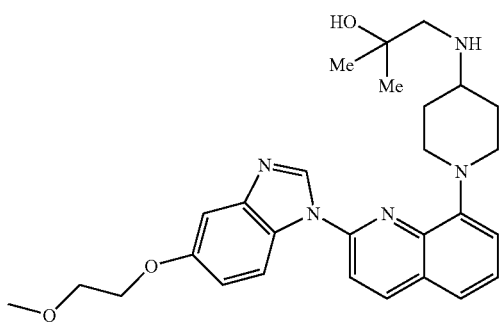

Example 58A (1-(2-[5-(2-Methoxy-ethoxy)-benzoimidazol-1-yl]-quinolin-8-yl)-piperidin-4-ylamino)-acetic acid ethyl ester Bromo-acetic acid ethyl ester (80 μL, 0.710 mMol), diisopropylethylamine (180 μL, 1.00 mMol) and 1-(2-[5-(2-methoxy-ethoxy]benzoimidazol-1-yl]-quinolin-8-yl}-piperidin-4-ylamine 33 (270 mg, 0.647 mMol) were dissolved in 3 mL of anhydrous DCM under an atmosphere of dry N₂ and stirred overnight at ambient temperature. The reaction mixture was then partitioned between DCM and 0.1 N aqueous NaOH. The organic layer was saved and washed sequentially with 0.1 N aqueous NaOH and brine, dried over Na₂SO₄, filtered and concentrated under vacuum to give a yellow residue. The residue was chromatographed on flash silica gel eluting with MeOH/DCM (298) to give 220 mg of the title compound 58A.

Example 58B 1-(1-{2-[5-(2-Methoxy-ethoxy)-benzoimidazol-1-yl]-quinolin-8-yl}-piperidin-4-ylamino)-2-methyl-propan-2-ol (1-(2-[5-(2-Methoxy-ethoxy)-benzoimidazol-1-yl]-quinolin-8-yl}-piperidin-4-ylamino)-acetic acid ethyl ester (110 mg, 0.218 mMol) 58A was dissolved in 2 mL of anhydrous THF under an atmosphere of dry N₂. The reaction mixture was cooled to ~78° C. and then 260 μL of a solution of 1.0 M methylmagnesium bromide in THF was added. The reaction mixture was slowly warmed up to ambient temperature and stirred overnight. The reaction mixture was then partitioned between DCM and saturated aqueous NaHCO₃. The organic layer was saved and washed again with saturated aqueous NaHCO₃, dried over Na₂SO₄, filtered and concentrated under vacuum to give a yellow residue. The residue was chromatographed on flash silica gel eluting with MeOH/DCM/NH4OH (297.90.1) to give 20 mg of the title compound 58 as a yellow residue.

C.I. m/z 490 [M+1]; ¹H NMR (CDCl₃) δ 8.65 (s, 1H), 8.35 (d, J=9.1 Hz, 1H), 8.28 (d, J=8.7 Hz, 1H), 7.66 (d, J=8.7 Hz, 1H), 7.44 (m, 2H), 7.33 (d, J=2.5 Hz, 1H), 7.22 (m, 1H), 7.12 (m, 1H), 4.21 (m, 2H), 3.88 (m, 2H), 3.80 (m, 2H), 3.47 (s, 3H), 2.88 (m, 2H), 2.67 (m, 1H), 2.62 (s, 2H), 2.13 (m, 2H), 1.78 (m, 2H), 1.19 (s, 6H).

Example 59

(1-{2-[5-(2-Methoxy-ethoxy)-benzoimidazol-1-yl]-quinolin-8-yl}-piperidin-4-yl)-pyridin-2-ylmethyl-amine

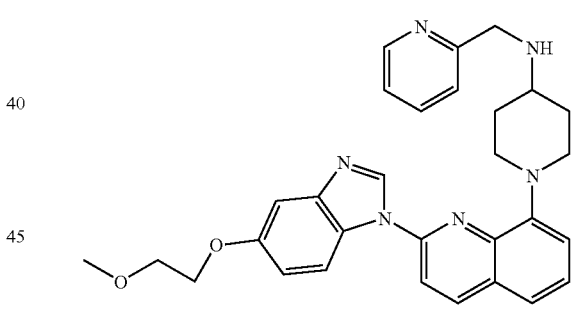

1-{2-[5-(2-methoxy-ethoxy)-benzoimidazol-1-yl]-quinolin-8-yl}-piperidin-4-ylamine 33 (50 mg, 0.119 mMol) and pyridine-2-carbaldehyde (11 μL, 0.119 mMol) were dissolved in a solution of 2 mL of EtOH and 500 μL of DCE under an atmosphere of dry N₂. The reaction mixture was subsequently heated to reflux and stirred at this temperature for 1.5 hours. The reaction mixture was then cooled to ambient temperature and NaBH₄ (14 mg, 0.357 mMol) was added. The reaction mixture was stirred overnight at ambient temperature. The solvent was removed under vacuum and the resulting residue was partitioned between DCM- and 0.1 1 N aqueous NaOH. The DCM layer was dried over Na₂SO₄, filtered and concentrated under vacuum to give 47 mg of the title compound 59 as a yellow residue.

C.I. m/z 509 [M+1]; ¹H NMR (CDCl₃) δ 8.63 (s, 1H), 8.55 (m, 1H), 8.39 (d, J=9.1 Hz, 1H), 8.26 (d, J=8.7 Hz, 1H), 7.65 (m, 2H), 7.44 (m, 2H), 7.36 (d, J=8.9 Hz, 1H), 7.32 (d, J=2.5 Hz, 1H), 7.22 (m, 1H), 7.12 (m, 2H), 4.20 (m, 2H), 4.01 (s, 2H), 3.89 (m, 2H), 3.79 (m, 2H), 3.46 (s, 3H), 2.90 (m, 2H), 2.77 (m, 1H), 2.13 (m, 2H), 1.88 (m, 3H).

Example 60

(1-{2-[5-(2-Methoxy-ethoxy)-benzoimidazol-1-yl]-quinolin-8-yl}-piperidin-4-yl)-pyridin-3-ylmethyl-amine

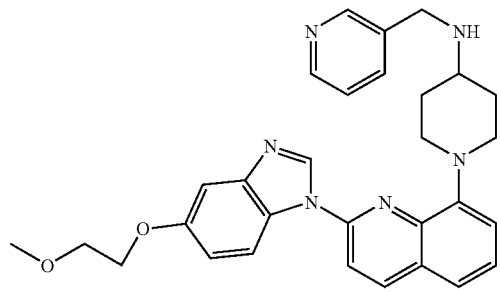

The same procedure that was used in example 59 was followed except that pyridine-3-carbaldehyde was used in the place of pyridine-2-carbaldehyde to give the title compound 60 as a yellow residue.

C.I. m/z 509 [M+1]; $^1$H NMR (CDCl$_3$) δ 8.65 (s, 1H), 8.59 (d, J=2.7 Hz, 1H), 8.50 (dd, J=2.7, 5.0, 1H), 8.38 (d, J=8.7 Hz, 1H), 8.29 (d, J=8.7 Hz, 1H), 7.76 (m, 1H), 7.67 (m, 1H), 7.45 (m, 2H), 7.34 (d, J=2.5 Hz, 1H), 7.27 (m, 1H), 7.22 (m, 1H), 7.12 (dd, J=2.5, 8.7, 1H), 4.22 (m, 2H), 3.91 (s, 2H), 3.88 (m, 2H), 3.80 (m, 2H), 3.47 (s, 3H), 2.90 (m, 2H), 2.75 (m, 1H), 2.14 (m, 2H), 1.85 (m, 2H), 1.75 (brs, 1H).

Example 61

4-{2-[5-(2-Methoxy-ethoxy)-benzoimidazol-1-yl]-quinolin-8-yl}phenol

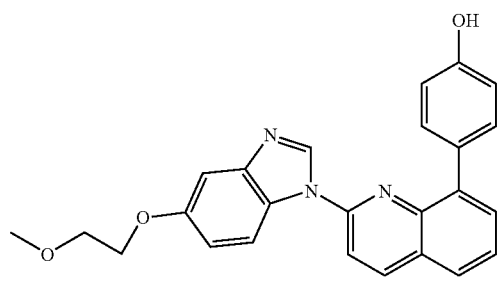

Example 61A

N-(2-Bromo-phenyl)-3-phenyl-acrylamide

2-Bromoaniline (48.41 g, 281.4 mMol) was dissolved in 500 mL of anhydrous DCM under an atmosphere of dry N$_2$. Pyridine (45.5 mL, 563 mMol) was then added and the reaction was subsequently cooled to 0° C. after which time cinnamyl chloride (46.9 g, 281.4 mMol) was added. The reaction mixture was slowly warmed up to ambient temperature and then stirred overnight at ambient temperature. The reaction was diluted with 300 mL of saturated aqueous NaHCO$_3$ and then extracted with DCM. The DCM layer was then washed three times with 10% aqueous NaHSO$_4$ followed by saturated aqueous NaHCO$_3$ and finally brine. The DCM layer was then dried over Na$_2$SO$_4$, filtered and concentrated under vacuum to give 85.08 g of a tan solid as the title compound 61A.

Example 61B

8-Bromo-quinolin-2-ol

N-(2-Bromo-phenyl)-3-phenyl-acrylamide 61A (85.0 g, 281.3 mMol) was dissolved in 500 mL of chlorobenzene under an atmosphere of dry N$_2$. Aluminum trichloride (187.5 g, 1.40 mMol) was then added to the solution and the reaction mixture was subsequently heated to 90° C. for 3 hours after which time the temperature was raised to 120° C. After stirring for 1 hour at 120° C. for 1 hour, an additional 40 g of aluminum trichloride was added and the reaction mixture was stirred for an additional hour. The reaction mixture was then cooled to ambient temperature and then slowly poured into absolution of 2 L of ice water and 1 L of DCM. The DCM layer was washed with brine, dried over Na$_2$SO$_4$, filtered and concentrated under vacuum to give a volume ~100 mL. The pink precipitate was collected and washed with hexanes and then dried to give 44.1 g of the title compound 61B.

Example 61C

Trifluoro-methanesulfonic acid 8-bromo-quinolin-2-yl ester

8-Bromo-quinolin-2-ol 61B (24.4 g, 109 mMol) and 2,6-dimethylpyridine (19 mL, 163 mMol) were dissolved in 500 mL of anhydrous DCM under an atmosphere of dry N$_2$. The reaction mixture was then cooled to 0° C. and trifluoromethanesulfonic anhydride (22.0 mL, 131 mMol) was added to the solution dropwise. After the addition was complete, the reaction was warmed to ambient temperature and stirred for 1 hour. The reaction mixture was then quenched with water and partitioned between DCM and aqueous NaHCO$_3$. The DCM layer was then washed four times with 10% aqueous citric acid, twice with aqueous NaHCO$_3$ and once with brine. The DCM layer was then dried over Na$_2$SO$_4$, filtered and concentrated under vacuum to give the title compound 61C.

Example 61D (8-Bromo-quinolin-2-yl)-[4-(2-methoxy-ethoxy)-2-nitro-phenyl]-amine

Trifluoro-methanesulfonic acid 8-bromo-quinolin-2-yl ester 61C (40.8 g, 114 mMol) and 5-(2-methoxy-ethoxy)-2-nitro-phenylamine 42A (25.2 g, 119 mMol) were dissolved in 300 mL of toluene under an atmosphere of dry N$_2$. To this solution was added (49.3 g, 151 mMol) Cs$_2$CO$_3$, (3.91 g, 6.50 mMol) racemic-2,2'-bis(diphenylposphino)-1, 1'-binapthyl (BINAP) and (1.98 g, 2.16 mMol) tris(dibenzylideneacetone)dipalladium (0) and the reaction mixture was heated to 80° C. and reacted overnight at this temperature. The mixture was then cooled to ambient temperature, concentrated under vacuum, treated with DCM, filtered and concentrated under vacuum to give a red solid. The solid was triturated with EtOAc and dried under vacuum to give 22.0 g of the title compound 61 D.

Example 61E

N¹-(8-Bromo-quinolin-2-yl)-4-(2-methoxy-ethoxy)-benzene-1,2-diamine (8-Bromo-quinolin-2-yl)-[4-(2-methoxy-ethoxy)-2-nitrophenyl]-amine 61D (22.0 g, 52.6 mMol) was suspended in a solution of 500 mL of EtOH and 100 mL of water under an atmosphere of dry $N_2$. To this heterogeneous solution were added ammonium chloride (1.75 g, 63.1 mMol) and iron powder (23.5 g, 421 mMol). The reaction mixture was then heated to 100° C. and reacted at this temperature for 6 hours. The reaction mixture was then cooled to ambient temperature, filtered and the filtrate was concentrated under vacuum. The resulting slurry was partitioned between DCM and water. The DCM layer was then washed two more times with water and once with brine. The DCM layer was then dried over $Na_2SO_4$, filtered and concentrated under vacuum to give 20.5 g of the title compound 61 E. This material was used without further purification.

Example 61F

8-Bromo-2-[5-(2-methoxy-ethoxy)-benzoimidazol-1-yl]-quinoline

N¹-(8-Bromo-quinolin-2-yl)-4-(2-methoxy-ethoxy)-benzene-1,2-diamine 61E (20.5 g, 52.7 mMol) and formamidine acetate (6.03 g, 58.0 mMol) were dissolved in 150 mL of 2-methoxyethanol under an atmosphere of dry $N_2$. The reaction mixture was heated to reflux and stirred overnight. The reaction mixture was then cooled to ambient temperature that caused the product to precipitate. The pink solid was collected via suction filtration, washed with 2-methoxyethanol and then dried under vacuum to give 16.1 g of the title compound 61F. The filtrate was concentrated under vacuum and the resulting residue was chromatographed on flash silica gel eluting with a gradient of DCM to MeOH/DCM (199) to give an additional 4.40 g of the title compound 61F.

Example 61

4-{2-[5-(2-Methoxy-ethoxy)-benzoimidazol-1-yl]-quinolin-8-yl)-phenol

8-Bromo-2-[5-(2-methoxy-ethoxy)-benzoimidazol-1-yl]-quinoline 61F (585 mg, 1.47 mMol), was dissolved in 10 mL of dioxane under an atmosphere of dry $N_2$. To this solution were added 4-hydroxyphenyl boronic acid (240 mg, 1.74 mMol), potassium phosphate (620 mg, 2.92 mMol) and tetrakis(triphenylphosphine)palladium (0) (85 mg, 0.074 mMol). The reaction mixture was heated to 105° C. and reacted at this temperature for 48 hours. The reaction mixture was then cooled to ambient temperature, concentrated under vacuum and partitioned between DCM and aqueous saturated $NaHCO_3$. The DCM layer was then washed with brine, dried over $Na_2SO_4$, filtered and concentrated under vacuum to give a yellow residue. The residue was chromatographed on flash silica gel eluting with MeOH/DCM/$NH_4OH$ (297.90.1) to give 365 mg of a white foam as the title compound 61.

C.I. m/z 412 [M+1]; ¹H NMR (CDCl₃) δ 8.64 (s, 1H), 8.21 (d, J=8.7 Hz, 1H), 7.93 (d, J=9.1 Hz, 1H), 7.68 (d, J=7.9 Hz, 2H), 7.56 (d, J=9.1 Hz, 1H), 7.49 (m, 3H), 7.20 (d, J=2.5 Hz, 1H), 7.07 (d, J=7.9 Hz, 2H), 6.90 (m, 1H), 4.02 (m, 2H), 3.65 (m, 2H), 3.37 (s, 3H).

Example 62

[2-(4-2-[5-(2-Methoxy-ethoxy)-benzoimidazol-1-yl]-quinolin-8-yl}-phenoxy)-ethyl]-dimethylamine

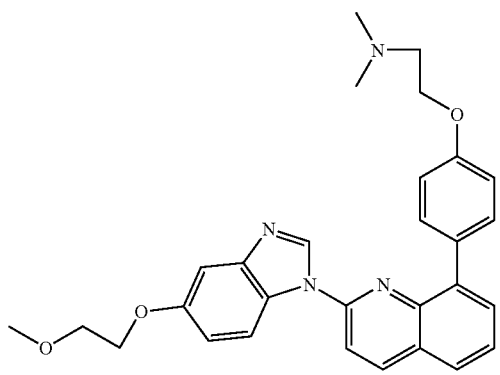

4-{2-[5-(2-Methoxy-ethoxy)-benzoimidazol-1-yl]-quinolin-8-yl}-phenol 61 (160 mg, 0.243 mMol) was dissolved in 600 μL of anhydrous DMF under an atmosphere of dry $N_2$. $Cs_2CO_3$ (237 mg, 0.729 mMol) and (2-chloro-ethyl)dimethyl-amine hydrochloride (39 mg, 267 mMol) were added to the reaction mixture. The reaction was heated to 80° C. and reacted at this temperature for 3 hours. The reaction mixture was partitioned between DCM and 0.1 N aqueous NaOH. The DCM layer was washed two more times with 0.1 N aqueous NaOH, dried over $Na_2SO_4$, filtered and concentrated under vacuum to give 125 mg of a brown oil. The oil was dissolved into 1 mL of DCM to which was added a 3.0 mL of a solution of 1 N hydrochloric acid (HCl) in ethyl ether. The precipitate was collected, washed with ether, dissolved in methanol and finally concentrated under vacuum to give 92 mg of the bishydrochloride salt of the title compound 62 as a tan solid.

C.I. m/z 483 [M+1]; ¹H NMR (CD₃OD) δ 10.2 (s, 1H), 8.73 (d, J=9.1 Hz, 1H), 8.21 (d, J=9.1 Hz, 1H), 8.17 (d, J=8.7 Hz, 1H), 8.07 (d, J=8.3 Hz, 1H), 7.88 (d, J=6.2 Hz, 1H), 7.78 (m, 1H), 7.64 (d, J=8.7 Hz, 2H), 7.34 (d, J=2.1 Hz, 1H), 7.21 (d, J=8.3 Hz, 2H), 7.01 (m, 1H), 4.46 (m, 2, H), 4.22 (m, 2H), 3.80 (m, 2H), 3.69 (m, 2H), 3.44 (s, 3H), 3.04 (s, 6H).

Example 63

2-[5-(2-Methoxy-ethoxy)-benzoimidazol-1-yl]-8-piperazin-1-yl]-8-quinoline

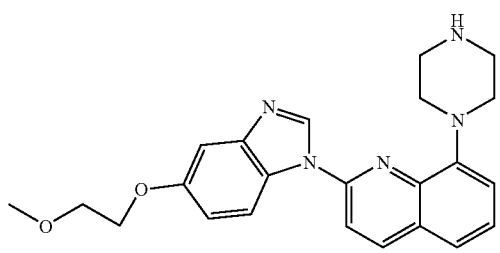

The same procedure that was used in example 1 was followed except that 8-bromo-2-[5-(2-methoxy-ethoxy)-benzoimidazol-1-yl]-quinoline 61F was used in the place of trifluoromethane sulfonic acid 2-(5-methoxy-benzoimidazol-1-yl)-quinolin-8-yl ester 1E and t-butyl-1-piperazine-carboxylate in the place of piperidin-4-yl-carbamic acid tert-butyl ester in example 1F to give the title compound 63 as a tan solid.

C.I. m/z 404 [M+1]; $^1$H NMR (CDCl$_3$) δ 8.62 (s, 1H), 8.41 (d, J=9.1 Hz, 1H), 8.30 (d, J=8.7 Hz, 1H), 7.67 (d, J=9.1Hz, 1H), 7.48 (m, 2H), 7.34 (d, J=2.1 Hz, 1H), 7.23 (m, 1H), 7.13 (dd, J=2.5, 9.1 Hz, 1H), 4.22 (m, 2H), 3.80 (m, 2H), 3.46 (s, 3H), 3.42 (m, 4H), 3.25 (m, 4H).

Example 64

[2-(4-{2-[5-(2-Methoxy-ethoxy)-benzoimidazol-1-yl]-quinolin-8-yl}-piperazin-1-yl)-ethyl]dimethyl-amine

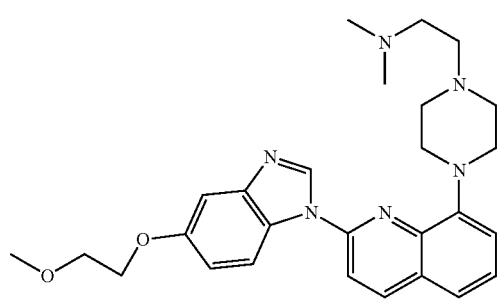

2-[5-(2-Methoxy-ethoxy)-benzoimidazol-1-yl]-8-piperazin-1-yl-quinoline 63 (100 mg, 0.248 mMol), 2-dimethylamino ethyl chloride hydrochloride (53 mg, 0.37 mMol) and N,N-diisopropylethylamine (130 μL, 0.743 mMol) were dissolved in 1 mL of ACN under an atmosphere of dry N$_2$. The reaction mixture was heated to 82° C. and reacted at this temperature overnight. The reaction mixture was then concentrated under vacuum and then partitioned between DCM and 1 N aqueous NaOH. The DCM layer was then washed again with 1 N aqueous NaOH, dried over Na$_2$SO$_4$, filtered and concentrated under vacuum to give a tan residue. The residue was chromatographed on flash silica gel eluting first with MeOH/DCM (595) to remove less polar impurities and then with MeOH/DCM/NH$_4$OH (891.90.1) to give the title compound 64.

C.I. m/z 475 [M+1]; $^1$H NMR (CDCl$_3$) δ 8.63 (s, 1H), 8.44 (d, J=8.7, 1H), 8.27 (d, J=8.7 Hz, 1H), 7.66 (d, J=8.7 Hz, 1H), 7.45 (m, 2H), 7.33 (d, J=2.5 Hz, 1H), 7.22 (m, 1H), 7.12 (m, 1H), 4.22 (m, 2H), 3.81 (m, 2H), 3.47 (s, 3H), 3.46 (m, 4H), 2.83 (m, 4H), 2.63 (m, 2H), 2.52 (m, 2H) 2.30 (s, 6H).

Example 65

2-[5-(2-Methoxy-ethoxy)-benzoimidazol-1-yl]-8-(4-pyridin-2-ylmethyl-piperazin-1-yl)-quinoline

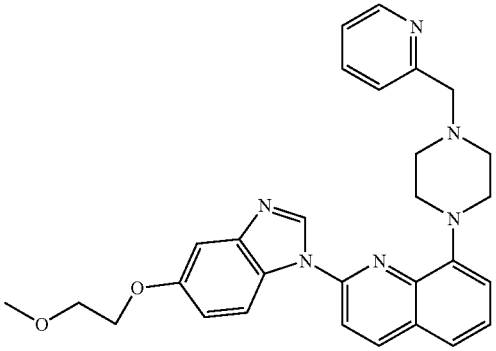

The same procedure that was used in example 64 was used except that 2-picolyl chloride hydrochloride was used in the place of 2-dimethylamino ethyl chloride hydrochloride to give the title compound 65 as a yellow solid.

C.I. m/z 495 [M+1]; $^1$H NMR (CDCl$_3$) δ 8.62 (s, 1H), 8.413 (d, J=9.1, 1H), 8.28 (d, J=9.1 Hz, 1H), 7.68 (m, 2H), 7.48 (m, 3H), 7.33 (d, J=2.1 Hz, 1H), 7.23 (m, 2H), 7.10 (m, 1H), 4.22 (m, 2H), 3.82 (m, 4H), 3.49 (s, 3H), 3.47–3.49 (m, 4H), 2.92 (m, 4H).

Example 66

2-[5-(2-Methoxy-ethoxy)-benzoimidazol-1-yl]-8-(4-pyridin-3-ylmethyl-piperazin-1-yl)-quinoline

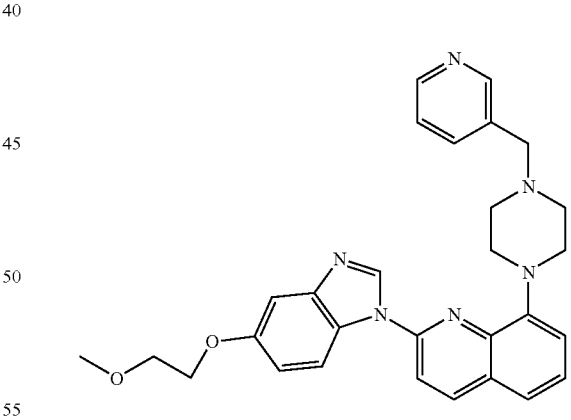

The same procedure that was used in example 64 was used except that 3-picolyl chloride hydrochloride was used in the place of 2-dimethylamino ethyl chloride hydrochloride to give the title compound 66 as a yellow solid.

C.I. m/z 495 [M+1]; 1H NMR (CDCl$_3$) δ 8.63 (m, 2H), 8.52 (dd, J=2.6, 5.0 Hz, 1H), 8.43 (d, J=9.1, 1H), 8.27 (d, J=8.7 Hz, 1H), 7.75 (brd, J=7.5 Hz, 1H), 7.66 (d, J=9.1 Hz, 1H), 7.46 (m, 2H), 7.33 (d, J=2.1 Hz, 1H), 7.27 (m, 1H), 7.22 (m, 1H), 7.10 (m, 1H), 4.23 (m, 2H), 3.82 (m, 2H), 3.67 (s, 2H) 3.48 (s, 3H), 3.47 (m, 4H), 2.82 (m, 4H).

Example 67

2-Amino-1-(4-{2-[5-(2-methoxy-ethoxy]benzoimidazol-1-yl]-quinolin-8-yl}-piperazin-1-yl)-2-methyl-propan-1-one

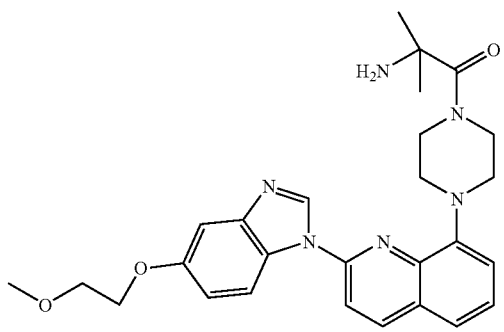

The same procedure used in example 54 was followed except that 2-[5-(2-methoxy-ethoxy)-benzoimidazol-1-yl]-8-piperazin-1-yl-quinoline 63 was used in the place of 1-{2-[5-(2-methoxy-ethoxy)-benzoimidazol-1-yl]-quinolin-8-yl}-piperidin-4-ylamine 33 and N-t-boc-α-methylalanine was used in the place of N-(tert-butoxycarbonyl)glycine to give the title compound 67.

$^1$H NMR (CDCl$_3$) δ 8.62 (s, 1H), 8.42 (d, J=8.7 Hz, 1H), 8.31 (d, J=8.7 Hz, 1H), 7.68 (d, J=8.7 Hz, 1H), 7.46 (m, 2H), 7.34 (d, J=2.5 Hz, 1H), 7.21 (dd, J=2.2, 7.5 Hz, 1H), 7.11 (dd, J=2.5, 8.7 Hz, 1H), 4.22 (m, 2H), 4.17 (m, 4H), 3.81 (m, 2H), 3.47 (s, 3H), 3.39 (m, 4H), 2.13 (brs, 2H), 1.49 (s, 6H).

Example 68

(S)-2-Amino-1-(4-{2-[5-(2-methoxy-ethoxy)-benzoimidazol-1-yl]-quinolin-8-yl}-piperazin-1-yl)propan-1-one

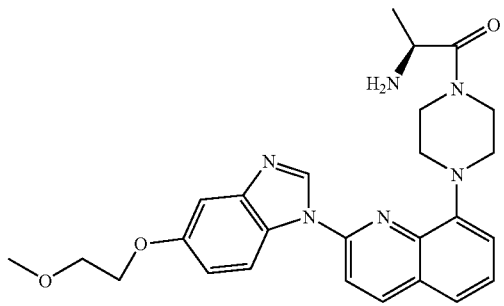

The same procedure used in example 54 was followed except that 2-[5-(2-methoxy-ethoxy)benzoimidazol-1-yl]-8-piperazin-1-yl-quinoline 63 was used in the place of 1-(2-[5-(2-methoxyethoxy)-benzoimidazol-1-yl]-quinolin-8-yl}-piperidin-4-ylamine 33 and N-(tert-butoxycarbonyl) L-alanine was used in the place of N-(tert-butoxycarbonyl)glycine to give the title compound 68 as a yellow solid.

$^1$H NMR (CDCl$_3$) δ 8.60 (s, 1H), 8.40 (d, J=8.7 Hz, 1H), 8.30 (d, J=9.1 Hz, 1H), 7.67 (d, J=8.7 Hz, 1H), 7.46 (m, 2H), 7.33 (d, J=2.5 Hz, 1H), 7.19 (dd, J=2.3, 7.5 Hz, 1H), 7.10 (m, 1H), 4.20 (m, 2H), 3.96 (m, 2H), 3.88 (m, 1H), 3.79 (m, 4H), 3.46 (s, 3H), 3.38 (m, 4H), 2.11 (brs, 2H), 1.30 (d, J=7.0 Hz, 3H).

Example 69

(S)-2-Amino-1-(4-{2-[5-(2-methoxy-ethoxy)-benzoimidazol-1-yl]-quinolin-8-yl}-piperazin-1-yl)propan-1-one

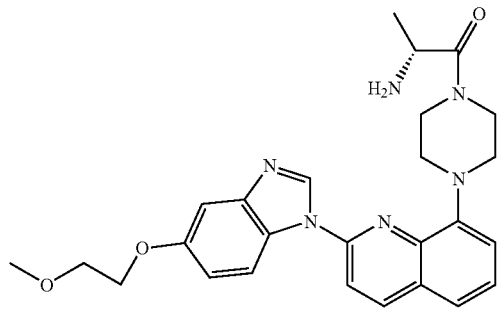

The same procedure used in example 54 was followed except that 2-[5-(2-methoxy-ethoxy)-benzoimidazol-1-yl]-8-piperazin-1-yl-quinoline 63 was used in the place of 1-2-[5-(2-methoxy-ethoxy)-benzoimidazol-1-yl]-quinolin-8-yl}-piperidin-4-ylamine 33 and N-(tert-butoxycarbonyl)-D-alanine was used in the place of N-(tert-butoxycarbonyl) glycine to give the title compound 69 as a yellow solid.

$^1$H NMR (CDCl$_3$) δ8.60 (s, 1H), 8.40 (d, J=9.1 Hz, 1H), 8.30 (d, J=8.7 Hz, 1H), 7.66 (d, J=8.7 Hz, 1H), 7.46 (m, 2H), 7.33 (m, 1H), 7.18 (m, 1H), 7.11 (m, 1H), 4.20 (m, 2H), 3.96 (m, 2H), 3.88 (m, 1H), 3.79 (m, 4H), 3.46 (s, 3H), 3.36 (m, 4H), 2.10 (brs, 2H), 1.29 (d, J=6.2 Hz, 3H).

Example 70

2-Amino-1-(4-(2-[5-(2-methoxy-ethoxy)-benzoimidazol-1-yl]-quinolin-8-yl}-piperazin-1-yl]ethanone

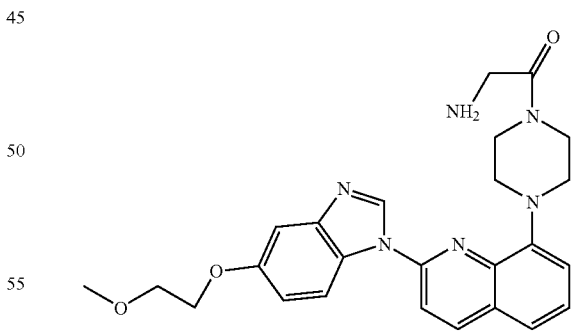

The same procedure used in example 54 was followed except that 2-[5-(2-methoxy-ethoxy]benzoimidazol-1-yl]-8-piperazin-1-yl-quinoline 63 was used in the place of 1-(2-[5-(2-methoxyethoxy)-benzoimidazol-1-yl]-quinolin-8-yl}-piperidin-4-ylamine 33 to give the title compound 70.

$^1$H NMR (CDCl$_3$) δ8.59 (s, 1H), 8.40 (d, J=8.7 Hz, 1H), 8.29 (d, J=8.7 Hz, 1H), 7.66 (d, J=8.7 Hz, 1H), 7.51 (dd, J=2.2, 7.9, 1H), 7.45 (m, 1H), 7.33 (d, J=2.5 Hz, 1H), 7.18 (dd, J= 2.2, 7.5 Hz, 1H), 7.09 (d, J=2.5, 8.7 Hz, 1H), 4.19

(m, 2H), 3.96 (m, 2H), 3.79 (m, 2H), 3.68 (m, 2H), 3.54 (m, 2H), 3.46 (s, 3H), 3.39 (m, 2H), 3.33 (m, 2H), 2.05 (brs, 2H).

Example 71

(1-Amino-cyclopropyl)-(4-(2-[5-(2-methoxy-ethoxy)-benzoimidazol-1-yl]-quinolin-8-yl}piperazin-1-yl)-methanone

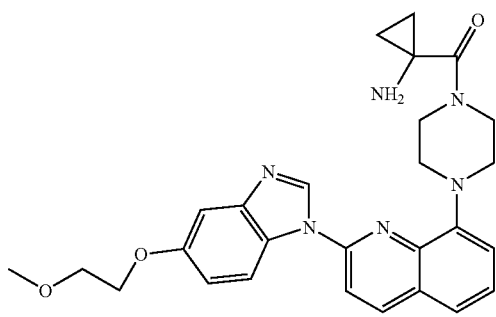

The same procedure used in example 54 was followed except that 2-[5-(2-methoxy-ethoxy)benzoimidazol-1-yl]-8-piperazin-1-yl-quinoline 63 was used in the place of 1-(2-[5-(2-methoxyethoxy)-benzoimidazol-1-yl]-quinolin-8-yl}piperidin-4-ylamine 33 and 1-tert-butoxycarbonylamino-cyclopropanecarboxylic acid was used in the place of N-(tert-butoxycarbonyl)glycine to give the title compound 71.

C.I. m/z 487 [M+1]; $^1$H NMR (CDCl$_3$) δ 8.62 (s, 1H), 8.40 (d, J=9.1 Hz, 1H), 8.31 (d, J=, 8.7 Hz, 1H), 7.68 (d, J=8.7 Hz, 1H), 7.52 (dd, J=2.2, 7.9, 1H), 7.45 (m, 1H), 7.34 (d, J=2.1 Hz, 1H), 7.20 (dd, J=2.2, 7.5 Hz, 1H), 7.10 (m, 1H), 4.20 (m, 2H), 4.00 (m, 4H), 3.79 (m, 2H), 3.46 (s, 3H), 3.39 (m, 4H), 2.02 (brs, 2H), 1.04 (m, 2H), 0.84 (m, 2H).

Example 72

2-(4-{2-[5-(2-Methoxy-ethoxy)-benzoimidazol-1-yl]-quinolin-8-yl}-piperazin-1-yl)-ethylamine

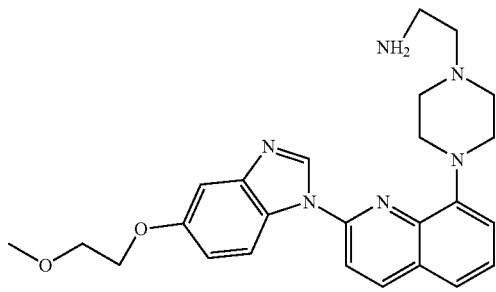

2-[5-(2-methoxy-ethoxy)-benzoimidazol-1-yl]-8-piperazin-1-yl-quinoline 63 (100 mg, 0.248 mMol), and t-butyl-N-(2-oxoethyl)-carbamate (39.5 mg, 0.248 mMol) were dissolved in 1 mL of methanol under an atmosphere of dry N$_2$. To this solution was added 200 µL of AcOH followed by NaCNBH$_3$ (19 mg, 0.297 mMol) and the reaction mixtur was then stirred at ambient temperature overnight. The reaction mixture was then concentrated under vacuum and the resulting residue was partitioned between DCM and 1 N aqueous NaOH. The DCM layer was then successively washed with 1 N aqueous NaOH and brine, dried over Na$_2$SO$_4$, filtered and concentrated under vacuum to give a yellowish-green film. The film was then dissolved in a solution of 1 mL of DCM and 2 mL of TFA under an atmosphere of dry N$_2$. The reaction mixture was stirred at ambient temperature for 30 minutes after which time it was concentrated under the vacuum. The resulting residue was partitioned between 0.1 N aqueous NaOH. The DCM layer was dried over Na$_2$SO$_4$, filtered and concentrated under vacuum to give a green film. The film was chromatographed on flash silica gel eluting with MeOH/DCM (595) to remove the less polar impurities and then MeOH/DCM/NH$_4$OH (594.90.1) to give 71 mg of the title compound 72.

C.I. m/z 447 [M+1]; $^1$H NMR (CDCl$_3$) δ 8.63 (s, 1H), 8.45 (d, J=9.1 Hz, 1H), 8.27 (d, J=8.7 Hz, 1H), 7.66 (d, J=8.7 Hz, 1H), 7.46 (m, 2H), 7.33 (d, J=2.5 Hz, 1H), 7.22 (m, 1H), 7.11 (dd, J=2.5 Hz, 8.7 Hz, 1H), 4.20 (m, 2H), 3.80 (m, 2H), 3.47 (s, 3H), 3.43 (m, 4H), 2.89 (t, J=5.8 Hz, 2H), 2.80 (m, 4H), 2.59 (t, J=5.8 Hz, 2H), 2.17 (brs, 2H).

Example 73

(R)-2-Amino-3-(4-{2-[5-(2-methoxy-ethoxy)-benzoimidazol-1-yl]-quinolin-8-yl}-piperazin-1-yl)propan-1-ol

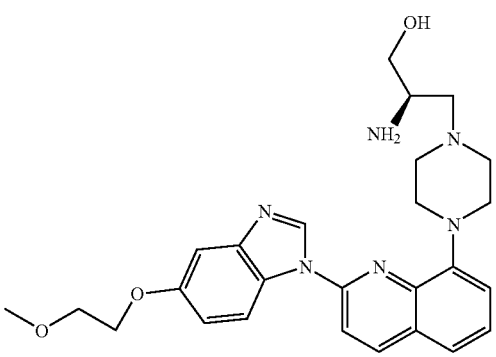

The same procedure that was used in example 72 was followed except that t-butyl-(S)-(−)-4-formyl-2,2-dimethyl-3-oxazolidinecarboxylate was used in the place of t-butyl-N-(2-oxoethyl)carbamate to give the title compound 73.

C.I. m/z 477 [M+1]; $^1$H NMR (CDCl$_3$) δ 8.61 (s, 1H), 8.43 (d, J=9.1 Hz, 1H), 8.27 (d, J=8.7 Hz, 1H), 7.64 (d, J=8.7 Hz, 1H), 7.45 (m, 2H), 7.32 (d, J=2.1 Hz, 1H), 7.20 (dd, J=2.6, 7.1 Hz, 1H), 7.10 (dd, J=2.5 Hz, 9.1 Hz, 1H), 4.20 (m, 2H), 3.80 (m, 2H), 3.66 (m, 2H), 3.46 (s, 3H), 3.45 (m, 4H), 3.25 (m, 1H), 2.82 (m, 4H), 2.65 (m, 1H), 2.50 (m, 3H).

Example 74

3-{2-[5-(2-Methoxy-ethoxy)-benzoimidazol-1-yl]-quinolin-8-yl}-3-aza-bicyclo[3.1.0]hex-6-ylamine

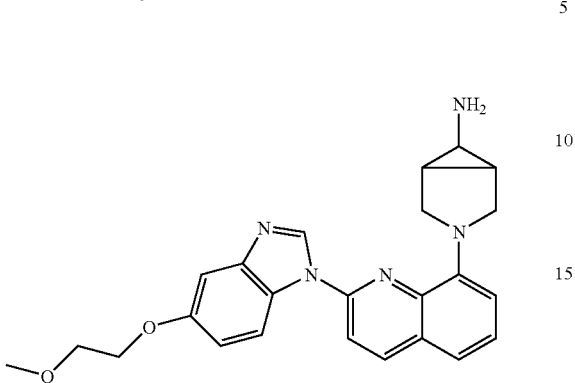

The same procedure that was used in example 33 was followed except that (3-aza-bicyclo[3.1.0]hex-6-yl]carbamic acid tert-butyl ester was used in the place of piperidin-4-yl-carbamic acid tert-butyl ester in example 1F to give the title compound 74 as a yellow solid.

$^1$H NMR (CDCl$_3$) δ 8.59 (s, 1H), 8.22 (d, J=8.7 Hz, 1H), 7.99 (d, J=9.1 Hz, 1H), 7.59 (d, J=8.7 Hz, 1H), 7.37 (m, 2H), 7.35 (d, J=2.5 Hz, 1H), 7.09 (dd, J=2.5, 9.1 Hz, 1H), 6.83 (d, J=7.9 Hz, 1H), 4.34 (d, J=9.6 Hz, 2H), 4.20 (m, 2H), 3.80 (m, 2H), 3.46 (s, 3H), 3.42 (d, J=9.6 Hz, 2H), 2.93 (brs, 2H), 2.65 (s, 1H), 1.73 (s, 0.2H).

Example 75

(S)-1-{2-[5-(2-Methoxy-ethoxy)-benzoimidazol-1-yl]-quinolin-8-yl)-pyrrolidin-3-ylamine

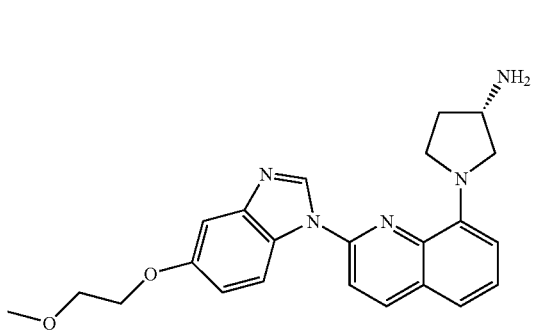

The same procedure that was used in example 33 was followed except that (3S)-(−)-3-(tert-butoxycarbonyl-amino)pyrrolidine was used in the place of piperidin-4-yl-carbamic acid tert-butyl ester in example 1F to give the title compound 75 as a tan solid.

$^1$H NMR (CD$_3$OD) δ 8.75 (d, J=1.7 Hz, 1H), 8.30 (d, J=8.7 Hz, 1H), 8.00 (d, J=9.1 Hz, 1H), 7.70 (dd, J=2.1, 8.7 Hz, 1H), 7.38 (t, J=7.9 Hz, 1H), 1.24 (m, 2H), 7.04 (dd, J=2.6, 9.1 Hz, 1H), 6.90 (d, J=7.9 Hz, 1H), 4.16 (m, 2H), 3.90 (m, 1H), 3.82 (m, 1H), 3.77 (m, 2H), 3.66 (m, 1H), 3.60 (m, 1H), 3.48 (m, 1H), 3.43 (s, 3H), 2.21 (m, 1H), 1.80 (m, 1H).

Example 76

(R)-1-{2-[5-(2-Methoxy-ethoxy)-benzoimidazol-1-yl]-quinolin-8-yl)-pyrrolidin-3-ylamine

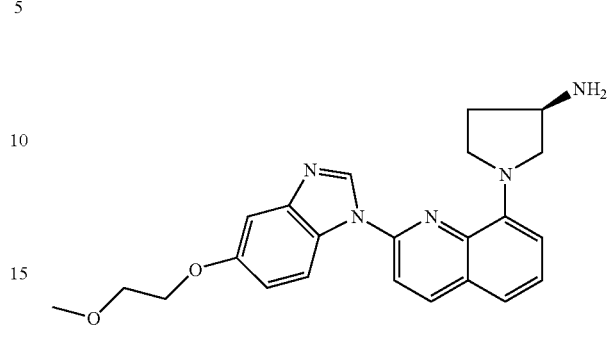

The same procedure that was used in example 33 was followed except that (3R)-(−)-3-(tert-butoxycarbonyl-amino)pyrrolidine was used in the place of piperidin-4-yl-carbamic acid tert-butyl ester in example 1F to give the title compound 76 as a tan solid.

$^1$H NMR (CD$_3$OD) δ 8.80 (s, 1H), 8.35 (d, J=8.7 Hz, 1H), 8.05 (d, J=8.7 Hz, 1H), 7.76 (d, J=8.7 Hz, 1H), 7.41 (t, J=7.9 Hz, 1H), 7.28 (m, 2H), 7.09 (dd, J=2.5, 9.1 Hz, 1H), 6.93 (d, J=7.5 Hz, 1H), 4.18 (m, 2H), 3.91 (m, 1H), 3.84 (m, 1H), 3.78 (m, 2H), 3.66 (m, 1H), 3.62 (m, 1H), 3.48 (m, 1H), 3.44 (s, 3H), 2.23 (m, 1H), 1.82 (m, 1H).

Example 77

2-[5-(2-Methoxy-ethoxy)-benzoimidazol-1-yl]-8-pyridin-3-yl)-quinoline

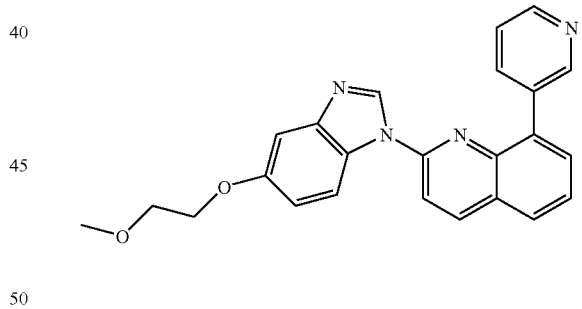

Example 77A

8-Benzyloxy-quinolin-2-ol 2,8-Quinolinediol (133.3 g, 0.827 Mol) was dissolved in 800 mL of anhydrous DMF under an atmosphere of dry N$_2$. To this solution was added potassium carbonate (183 g, 1.32 Mol) followed by benzyl bromide (110 mL, 0.909 Mol) and the solution was then warmed up to 65° C. and reacted at this temperature overnight. The reaction mixture was then poured into 9 L of water and the resulting solution was stirred at ambient temperature for 5.5 hours after which time it was filtered. The solid was washed with water, collected and suspended in toluene and finally the solution was concentrated under vacuum to give 142 g of the title compound 77A.

Example 77B

8-Benzyloxy-2-chloro-quinoline

8-Benzyloxy-quinolin-2-ol 77A (142 g, 0.565 Mol) was dissolved in 500 mL of DCE under an atmosphere of dry $N_2$. Oxalyl chloride (99 mL, 1.13 Mol) was added dropwise to this solution followed by 1 mL of DMF. After the addition was complete, the reaction was stirred at ambient temperature for 30 minutes after which time the reaction was warmed to 84° C. The reaction mixture was stirred at this temperature for 10 hours and then concentrated under vacuum. The resulting residue was partitioned between DCM and aqueous saturated $NaHCO_3$. The DCM layer was washed again with aqueous saturated $NaHCO_3$, dried over $Na_2SO_4$, filtered and concentrated under vacuum to give a brown solid. The solid was recrystallised from toluene to give two crops of (68.3 g and 38.3 g) of the title compound 77B.

Example 77C

(8-Benzyloxy-quinolin-2-yl)[4-(2-methoxy-ethoxy)-2-nitro-phenyl]-amine

8-Benzyloxy-2-chloro-quinoline 77B (25.53 g, 94.64 mMol) was added to 350 mL of anhydrous toluene under an atmosphere of dry $N_2$. To this solution was added 5-(2-methoxyethoxy)-2-nitro-phenylamine 42A (20.08 g, 94.64 mMol), palladium acetate (433 mg, 1.89 mMol), $Cs_2CO_3$ (43.2 g, 132 mMol), phenyl boronic acid (584 mg, 4.79 mMol) and 1,2-bis(diphenylphosphino)-ethane (2.33 g, 5.68 mMol) and the mixture was then deoxygenated by bubbling argon through for ten minutes. The reaction mixture was then heated to 95° C. and reacted at this temperature for two hours. Then the reaction was diluted (while still hot) with 350 mL of DCE and then filtered while still hot. The filter cake was washed with 100 mL of hot DCE. The filtrate was concentrated to ~175 mL during which time a large amount of precipitate formed. To this mixture was added 400 mL of EtOH and the reaction mixture was stirred overnight. The resulting red precipitate was collected via suction filtration and dried under vacuum to give 36.8 g of the title compound as a red solid 77C.

Example 77D

2-[5-(2-Methoxy-ethoxy)-benzoimidazol-1-yl]-quinolin-8-ol (8-Benzyloxy-quinolin-2-yl)-[4-(2-methoxy-ethoxy)-2-nitro-phenyl]-amine 77C (36.8 g, 85.4 mMol) was suspended in 275 mL of EtOH under an atmosphere of dry $N_2$. The reaction mixture was then cooled to 0° C. after which time 119 mL of triethylamine ($NEt_3$) followed by 34 mL of formic acid (slowly) were added. The ice bath was removed and the reaction mixture was then heated to ~80° C. and reacted at this temperature until the nitro group has been fully reduced to the amine and the benzyl group has been fully removed (as determined by mass sprectral analysis) which, in this case, was ~2 hours. To this mixture is then added formamidine acetate (11.56 g, 111 mMol) and the reaction temperature was increased to reflux. After a couple of hours more formamidine acetate (3.20 g) was added and the reaction mixture was stirred at reflux for an additional 4 hours. The reaction mixture was then cooled to ambient temperature and the filtered through Celite™. The Celite™ was washed with copious amounts of a 1:1 MeOH/DCM solution and the combined filtrates were concentrated under vacuum and the resulting solids were triturated with 200 mL of EtOH. The solution was filtered and the precipitate was dried under vacuum to give 23.03 g of the title compound 77D was a white solid.

Example 77E

Trifluoro-methanesulfonic acid 2-[5-(2-methoxy-ethoxy)-benzoimidazol-1-yl]-quinolin-8-yl ester 2-[5-(2-Methoxy-ethoxy]benzoimidazol-1-yl]-quinolin-8-ol 77D (23.0 g, 68.6 mMol) was dissolved in a solution of 120 mL of anhydrous DMF and 250 mL of THF under an atmosphere of dry $N_2$. To this solution were added N-phenyl-bis(trifluoromethanesulfonimide) (26.95 g, 75.5 mMol) and $NEt_3$ (6.75 mL, 137.2 mMol). The reaction mixture was stirred over night at ambient temperature after which time an additional 2.70 g of N-phenyl-bis(trifluoromethanesulfonimide) and an 700 µL of $NEt_3$ were added. The reaction mixture was stirred an additional 1 hour and then was filtered and the filter cake was washed with ethyl ether. The filter cake was dried under vacuum to give 6.70 g of the title compound 77E as a white solid. A second crop was obtained by concentrating the filtrate to ~75 mL. To this solution was added 200 mL of ethyl ether and the resulting mixture was stirred for 1 hour and then filtered. The filter cake was washed with ethyl ether and then vacuum dried to give an additional 19.91 g of the title compound 77E for a total of 28.61 g.

Example 77F

2-[5-(2-Methoxy-ethoxy)-benzoimidazol-1-yl]-8-pyridin-3-yl-quinoline

Trifluoro-methanesulfonic acid 2-[5-(2-methoxy-ethoxy]benzoimidazol-1-yl]-quinolin-8-yl ester 77E (1.00 g, 2.14 mMol), diethyl(3-pyridyl)-borane (620 mg, 4.36 mMol), lithium chloride (188 mg, 4.36 mMol) and tetrakis(triphenyl phosphine)palladium (0) (248 mg, 0.215 mMol) were dissolved in a solution of 14 mL of toluene, 4 mL of EtOH and 1.5 mL of 2 N aqueous sodium carbonate ($Na_2CO_3$) under an atmosphere of dry $N_2$. The reaction mixture was heated to 90° C. and reacted at this temperature overnight. The reaction mixture was then cooled to ambient temperature, concentrated under vacuum and partitioned between DCM and aqueous saturated $NaHCO_3$. The DCM layer was then washed with brine, dried over $Na_2SO_4$, filtered and concentrated under vacuum. The resulting residue was chromatographed on flash silica gel eluting with a gradient from MeOH/DCM (1/99) to MeOH/DCM (298) to give 460 mg of the title compound 77.

C.I. m/z 397 [M+1]; $^1$H NMR ($CDCl_3$) δ 8.86 (d, J=1.6 Hz, 1H), 8.67 (dd, J=1.3, 4.6 Hz, 1H), 8.56 (s, 1H), 8.35 (d, J=8.7 Hz, 1H), 8.08 (m, 1H), 7.88 (m, 1H), 7.78 (m, 2H), 7.70 (d, J=8.7 Hz, 1H), 7.62 (m, 1H), 7.42 (m, 1H), 7.25 (m, 1H), 6.84 (dd, J=2.5 Hz, 9.1 Hz, 1H), 4.15 (m, 2H), 3.77 (m, 2H), 3.45 (s, 3H).

Example 78

2-[5-(2-Methoxy-ethoxy)-benzoimidazol-1-yl]-8-(6-methoxy-pyridin-3-yl)-quinoline

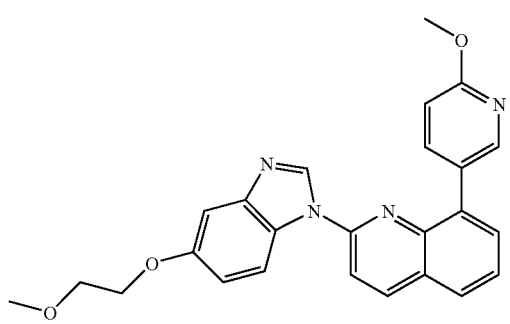

Trifluoro-methanesulfonic acid 2-[5-(2-methoxy-ethoxy)-benzoimidazol-1-yl]-quinolin-8-yl ester 77E (850 mg, 1.82 mMol), 2-methoxy-5-pyridineboronic acid (305 mg, 2.00 mMol), potassium phosphate ($K_2CO_3$) (772 mg, 3.64 mMol) and tetrakis(triphenylphosphine)palladium (0) (208 mg, 0.182 mMol) were dissolved in 5 mL of 1,4-dioxane under an atmosphere of dry $N_2$. The reaction mixture was heated to 100° C. and reacted at this temperature overnight. The reaction mixture was then cooled to ambient temperature, concentrated under vacuum and partitioned between DCM and aqueous saturated $NaHCO_3$. The DCM layer was then washed with brine, dried over $Na_2SO_4$, filtered and concentrated under vacuum. The resulting residue was chromatographed on flash silica gel eluting with a gradient from EtOAc/DCM (2080) to EtOAc/DCM (7525) to give 856 mg of the title compound 78.

C.I. m/z 427 [M+1]; $^1$H NMR (CDCl$_3$) δ 8.63 (s, 1H), 8.39 (d, J=2.1 Hz, 1H), 8.31 (d, J=8.7 Hz, 1H), 7.96 (m, 1H), 7.91 (d, J=9.1 Hz, 1H), 7.80 (dd, J=2.2, 8.3 Hz, 1H), 7.72 (m, 2H), 7.56 (m, 1H), 7.24 (m, 1H), 6.87 (m, 1H), 6.83 (d, J=8.7 Hz, 1H), 4.14 (m, 2H); 4.00 (s, 3H), 3.76 (m, 2H), 3.44 (s, 3H).

Example 79

4-(2-[5-(2-Methoxy-ethoxy)-benzoimidazol-1-yl]-quinolin-8-yl}-benzoic acid methyl ester

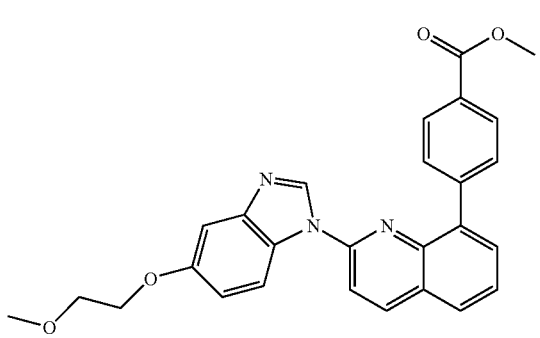

The same procedure that was used in example 78 was followed except that 4-methoxycarbonylphenylboronic acid was used in the place of 2-methoxy-5-pyridineboronic acid to give the title compound 79 as a white solid.

C.I. m/z 454 [M+1]; $^1$H NMR (CDCl$_3$) δ 8.77 (s, 1H), 8.37 (d, J=8.7 Hz, 1H), 8.13 (d, J=8.3 Hz, 2H), 7.91 (d, J=9.1 Hz, 1H), 7.88 (dd, J=2.2, 7.9 Hz, 1H), 7.77 (m, 4H), 7.62 (m, 1H), 7.26 (d, J=2.1 Hz, 1H), 6.82 (dd, J=2.5, 9.1 Hz, 1H), 4.16 (m, 2H), 3.99 (s, 3H), 3.77 (m, 2H), 3.46 (s, 3H).

Example 80

1-{2-[5-(2-Methoxy-ethoxy)-benzoimidazol-1-yl]-quinolin-8-yl}-4-methyl-piperidin-4-ylamine

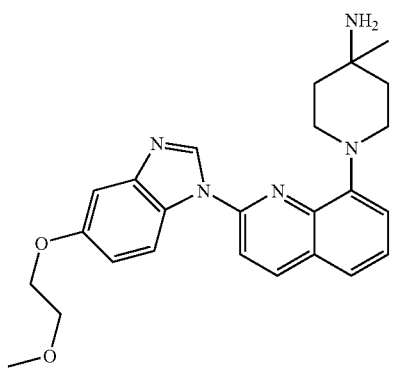

Example 80A

Piperidine-1,4-dicarboxylic acid tert-butyl ester ethyl ester

Piperidine-4-carboxylic acid ethyl ester (9.80 mL, 63.2 mMol) was dissolved in 60 mL of DCM at ambient temperature under an atmosphere of dry $N_2$. Di-tert-butyl dicarbonate (13.77 g, 63.16 mMol) was slowly added to the reaction mixture after which time the reaction mixture was stirred overnight. The reaction mixture was then partitioned between DCM and saturated aqueous $NaHCO_3$. The DCM layer was washed two more times with saturated aqueous $NaHCO_3$, dried over $Na_2SO_4$, filtered and concentrated under vacuum to give 16.13 g of the title compound 80A as an oil.

Example 80B

4-Methyl-piperidine-1,4-dicarboxylic acid tert-butyl ester ethyl ester

Piperidine-1,4-dicarboxylic acid tert-butyl ester ethyl ester 80A (10.9 g, 42.3 mMol) was dissolved in 44 mL anhydrous THF under an atmosphere of dry $N_2$. The solution was then cooled to −40° C. and 85 mL of a solution of 1 M lithium bis(trimethylsilyl)amide in terahydrofuran was slowly added. The reaction mixture was stirred at −40° C. for 1 hour after which time iodomethane (5.3 mL, 85 mMol) was added the solution was allowed to warm up to ambient temperature and after 1 hour was quenched with water. The reaction mixture was partitioned between DCM and aqueous saturated $NaHCO_3$. The DCM layer was washed two more times with aqueous saturated $NaHCO_3$, dried over $Na_2SO_4$, filtered and concentrated under vacuum to give 14.78 g of the title compound 80B as an orange oil. The compound was used without further purification.

Example 80C

4-Methyl-piperidine-1,4-dicarboxylic acid mono-tert-butyl ester

4-Methyl-piperidine-1,4-dicarboxylic acid tert-butyl ester ethyl ester 80B (12.8 g, 47.2 mMol) was dissolved in a solution of 94 mL of EtOH and 47 ml of aqueous 2 N NaOH. The reaction mixture was heated to 60° C. and reacted at this temperature for 6 hours. The reaction mixture was concentrated under vacuum to remove the EtOH. The remaining aqueous solution was washed three times with ethyl ether. The pH was then adjusted to 3 with the careful addition of 1 N HCl. The aqueous layer was then washed 4 times with EtOAc. The EtOAc extracts were combined, dried over $Na_2SO_4$, filtered and concentrated under vacuum to give 9.54 g of the title compound 80C as white solid. The compound was used without further purification.

Example 80D

4-Carbamoyl-4-methyl-piperidine-1-carboxylic acid tert-butyl ester

4-Methyl-piperidine-1,4-dicarboxylic acid mono-tert-butyl ester 80C (9.54 g, 39.2 mMol) was dissolved in 115 mL of anhydrous THF under an atmosphere of dry $N_2$. The reaction mixture was cooled to 0° C. after which time $NEt_3$ (4.50 mL, 47.1 mMol) followed by ethyl chloroformate (7.10 mL, 60.0 mMol) were added. The mixture was warmed to ambient temperature and stirred for 15 minutes after which time it was cooled back down to 0° C. To this mixture, was added 65 mL of $NH_4OH$. The reaction mixture was warmed to ambient temperature and the THF was removed under vacuum. The resulting aqueous solution was washed three times with DCM. The DCM extracts were combined, dried over $Na_2SO_4$, filtered and concentrated under vacuum to give 6.19 g of the title compound 80D as an oil. The compound was used without further purification.

Example 80E

4-Amino-4-methyl-piperidine-1-carboxylic acid tert-butyl ester

4-Carbamoyl-4-methyl-piperidine-1-carboxylic acid tert-butyl ester 80D (6.19 g, 25.6 mMol), [Bis(trifluoroacetoxy) iodo]-benzene (16.5 g, 38.3 mMol) and pyridine (6.20 mL, 76.9 mMol) were dissolved in a solution of 40 mL of ACN and 20 mL of water under an atmosphere of dry $N_2$. The reaction mixture was stirred for 2 hours at ambient temperature after which time it was diluted with aqueous 1 N NaOH. The resulting solution was washed three times with DCM. The DCM extracts were combined, dried over $Na_2SO_4$, filtered and concentrated under vacuum to give an oil. The oil was partitioned between DCM and aqueous HCl (pH~3). The aqueous layer was washed 2 more times with DCM, and then was basified with 2 N aqueous NaOH until the pH~1.0. The basic aqueous layer was washed three times with DCM. The DCM extracts were combined, dried over $Na_2SO_4$, filtered and concentrated under vacuum to give 4.19 g of the title compound 80E as a yellow oil. The compound was used without further purification.

Example 80F

(4-Methyl-piperidin-4-yl)-carbamic acid benzyl ester

4-Amino-4-methyl-piperidine-1-carboxylic acid tert-butyl ester 80E (4.19 g, 19.6 mMol) was dissolved in a solution of 50 mL of dioxane and 20 mL of aqueous 2 N NaOH under an atmosphere of dry $N_2$. To this solution was slowly added benzyl chloroformate (5.6 mL, 39 mMol) and the reaction was stirred for 3 hours at ambient temperature. The reaction mixture was concentrated under vacuum. The reaction mixture was dissolved in DCM and successively washed three with aqueous 1 N NaOH. The DCM layer was dried over $Na_2SO_4$, filtered and concentrated under vacuum to give a yellow oil. The oil was dissolved in 15 mL of TFA under an atmosphere of dry $N_2$. The reaction mixture was concentrated under vacuum and partitioned between DCM and 0.1 N aqueous NaOH. The DCM layer was dried over $Na_2SO_4$, filtered and concentrated under vacuum to give 3.06 g of an oil. The oil was chromatographed on flash silica gel eluting with DCM to remove less polar impurities then with MeOH/DCM/$NH_4OH$ (20179.90.1) to give 2.85 g of the title compound 80F as an oil.

Example 80G

1-{2-[5-(2-Methoxy-ethoxy)-benzoimidazol-1-yl]-quinolin-8-yl}-4-methyl-piperidin-4-ylamine The same procedure that was used in example 1 was followed except that trifluoromethanesulfonic acid 2-[5-(2-methoxy-ethoxy)-benzoimidazol-1-yl]-quinolin-8-yl ester 77E was used in the place of trifluoro-methanesulfonic acid 2-(5-methoxy-benzoimidazol-1-yl)quinolin-8-yl ester 1E and (4-methyl-piperidin-4-yl)-carbamic acid benzyl ester 80F was used in the place of piperidin-4-yl-carbamic acid tert-butyl ester in example 1F to give the title compound 80 as a yellow solid.

C.I. m/z 432 [M+1]; $^1$H NMR ($CD_3OD$) δ 8.80 (s, 1H), 8.49 (d, J=9.1 Hz, 1H), 8.24 (d, J=9.1 Hz, 1H), 7.70 (d, J=8.7 Hz, 1H), 7.44 (m, 2H), 7.24 (dd, J=1.2, 8.7 Hz, 1H), 7.18 (d, J=2.5 Hz, 1H), 7.00 (m, 1H), 4.12 (m, 2H), 3.76 (m, 2H), 3.43 (s, 3H), 3.26 (m, 2H), 3.13 (m, 2H), 1.75 (m, 4H), 1.17 (s, 3H).

Example 81

1-[2-(6,7-Dihydro-5,8-dioxa-1,3-diaza-cyclopenta[b]naphthalen-1-yl)-quinolin-8-yl]-piperidin-4-ylamine

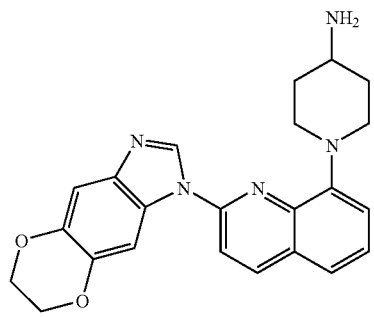

Example 81A

8-Bromo-2-chloro-quinoline

8-Bromo-quinolin-2-ol 61B (44.11 g, 196.7 mMol) was dissolved in 450 mL of DCE under an atmosphere of dry $N_2$. To this solution was added oxalyl chloride (65.3 mL, 749 mMol) dropwise followed by the addition of 400 μL of dimethylformamide. After the addition was complete, the reaction mixture was heated to reflux and reacted for 3 hours. The reaction mixture was concentrated under vacuum. The resulting residue was partitioned between DCM and saturated aqueous $NaHCO_3$, washed again with saturated aqueous $NaHCO_3$, dried over $Na_2SO_4$, filtered and concentrated under vacuum to give 48.40 g of the title compound 81A as an orange solid.

Example 81B

6,7-Dihydro-1H-5,8-dioxa-1,3-diaza-cyclopenta[b]naphthalene 5-6-Ethylenedioxy-2-mercaptobenzimidazole (1.27 g, 6.10 mMol) and 3.5 mL of Raney® nickel (50% slurry in water) were suspended in 30 mL of EtOHI under an atmosphere of dry $N_2$. The reaction mixture was heated to 80° C. and reacted at this temperature for 3 hours. The reaction mixture was then filtered through Celite™ and then the Celite was washed with ethanol and DCM. The filtrates were combined and concentrated under vacuum to give 750 mg of the title compound 81B as a foam.

Example 81C

1-(8-Bromo-quinolin-2-yl)-6,7-dihydro-1H-5,8-dioxa-1,3-diaza-cyclopenta[b]naphthalene 6,7-Dihydro-1H-5,8-dioxa-1,3-diaza-cyclopenta[b]naphthalene 81B (600 mg, 3,4 mMol) was dissolved in 15 mL of 1-methyl-2-pyrrolidinone under an atmosphere of dry $N_2$. To this solution was added 60% sodium hydride in oil (136 mg, 3.40 mMol) and the reaction mixture was stirred for 15 minutes. 8-Bromo-2-chloro-quinoline 81A (750 mg, 3.10 mMol) was then added to the reaction mixture which was subsequently heated to 65° C. and reacted at this temperature overnight. The reaction mixture was then cooled to ambient temperature, partitioned between DCM and saturated aqueous $NaHCO_3$, washed again with saturated aqueous $NaHCO_3$, dried over $Na_2SO_4$, filtered and concentrated under vacuum to give 1.60 g of an orange solid. The solid was chromatographed on flash silica gel eluting with a gradient from DCM to MeOH/DCM (0.5/99.5) to give 700 mg of the title compound 81C as a light yellow solid.

Example 81D

{1-[2-(6,7-Dihydro-5,8-dioxa-1,3-diaza-cyclopenta[b]naphthalen-1-yl)-quinolin-8-yl]-piperidin-4-yl}-carbamic acid tert-butyl ester 1-(8-Bromo-quinolin-2-yl)-6,7-dihydro-1H-5,8-dioxa-1,3-diaza-cyclopenta[b]naphthalene 81C (700 mg, 1.83 mMol) and piperidin-4-yl-carbamic acid tert-butyl ester (733 mg, 3.66 mMol) were dissolved in 6.0 mL of dioxane under an atmosphere of dry $N_2$. To this solution was added $Cs_2CO_3$ (835 mg, 2.56 mMol), racemic-BINAP (68 mg, 0.109 mMol) and tris(dibenzylideneacetone)dipalladium (0) (34 mg, 0.037 mMol) and the reaction mixture was heated to reflux and reacted at this temperature overnight. The mixture was then cooled to ambient temperature, filtered; and concentrated under vacuum to give 1.12 g of an orange film. The film was dissolved in a solution of 5 mL of TFA and 5 mL of DCM under an atmosphere of dry $N_2$. The reaction mixture was stirred at ambient temperature for 30 minutes after which time it was concentrated under vacuum to give a yellow oil. The oil was partitioned between ethyl ether and 0.1 N aqueous HCl. The aqueous layer was then washed with DCM. The aqueous layer was basified to pH~11 with NaOH. The resulting solution was washed three times with DCM. The DCM extracts were combined, dried over $Na_2SO_4$, filtered and concentrated to give 500 mg of a yellow solid. The solid was chromatographed on flash silica gel eluting with MeOH/DCM (1090) to give 127 mg of the title compound 81 as a yellow solid.

C.I. m/z 402 [M+1]; $^1$H NMR ($CD_3OD$) δ 8.63 (s, 1H), 8.19 (s, 1H), 8.08 (d, J=8.7 Hz, 1H), 7.56 (d, J=9.1 Hz, 1H), 7.30 (m, 2H), 7.08 (dd, J=2.1 Hz, 6.7 Hz, 1H), 7.06 (s, 1H), 4.21 (m, 4H), 3.57 (m, 2H), 2.63 (m, 3H), 1.86 (m, 2H), 1.73 (m, 2H).

Example 82

4-Cyclopropylaminomethyl-1-{2-[5-(2-methoxy-ethoxy)-benzoimidazol-1-yl]-quinolin-8-yl}piperidin-4-ol

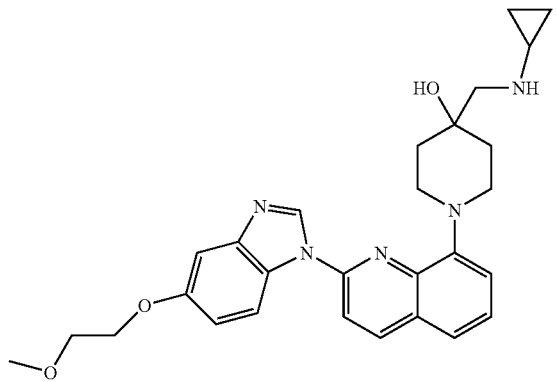

The same procedure that was used in example 24 was followed except that 5-(2-Methoxyethoxy)-2-nitro-phenylamine 42A was used in the place of 4-methoxy-2-nitroaniline in example 1B and cyclopropylamine was used in the place of 2.o M solution of dimethylamine in THF to give the title compound 82 as a yellow foam 82.

C.I. m/z 488 [M+1]; $^1$H NMR ($CDCl_3$) δ 8.63 (s, 1H), 8.33 (d, J=9.1 Hz, 1H), 8.28 (d, J=8.7 Hz, 1H), 7:65 (d, J=8.7 Hz, 1H), 7.44 (m, 2H), 7.33 (d, J=2.1 Hz, 1H), 7.27 (m, 1H), 7.08 (m, 1H), 4.21 (m, 2H), 3.81 (m, 2H), 3.68 (m, 2H), 3.47 (s, 3H), 3.22 (m, 2H), 2.80 (brs, 2H), 2.28 (m, 1H), 1.99 (m, 2H), 1.73 (m, 2H), 0.51 (m, 2H), 0.40 (m, 2H).

Example 83

2-(1-[8-(4-Amino-piperidin-1-yl)-quinolin-2-yl]-1H-benzoimidazol-5-yloxy]ethanol

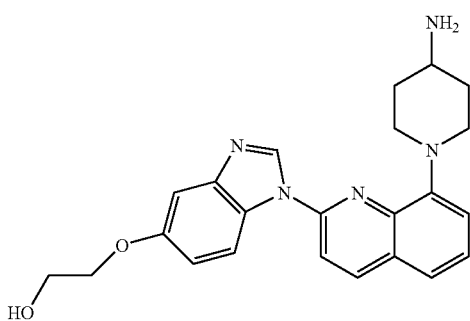

The procedure that was used in example 2 was followed except that 1-{2-[5-(2-methoxyethoxy)-benzoimidazol-1-yl]-quinolin-8-yl}piperidin-4-ylamine 33 was used in the place of 1-[2-(5-methoxy-benzoimidazol-1-yl)-quinolin-8-yl]-piperidin-4-ylamine 1 to give the title compound 83 as a yellow solid.

C.I. m/z 404 [M+1]; $^1$H NMR (CD$_3$OD) δ 8.96 (s, 1H), 8.69 (d, J=8.7 Hz, 1H), 8.42 (d, J=8.7 Hz, 1H), 7.93 (d, J=8.7 Hz, 1H), 7.56 (d, J=6.5 Hz, 1H), 7.48 (t, J=7.9 Hz, 1H), 7.33 (d, J=7.5 Hz, 1H), 7.29 (d, J=2.5 Hz, 1H), 7.22 (m, 1H), 4.14 (m, 2H), 3.92 (m, 2H), 3.85 (m, 2H), 2.83 (m, 3H), 2.00 (m, 2H), 1.83 (m, 2H).

Example 84

1-[8-(4-Amino-piperidin-1-yl)-quinolin-2-yl]-1H-benzoimidazole-5-sulfonic acid dimethylamide

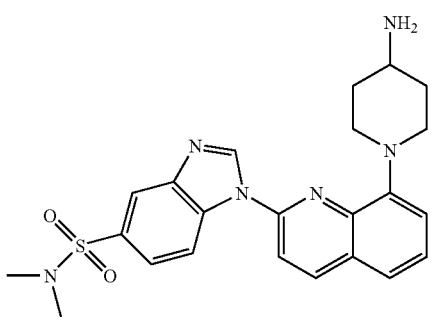

Example 84A

4-Amino-N,N-dimethyl-3-nitro-benzenesulfonamide 6.00 g (25.0 mmol) sodium 2-nitroaniline-4-sulfonate was taken into 25.0 mL carbon tetrachloride (CCl$_4$) with 13.0 g (62.4 mmol) phosphorus pentachloride (PCl$_5$) and allowed to heat to reflux for five hours. The reaction was allowed to cool to room temperature and was poured into ice water. Chloroform (CHCl$_3$) was added and normal aqueous work-up yielded a bright yellow solid. Half of the isolated material was taken into 10.0 mL H$_2$O and cooled to 0° C. To this solution was slowly added 44.0 mL (87.5 mmol) 2.0 M dimethyl amine in methanol. After the initial exotherm and gas discharge had subsided, reaction was heated to 80° C. for four hours. The reaction was allowed to cool to room temperature and the pH was adjusted to 3.0 using dilute HCl. The quenched reaction was allowed to slowly stir at room temperature overnight. 1.13 g (4.62 mmol, 37%) of the desired product 84A was isolated as a bright yellow solid through filtration.

Example 84B

{1-[2-(5-Dimethylsulfamoyl-benzoimidazol-1-yl)-quinolin-8-yl]-piperidin-4-yl}-carbamic acid tert-butyl ester The same procedure that used for Example 1 was followed with the exception that 4-amino-N,N-dimethyl-3-nitro-benzenesulfonamide 84A was used in the place of that 4-methoxy-2-nitroaniline in example 1B to give the title compound 84B solid.

Example 84C

1-[8-(4-Amino-piperidin-1-yl)-quinolin-2-yl]-1H-benzoimidazole-5-sulfonic acid dimethylamide {1-[2-(5-Dimethylsulfamoyl-benzoimidazol-1-yl)-quinolin-8-yl]-piperidin-4-yl}-carbamic acid tert-butyl ester 84B (129 mg, 0.234 mMol) was dissolved into 1.0 mL of 1,4-dioxane. To this solution, was slowly added 234 µL (0.936 mmol) of a solution of 4.0 M HCl in 1,4-dioxane. Solid formation was noted and the slurry was allowed to stir at room temperature for two hours. Diethyl ether was added to the reaction mixture, and the crude reaction product was isolated through filtration (141 mg yellow solid). This yellow solid was taken into DCM and washed once with 10% K$_2$CO$_3$. Organic layer was dried over MgSO$_4$ and evaporated under reduced pressure. The resulting yellow solid was purified over silica gel (94 CHCl$_3$: 6 CH$_3$OH: 0.6 NH$_4$OH) to give 10 mg of the title compound 84 a brownish solid.

C.I. m/z 451 [M+1]; $^1$H NMR (CDCl$_3$): δ 8.81 (s, 1H), 8.64 (m, 1H), 8.38 (m, 1H), 8.34 (s, 1H), 7.88 (m, 1H), 7.71 (m, 1H), 7.52 (m, 2H), 7.29 (m, 1H), 3.89 (m, 1H), 2.98 (m, 2H), 2.74 (s, 6H), 2.09 (m, 2H), 1.80 (m, 2H), 1.78 (m, 2H).

Example 85

1-[2-(6-Methoxy-benzoimidazol-1-yl)quinolin-8-yl]-piperidin-4-ylamine

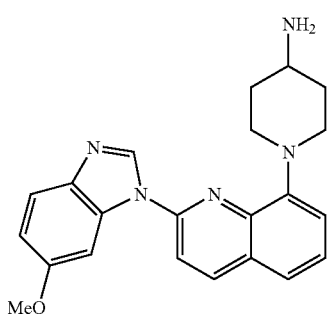

The same procedure that was used in example 84 was followed except that 5-methoxy-2-nitroaniline was used in the place of 4-methoxy-2-nitroaniline in example 1B to give the title compound 85 as an off-white solid.

C.I. m/z 374.1 [M+1]; $^1$H NMR (CDCl$_3$): δ 8.60 (s, 1H), 8.31 (d, J=8.7 Hz, 1H), 7.90 (s, 1H), 7.77 (d, J=8.7 Hz, 1H), 7.67 (d, J=8.7 Hz, 1H), 7.46 (m, 2H), 7.23 (m, 1H), 7.02 (m, 1H), 3.92 (s, 3H), 3.91 (m, 2H), 2.90 (m, 3H), 2.10 (m, 2H), 1.89 (m, 2H), 1.58 (brs, 2H).

Example 86

1-[2-(5,6-Dimethoxy-benzoimidazol-1-yl)-quinolin-8-yl]-piperidin-4-ylamine

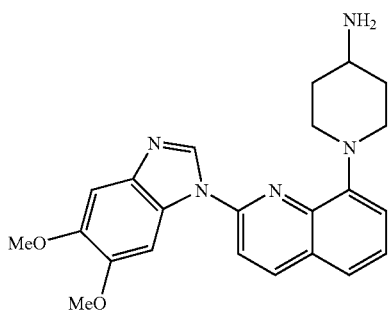

Example 86A 4,5-Dimethoxy-2-nitroaniline 4.50 g (20.0 mmol) 4,5-dimethoxy-1,2-dinitrobenzene was taken into 50.0 mL EtOH/8.4 mL AcOH mixture. To this was added 4.00 g powdered iron (O). The reaction was heated to an oil bath temperature of 70° C. overnight. The reaction was allowed to cool to room temperature and was poured into 400 mL H$_2$O. Aqueous layer was extracted several times with diethyl ether. Organic layers were dried over magnesium sulfate and evaporated under reduced pressure to give 4.73 g orange solid as a mixture of starting material and product. This solid was purified over silica gel (30% DCM in hexanes) to give the title compound 86A as an orange solid (1.15 g, 5.80 mmol).

Example 86B

1-[2-(5,6-Dimethoxy-benzoimidazol-1-yl)-quinolin-8-yl]-piperidin-4-ylamine

The same procedure that was used in example 84 was followed except that 4-5-dimethoxy-2-nitroaniline 86A was used in the place of 4-methoxy-2-nitroaniline in example 1B to give the title compound 86 as an off-white solid.

C.I. m/z 404 [M+1]; $^1$H NMR (CDCl$_3$): δ 8.54 (s, 1H), 8.30 (d, J=8.7 Hz, 1H), 7.86 (s, 1H), 7.64 (d, J=8.7 Hz, 1H), 7.45 (m, 1H), 7.33 (s, 1H), 7.30 (m, 1H), 7.20 (m, 1H), 4.00 (s, 3H), 3.97 (s, 3H), 3.90 (m, 2H), 2.90 (m, 3H), 2.02 (m, 2H), 1.89 (m, 2H).

Example 87

2-Dimethylamino-1-(4-{2-[5-(2-methoxy-ethoxy)-benzoimidazol-1-yl]-quinolin-8-yl}-piperazin-1-yl)-ethanone

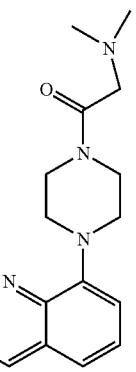

Example 87A

2-Chloro-1-(4-{2-[5-(2-methoxy-ethoxy)-benzoimidazol-1-yl]-quinolin-8-yl}-piperazin-1-yl)ethanone 2-[5-(2-methoxy-ethoxy)-benzoimidazol-1-yl]-8-piperazin-1-yl-quinoline 63 (215 mg, 0.53 mMol) was dissolved in 2.5 mL of anhydrous DCM under an atmosphere of dry N$_2$. To this solution, was sequentially added 2,6-lutidine (120 µL, 1.06 mMol) and chloroacetyl chloride (630 µL, 0.800 mMol) and then reaction was then stirred overnight at ambient temperature. The reaction mixture was filtered and the solid was collected and dried under vacuum to give 50 mg of the title compound 87A.

Example 87B

2-Dimethylamino-1-(4-2-[5-(2-methoxy-ethoxy)-benzoimidazol-1-yl]-quinolin-8-yl}-piperazin-1-yl)-ethanone 2-Chloro-1-(4-[(2-[5-(2-methoxy-ethoxy)-benzoimidazol-1-yl]-quinolin-8-yl}-piperazin-1-yl)ethanone 87A (50 mg, 0.10 mMol) was dissolved in 2.0 mL of a 2.0 M solution of dimethylamine in methanol and the reaction mixture was subsequently stirred for 2 hours at ambient temperature. The reaction mixture was concentrated under vacuum and the residue was chromatographed on flash silica gel eluting with MeOH/DCM (298) then MeOH/DCM/NH$_4$OH (4195.9/0.1) and finally MeOH/DCM/NH$_4$OH (6193.9/0.1) to give 32.5 mg of the title compound 87.

C.I. m/z 489 [M+1]; $^1$H NMR (CD$_3$OD): δ 8.79 (s, 1H), 8.49 (d, J=9.1 Hz, 1H), 8.24 (d, J=8.7 Hz, 1H), 7.69 (d, J=9.1 Hz, 1H), 7.48 (m, 1H), 7.39 (m, 1H), 7.17 (m, 2H), 6.98 (dd, J=2.5, 9.1 Hz, 1H), 4.11 (m, 2H), 3.76 (m, 6H), 3.42 (s, 3H), 3.14–3.21 (m, 6H), 2.28 (s, 6H).

Example 88

1-[2-(5Benzyloxy-benzoimidazol-1-yl)-quinolin-8-yl]-4-methyl-piperidin-4-ol

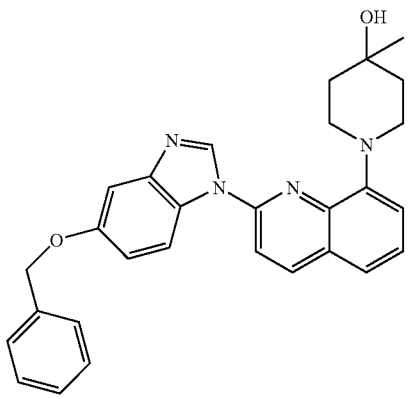

Example 88A

1-[2-(5-Benzyloxy-benzoimidazol-1-yl)-quinolin-8-yl]-piperidin-4-one 2-(5-benzyloxy-benzoimidazol-1-yl)-8-bromo-quinoline (3.46 g, 8.05 mMol), which was prepared using the procedure outlined in example 61 except that 4-benzyloxy-2-nitrophenylamine was used in the place of 5-(2-methoxy-ethoxy-2-nitro-phenylamine 42A in example 61D, and 4-piperidone hydrochloride hydrate (2.47 g, 16.1 mMol) were dissolved in ~40 mL of 1,4-dioxane under an atmosphere of dry $N_2$. To this solution was added $CS_2CO_3$ (8.91 g, 27.4 mMol), racemic-BINAP (300 mg, 0.482 mMol) and tris(dibenzylideneacetone)dipalladium (0) (147 mg, 0.160 mMol) and the reaction mixture was heated to 100° C. and reacted at this temperature overnight. The mixture was then cooled to ambient temperature, filtered, and the precipitate was washed several times with DCM/MeOH. The combined filtrates were concentrated under vacuum and the resulting residue was purified via flash silica gel chromatography eluting with MeOH/DCM/$NH_4OH$ (1.5/98.3/0.2) to give 1.91 g of the title compound 88A as an orange solid.

Example 88B

1-[2-(5-Benzyloxy-benzoimidazol-1-yl)-quinolin-8-yl]4-methyl-piperidin-4-ol

1-[2-(5-Benzyloxy-benzoimidazol-1-yl)-quinolin-8-yl]-piperidin-4-one 88A (832 mg, 1.85 mMol) was dissolved in 10 mL of anhydrous THF under an atmosphere of dry $N_2$. The solution was then cooled to −78° C. after which time 1.2 mL of a 3 M solution methylmagnesium bromide in THF was added. The reaction mixture warmed up to ambient temperature overnight after which time it was quenched with water. The mixture was then concentrated under vacuum and subsequently partitioned between DCM and saturated aqueous $NaHCO_3$. The organic layer was then saved, washed again with saturated aqueous $NaHCO_3$, then with brine, dried over $Na_2SO_4$, filtered and concentrated under vacuum to give a yellow foam. The foam was chromatographed over flash silica gel eluting with MeOH/DCM/$NH_4OH$ (1.5/98.3/0.2) to give 585 mg of the title compound 88 as yellow solid.

C.I. m/z 465 [M+1]; $^1$H NMR ($CDCl_3$): δ8.63 (s, 1H), 8.35 (d, J=8.7 Hz, 1H), 8.23 (d, J=8.7 Hz, 1H), 7.60 (d, J=8.7 Hz, 1H), 7.24–7.48 (m, 9H), 7.10 (dd, J=2.5, 8.7 Hz, 1H), 5.12 (s, 2H), 3.58 (m, 2H), 3.26 (m, 2H), 2.08 (m, 2H), 1.98 (brs, 1H), 1.84 (m, 2H), 1.37 (s, 3H).

Example 89

(4-{2-[5-(2-Methoxy-ethoxy)-benzoimidazol-1-yl]-quinolin-8-yl}-benzyl)-dimethyl-amine

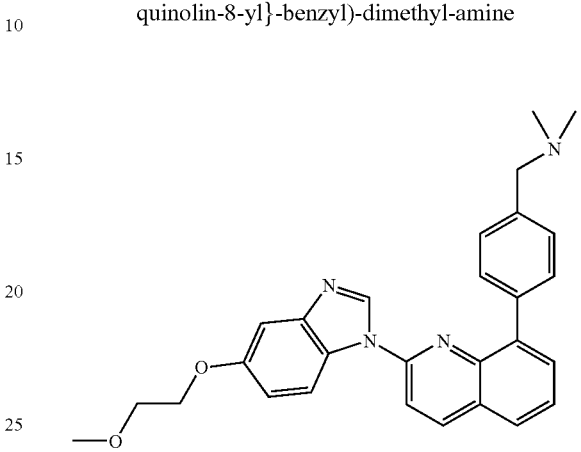

The same procedure that used for Example 6 was followed with the exception that trifluoromethanesulfonic acid 2-[5-(2-methoxy-ethoxy)-benzoimidazol-1-yl]-quinolin-8-yl ester 77E was used in the place of trifluoro-methanesulfonic acid 2-(5-methoxy-benzoimidazol-1-yl)quinolin-8-yl ester 1 E in example 1F to give the title compound 89.

C.I. m/z 453 [M+1]; $^1$H NMR ($CDCl_3$) δ 8.57 (s, 1H), 8.31 (d, J=9.1 Hz, 1H), 7.99 (d, J=9.1 Hz, 1H), 7.80 (m, 1H), 7.77 (m, 1H), 7.65 (m, 3H), 7.57 (m, 1H), 7.44 (d, J=8.1 Hz, 2H), 7.26 (d, J=2.5 Hz, 1H), 6.81 (dd, J=2.5, 9.1, 1H), 4.15 (m, 2H), 3.77 (m, 2H), 3.56 (s, 2H), 3.45 (s, 3H), 2.33 (s, 6H).

Example 90

(4-(2-[5-(2-Methoxy-ethoxy)-benzoimidazol-1-yl]-quinolin-8-yl}-benzyl)-methyl-amine

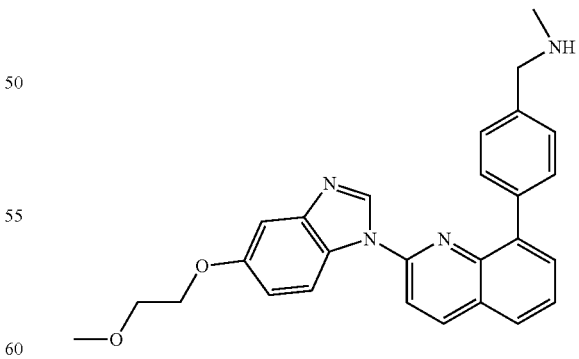

The same procedure that used for Example 5 was followed with the exception trifluoromethanesulfonic acid 2-[5-(2-methoxy-ethoxy)-benzoimidazol-1-yl]-quinolin-8-yl ester 77E was used in the place of trifluoro-methanesulfonic acid 2-(5-methoxy-benzoimidazol-1-yl]quinolin-8-yl ester 1E in example 1F to give the title compound 90.

C.I. m/z 439 [M+1]; $^1$H NMR (CDCl$_3$) δ 8.56 (s, 1H), 8.31 (d, J=9.1. Hz, 1H), 7.94 (d, J=9.1 Hz, 1H), 7.80 (m, 1H), 7.75 (m, 1H), 7.63 (m, 3H), 7.56 (m, 1H), 7.43 (d, J=7.9 Hz, 2H), 7.23 (d, J=2.5 Hz, 1H), 6.80 (m, 1H), 4.14 (m, 2H), 3.87 (s, 2H), 3.76 (m, 2H), 3.43 (s, 3H), 2.53 (s, 3H)

Example 91

2-[5-(2-Methoxy-ethoxy)-benzoimidazol-1-yl]-8-(4-morpholin-4-ylmethyl-phenyl)-quinoline

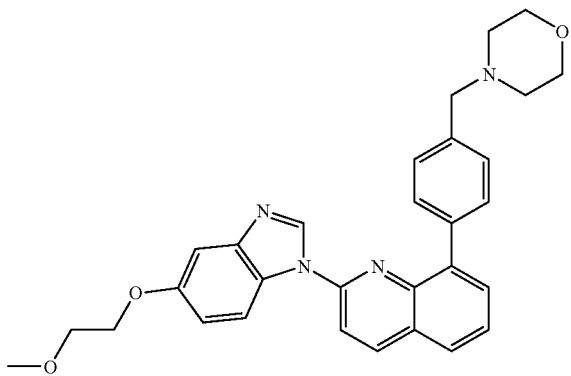

The same procedure that used for Example 5 was followed with the exception that trifluoromethanesulfonic acid 2-[5-(2-methoxy-ethoxy)-benzoimidazol-1-yl]-quinolin-8-yl ester 77E was used in the place of trifluoro-methanesulfonic acid 2-(5-methoxy-benzoimidazol-1-yl)quinolin-8-yl ester 1E in example 1F and morpholine was used in the place of methylamine in example 5B to give the title compound 91.

C.I. m/z 495 [M+1]; $^1$H NMR (CDCl$_3$) δ 8.56 (s, 1H), 8.31 (d, J=8.7 Hz, 1H), 7.98 (d, J=8.7 Hz, 1H), 7.81 (m, 1H), 7.76 (m, 1H), 7.65 (m, 3H), 7.57 (m, 1H), 7.43 (d, J=7.9 Hz, 2H), 7.25 (d, J=2.5 Hz, 1H), 6.80 (dd, J=2.5, 9.1, 1H), 4.15 (m, 2H), 3.78 (m, 6H), 3.62 (s, 2H), 3.46 (s, 3H), 2.85 (m, 4H)

Example 92

2-(4-[(2-[5-(2-Methoxy-ethoxy)-benzoimidazol-1-yl]-quinolin-8-yl}-benzylamino)-ethanol

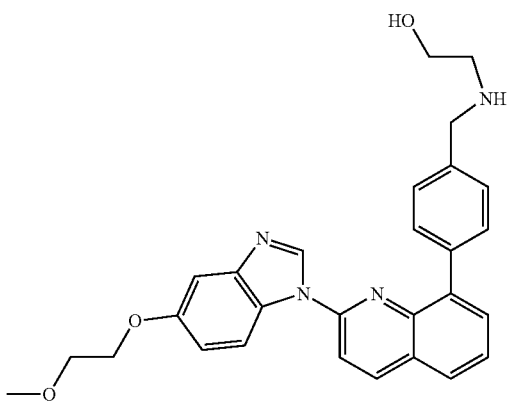

The same procedure that used for Example 5 was followed with the exception that trifluoromethanesulfonic acid 2-[5-(2-methoxy-ethoxy)-benzoimidazol-1-yl]-quinolin-8-yl ester 77E was used in the place of trifluoro-methanesulfonic acid 2-(5-methoxy-benzoimidazol-1-yl)quinolin-8-yl ester 1E in example 1F and ethanolamine was used in the place of methylamine in example 5B to give the title compound 92.

C.I. m/z 469 [M+1]; $^1$H NMR (CD$_3$OD) δ 8.63 (s, 1H), 8.14 (d, J=9.1 Hz, 1H), 7.71 (d, J=9.1 Hz, 1H), 7.68 (dd, J=2.2, 7.9 Hz, 1H), 7.59 (d, J=9.1 Hz, 1H), 7.54 (dd, J=2.2, 7.0 Hz, 1H), 7.43 (m, 1H), 7.35 (d, J=8.3 Hz, 2H), 7.28 (d, J=8.3 Hz, 2H), 6.99 (d, J=2.5 Hz, 1H), 6.50 (m, 1H), 4.00 (m, 2H), 3.83 (s, 2H), 3.70 (m, 4H), 3.41 (s, 3H), 3.21 (m, 2H)

Example 93

4-{2-[5-(2-Methoxy-ethoxy)-benzoimidazol-1-yl]-quinolin-8-yl}-benzylamine

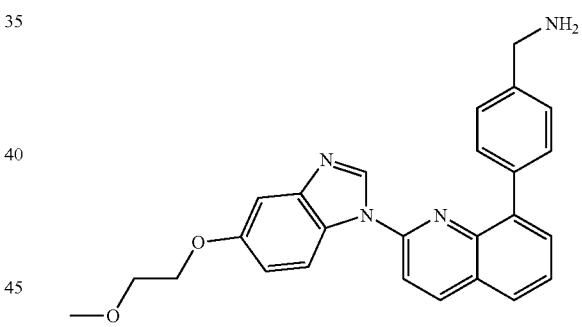

The same procedure that used for Example 78 was followed with the exception that 4-aminomethylphenylboronic acid hydrochloride was used in the place 2-methoxy-5-pyridineboronic acid and the number of equivalents of potassium phosphate was doubled to give the title compound 93.

C.I. m/z 425 [M+1]; $^1$H NMR (CD$_3$OD) δ 8.69 (s, 1H), 8.21 (d, J=9.1 Hz, 1H), 7.77 (d, J=8.7 Hz, 1H), 7.73 (m, 1H), 7.66 (d, J=9.1 Hz, 1H), 7.59 (dd, J=1.7, 7.0 Hz, 1H), 7.48 (m, 1H), 7.41 (d, J=8.3 Hz, 2H), 7.32 (d, J=8.3 Hz, 2H), 7.01 (d, J=2.5 Hz, 1H), 6.54 (d, J=2.5, 9.1 Hz, 1H), 4.02 (m, 2H), 3.86 (s, 2H), 3.71 (m, 2H), 3.41 (s, 3H).

Example 94

2-[5-(2-Methoxy-ethoxy)-benzoimidazol-1-yl]-8-(4-pyrrolidin-1-ylmethyl-phenyl)-quinoline

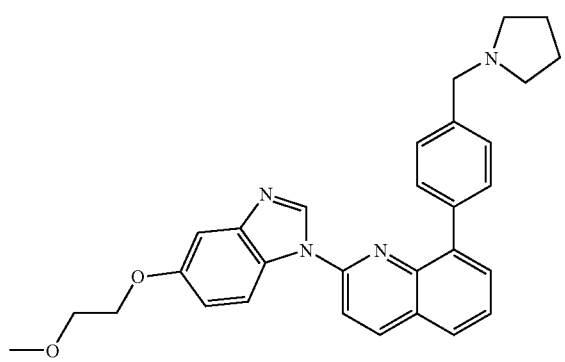

The same procedure that used for Example 5 was followed with the exception that trifluoromethanesulfonic acid 2-[5-(2-methoxy-ethoxy)-benzoimidazol-1-yl]-quinolin-8-yl ester 77E was used in the place of trifluoro-methanesulfonic acid 2-(5-methoxy-benzoimidazol-1-yl)quinolin-8-yl ester 1E in example 1F and pyrrolidine was used in the place of methylamine in example 5B to give the title compound 94.

C.I. m/z 479 [M+1]; $^1$H NMR (CD$_3$OD) δ 8.72 (s, 1H), 8.22 (d, J=9.1 Hz, 1H), 7.79 (d, J=9.1 Hz, 1H), 7.74 (m, 1H), 7.69 (d, J=8.7 Hz, 1H), 7.57 (dd, J=1.7, 7.0 Hz, 1H), 7.48 (m, 1H), 7.36 (d, J=8.3 Hz, 2H), 7.27 (d, J=8.3 Hz, 2H), 7.03 (d, J=2.5 Hz, 1H), 6.50 (m, 1H), 4.02 (m, 2H), 3.70 (m, 2H), 3.65 (s, 2H), 3.41 (s, 3H), 2.55 (m, 4H), 1.80 (m, 4H).

Example 95

2-[5-(2-Methoxy-ethoxy)-benzoimidazol-1-yl]-8-(4-pyrrolidin-1-ylmethyl-phenyl)-quinoline

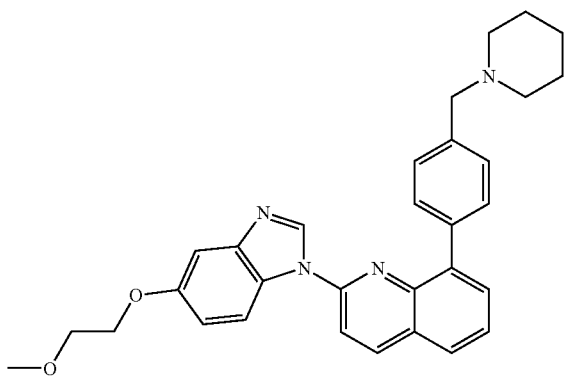

The same procedure that used for Example 5 was followed with the exception that trifluoromethanesulfonic acid 2-[5-(2-methoxy-ethoxy)-benzoimidazol-1-yl]-quinolin-8-yl ester 77E was used in the place of trifluoro-methanesulfonic acid 2-(5-methoxy-benzoimidazol-1-yl)-quinolin-8-yl ester 1E in example 1F and piperidine was used in the place of methylamine in example 5B to give the title compound 95.

C.I. m/z 493 [M+1], $^1$H NMR (CDCl$_3$) δ 8.56 (s, 1H), 8.30 (d, J=8.7 Hz, 1H), 8.00 (d, J=9.1 Hz, 1H), 7.78 (dd, J=1.2, 7.9 Hz, 1H), 7.76 (m, 1H), 7.64 (m, 3H), 7.56 (m, 1H), 7.45 (d, J=7.9 Hz, 2H), 7.25 (d, J=2.5 Hz, 1H), 6.81 (d, J=2.5, 9.1 Hz, 1H), 4.15 (m, 2H), 3.77 (m, 2H), 3.60 (s, 2H), 3.46 (s, 3H), 2.48 (m, 4H), 1.63 (m, 4H), 1.47 (m, 2H).

Example 96

2-[5-(2-Methoxy-ethoxy)-benzoimidazol-1-yl]-8-(4-pyrrolidin-1-ylmethyl-phenyl)-quinoline

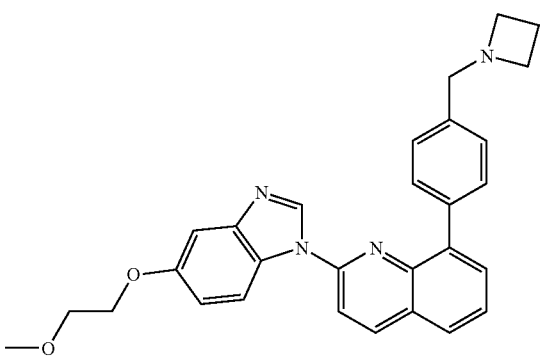

The same procedure that used for Example 5 was followed with the exception that trifluoromethanesulfonic acid 2-[5-(2-methoxy-ethoxy)-benzoimidazol-1-yl]-quinolin-8-yl ester 77E was used in the place of trifluoro-methanesulfonic acid 2-(5-methoxy-benzoimidazol-1-yl)quinolin-8-yl ester 1E in example 1F and azetidine was used in the plac of methylamine in example 5B to give the title compound 96.

C.I. m/z 465 [M+1]; $^1$H NMR (CD$_3$OD) δ 8.68 (s, 1H), 8.17 (d, J=9.1 Hz, 1H), 7.72 (d, J=9.1 Hz, 1H), 7.71 (m, 1H), 7.62 (d, J=9.1 Hz, 1H), 7.54 (d, J=1.7, 7.0 Hz, 1H), 7.44 (m, 1H), 7.32 (d, J=7.9 Hz, 2H), 7.19 (d, J=7.9 Hz, 2H), 7.02 (d, J=2.5 Hz, 1H), 6.49 (dd, J=2.5, 9.1 Hz, 1H), 4.01 (m, 2H), 3.70 (m, 2H), 3.60 (s, 2H), 3.41 (s, 3H), 3.26 (m, 4H), 2.09 (m, 2H).

Example 97

1-(4-{2-[5-(2-Methoxy-ethoxy)-benzoimidazol-1-yl]-quinolin-8-yl}-benzyl)-cis-pyrrolidine-3,4-diol

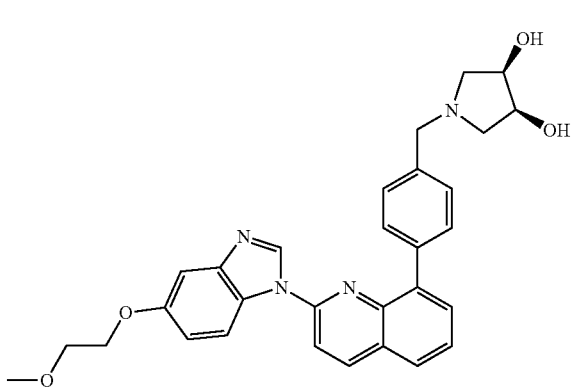

The same procedure that used for Example 5 was followed with the exception that trifluoromethanesulfonic acid 2-[5-(2-methoxy-ethoxy)-benzoimidazol-1-yl]-quinolin-8-yl ester 77E was used in the place of trifluoro-methanesulfonic acid 2-(5-methoxy-benzoimidazol-1-yl)-quinolin-8-yl ester 1E in example 1F and cis-pyrrolidine-3,4-diol was used in the place of methylamine in example 5B to give the title compound 97.

C.I. m/z 511 [M+1]; $^1$H NMR (CD$_3$OD) δ 8.68 (s, 1H), 8.18 (d, J=9.1 Hz, 1H), 7.74 (d, J=9.1 Hz, 1H), 7.71 (dd, J=1.3, 8.3 Hz, 1H), 7.63 (d, J=9.1 Hz, 1H), 7.54 (dd, J=1.3, 7.0 Hz, 1H), 7.44 (m, 1H), 7.33 (d, J=8.0 Hz, 2H), 7.25 (d, J=8.0 Hz, 2H), 7.00 (d, J=2.5 Hz, 1H), 6.50 (m, 1H), 4.14 (m, 2H), 4.01 (m, 2H), 3.71 (m, 2H), 3.66 (s, 2H), 3.42 (s, 3H), 2.96 (m, 2H), 2.55 (m, 2H).

Example 98

R,R-(1-(4-(2-[5-(2-Methoxy-ethoxy)-benzoimidazol-1-yl]-quinolin-8-yl}-benzyl)-trans-pyrrolidine-3,4-diol)

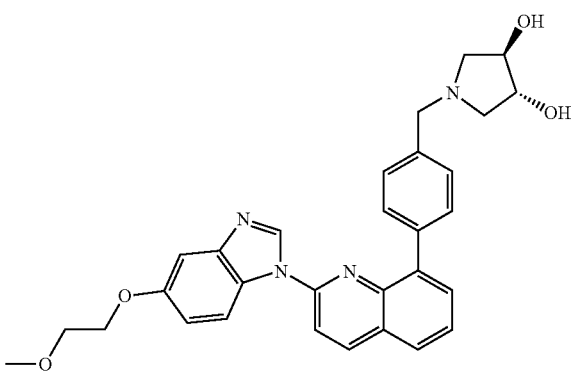

The same procedure that used for Example 5 was followed with the exception that trifluoromethanesulfonic acid 2-[5-(2-methoxy-ethoxy)-benzoimidazol-1-yl]-quinolin-8-yl ester 77E was used in the place of trifluoro-methanesulfonic acid 2-(5-methoxy-benzoimidazol-1-yl)quinolin-8-yl ester 1E in step 1F and R,R-trans-pyrrolidine-3,4-diol was used in the place of methylamine in step 5B to give the title compound 98.

C.I. m/z 511 [M+1]; $^1$H NMR (CD$_3$OD) δ 8.87 (s, 1H), 8.40 (d, J=8.7 Hz, 1H), 7.96 (d, J=9.1 Hz, 1H), 7.88 (m, 2H), 7.71 (dd, J=1.2, 7.0 Hz, 1H), 7.58 (m, 1H), 7.54 (d, J=8.3 Hz, 2H), 7.44 (d, J=8:3 Hz, 2H), 7.12 (d, J=2.5 Hz, 1H), 6.67 (dd, J=2.5, 9.1 Hz, 1H), 4.10 (m, 4H), 3.77 (m, 4H), 3.44 (s, 3H), 3.04 (m, 2H), 2.60 (m, 2H).

Example 99

1-(4-(2-[5-(2-Methoxy-ethoxy]benzoimidazol-1-yl]-quinolin-8-yl}benzyl)-pyrrolidin-3-ol The same procedure that used for Example 5 was followed with the exception that trifluoromethanesulfonic acid 2-[5-(2-methoxy-ethoxy)-benzoimidazol-1-yl]-quinolin-8-yl ester 77E was used in the place of trifluoro-methanesulfonic acid 2-(5-methoxy-benzoimidazol-1-yl)quinolin-8-yl ester 1E in example 1F and racemic 3-pyrrolidinol was used in the place of methylamine in example 5B to give the title compound 99.

C.I. m/z 495 [M+1]; $^1$H NMR (CD$_3$OD) δ 8.60 (s, 1H), 8.08 (d, J=8.7 Hz, 1H), 7.67 (d, J=8.7 Hz, 1H), 7.63 (m, 1H), 7.53 (d, J=9.1 Hz, 1H), 7.49 (dd, J=1.2, 7.1 Hz, 1H), 7.39 (m, 1H), 7.39 (d, J=8.3 Hz, 2H), 7.26 (d, J=8.3 Hz, 2H), 6.97 (d, J=2.5 Hz, 1H), 6.44 (dd, J=2.5, 9.1 Hz, 1H), 4.35 (m, 1H), 3.98 (m, 2H), 3.69 (m, 2H), 3.61 (d, J=12.5 Hz, 1H), 3.57 (d, J=12.5 Hz, 1H), 3.41 (s, 3H), 2.82 (m, 1H), 2.67 (m, 1H), 2.48 (m, 2H), 2:12 (m, 1H), 1.70 (m, 1H).

Example 100

R-(1-(4-{2-[5-(2-Methoxy-ethoxy)-benzoimidazol-1-yl]-quinolin-8-yl}-benzyl)-pyrrolidin-3-ol)

The same procedure that used for Example 5 was followed with the exception that trifluoromethanesulfonic acid 2-[5-(2-methoxy-ethoxy)-benzoimidazol-1-yl]-quinolin-8-yl ester 77E was used in the place of trifluoro-methanesulfonic acid 2-(5-methoxy-benzoimidazol-1-yl)quinolin-8-yl ester 1E in example 1F and R-3-pyrrolidinol was used in the place of methylamine in example 5B to give the title compound 100.

C.I. m/z 495 [M+1]; $^1$H NMR (CD$_3$OD) δ 8.69 (s, 1H), 8.19 (d, J=9.1 Hz, 1H), 7.76 (d, J=9.1 Hz, 1H), 7.71 (m, 1H), 7.64 (d, J=8.7 Hz, 1H), 7.55 (dd, J=1.3, 7.0 Hz, 1H), 7.46 (m, 1H), 7.34 (d, J=8.3 Hz, 2H), 7.27 (d, J=8.3 Hz, 2H), 7.01

(d, J=2.5 Hz, 1H), 6.49 (dd, J=2.5, 9.1 Hz, 1H), 4.36 (m, 1H), 4.01 (m, 2H), 3.70 (m, 2H), 3.67 (d, J=12.5 Hz, 1H), 3.62 (d, J=12.5 Hz, 1H), 3.42 (s, 3H), 2.84 (m, 1H), 2.70 (m, 1H), 2.55 (m, 1H), 2.50 (m, 1H), 2.15 (m, 1H), 1.72 (m, 1H).

Example 101

S-(1-(4-{2-[5-(2-Methoxy-ethoxy)-benzoimidazol-1-yl]-quinolin-8-yl)benzyl)-pyrrolidin-3-ol)

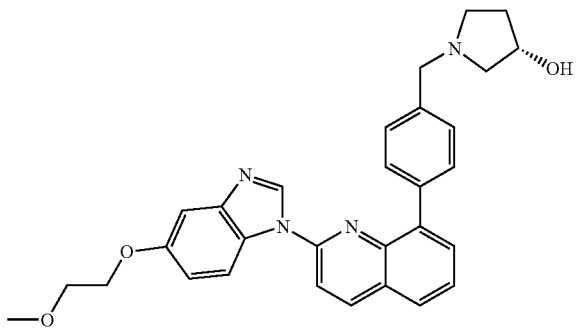

The same procedure that used for Example 5 was followed with the exception that trifluoromethanesulfonic acid 2-[5-(2-methoxy-ethoxy)-benzoimidazol-1-yl]-quinolin-8-yl ester 77E was used in the place of trifluoro-methanesulfonic acid 2-(5-methoxy-benzoimidazol-1-yl)quinolin-8-yl ester 1E in example 1F and S-3-pyrrolidinol was used in the place of methylamine in example 5B to give the title compound 101.

C.I. m/z 495 [M+1]; $^1$H NMR (CD$_3$OD) δ 8.84 (s, 1H), 8.37 (d, J=8.7 Hz, 1H), 7.93 (d, J=9.1 Hz, 1H), 7.86 (m, 2H), 7.68 (dd, J=1.7, 7.1 Hz, 1H), 7.56 (m, 1H), 7.53 (d, J=7.9 Hz, 2H), 7.40 (d, J=7.9 Hz, 2H), 7.11 (d, J=2.5 Hz, 1H), 6.63 (dd, J=2.5, 9.1 Hz, 1H), 4.39 (m, 1H), 4.09 (m, 2H), 3.74 (m, 4H), 3.43 (s, 3H), 2.90 (m, 1H), 2.76 (m, 1H), 2.62 (m, 1H), 2.52 (m, 1H), 2.19 (m, 1H), 1.75 (m, 1H).

Example 102

1-(4-(2-[5-(2-Methoxy-ethoxy)-benzoimidazol-1-yl]-quinolin-8-yl]benzyl)-azetidin-3-ol

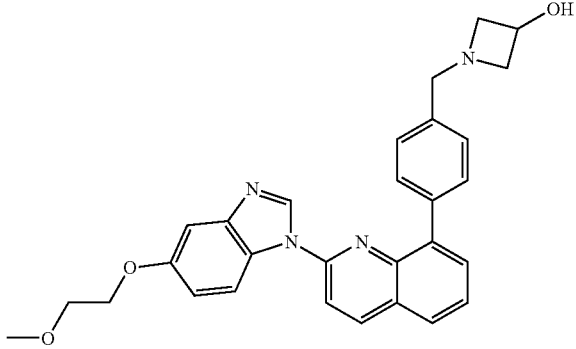

The same procedure that used for Example 5 was followed with the exception that trifluoromethanesulfonic acid 2-[5-(2-methoxy-ethoxy)-benzoimidazol-1-yl]-quinolin-8-yl ester 77E was used in the place of trifluoro-methanesulfonic acid 2-(5-methoxy-benzoimidazol-1-yl)quinolin-8-yl ester 1E in example 1F and azetidin-3-ol was used in the place of methylamine in example 5B to give the title compound 102.

C.I. m/z 481 [M+1]; $^1$H NMR (CD$_3$OD) δ 8.52 (s, 1H), 8.00 (d, J=9.1 Hz, 1H), 7.63 (d, J=8.7 Hz, 1H), 7.56 (dd, J=2.3, 7.9 Hz, 1H), 7.45 (m, 2H), 7.33 (m, 1H), 7.26 (d, J=8.3 Hz, 2H), 7.15 (d, J=8.3 Hz, 2H), 6.96 (d, J=2.5 Hz, 1H), 6.46 (dd, J=2.5, 8.7 Hz, 1H), 4.86 (brs, 1 H), 4.37 (m, 1H), 3.96 (m, 2H), 3.68 (m, 2H), 3.63 (s, 2H), 3.59 (m, 2H), 3.40 (s, 3H), 2.98 (m, 2H).

Example 103

2-[5-(2-Methoxy-ethoxy)-benzoimidazol-1-yl]-8-[4-(4-methyl-piperazin-1-ylmethyl)-phenyl]-quinoline

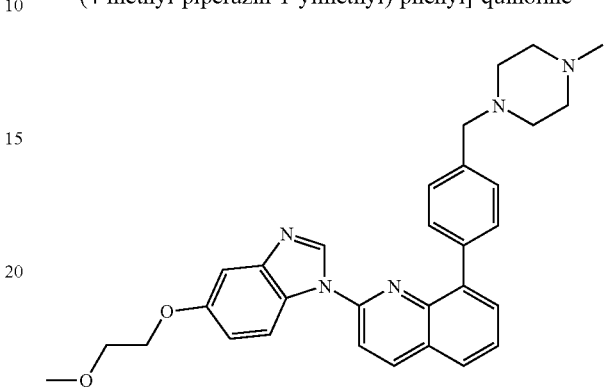

The same procedure that used for Example 5 was followed with the exception that trifluoromethanesulfonic acid 2-[5-(2-methoxy-ethoxy)-benzoimidazol-1-yl]-quinolin-8-yl ester 77E was used in the place of trifluoro-methanesulfonic acid 2-(5-methoxy-benzoimidazol-1-yl)quinolin-8-yl ester 1E in example 1F and 1-methylpiperazine was used in the place of methylamine in example 5B to give the title compound 103.

C.I. m/z 508 [M+1]; $^1$H NMR (CDCl$_3$) δ 8.56 (s, 1H), 8.30 (d, J=9.1 Hz, 1H), 7.98 (d, J=8.7 Hz, 1H), 7.80 (m, 1H), 7.75 (m, 1H), 7.62 (m, 3H), 7.57 (m, 1H), 7.44 (d, J=8.3 Hz, 2H), 7.24 (d, J=2.1 Hz, 1H), 6.80 (dd, J=2.5, 8.7 Hz, 1H), 4.15 (m, 2H), 3.77 (m, 2H), 3.62 (s, 2H), 3.45 (s, 3H), 2.70 (m, 8H), 2.30 (s, 3H).

Example 104

4-(4-(2-[5-(2-Methoxy-ethoxy)-benzoimidazol-1-yl]-quinolin-8-yl}-benzyl)-piperazine-1-carboxylic acid tert-butyl ester

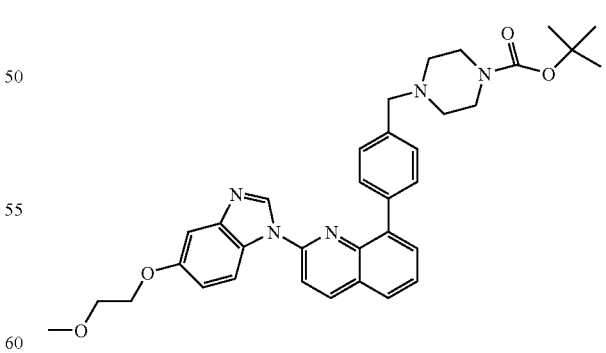

The same procedure that used for Example 5 was followed with the exception that trifluoromethanesulfonic acid 2-[5-(2-methoxy-ethoxy)-benzoimidazol-1-yl]-quinolin-8-yl ester 77E was used in the place of trifluoro-methanesulfonic acid 2-(5-methoxy-benzoimidazol-1-yl)quinolin-8-yl ester 1E in example 1F and 1-tert-butoxycarbonylpiperazine was used in the place of methylamine in example 5B to give the title compound 104.

C.I. m/z 594 [M+1]; ¹H NMR (CDCl₃) δ 8.58 (s, 1H), 8.35 (d, J=9.1 Hz, 1H), 8.00 (d, J=9.1 Hz, 1H), 7.82 (m, 1H), 7.78 (m, 1H), 7.67 (m, 3H), 7.60 (m, 1H), 7.47 (d, J=7.9 Hz, 2H), 7.26 (d, J=2.1 Hz, 1H), 6.83 (dd, J=2.5, 8.7 Hz, 1H), 4.17 (m, 2H), 3.79 (m, 2H), 3.64 (s, 2H), 3.49 (m, 4H), 3.46 (s, 3H), 2.50 (m, 4H), 1.45 (s, 9H).

Example 105

[1-(4-{2-[5-(2-Methoxy-ethoxy)-benzoimidazol-1-yl]-quinolin-8-yl}-benzyl)-piperidin-4-yl]-carbamic acid tert-butyl ester

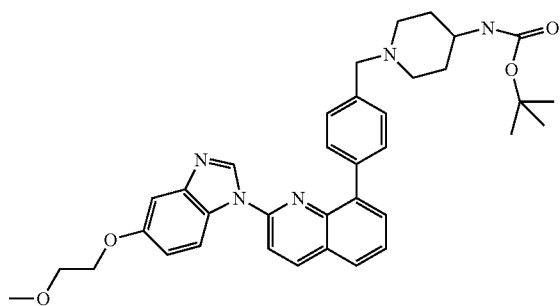

The same procedure that used for Example 5 was followed with the exception that trifluoromethanesulfonic acid 2-[5-(2-methoxy-ethoxy)-benzoimidazol-1-yl]-quinolin-8-yl ester 77E was used in the place of trifluoro-methanesulfonic acid 2-(5-methoxy-benzoimidazol-1-yl quinolin-8-yl ester 1E in example 1F and 4-N-tert-butoxycarbonyl-aminopiperidine was used in the place of methylamine in example 5B to give the title compound 105.

C.I. m/z 608 [M+1]; ¹H NMR (CD₃OD) δ8.92 (s, 1H), 8.48 (d, J=9.1 Hz, 1H), 8.04 (d, J=9.1 Hz, 1H), 7.96 (d, J=9.1 Hz, 1H), 7.92 (m, 1H), 7.75 (m, 1H), 7.61 (m, 3H), 7.45 (d, J=7.9 Hz, 2H), 7.16 (d, J=2.5 Hz, 1H), 6.65 (dd, J=2.5, 8.7 Hz, 1H), 4.12 (m, 2H), 3.77 (m, 2H), 3.65 (s, 2H), 3.44 (s, 3H), 3.41 (m, 1H), 3.00 (m, 2H), 2.22 (m, 2H), 1.88 (m, 2H), 1.75 (m, 2H), 1.42 (s, 9H).

Example 106

1-(4-(2-[5-(2-Methoxy-ethoxy)-benzoimidazol-1-yl]-quinolin-8-yl}-benzyl)-piperidin-4-ylamine

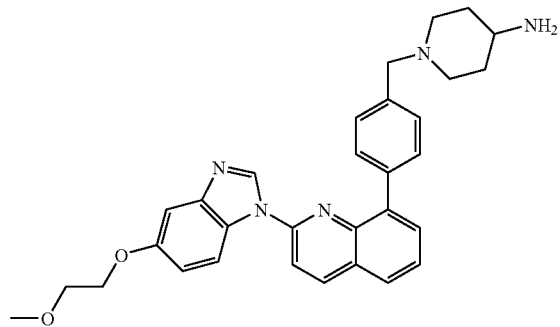

[1-(4-(2-[5-(2-Methoxy-ethoxy)-benzoimidazol-1-yl]-quinolin-8-yl}-benzyl)-piperidin-4-yl]-carbamic acid tert-butyl ester 105 (110 mg, 0181 mMol) was dissolved in a solution of 3 mL of TFA and 3 mL of DCM under an atmosphere of dry N₂. The reaction mixture was stirred for 40 minutes after which time it was concentrated under vacuum and the resulting residue was partitioned between DCM and 1 N aqueous NaOH. The DCM layer was then washed with again with 1 N aqueous NaOH, dried over Na₂SO₄, filtered and concentrated under vacuum to give 45 mg of the title compound 106.

C.I. m/z 508 [M+1]; ¹H NMR (CDCl₃) δ 8.55 (s, 1H), 8.29 (d, J=8.7 Hz, 1H), 7.98 (d, J=9.1 Hz, 1H), 7.78 (d, J=8.3 Hz, 1H), 7.76 (m, 1H), 7.60 (m, 4H), 7.42 (d, J=7.9 Hz, 2H), 7.23 (d, J=2.5 Hz, 1H), 6.80 (m, 1H), 4.14 (m, 2H), 3.76 (m, 2H), 3.59 (s, 2H), 3.44 (s, 3H), 2.93 (m, 2H), 2.68 (m, 1H), 2.11 (m, 2H), 1.94 (brs, 2H), 1.80 (m, 2H), 1.45 (m, 2H).

Example 107

(1-[(2-[5-(2-Methoxy-ethoxy)-benzoimidazol-1-yl]-quinolin-8-yl}-piperidin-4-yl)-methanol

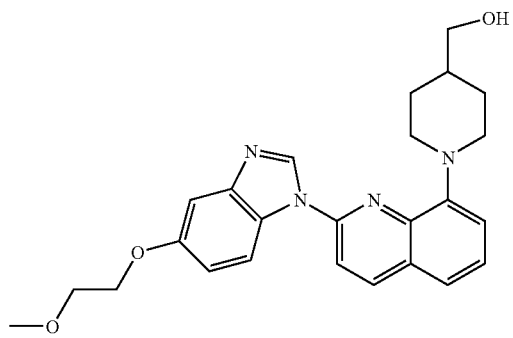

The same procedure that was used in example 1 was followed except that trifluoromethanesulfonic acid 2-[5-(2-methoxy-ethoxy)-benzoimidazol-1-yl]quinolin-8-yl ester 77E was used in the place of trifluoro-methanesulfonic acid 2-(5-methoxy-benzoimidazol-1-yl)-quinolin-8-yl ester 1E and 4-(hydroxymethyl]piperidine was used in the place of piperidin-4-yl-carbamic acid tert-butyl ester in example 1F to give the title compound 107 as a yellow solid.

C.I. m/z 433 [M+1]; ¹H NMR (CDCl₃) δ 8.66 (s, 1H), 8.38 (d, J=9.1 Hz, 1H), 8.29 (d, J=9.1 Hz, 1H), 7.67 (d, J=8.7 Hz, 1H), 7.47 (m, 2H), 7.33 (d, J=2.5 Hz, 1H), 7.28 (m, 1H), 7.10 (dd, J=2.5, 9.1 Hz, 1H), 4.21 (m, 2H), 3.95 (m, 2H), 3.80 (m, 2H), 3.63 (m, 2H), 3.47 (s, 3H), 2.83 (m, 2H), 95 (m, 1H), 75 (m, 3H).

Example 108

(1-{2-[5-(2-Methoxy-ethoxy)-benzoimidazol-1-yl]-quinolin-8-yl}-piperidin-4-ylmethyl)-methyl-amine

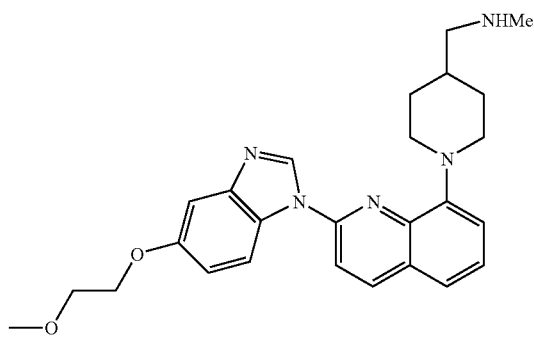

Example 108A 1-(2-[5-(2-Methoxy-ethoxy)-benzoimidazol-1-yl]-quinolin-8-yl}-piperidine-4-carbaldehyde (1-{2-[5-(2-Methoxy-ethoxy)-benzoimidazol-1-yl]-quinolin-8-yl}-piperidin-4-yl)-methanol 107 (1.47 g, 3.40 mMol) was dissolved in 15 mL of anhydrous DCM under an atmosphere of dry $N_2$. To this mixture was added ~2 gm of 4A molecular sieves, 4-methylmorpholine N-oxide (1.19 g, 10.2 mMol) and finally tetrapropylammonium perruthenate (119 mg, 0.340 mMol). The mixture was stirred at ambient temperature over night after which time it was filtered through Celite™. The Celite™ was washed with DCM and the resulting combined filtrate was concentrated under vacuum. The resulting residue was chromatographed on flash silica gel eluting with a gradient from MeOH/DCM (199) to MeOH/DCM (298) to give 446 mg of the title compound 108A.

Example 108B (1-{2-[5-(2-Methoxy-ethoxy)-benzoimidazol-1-yl]-quinolin-8-yl}-piperidin-4-ylmethyl)-methyl-amine 1-{2-[5-(2-Methoxy-ethoxy)-benzoimidazol-1-yl]-quinolin-8-yl}piperidine-4-carbaldehyde 108A (100 mg, 0.232 mMol) was dissolved in 1 mL of MeOH under an atmosphere of dry $N_2$. To this solution was added 580 µL of a 2.0 M solution of methylamine in MeOH. AcOH (~100 LL) was added to this solution until the pH ~5 after which time $NaCNBH_3$ (30 mg, 0.46 mMol) was added to the mixture. The reaction mixture was stirred overnight at ambient temperature. The reaction mixture was then concentrated under vacuum and partitioned between DCM and 1 N aqueous NaOH. The DCM layer was saved and washed again with 1 N aqueous NaOH, dried over $Na_2SO_4$, filtered and concentrated under vacuum. The resulting residue was chromatographed on flash silica gel eluting with a gradient from MeOH/DCM (397) to MeOH/DCM (5/95) and then a gradient from $MeOH/DCM/NH_4OH$ (792.90.1) to $MeOH/DCM/NH_4OH$ (990.90.1) to give 60 mg of the title compound 108 as a yellow solid.

C.I. m/z 446 [M+1]; $^1$H NMR ($CD_3OD$) δ8.96 (s, 1. H), 8.68 (d, J=9.1 Hz, 1H), 8.44 (d, J=9.1 Hz, 1H), 7.93 (d, J=8.7 Hz, 1H), 7.57 (d, J=7.9 Hz, 1H), 7.49 (m, 1H), 7.34 (d, J=7.9 Hz, 1H), 7.27 (d, J=2.5 Hz, 1H), 7.10 (dd, J=2.5, 9.1 Hz, 1H), 4.19 (m, 2H), 3.86 (m, 2H), 3.79 (m, 2H), 3.45 (s, 2H), 2.78 (m, 2H), 2.63 (m, 2H), 2.45 (s, 3H), 1.92 (m, 2H), 1.68 (m, 3H).

Example 109

2-[5-(2-Methoxy-ethoxy)-benzoimidazol-1-yl]-8-[4-(4-methyl-piperazin-1-ylmethyl)-piperidin-1-yl]-quinoline

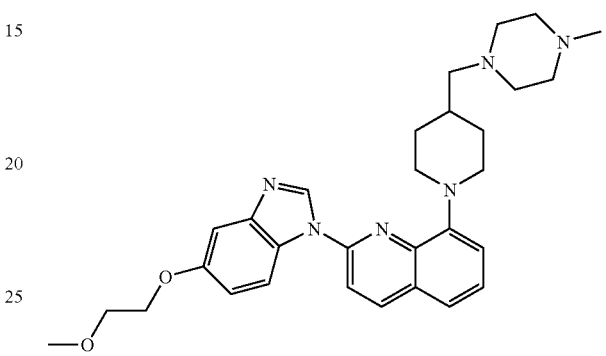

The same procedure that was used in example 108 was followed except that 1-methylpiperazine was used in the place of methylamine in example 108B to give the title compound 109.

C.I. m/z 515 [M+1]; $^1$H NMR ($CD_3OD$) δ 8.79 (s, 1H), 8.48 (d, J=9.1 Hz, 1H), 8.19 (d, J=8.7 Hz, 1H), 7.67 (d, J=9.1 Hz, 1H), 7.38 (m, 2H), 7.16 (d, J=2.1 Hz, 1H), 7.12 (d, J=7.4 Hz, 1H), 6.90 (m, 1H), 4.11 (m, 2H), 3.75 (m, 2H), 3.63 (m, 2H), 3.43 (s, 3H), 2.20–2.60 (m, 15 H), 1.76 (m, 2H), 1.55 (m, 1H), 1.45 (m, 2H).

Example 110

(1-{2-[5-(2-Methoxy-ethoxy)-benzoimidazol-1-yl]-quinolin-8-yl}-piperidin-4-ylmethyl)-dimethyl-amine

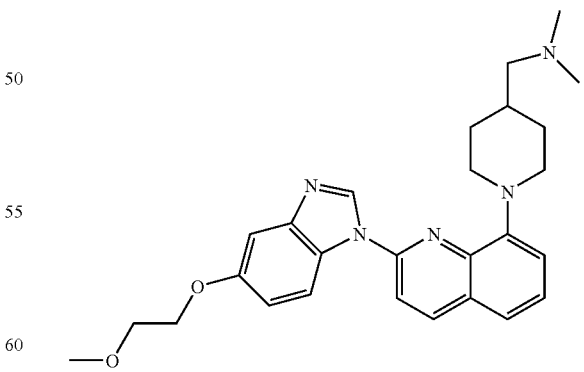

The same procedure that was used in example 108 was followed except that dimethylamine was used in the place of methylamine in step 108B to give the title compound 110.

C.I. m/z 460 [M+1]; $^1$H NMR ($CD_3OD$) δ 8.85 (s, 1H), 8.55 (d, J=9.1 Hz, 1H), 8.28 (d, J=8.7 Hz, 1H), 7.76 (d, J=8.7

Hz, 1H), 7.45 (d, J=7.9 Hz, 1H), 7.40 (m, 1H), 7.21 (m, 2H), 6.98 (dd, J=2.1, 9.1 Hz, 1H), 4.14 (m, 2H), 3.75 (m, 4H), 3.43 (s, 3H), 2.64 (m, 2H), 2.27 (m, 2H), 2.24 (s, 6H), 1.83 (m, 2H), 1.63 (m, 1H), 1.54 (m, 2H).

Example 111

1-(1-{2-[5-(2-Methoxy-ethoxy)-benzoimidazol-1-yl]-quinolin-8-yl}-piperidin-4-ylmethyl)pyrrolidin-3-ol

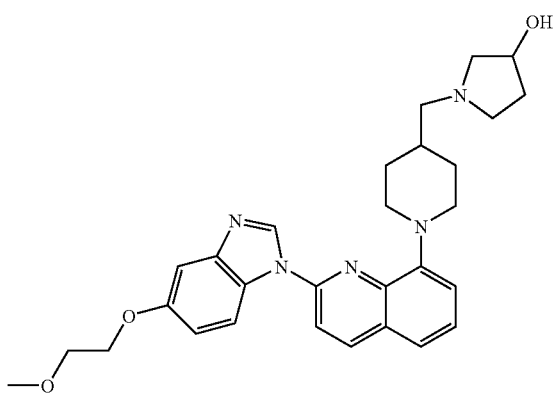

The same procedure that was used in example 108 was followed except that racemic 3-pyrrolidinol was used in the place of methylamine in example 108B to give the title compound 111.

C.I. m/z 502 [M+1]; $^1$H NMR (CD$_3$OD) δ 8.93 (s, 1H), 8.65 (d, J=8.7 Hz, 1H), 8.39 (d, J=8.7 Hz, 1H), 7.88 (d, J=8.7 Hz, 1H), 7.55 (m, 1H), 7.46 (m, 1H), 7.30 (dd, J=1.3, 7.5 Hz, 1H), 7.25 (d, J=2.1 Hz, 1H), 7.06 (m, 1H), 4.35 (m, 1H), 4.18 (m, 2H), 3.78 (m, 4H), 3.45 (s, 3H), 2.86 (m, 1H), 2.74 (m, 3H), 2.58 (m, 1H), 2.50 (m, 3H), 2.12 (m, 1H), 1.93 (m, 2H), 1.60–1.75 (m, 4H).

Example 112

C-(1-(2-[5-(2-Methoxy-ethoxy)-benzoimidazol-1-yl]-quinolin-8-yl}-piperidin-4-yl)-methylamine

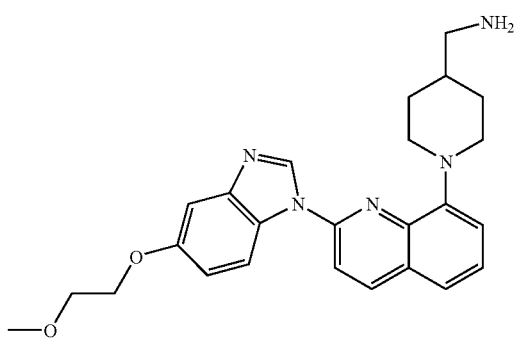

The same procedure that was used in example 108 was followed except that ammonium acetate was used in the place of methylamine in example 108B to give the title compound 112.

C.I. m/z 432 [M+1]; $^1$H NMR (CD$_3$OD) δ 8.91 (s, 1H), 8.61 (d, J=8.7 Hz, 1H), 8.37 (d, J=8.7 Hz, 1H), 7.85 (d, J=8.7 Hz, 1H), 7.52 (d, J=7.1 Hz, 1H), 7.45 (m, 1H), 7.29 (d, J=7.5 Hz, 1H), 7.23 (d, J=2.1 Hz, 1H), 7.04 (dd, J=2.5, 9.1 Hz, 1H), 4.17 (m, 2H), 3.79 (m, 4H), 3.44 (s, 3H), 2.65–2.80 (m, 4H), 1.89 (m, 2H), 1.60 (m, 3H).

Example 113

1-(2-[5-(2-Dimethylamino-ethoxy)-benzoimidazol-1-yl]-quinolin-8-yl}-4-methyl-piperidin-4-ol

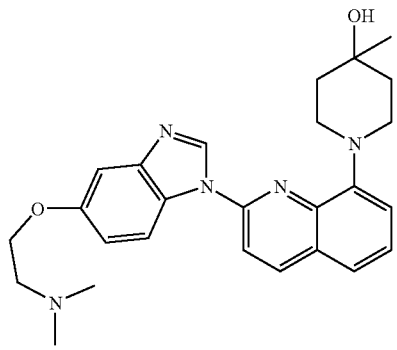

Example 113A

1-[8-(4-Hydroxy-4-methyl-piperidin-1-yl)-quinolin-2-yl]-1H-benzoimidazol-5-ol

1-[2-(5-Benzyloxy-benzoimidazol-1-yl)-quinolin-8-yl]-4-methyl-piperidin-4-ol 88 (535 mg, 1.15 mMol) was dissolved in 5 mL of anhydrous DCM under an atmosphere of dry N$_2$. The solution was then cooled to 0° C. after which time 32 µL of NEt$_3$ and 1.50 mL of a 1 M solution of dimethylbromoborane in DCM were added. The reaction mixture was allowed to warm up to ambient temperature and reacted at this temperature for ~2 hours. The mixture was then partitioned between iso-propanol/DCM (1882) and saturated aqueous NaHCO$_3$— The aqueous layer was extracted two more times with iso-propanol/DCM. The organic extracts were combined, dried over Na$_2$SO$_4$, filtered and concentrated under vacuum to give a yellow solid. The solid was chromatographed over flash silica gel eluting with MeOH/DCM/NH$_4$OH (4/195.8/0.2) to give 189 mg of the title compound 113A as yellow solid.

Example 113B

1-{2-[5-(2-Dimethylamino-ethoxy)-benzoimidazol-1-yl]-quinolin-8-yl}-4-methyl-piperidin-4-ol 1-[8-(4-Hydroxy-4-methyl-piperidin-1-yl]quinolin-2-yl]-1H-benzoimidazol-5-ol 113A (189 mg, 0.505 mMol), Cs$_2$CO$_3$ (592 mg, 1.81 mMol), sodium iodide (76 mg, 0.505 mMol) and (2-dimethylamino)ethyl chloride hydrochloride (87 mg, 0.61 mMol) were added to 2 mL of anhydrous DMF and the resulting mixture was heated to 80° C. under an atmosphere of dry N$_2$. The reaction was run for 48 hours after which time it was cooled to ambient temperature and concentrated under vacuum. The residue was chromatographed over flash silica gel eluting with a gradient starting from MeOH/DCM (397) to MeOH/DCM (892) then switched to MeOH/DCM/NH$_4$OH (891.80.2) to give 67 mg of the title compound 113 as a yellow oil.

C.I. m/z 446 [M+1]; $^1$H NMR (CDCl$_3$): δ 8.64 (s, 1H), 8.33 (d, J=8.7 Hz, 1H), 8.29 (d, J=8.7 Hz, 1H), 7.66 (d, J=8.7 Hz, 1H); 7.46 (m, 2H), 7.33 (d, J=2.5 Hz, 1H), 7.28 (dd, J=2.9, 5.8 Hz, 1H), 7.08 (dd, J=2.5, 9.1 Hz, 1H), 4.20 (m, 2H), 3.60 (m, 2H), 3.26 (m, 2H), 2.86 (m, 2H), 2.41 (s, 6H), 2.10 (m, 2H), 1.85 (m, 2H), 1.38 (s, 3H).

Example 114

1-{2-[5-(2-Dimethylamino-ethoxy)-benzoimidazol-1-yl]-quinolin-8-yl}-piperidin-4-ol

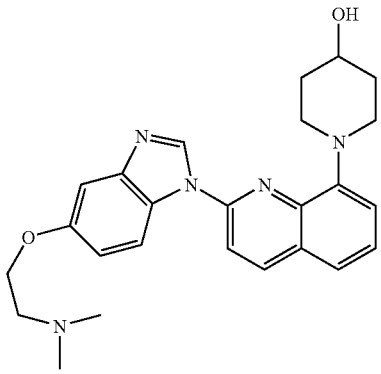

Example 114A

1-[2-(5-Benzyloxy-benzoimidazol-1-yl)-quinolin-8-yl]-piperidin-4-ol

1-[2-(5-Benzyloxy-benzoimidazol-1-yl)-quinolin-8-yl]-piperidin-4-one 88A (790 mg, 1.76 mMol) was dissolved in 6 mL of MeOH under an atmosphere of dry N$_2$. To this solution was added sodium borohydride (66 mg, 1.76 mMol) and the reaction mixture was stirred at ambient temperature overnight. The mixture was then concentrated under vacuum and the resulting residue was partitioned between DCM and 0.1 N aqueous NaOH. The DCM layer was saved and washed again with 0.1 N aqueous NaOH and then two times with brine. The DCM layer was dried over Na$_2$SO$_4$, filtered and concentrated under vacuum to give a yellow solid. The solid was purified via flash silica gel chromatography eluting with MeOH/DCM/NH$_4$OH (1.5/98.30.2) to give 690 mg of the title compound 114A.

Example 114B

1-[8-(4-Hydroxy-piperidin-1-yl)-quinolin-2-yl]-1H-benzoimidazol-5-ol

1-[2-(5-Benzyloxy-benzoimidazol-1-yl)-quinolin-8-yl]-piperidin-4-ol 114A (440 mg, 0.976 mMol) was suspended in 10 mL of DCE under an atmosphere of dry N$_2$. To this heterogeneous solution was added 5 mL of a 1 M solution of boron tribromide in DCM. The reaction mixture was stirred for 1 hour at ambient temperature and then heated to reflux and reacted at that temperature for 2 hours. The reaction mixture was then cooled to ambient temperature and was added to ice water. The pH of the resulting reaction mixture was adjusted to 8 with the addition of Na$_2$CO$_3$ and the solution was extracted 5 times with isopropanol/DCM (1882). The organic extracts were combined and dried over Na$_2$SO$_4$, filtered and concentrated under vacuum to give a yellow solid. The solid was purified via flash silica gel chromatography eluting with MeOH/DCM/NH$_4$OH (396.80.2) to give 201 mg of the title compound 114B.

Example 114C 1-(2-[5-(2-Dimethylamino-ethoxy)-benzoimidazol-1-yl]-quinolin-8-yl}-piperidin-4-ol 1-[8-(4-Hydroxy-piperidin-1-yl)-quinolin-2-yl]-1H-benzoimidazol-5-ol 114B (201 mg, 0.558 mMol), Cs$_2$CO$_3$ (400 mg, 1.22 mMol), sodium iodide (84 mg, 0.559 mMol) and (2-dimethylamino)ethyl chloride hydrochloride (88 mg, 0.62 mMol) were added to 5 mL of anhydrous DMF and the resulting mixture was heated to 65° C. under an atmosphere of dry N$_2$. After one hour, the reaction temperature was increased to 100° C. After reacting at 100° C. for 1 hour, an additional 44 mg of (2-dimethylamino)ethyl chloride hydrochloride and 200 mg of Cs$_2$CO$_3$ were added. After reacting overnight at 100° C., the reaction mixture was cooled to ambient temperature and concentrated under vacuum. The resulting residue was partitioned between DCM and aqueous 0.1 N NaOH. The aqeuous layer was extracted 2 more times with DCM and the organic extracts were combined, dried over Na$_2$SO$_4$, filtered and concentrated under vacuum to give a yellow oil. The residue was purified via High Pressure Liquid Chromatography (C-8 reverse phase; linear gradient from 0.1% TFA in water to 0.1% TFA in water/acetonitrile (5050) over 8 minutes) to give 43 mg of the title compound 114 as a yellow oil.

C.I. m/z 432 [M+1]; $^1$H NMR (CD$_3$OD) δ8.92 (s, 1H), 8.68 (d, J=9.1 Hz, 1H), 8.38 (d, J=9.1 Hz, 1H), 7.87 (d, J=9.1 Hz, 1H), 7.52 (dd, J=2.3, 7.9 Hz, 1H), 7.45 (m, 1H), 7.30 (dd, J=1.2, 7.5 Hz, 1H), 7.25 (d, J=2.1 Hz, 1H), 7.13 (m, 1H), 4.17 (m, 2H), 3.80 (m, 1H), 3.70 (m, 2H), 2.91 (m, 2H), 2.81 (m, 2H), 2.37 (s, 6H), 2.05 (m, 2H), 1.92 (m, 2H).

Example 115

S,S-(1-(4-(2-[5-(2-Methoxy-ethoxy)-benzoimidazol-1-yl]-quinolin-8-yl}-benzyl)-trans-pyrrolidine-3,4-diol)

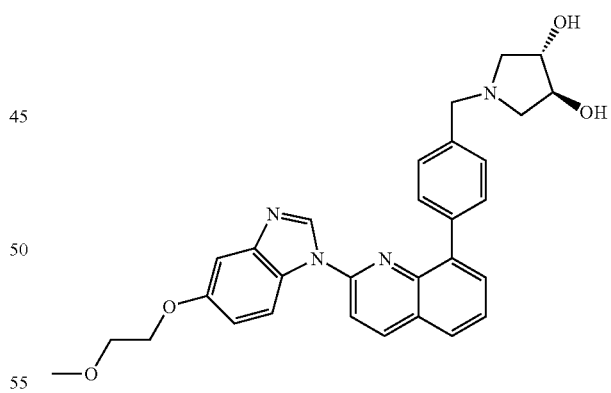

The same procedure that used for Example 98 was followed with the exception S,S-trans-pyrrolidine-3,4-diol was used in the place of R,R-trans-pyrrolidine-3,4-diol to give the title compound 115.

C.I. m/z 511 [M+1]; $^1$H NMR (CD$_3$OD) δ 8.95 (s, 1H), 8.49 (d, J=9.1 Hz, 1H), 8.04 (d, J=9.1 Hz, 1H), 7.98 (d, J=9.1 Hz, 1H), 7.94 (m, 1H), 7.761 (m, 1H), 7.65 (m, 1H), 7.62 (d, J= 8.3 Hz, 2H), 7.51 (d, J=8.3 Hz, 2H), 7.17 (d, J=2.5 Hz, 1H), 6.74 (dd, J=2.5, 9.1 Hz, 1H), 4.13 (m, 4H), 3.88 (d J=12.5 Hz, 1H), 3.82 (d, J=12.5 Hz, 1H), 3.77 (m, 2H), 3.44 (s, 3H), 3.11 (m, 2H), 2.67 (m, 2H).

Example 116

4-{2-[5-(3-Amino-propoxy)-benzoimidazol-1-yl]-quinolin-8-yl}-phenol

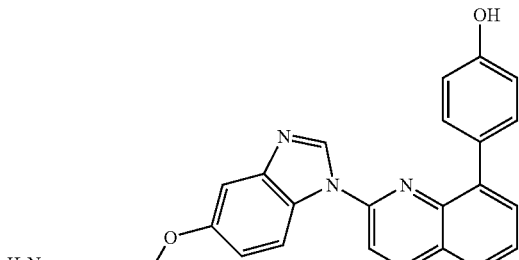

Example 116A

Trifluoro-methanesulfonic acid 2-(5-hydroxy-benzoimidazol-1-yl)-quinolin-8-yl ester Trifluoro-methanesulfonic acid 2-[5-(2-methoxy-ethoxy]benzoimidazol-1-yl]-quinolin-8-yl ester 77E (2.00 g, 4.28 mMol) was suspended in 20 mL of anydrous DCM under an atmosphere of dry $N_2$. To this heterogeneous solution was added 12.9 mL of a solution of 1 M borontribromide in DCM and the resulting mixture was stirred at ambient temperature for 24 hours. The reaction mixture was then poured into ice water. The resulting heterogeneous mixture was neutralised with the addition of $NaHCO_3$ and then partitioned between isopropanol/DCM (1882) and aqueous saturated $NaHCO_3$. The organic layer was washed again aqueous saturated $NaHCO_3$, dried over $Na_2SO_4$, filtered, concentrated under vacuum to give 890 mg of a brownish yellow solid as the title compound 116A.

Example 116B

Trifluoro-methanesulfonic acid 2-[5-(3-tert-butoxy-carbonylamino-propoxy)-benzoimidazol-1-yl]-quinolin-8-yl ester (3-Hydroxy-propyl)-carbamic acid tert-butyl ester (180 mg, 1.03 mMol) was dissolved in 7 mL of anhydrous THF was under an atmosphere of dry $N_2$. Trifluoro-methanesulfonic acid 2-(5-hydroxy-benzoimidazol-1-yl)-quinolin-8-yl ester 116A (420 mg, 1.03 mMol) and triphenyl phosphine (538 mg, 2.05 mMol) were added to the solution resulting in a brown heterogen ous solution. A solution of 320 μL of diethyl azodicarboxylate dissolved in 3 mL of anhydrous THF was then added. After ~30 minutes, the reaction mixtured was concentrated under vacuum and the residue was chromatographed on flash silica gel eluting with MeOH/DCM/NH$_4$OH (198.80.2) to give 184 mg of the title compound 116B.

Example 116C

[3-(1-{8-[4-(Tetrahydro-pyran-2-yloxy)-phenyl]-quinolin-2-yl}-1H-benzoimidazol-5-yloxy)-propyl]-carbamic acid tert-butyl ester Trifluoro-methanesulfonic acid 2-[5-(3-tert-butoxycarbonylamino-propoxy)-benzoimidazol-1-yl]-quinolin-8-yl ester 116B (144 mg, 0.254 mMol), was dissolved in 1.0 mL of 1,4-dioxane under an atmosphere of dry $N_2$. To this solution were added 4-hydroxyphenyl boronic acid tertrahydropyranyl ether (67 mg, 0.31 mMol), potassium phosphate (108 mg, 0.508 mMol) and tetrakis(triphenylphosphine)palladium (0) (15 mg, 0.013 mMol). The reaction mixture was heated to 100° C. and reacted overnight at this temperature in a seal tube. The reaction mixture was then cooled to ambient temperature, concentrated under vacuum and the residue was taken up in DCM. The resulting heterogeneous solution was filtered and the filter cake was washed several times with DCM/MeOH (~1:1). The filtrates were combined and concentrated under vacuum and the resulting residue was chromatographed on flash silica gel eluting with MeOH/DCM/NH$_4$OH (1.5/98.3/0.2) to give 128 mg of the title compound 116C.

Example 116D

4-{2-[5-(3-Amino-propoxy)-benzoimidazol-1-yl]-quinolin-8-yl}-phenol

[3-(1-{8-[4-(Tetrahydro-pyran-2-yloxy)-phenyl]-quinolin-2-yl}-1H-benzoimidazol-5-yloxy)-propyl]-carbamic acid tert-butyl ester 116C (128 mg, 0.215 mMol) was dissolved in 1 mL of TFA under an atmosphere of dry $N_2$ and was then stirred for 10 minutes. The reaction mixture was concentrated under vacuum and the resulting residue was partitioned between isopropanol/DCM (18/82) and aqueous saturated NaHCO$_3$. The organic layer was dried over Na$_2$SO$_4$, filtered and concentrated under vacuum to give a brown oil. The oil was purified via High Pressure Liquid Chromatography (C-8 reverse phase; linear gradient from 0.01% HCl in water to 0.01% HCl acetonitrile (over 15 minutes) to give 19 mg of the title compound 116 as a white solid which was further purified by recrystallizing from EtOH to give 9 mg of the title compound as the bis-HCl salt.

C.I. m/z 411 [M+1]; $^1$H NMR (CD$_3$OD) δ 9.75 (s, 1H), 8.61 (d, J=8.7 Hz, 1H), 8.19 (d, J=9.1 Hz, 1H), 8.03 (d, J=8.7 Hz, 1H), 7.95 (m, 1H), 7.80 (d, J=6.2 Hz, 1H), 7.70 (m, 1H), 7.45 (d, J=8.3 Hz, 2H), 7.30 (m, 1H), 6.95 (m, 1H), 6.94 (d, J=8.3 Hz, 2H), 4.20 (m, 2H), 3.29 (m, 2H), 2.20 (m, 2H).

Example 117

4-{2-[5-(3-Dimethylamino-propoxy)-benzoimidazol-1-yl]-quinolin-8-yl)-phenol

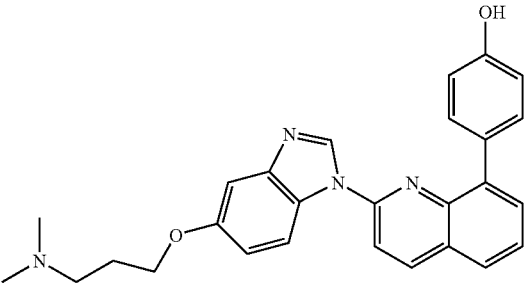

The same procedure that was used in example 4 was followed except that 4-{2-[5-(3-aminopropoxy)-benzoimidazol-1-yl]-quinolin-8-yl}-phenol 116 was used in the place of 1-[2-(5-methoxy-benzoimidazol-1-yl)-quinolin-8-yl]-piperidin-4-ylamine to give the title compound 117.

C.I. m/z 439 [M+1]; $^1$H NMR (CD$_3$OD) δ 8.82 (s, 1H), 8.33 (d, J=8.7 Hz, 1H), 7.99 (d, J=9.1 Hz, 1H), 7.80 (m, 2H), 7.66 (m, 1H), 7.52 (m, 1H), 7.39 (d, J=8.3 Hz, 2H), 7.07 (d, J=2.5 Hz, 1H), 6.90 (d, J=8.3 Hz, 2H), 6.65 (dd, J=2.5, 9.1 Hz, 1H), 3.99 (m, 2H), 2.75 (m, 2H), 2.46 (s, 6H), 2.00 (m, 2H).

Example 118

1-[2-(5-Phenyl-benzoimidazol-1-yl)-quinolin-8-yl]-piperidin-4-ylamine

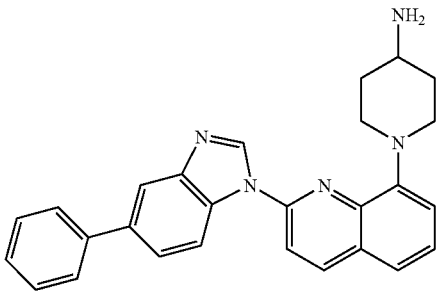

Example 118A

Trifluoro-methanesulfonic acid 1-[8-(4-tert-butoxy-carbonylamino-piperidin-1-yl)-quinolin-2-yl]-1H-benzoimidazol-5-yl ester {1-[2-(5-Hydroxy-benzoimidazol-1-yl)-quinolin-8-yl]-piperidin-4-yl}-carbamic acid tert-butyl ester 3A (2.37 g, 5.17 mMol) was dissolved in 35 mL of anhydrous THF under an atmosphere of dry $N_2$. To this solution were added triethylamine (790 μL, 5.68 mMol) followed by N-phenyl-bis(trifluoromethanesulfonamide) (2.02 g, 5.68 mMol). The reaction mixture was reacted at this temperature for 2 days. The yellow precipitate was collected via suction filtration, washed with isopropylether and dried under vacuum to give 1.48 g of the title compound as a yellow solid.

Example 118B (1-[2-(5-Phenyl-benzoimidazol-1-yl)-quinolin-8-yl]-piperidin-4-yl}-carbamic acid tert-butyl ester Trifluoro-methanesulfonic acid 1-[8-(4-tert-butoxycarbonylamino-piperidin-1-yl)-quinolin-2-yl]1H-benzoimidazol-5-yl ester 118A (150 mg, 0.253 mMol), was dissolved in 2.0 mL of 1,4-dioxane under an atmosphere of dry $N_2$. To this solution were added phenylboronic acid (46 mg, 0.38 mMol), potassium phosphate (161 mg, 0.759 mMol) and tetrakis(triphenylphosphine)palladium (0) (15 mg, 0.013 mMol). The reaction mixture was heated to 100° C. and reacted overnight at this temperature. The reaction mixture was then cooled to ambient temperature, concentrated under vacuum and the residue was partitioned between DCM and aqueous saturated $NaHCO_3$. The DCM layer was washed again with aqueous saturated $NaHCO_3$, dried over $Na_2SO_4$, filtered and concentrated under vacuum to give a yellow oil. The resulting oil was chromatographed on flash silica gel eluting with EtOAc/Hexanes (70:30) to give 121 mg of the title compound 118B.

Example 118C

1-[2-(5-Phenyl-benzoimidazol-1-yl)-quinolin-8-yl]-piperidin-4-ylamine

{1-[2-(5-Phenyl-benzoimidazol-1-yl)-quinolin-8-yl]-piperidin-4-yl}-carbamic acid tert-butyl ester 118B (121 mg, 0.233 mMol) was dissolved in 0.50 mL of TFA under an atmosphere of dry $N_2$ and was then stirred for 45 minutes. The reaction mixture was concentrated under vacuum and the resulting residue was partitioned between DCM and aqueous 1 N NaOH. The DCM layer was washed again with concentrated under vacuum and the resulting residue was partitioned between DCM and aqueous, dried over $Na_2SO_4$, filtered and concentrated under vacuum to give a yellow oil as the title compound 118. Compound 118 was dissolved in DCM and then 3 mL of 1 N HCl in ethyl ether was added to the mixture. The resulting precipitate was collected via suction filtration and dried under vacuum to give 91 mg of the title compound 118 as the bis-HCl salt.

C.I. m/z 420 [M+1]; $^1$H NMR ($CD_3OD$) δ 10.49 (s, 1H), 8.84 (d, J=8.7 Hz, 1H), 8.80 (d, J=9.1 Hz, 1H), 8.27 (d, J=8.7 Hz, 1H), 8.16 (m, 2H), 7.91 (m, 1H), 7.80 (m, 4H), 7.53 (m, 2H), 7.44 (m, 1H), 4.12 (m, 2H), 3.50 (m, 1H), 3.38 (m, 2H), 2.36 (m, 4H).

Example 119

1-[2-(5-Pyridin-4-yl-benzoimidazol-1-yl)-quinolin-8-yl]-piperidin-4-ylamine

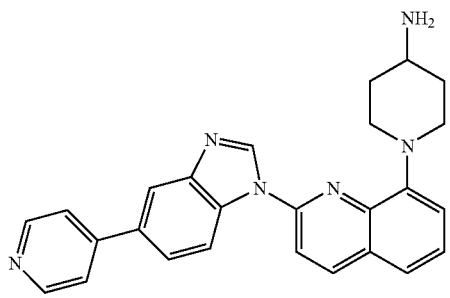

The same procedure that was used in example 118 was followed except that 4-pyridylboronic acid was used in the place of phenylboronic acid in step 118B to give the title compound 119 as the free base.

C.I. m/z 421 [M+1]; $^1$H NMR ($CD_3OD$) δ9.00 (s, 1H), 8.80 (d, J=8.5 Hz, 1H), 8.52 (d, J=6.0 Hz, 2H), 8.33 (d, J=8.7 Hz, 1H), 8.03 (s, 1H), 7.84 (m, 2H), 7.72 (d, J=6.0 Hz, 2H), 7.44 (m, 2H), 7.27 (d, J=8.5 Hz, 1H), 3.78 (m, 2H), 2.84 (m, 1H), 2.76 (m, 2H), 1.99 (m, 2H), 1.85 (m, 2H).

Example 120

1-(2-[5-(3-Methoxy-phenyl)-benzoimidazol-1-yl]-quinolin-8-yl}-piperidin-4-ylamine

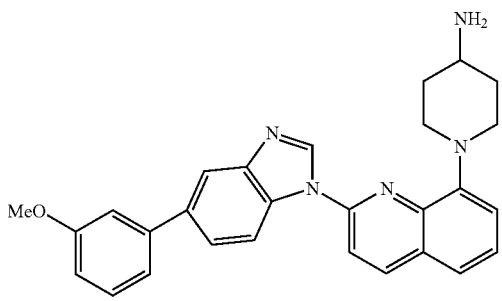

The same procedure that was used in example 118 was followed except that (3-methoxyphenyl)boronic acid was used in the place of phenylboronic acid in example 118B to give the title compound 120 as the free base.

C.I. m/z 450 [M+1]; $^1$H NMR ($CDCl_3$) δ 8.74 (s, 1H), 8.46 (d, J=8.5 Hz, 1H), 8.30 (d, J=8.7 Hz, 1H), 8.08 (d, J=1.3 Hz, 1H), 7.69 (d, J=8.7 Hz, 1H), 7.66 (dd, J=1.7, 8.5 Hz,

1H), 7.46 (m, 2H), 7.38 (m, 1H), 7.22–28 (m, 3H), 6.90 (m, 1H), 3.89 (m, 2H), 3.87 (s, 3H), 2.90 (m, 3H), 2.05 (m, 2H), 1.83 (m, 2H).

Example 121

1-[2-(5-Pyridin-3-yl-benzoimidazol-1-yl)-quinolin-8-yl]-piperidin-4-ylamine

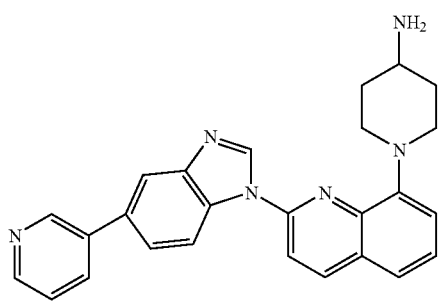

The same procedure that was used in example 77 was followed except that (1-[2-(5-phenyl-benzoimidazol-1-yl)-quinolin-8-yl}-carbamic acid tert-butyl ester 118B was used in the place of trifluoro-methanesulfonic acid 2-[5-(2-methoxy-ethoxy)-benzoimidazol-1-yl]quinolin-8-yl ester 77E in example 77F. The resulting compound was deprotected using the procedure outlined in example 118C to give the title compound 121 as the free base.

C.I. m/z 421 [M+1]; $^1$H NMR (CD$_3$OD) δ 9.32 (s, 1H), 9.27 (s, 1H), 8.93 (m, 1H), 8.87 (d, J=8.7 Hz, 1H), 8.82 (d, J=5.7 Hz, 1H), 8.55 (d, J=8.9 Hz, 1H), 8.24 (s, 1H), 8.13 (m, 1H), 8.03 (m, 2H), 7.70 (d, J=8.1 Hz, 1H), 7.57 (m, 1H), 7.47 (d, J=7.7 Hz, 1H), 4.01 (m, 2H), 3.38 (m, 1H), 3.05 (m, 2H), 2.13–2.24 (m, 4H).

Example 122

1-(2-[5-(6-Methoxy-pyridin-3-yl)-benzoimidazol-1-yl]-quinolin-8-yl)-piperidin-4-ylamine

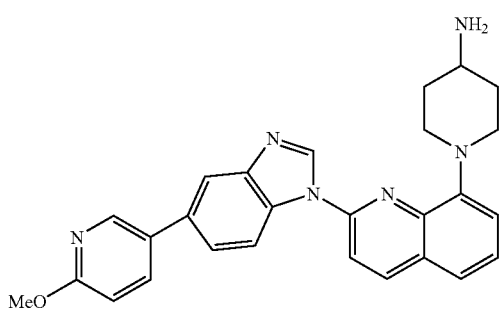

The same procedure that was used in example 118 was followed except that 2-methoxy-5-pyridineboronic acid was used in the place of phenylboronic acid in example 118B to give the title compound 122 as the HCl salt.

C.I. m/z 451 [M+1]$^1$H NMR (DMSO) δ9.27 (s, 1H), 9.02 (d, J=8.7 Hz, 1H), 8.61 (d, J=1.5 Hz, 1H), 8.57 (d, J=9.1 Hz, 1H), 8.19 (d, J=8.7 Hz, 1H), 8.15 (m, 1H), 8.07 (s, 1H), 8.02 (d, J=8.7 Hz, 1H), 7.63 (d, J=7.9 Hz, 1H), 7.50 (m, 1H), 7.31 (d, J=7.5 Hz, 1H), 6.92 (d, J=8.3 Hz, 1H), 3.89 (s, 3H), 3.87 (m, 2H), 3.22 (m, 1H), 2.79 (m, 2H), 2.07 (m, 4H).

Example 123

1-{2-[5-(4-Aminomethyl-phenyl)-benzoimidazol-1-yl]-quinolin-8-yl}-piperidin-4-ylamine

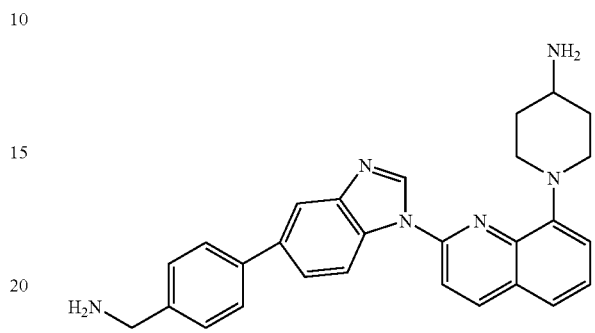

The same procedure that was used in example 118 was followed except that the HCl salt of 4-aminomethylphenylboronic acid was used in the place of phenylboronic acid in example 118B and 2.5 equivalents of N,N-diisopropylethylamine was added to the reaction mixture to give the title compound 123 as the HCl salt.

C.I. m/z 449 [M+1]; $^1$H NMR (CD$_3$OD) δ9.10 (s, 1H), 8.71 (d, J=8.7 Hz, 1H), 8.55 (d, J=8.7 Hz, 1H), 8.04 (m, 2H), 7.87 (dd, J=1.7, 8.7 Hz, 1H), 7.83 (m, 2H), 7.66 (d, J=7.1 Hz, 1H), 7.58 (m, 3H), 7.40 (m, 1H), 4.18 (s, 2H), 4.03 (m, 2H), 3.34 (m, 1H), 2.95 (m, 2H), 2.20 (m, 2H), 2.10 (m, 2H).

Example 124

4-(1-[8-(4-Amino-piperidin-1-yl)-quinolin-2-yl]-1H-benzoimidazol-5-yl]benzoic acid methyl ester

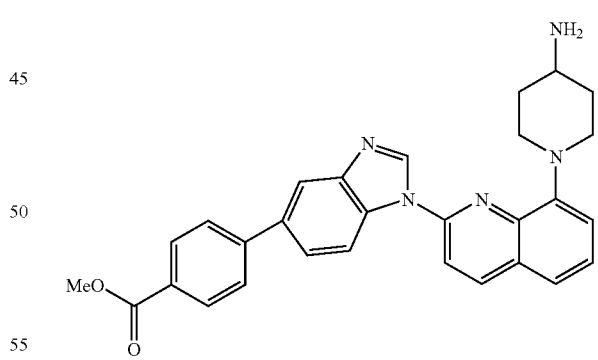

The same procedure that was used in example 118 was followed except that 4-methoxycarbonylphenylboronic acid was used in the place of phenylboronic acid in example 118B to give the title compound 124 as the HCl salt.

C.I. m/z 478 [M+1]; $^1$H NMR (CD$_3$OD) δ 9.08 (s, 1H), 8.79 (d, J=8.7 Hz, 1H), 8.52 (d, J=8.7 Hz, 1H), 8.11 (m, 2H), 8.07 (d, J=1.3 Hz, 1H), 8.02 (d, J=9.1 Hz, 1H), 7.87 (m, 1H), 7.83 (m, 2H), 7.65 (m, 1H), 7.55 (m, 1H), 7.39 (m, 1H), 4.03 (m, 2H), 3.93 (s, 3H), 3.33 (m, 1H), 2.93 (m, 2H), 2.19 (m, 2H), 2.11 (m, 2H).

Example 125

4-{1-[8-(4-Amino-piperidin-1-yl)-quinolin-2-yl]-1H-benzoimidazol-5-yl}-phenol

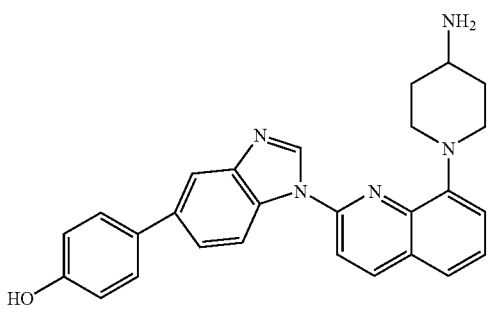

The same procedure that was used in example 118 was followed except that 4-hydroxyphenylboronic acid tetrahydropyranyl ether was used in the place of phenylboronic acid in example 118B to give the title compound 125 as the HCl salt.

C.I. m/z 436 [M+1]; $^1$H NMR (CD$_3$OD) δ 9.20 (s, 1H), 8.72 (d, J=8.3 Hz, 1H), 8.49 (d, J=8.7 Hz, 1H), 7.98 (d, J=8.7 Hz, 1H), 7.90 (s, 1H), 7.79 (m, 1H), 7.64 (d, J=7.5 Hz, 1H), 7.53 (m, 3H), 7.39 (d, J=7.9 Hz, 1H), 6.88 (m, 2H), 4.03 (m, 2H), 3.34 (m, 1H), 2.93 (m, 2H), 2.19 (m, 2H), 2.10 (m, 2H).

Example 126

2-(5-Methoxy-benzoimidazol-1-yl)-quinoline-8-carboxylic acid methyl ester

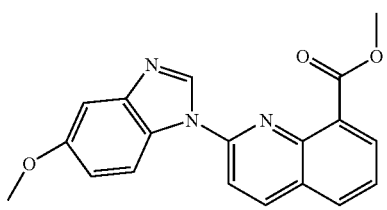

Trifluoro-methanesulfonic acid 2-(5-methoxy-benzoimidazol-1-yl)-quinolin-8-yl ester 1E (1.0 g, 2.3 mMol), palladium acetate (16 mg, 0.07 mMol), 1,3-bis(diphenylphosphine)propan (30 mg, 0.07 mMol) and triethylamine (730 µL, 5.20 mMol) were dissolved in a solution of 8 mL of DMF and 4 mL of MeOH in a Paar bottle. The reaction vessel was evacuated under vacuum and then filled with carbon monoxide (50 psi). The reaction mixture was shaken for 24 hours after which time it was concentrated under vacuum. The resulting residue was partitioned between DCM and aqueous saturated NaHCO$_3$. The DCM layer was then washed again with aqueous saturated NaHCO$_3$ and then with brine, dried over Na$_2$SO$_4$, filtered and concentrated under vacuum to give a light tan foam. The foam was chromatographed on flash silica gel eluting with MeOH/DCM (1:99) to give 770 mg of the title compound 126.

C.I. m/z 334 [M+]; $^1$H NMR (CDCl$_3$) δ 8.63 (d, J=8.9 Hz, 1H), 8.56 (s, 1H), 8.25 (d, J=8.9 Hz, 1H), 8.10 (dd, J=1.5, 7.2 Hz, 1H), 7.90 (dd, J=1.5, 8.1 Hz, 1H), 7.64 (d, J=8.9 Hz, 1 H), 7.51 (m, 1H), 7.27 (d, J=2.5 Hz, 1H), 7.07 (dd, J=2.5, 9.1 Hz, 1H), 4.04 (s, 3H), 3.87 (s, 3H).

Example 127

2-[5-(2-Methoxy-ethoxy)-benzoimidazol-1-yl]-quinoline-8-carboxylic acid methyl ester

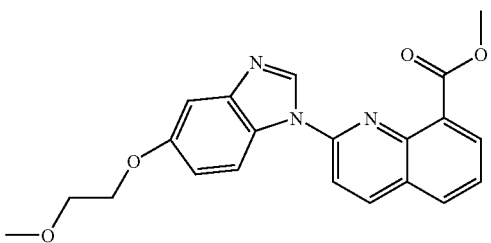

The same procedure that was used in example 126 was followed except that trifluoromethanesulfonic acid 2-[5-(2-methoxy-ethoxy)-benzoimidazol-1-yl]-quinolin-8-yl ester 77E was used in the place of trifluoro-methanesulfonic acid 2-(5-methoxy-benzoimidazol-1-yl)-quinolin-8-yl ester 1E to give the title compound 127 as a white solid.

C.I. m/z 378 [M+1]; $^1$H NMR (DMSO) δ 9.17 (s, 1H), 8.73 (d, J=9.1 Hz, 1H), 8.64 (d, J=9.1 Hz, 1H), 8.23 (d, J=8.7 Hz, 1H), 8.18 (m, 1H), 8.05 (m, 1H), 7.64 (m, 1H), 7.29 (d, J=2.5 Hz, 1H), 7.07 (dd, J=2.5, 9.1 Hz, 1H), 4.14 (m, 2H), 4.00 (s, 3H), 3.67 (m, 2H), 3.31 (s, 3H).

Example 128

2-(5-Methoxy-benzoimidazol-1-yl)-quinoline-8-carboxylic acid (2-dimethylamino-ethyl)-amide

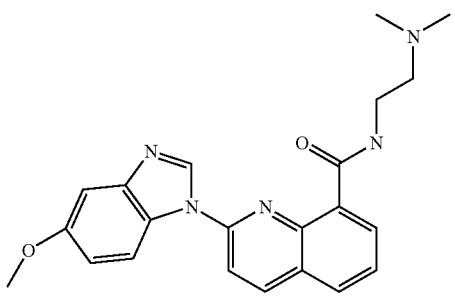

2-(5-Methoxy-benzoimidazol-1-yl)-quinoline-8-carboxylic acid methyl ester 126 (166.7 mg, 0.500 mMol) was dissolved in 2 mL of anhydrous DCM under an atmosphere of dry N$_2$. In a separate flask, N,N-dimethylethylenediamine (2.20 mL, 20 mMol) was dissolved in 20 mL of anhydrous DCM under an atmosphere of dry N$_2$. To this solution was slowly added 10 mL a solution of 2.0 M trimethylaluminum in toluene. The solution was stirred for 30 minutes after which time 1 mL of this solution was added to the solution containing compound 126. The temperature of the reaction mixture was raised to 40° C. and reacted over night after which time 1 mL of water was slowly added to quench the reaction. The resulting mixture was partitioned between DCM and aqueous 0.1 N NaOH. The DCM layer was washed again with aqueous 0.1 N NaOH and then with brine. The DCM layer was then dried over Na₂SO₄, filtered and concentrated under vacuum. The resulting residue was dissolved in 2 mL of DCM. To this solution was added 1.5 mL of a solution of HCl in ethyl ether which caused an immediate precipitate to form. The precipitate was collected via suction filtration, washed with ethyl ether, and dried under vacuum to give 165 mg of the bis-HCl salt of the title compound 128 as a white solid.

C.I. m/z 390 [M+1]; ¹H NMR (CD₃OD) δ 10.22 (s, 1H), 8.85 (d, J=8.9 Hz, 1H), 8.54 (d, J=9.0 Hz, 1H), 8.49 (dd, J=1.5, 7.2 Hz, 1H), 8.30 (dd, J=1.4, 8.1 Hz, 1H), 8.18 (d, J=8.9 Hz, 1H), 7.86 (m, 1H), 7.42 (m, 2H), 3.97 (s, 3H), 3.90 (m, 2H), 3.44 (m, 2H), 2.96 (s, 6H).

Example 129

2-(5-Cyclopropylmethoxy-benzoimidazol-1-yl)-quinoline-8-carboxylic acid methyl ester

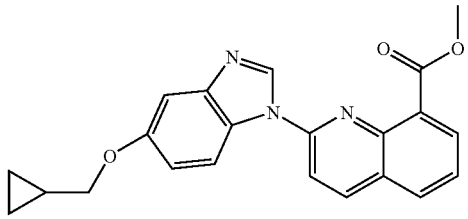

The same procedure that was used in example 126 was followed except that 4-cyclopropylmethoxy-2-nitro-phenylamine 52A was used in the place of 4-methoxy-2-nitroaniline in example 1B to give the titled compound 129.

C.I. m/z 374 [M+1]; ¹H NMR (CDCl₃) δ8.65 (d, J=9.1 Hz, 1H), 8.60 (s, 1H), 8.34 (d, J=8.7 Hz, 1H), 8.14 (m, 1H), 7.97 (m, 1H), 7.72 (d, J=9.1 Hz, 1H), 7.57 (m, 1H), 7.29 (d, J=2.5 Hz, 1H), 7.10 (m, 1H), 4.09 (s, 3H), 3.89 (d, J=7.1 Hz, 2H), 1.32 (m, 1H), 0.66 (m, 2H), 0.38 (m, 2H).

Example 130

[2-(5-Cyclopropylmethoxy-benzoimidazol-1-yl)-quinolin-8-yl]-pyrrolidin-1-yl-methanone

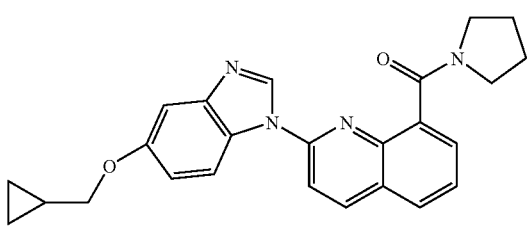

The same procedure that was used in example 128 was followed except that 2-(5-cyclopropylmethoxy-benzoimidazol-1-yl)-quinoline-8-carboxylic acid methyl ester 129 was used in the place of 2-(5-methoxy-benzoimidazol-1-yl]quinoline-8-carboxylic acid methyl ester 126 and pyrrolidine was used in the place of N,N-dimethylethylenediamine to give the title compound 130 as a white solid.

C.I. m/z 413 [M+1]; ¹H NMR (CDCl₃) δ8.58 (s, 1H), 8.51 (d, J=9.1 Hz, 1H), 8.26 (d, J=9.1 Hz, 1H), 7.80 (d, J=7.9 Hz, 1H), 7.76 (d, J=7.1 Hz, 1H), 7.67 (d, J=8.7 Hz, 1H), 7.52 (m, 1H), 7.25 (d, J=2.1 Hz, 1H), 7.07 (m, 1H), 3.92 (m, 1H), 3.88 (d, J=7.1 Hz, 2H), 3.85 (m, 1H), 3.19 (m, 1H), 3.10 (m, 1H), 1.95 (m, 2H), 1.75 (m, 2H), 1.32 (m, 1H), 0.67 (m, 2H), 0.39 (m, 2H).

Example 131

[2-(5-Cyclopropylmethoxy-benzoimidazol-1-yl)-quinolin-8-yl]-morpholin-4-yl-methanone

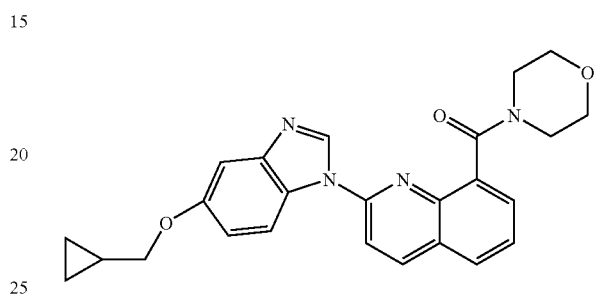

The same procedure that was used in example 128 was followed except that 2-(5-cyclopropylmethoxy-benzoimidazol-1-yl)-quinoline-8-carboxylic acid methyl ester 129 was used in the place of 2-(5-methoxy-benzoimidazol-1-yl)-quinoline-8-carboxylic acid methyl ester 126 and morpholine was used in the place of N,N-dimethylethylenediamine to give the title compound 131 as a white solid.

C.I. m/z 429 [M+1]

Example 132

[2-(5-Cyclopropylmethoxy-benzoimidazol-1-yl)-quinolin-8-yl]-piperidin-1-yl-methanone

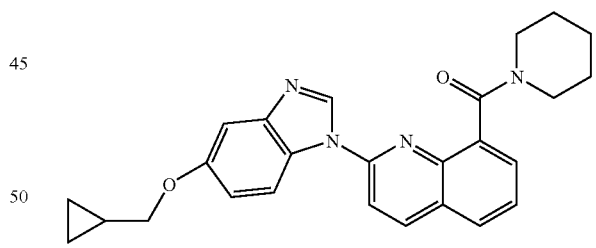

The same procedure that was used in example 128 was followed except that 2-(5-cyclopropylmethoxy-benzoimidazol-1-yl]quinoline-8-carboxylic acid methyl ester 129 was used in the place of 2-(5-methoxy-benzoimidazol-1-yl)-quinoline-8-carboxylic acid methyl ester 126 and piperdine was used in the place of N,N-dimethylethylenediamine to give the title compound 132 as a yellow solid.

C.I. m/z 427 [M+1]; ¹H NMR (CDCl₃) δ 8.61 (s, 1H), 8.49 (d, J=9.1 Hz, 1H), 8.31 (d, J=9.1 Hz, 1H), 7.85 (d, J=7.9 Hz, 1H), 7.72 (m, 2H), 7.56 (m, 1H), 7.29 (d, J=2.5 Hz, 1H), 7.09 (m, 1H), 4.09 (m, 1H), 3.88 (d, J=6.7 Hz, 2H), 3.78 (m, 1H), 3.13 (m, 2H), 1.20–1.80 (m, 7H), 0.66 (m, 2H), 0.39 (m, 2H).

Example 133

(3-Amino-pyrrolidin-1-yl)-[2-(5-cyclopropyl-methoxy-benzoimidazol-1-yl)-quinolin-8-yl]methanone

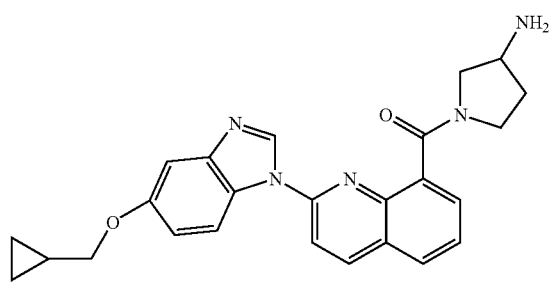

Example 133A

4-Cyclopropylmethoxy-2-nitro-phenylamine

4-Amino-3-nitrophenol (26.00 g, 165.5 mMol) was dissolved in 200 mL of anhydrous DMF under an atmosphere of dry $N_2$. The reaction mixture was then cooled to 0° C. and to this mixture was added $Cs_2CO_3$ (64.7 g, 199 mMol), and cyclopropyl methane bromide (17.7 mL, 182 mMol). After stirring for 15 minutes, the reaction mixture was then warmed up to ambient temperature and then stirred overnight. The reaction mixture is then poured into 800 mL of water. The precipitate was collected via suction filtration and partitioned between DCM and aqueous 0.1 N NaOH. The DCM layer was saved and washed again aqueous 0.1 N NaOH, then with brine, dried over $Na_2SO_4$, filtered and concentrated under vacuum to give 31.52 g of 4-cyclopropylmethoxy-2-nitro-phenylamine 133A as an orange solid.

Example 133B

{1-[2-(5-Cyclopropylmethoxy-benzoimidazol-1-yl)-quinoline-8-carbonyl]-pyrrolidin-3-yl}carbamic acid tert-butyl ester Trifluoro-methanesulfonic acid 2-(5-cyclopropyl-methoxy-benzoimidazol-1-yl)-quinolin-8-yl ester (602 mg, 1.30 mMol), (which was prepared by following example 77E except that 4-cyclopropylmethoxy-2-nitro-phenylamine 133A was used in the place of 5-(2-methoxyethoxy)-2-nitro-phenylamine 42A in example 77C) palladium acetate (9.0 mg, 0.04 mMol), 1,3-bis(diphenylphosphine)propane (16 mg, 0.04 mMol), (+−)-3-(tert-butoxycarbonylamino)pyrrolidine (484 mg, 2.60 mMol) and triethylamine (400 μL, 2.86 mMol) were dissolved in 6 mL of DMF and 4 mL of MeOH in a Paar bottle. The reaction vessel was evacuated under vacuum and then filled with carbon monoxide (50 psi). The reaction mixture was shaken for 24 hours after which time it was concentrated under vacuum. The resulting residue was partitioned between DCM and aqueous saturated $NaHCO_3$. The DCM layer was then washed again with aqueous saturated $NaHCO_3$ and then with brine, dried over $Na_2SO_4$, filtered and concentrated under vacuum. The resulting residue was chromatographed on flash silica gel eluting with MeOH/DCM (1:99) to give 139 mg of the title compound 133B.

Example 133C (3-Amino-pyrrolidin-1-yl)-[2-(5-cyclopropyl-methoxy-benzoimidazol-1-yl)-quinolin-8-yl]-methanone {1-[2-(5-Cyclopropylmethoxy-benzoimidazol-1-yl)-quinoline-8-carbonyl]-pyrrolidin-3-yl}-carbamic acid tert-butyl ester 133B (130 mg, 0.246 mMol) was dissolved in a solution of 1 mL of TFA and 1 mL of DCM under an atmosphere of dry $N_2$. The reaction mixture was stirred for 30 minutes. The reaction mixture was concentrated under vacuum and the resulting residue was partitioned between DCM and aqueous 1 N NaOH. The DCM layer was washed again with concentrated under vacuum and the resulting residue was partitioned between DCM and aqueous, dried over $Na_2SO_4$, filtered and concentrated under vacuum to give the title compound 133.

C.I. m/z 428 [M+1]

Example 134

8-Allyloxy-2-(5-methoxy-benzoimidazol-1-yl)-quinoline

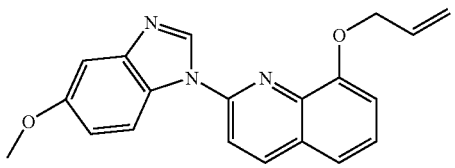

2-(5-Methoxy-benzoimidazol-1-yl)-quinolin-8-ol 1D (292 mg, 1.00 mMol) was dissolved in 5 mL of anhydrous THF under an atmosphere of dry $N_2$ and the reaction mixture was cooled to 0° C. To this solution was slowly added 60% sodium hydride in oil (44 mg, 1.1 mMol. After reacting for 30 minutes, allyl bromide (100 μL, 1.1 mMol) was added and the reaction mixture was then warmed to ambient temperature and 1 mL of DMF was added. After stirring overnight at ambient temperature, the reaction mixture was partitioned between DCM and aqueous saturated $NaHCO_3$. The DCM layer was washed again with aqueous saturated $NaHCO_3$, then with brine, dried over $Na_2SO_4$, filtered and concentrated under vacuum to give a red solid. The red solid was chromatographed over flash silica gel eluting with EtOAc to give 245 mg of the title compound 134 as a tan solid.

C.I. m/z 332 [M+1]; $^1$H NMR (CDCl$_3$) 8.60 (d, J=8.9 Hz, 1H), 8.57 (s, 1H), 8.19 (d, J=8.7 Hz, 1H), 7.59 (d, J=8.7 Hz, 1H), 7.37 (m, 2H), 7.30 (d, J=2.5 Hz, 1H), 7.07 (dd, J=1.9, 7.0 Hz, 1H), 7.02 (dd, J=2.5, 9.1 Hz, 1H), 6.21 (m, 1H), 5.62 (m, 1H), 5.36 (m, 1H), 4.76 (m, 2H), 3.87 (s, 3H).

Example 135

{2-[2-(5-Methoxy-benzoimidazol-1-yl)-quinolin-8-yloxy]-ethyl}-methyl-amine

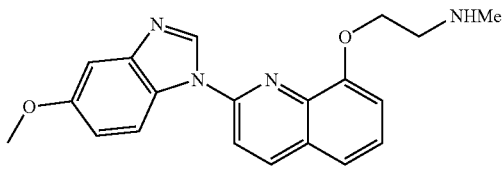

Example 135A

[2-(5-Methoxy-benzoimidazol-1-yl)-quinolin-8-yloxy]-acetaldehyde

8-Allyloxy-2-(5-methoxy-benzoimidazol-1-yl)-quinoline 134 (245 mg, 0.74 mMol), and trimethylamine-N-oxide dihydrate (101 mg, 0.88 mMol) were dissolved in 3 mL of anhydrous DCM under an atmosphere of dry $N_2$. To this solution was added osmium tetroxide (245 mg, 0.74 mMol) and the reaction mixture was stirred for ~1 hour at ambient temperature. The reaction mixture was then concentrated under vacuum and the resulting residue was, dissolved in 2 mL of THF. To this solution was added 2 mL of water followed by sodium periodate (238 mg, 1.11 mMol) and the reaction mixture was stirred overnight at ambient temperature. The reaction mixture was partitioned between DCM and aqueous saturated $NaHCO_3$ causing a precipitate to form. The brown solid was collected by suction filtration and dried under vacuum to give 214 mg of the title compound 135A.

Example 135B

{2-[2-(5-Methoxy-benzoimidazol-1-yl)-quinolin-8-yloxy]-ethyl}-methyl-amine

[2-(5-Methoxy-benzoimidazol-1-yl)-quinolin-8-yloxy]-acetaldehyde 135A (214 mg, 064 mMol), 400 μL of AcOH, 1.6 mL of a solution of 2 M methylamine in MeOH and $Na(OAc)_3BH$ (204, 0.96 mMol) were added to 3 mL of DCE under an atmosphere of dry $N_2$. The reaction mixture was stirred overnight at ambient temperature after which time it was partitioned between DCM and aqueous 1 N NaOH. The DCM layer was washed 2 more times with aqueous 1 N NaOH, then with brine, dried over $Na_2SO_4$, filtered and concentrated under vacuum. The resulting residue was chromatographed on flash silica gel initially eluting with MeOH/EtOAc (4:96), then MeOH/EtOAc/$NH_4OH$ (8:91.9:0.1), then MeOH/EtOAc/$NH_4OH$ (10:89.9:0.1) and finally MeOH/EtOAc/$NH_4OH$ (15:84.9:0.1) to give 28 mg of the title compound 135 as a white solid.

C.I. m/z 349 [M+1]; $^1$H NMR ($CDCl_3$) δ 8.63 (d, J=9.1 Hz, 1H), 8.60 (s, 1H), 8.27 (d, J=8.7 Hz, 1H), 7.66 (d, J=8.9 Hz, 1H), 7.43 (m, 2H), 7.33 (d, J=2.5 Hz, 1H), 7.14 (dd, J=2.1, 6.9 Hz, 1H), 7.05 (dd, J=2.5, 8.9 Hz, 1H), 4.35 (m, 2H), 3.89 (s, 3H), 3.21 (m, 2H), 2.61 (s, 3H), 2.02 (brs, 1H).

Example 136

{2-[2-(5-Methoxy-benzoimidazol-1-yl)-quinolin-8-yloxy]-ethyl}-dimethyl-amine

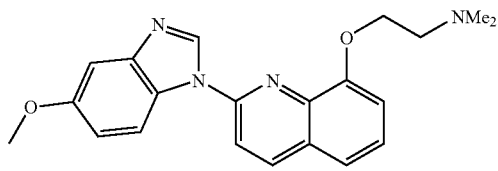

{2-[2-(5-Methoxy-benzoimidazol-1-yl)-quinolin-8-yloxy]-ethyl]methyl-amine 135 (23 mg, 0.066 mMol), 20 μL of 37% formaldehyde in water and 20 μL of formic acid were added to 500 μL of chloroform under an atmosphere of dry $N_2$. The reaction mixture was then heated to reflux for ~2 hours after which time it was concentrated under vacuum and partitioned between DCM and aqueous 1 N NaOH. The DCM layer was washed again with aqueous 1 N NaOH, then with brine, dried over $Na_2SO_4$, filtered and concentrated under vacuum to give 20 mg of the title compound 136.

C.I. m/z 363 [M+1]; $^1$H NMR ($CDCl_3$) δ 8.67 (d, J=9.1 Hz, 1H), 8.61 (s, 1H), 8.28 (d, J=8.7 Hz, 1H), 7.67 (d, J=8.9 Hz, 1H), 7.43 (m, 2H), 7.32 (d, J=2.3 Hz, 1H), 7.13 (d, J=7.3 Hz, 1H), 7.06 (dd, J=2.5, 8.9 Hz, 1H), 4.34 (m, 2H), 3.90 (s, 3H), 3.00 (m, 2H), 2.46 (s, 6H).

Example 137

2-[2-(5-Methoxy-benzoimidazol-1-yl)-quinolin-8-yloxy]-ethylamine

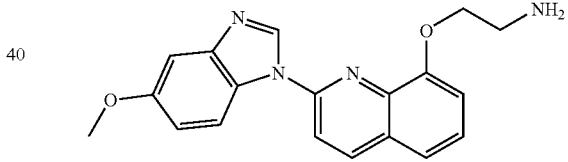

2-(5-Methoxy-benzoimidazol-1-yl)-quinolin-8-ol 1D (290 mg, 0.996 mMol) was dissolved in 5 mL of anhydrous DMF under an atmosphere of dry $N_2$. To this solution was slowly added 60% sodium hydride in oil (44.1 mg, 1.10 mMol). After reacting for 30 minutes, N-(2-bromoethyl)-pthalimide (280 mg, 1.10 mMol) was added and the reaction mixture was then heated to 80° C. After stirring for 2 hours at this temperature, $K_2CO_3$ (360 mg, 2.61 mMol) was added and the reaction mixture was stirred overnight at 80° C. The reaction mixture was then cooled to ambient temperature and partitioned between EtOAc and water. The EtOAc layer was then washed 4 more times with water, then with brine, dried over $MgSO_4$, filtered and concentrated under vacuum. The resulting residue was chromatographed over flash silica gel eluting with a gradient from DCM/Hex (50:50) to DCM and then to MeOH/DCM (2:98) to give a white solid. The white solid was dissolved in 5 mL of hot (reflux) EtOH to which was added 500 μL of anhydrous hydrazine. After reacting at reflux for two hours, the reaction mixture was cooled to ambient temperature, filtered and the filter cake was washed with EtOH. The combined filtrates were concentrated under vacuum and the resulting residue was chromatographed over flash silica gel eluting with a gradient of DCM to MeOH/DCM (8:92) then switched to MeOH/NH₄OH (8:91.9: 0.1) to give 110 mg of the title compound 137 as a white solid.

$^1$H NMR (CDCl₃) δ 8.60 (d, J=8.9 Hz, 1H), 8.58 (d, J=8.9 Hz, 1H), 8.57 (s, 1H), 8.21 (d, J=8.7 Hz, 1H), 7.60 (d, J=8.7 Hz, 1H), 7.39 (m, 2H), 7.29 (d, J=2.5 Hz, 1H), 7.08 (dd, J=1.9, 7.1 Hz, 1H), 7.03 (dd, J=2.5, 8.9 Hz, 1H), 4.21 (m, 2H), 3.86 (s, 3H), 3.27 (m, 2H), 2.26 (brs, 2H).

Example 138

1-[[2-[5-(3-Morpholinoethoxy)-1H-benzimidazol-1-yl]-quinolin-8-yl]-piperidin-4-ylamine trihydrochloride

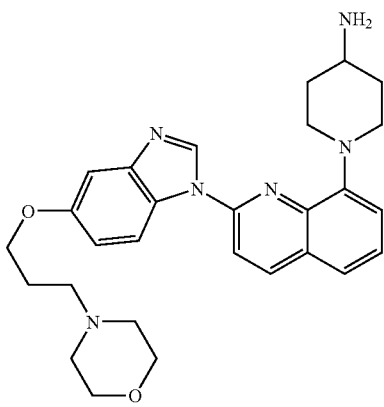

Example 138A,B

8-Chloro-2-(5-methoxy-1H-benzimidazol-1-yl)-quinoline and 8-Chloro-2-(6-methoxy-1H-benzimidazol-1-yl)-quinoline 2,8-Dichloroquinoline (11.89 g, 60 mMol), sodium hydride (60% dispersion in mineral oil, 2.88 g, 72 mMol) and 50 mL of toluene were combined under nitrogen, and a solution containing 5-methoxy-benzimidazole (10.67 g, 72 mMol) dissolved in 100 mL of anhydrous 1-methyl-2-pyrrolidinone was carefully added by syringe. The resultant mixture was warmed slowly to 110° C. and stirred at this temperature for 16 hrs. After cooling, the reaction mixture was quenched with 650 mL of water and then extracted multiple times with EtOAc. The combined EtOAc extracts were dried over Na₂SO₄ and evaporated to leave a semi-solid residue containing the title product isomers 138A,B. An $^1$H NMR spectrum of this product mixture revealed that formation of the 6-methoxybenzimidazol-1-yl isomer was favored over the 5-methoxybenzimidazol-1-yl isomer by about a 3:2 ratio. Fractional crystallization from EtOH provided three early crystalline crops that were combined to give 7.34 g, comprised of about 90% pure 6-methoxybenzimidazol-1-yl isomer. Recrystallization from EtOH gave needle-like crystals of the 6-methoxybenzimidazol-1-yl isomer 138A melting at 175–176° C.

C.I. m/z 310 [M+1]; $^1$H NMR (DMSO) δ 9.18 (s, 1H), 8.77 (d, J=2.5 Hz, 1H), 8.65 (d, J=9.0 Hz, 1H), 8.30 (d, J=9.0 Hz, 1H), 8.01 (m, 2H), 7.68 (d, 8.7 Hz, 1H), 7.58 (m, 1H), 7.00 (dd, J=2.5, 8.7 Hz, 1H), 3.92 (s, 3H).

Additional fractional crystallization efforts ultimately yielded two crops, 2.157 g combined weight, of the 5-methoxybenzimidazol-1-yl isomer 138B, melting at 184–185° C.

$^1$H NMR (DMSO) δ 9.27 (s, 1H), 8.98 (d, J=9.0 Hz, 1H), 8.67 (d, J=9.0 Hz, 1H), 8.31 (d, J=9.0 Hz, 1H), 8.02 (m, 2H), 7.59 (m, 1H), 7.35 (d, J=2.2 Hz, 1H), 7.12 (dd, J=2.2, 9.0 Hz, 1H), 3.87 (s, 3H).

Example 138C

8-Chloro-2-(5-hydroxy-1H-benzimidazol-1-yl] quinoline

To a pre-cooled (−78° C.) solution containing 8-chloro-2-(5-methoxy-1H-benzimidazol-1-yl)quinoline 138B (2.16 g, 7.0 mMol) in anhydrous DCM (28 mL) was added a 1.0 M solution of borontribromide in DCM (20.9 mL, 20.9 mMol). The cooling bath was removed and the reaction mixture stirred at ambient temperature under nitrogen for 22 hours. The reaction was quenched by the addition of aqueous 1 N NaOH to a pH of about 8.8. After stirring for about minutes, the suspended solids were removed by filtration. The solids were subsequently stirred briefly with 1 N NaOH (21 mL, 21 mMol) to hydrolyse remaining borate esters, and then neutralized by adding 1 N HCl (21 mL, 21 mMol). The solid precipitate was filtered off, stirred briefly with a small amount of warm EtOAc to remove traces of starting material, and re-filtered to give 1.91 g, mp>250° C., of the title product 138C.

C.I. m/z 296 [M+1]; $^1$H NMR (DMSO) δ 9.41 (br. s, 1H), 9.20 (s, 1. H), 8.86 (d, J=9.1 Hz, 1H), 8.65 (d, J=9.1 Hz, 1H), 8.28 (d, J=8.7 Hz, 1H), 8.00 (d, J=7.9 Hz, 2H), 7.57 (t, J=7.9 Hz, 1H), 7.08 (d, J=2.5 Hz, 1H), 6.93 (dd, J=2.5, 8.7 Hz, 1H).

Example 138D

8-Chloro-2-[5-(3-morpholinopropoxy)-1H-benzimidazol-1-yl]-quinoline

8-Chloro-2-(5-hydroxy-1H-benzimidazol-1-yl)-quinoline 138C (0.30 g, 1 mMol) and NaH (0.047 g of 60% dispersion in mineral oil, 1.1 mMol) were combined with 3 mL of anhydrous DMF under argon, and the mixture allowed to react for 1 hr at ambient temperature. To this was added 4-(3-chloropropyl)morpholine (0.199 g, 1.22 mMol) and the reaction mixture stirred at ambient temperature for 4 days. Remaining sodium hydride, if any, was quenched by water addition and the solvents evaporated under vacuum. Water (3mL) was added to the residue, and the mixture extracted (5×20 mL) with chloroform. The combined chloroform extracts were dried over Na₂SO₄ and evaporated to give an off-white solid. The solids were stirred with a small amount of EtOH and filtered to give 0.157 g of title product 138D.

C.I. m/z 423 [M+1]; $^1$H NMR (DMSO) δ 9.24 (s, 1H), 8.95 (d, J=9.1 Hz, 1H), 8.66 (d, J=9.1 Hz, 1H), 8.30 (d, J=9.1 Hz, 1H), 8.01 (d, J=7.9 Hz, 2H), 7.57 (t, J=7.9 Hz, 1H), 7.30 (d, J=2.1 Hz, 1H), 7.08 (dd, J=2.5, 9.1 Hz, 1H), 4.08 (t, J=6.4 Hz, 2H), 3.56 (m, 4H), 2.43 (t, J=7.3 Hz, 2H), 2.36 (m, 4H), 1.89 (m, 2H).

Example 138E

{1-[[2-[5-(3-Morpholinopropoxy)-1H-benzimidazol-1-yl]-quinolin-8-yl]]-piperidin-4-yl}-carbamic acid tert-butyl ester 8-Chloro-2-[5-(3-morpholinopropoxy)-1H-benzimidazol-1-yl]-quinoline 138D (226 mg, 0.53 mMol), racemic-BINAP (50 mg, 0.08 mMol), $Cs_2CO_3$ (243 mg, 0.75 mMol), piperidin-4-yl-carbamic acid tert-butyl ester (214 mg, 1.07 mMol), xylenes (1 mL), and $Pd(OAc)_2$ (12 mg, 0.053 mMol) were combined under argon and heated at reflux for 2 days. After allowing the mixture to cool, hexanes were added and decanted off, several times, to remove hexane solubles. The residue was stirred with EtOAc and filtered, and the solids washed with additional EtOAc. The combined EtOAc solutions were evaporated, and the residue chromatographed on silica gel with EtOAc/MeOH elution. Fractions containing the title product 138E were combined and concentrated to provide 130 mg.

C.I. m/z 587 [M+1]; $^1$H NMR (DMSO) δ 9.15 (s, 1H), 8.88 (d, J=9.6 Hz, 1H), 8.51 (d, J=8.7 Hz, 1H), 8.14 (d, J=9.1 Hz, 1H), 7.59 (d, J=7.0 Hz, 1H), 7.46 (t, J=7.9 Hz, 1H), 7.30 (m, 3H), 7.13 (d, J=8.3 Hz, 1H), 4.08 (t, J=6.2 Hz, 2H), 3.75 (m, 2H), 3.56 (m, 4H), 3.42 (m, 1H), 2.74 (t, J=10.8 Hz, 2H), 2.44 (m, 2H), 2.36 (m, 4H), 1.8–1.9 (m, 6H), 1.39 (s, 9H).

Example 138F

1-[[2-[5-(3-Morpholinopropoxy)-1H-benzimidazol-1-yl]-quinolin-8-yl]]-piperidin-4-ylamine trihydrochloride (1-[[2-[5-(3-Morpholinopropoxy)-1H-benzimidazol-1-yl]-quinolin-8-yl]]-piperidin-4-yl}-carbamic acid tert-butyl ester 138E (98 mg, 0.17 mMol) was stirred at ambient temperature with 4N HCl in dioxane (0.5 mL, 2 mMol). After 4 hr the mixture was rotoevaporated to provide the title product 138 as a pale yellow solid.

C.I. m/z 487 [M+1]; $^1$H NMR (DMSO) δ 9.55 (brs, 1H), 8.94 (d, J=8.7 Hz, 1H), 8.65 (d, J=9.0 Hz, 1H), 8.4 (brs, 3H), 8.24 (d, J=9.0 Hz, 1H), 7.72 (d, J=8.1 Hz, 1H), 7.58 (m, 2H), 7.42 (m, 2H), 4.24 (t, J=5.6 Hz, 2H), 4.0 (m, 2H), 3.9 (m, 4H), 3.5 (m, 2H), 3.3 (m, 3H), 3.1 (m, 2H), 2.88 (m, 2H), 2.29 (m, 2H), 2.12 (m, 4H).

Example 139

1-[[2-[5-(3-Morpholinoethoxy)-1H-benzimidazol-1-yl]-quinolin-8-yl]]-piperidin-4-ylamine trihydrochloride

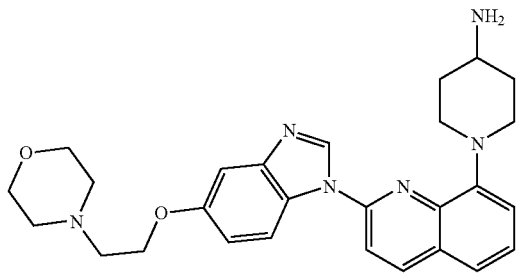

Example 139A

8-Chloro-2-[5-(3-morpholinoethoxy)-1H-benzimidazol-1-yl]-quinoline

8-Chloro-2-(5-hydroxy-1H-benzimidazol-1-yl)-quinoline 138B (296 mg, 1 mMol) and $Cs_2CO_3$ (717 mg, 2.2 mMol) and 3 ml anhydrous dioxane were combined and heated at 80° C. for 1.5 hr under nitrogen. Morpholinoethylchloride hydrochloride (223 mg, 1.2 mMol) was added and heating continued at 80° C. overnight. Additional morpholinoethylchloride hydrochloride (112 mg, 0.6 mMol) and $Cs_2CO_3$ (358 mg, 1.1 mMol) were added, and the mixture heated for an additional 2 days. After evaporation of the solvent, water (2 mL) was added to the residue, and the mixture extracted with EtOAc. The EtOAc extract was dried over $Na_2SO_4$ and evaporated to give 200 mg of title product 139A as an off-white solid.

Example 139B

{1-[[2-[5-(3-Morpholinoethoxy)-1H-benzimidazol-1-yl]-quinolin-8-yl]]-piperidin-4-yl}-carbamic acid tert-butyl ester 8-Chloro-2-[5-(3-morpholinoethoxy)-1H-benzimidazol-1-yl]-quinoline 139A (182 mg, 0.32 mMol), racemic-BINAP (30 mg, 0.05 mMol), $Cs_2CO_3$ (145 mg, 0.45 mMol), piperidin-4-yl-carbamic acid tert-butyl ester (127 mg, 0.64 mMol), xylenes (1 mL), and $Pd(OAc)_2$ (7.1 mg, 0.032 mMol) were combined under argon and heated at reflux for 2 days. This reaction was worked in the same way as in example 138E, including chromatography, to provide 120 mg of title product 139B.

Example 139C

1-[[2-[5-(3-Morpholinoethoxy)-1H-benzimidazol-1-yl]-quinolin-8-yl]]-piperidin-4-ylamine trihydrochloride {1-[[2-[5-(3-Morpholinoethoxy)-1H-benzimidazol-1-yl]-quinolin-8-yl]]-piperidin-4-yl}-carbamic acid tert-butyl ester 139B (121 mg, 0.21 mMol) was stirred at ambient temperature with 4N HCl in dioxane (0.63 mL, 2.5 mMol). After 4 hr the mixture was rotoevaporated, and the residue stirred briefly with fresh anhydrous dioxane. Filtration provided the title product 139 as a pale yellow solid.

C.I. m/z 473 [M+1]; $^1$H NMR (DMSO) δ 9.67 (brs, 1H), 8.92 (d, J=9.1 Hz, 1H), 8.62 (d, J=8.7 Hz, 1H), 8.50 (brs, 3H), 8.21 (d, J=8.7 Hz, 1H), 7.76 (m, 1H), 7.69 (d, J=8.3 Hz, 1H), 7.55 (t, J=7.9 Hz, 1H), 7.44 (d, J=2.5 Hz, 1H), 7.40 (m, 1H), 4.59 (m, 2H), 3.97 (d, J=11.2 Hz, 2H), 3.84 (m, 4H), 3.6–3.5 (m, 4H), 3.21–3.24 (m, 3H), 2.86 (m, 2H), 2.09 (m, 4H).

Example 140

5-{2-[5-(2-Methoxy-ethoxy)-benzoimidazol-1-yl]-quinolin-8-yl}-[1,3,4]oxadiazol-2-ylamine

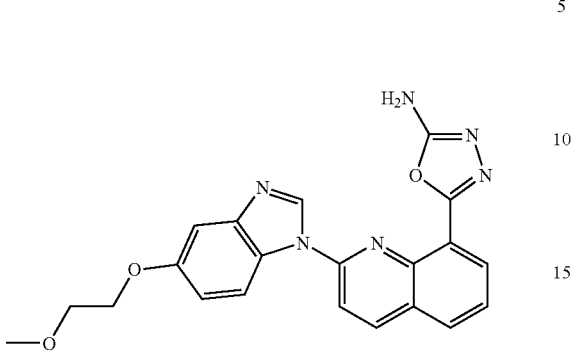

Example 140A

2-[5-(2-Methoxy-ethoxy)-benzoimidazol-1-yl]-quinoline-8-carboxylic acid hydrazide 2-[5-(2-Methoxy-ethoxy]benzoimidazol-1-yl]-quinoline-8-carboxylic acid methyl ester 127 (1.00 g, 2.66 mMol) was dissolved in 10 mL of anhydrous THF under an atmosphere of dry $N_2$. To this solution was added 400 µL of anhydrous hydrazine and the solution was then stirred for 18 hours at ambient temperature. The solution was concentrated under vacuum and the resulting residue was partitioned between DCM and aqueous saturated $NaHCO_3$. The DCM layer was washed again with aqueous saturated $NaHCO_3$, then with brine, dried over $Na_2SO_4$, filtered and concentrated under vacuum. The resulting residue was chromatographed on flash silica gel eluting with MeOH/DCM (595) to give 553 mg of the title compound 140A as a light yellow solid.

Example 140B

5-{2-[5-(2-Methoxy-ethoxy)-benzoimidazol-1-yl]-quinolin-8-yl}-[1,3,4]oxadiazol-2-ylamine 2-[5-(2-Methoxy-ethoxy)-benzoimidazol-1-yl]-quinoline-8-carboxylic acid hydrazide 140A (403 mg, 1.07 mMol) and $NaHCO_3$ (275 mg, 3.28 mMol) were dissolved in a solution of 5 mL of 1,4-dioxane and 5 mL of water. To this solution was added 500 µL of a 3 M solution of cyanogen bromide in DCM. The reaction mixture was heated to reflux and reacted at this temperature for 48 hours. The reaction mixture was concentrated under vacuum and then partitioned between EtOAc and aqueous saturated $NaHCO_3$. The DCM layer was then washed with brine, dried over $Na_2SO_4$ and filtered. A precipitate formed in the filtrate that was collected via suction filtration and dried under vacuum to give 83.7 mg of the title compound 140 as a yellow solid.

C.I. m/z 403 [M+1]; $^1$H NMR (DMSO) δ 9.18 (s, 1H), 8.75 (d, J=8.7 Hz, 1H), 8.68 (d, J=9.1 Hz, 1H), 8.27 (d, J=9.1 Hz, 1H), 8.20 (dd, J=1.2, 8.3 Hz, 1H), 8.12 (m, 1H), 7.70 (m, 1H), 7.30 (m, 1H), 7.28 (d, J=2.5 Hz, 3H), 6.97 (dd, J=2.5, 8.7 Hz, 1H), 4.14 (m, 2H), 3.67 (m, 2H), 3.31 (s, 3H).

Example 141

Ethyl 1-[8-(4-aminopiperidin-1-yl)-quinolin-2-yl]-benzimidazole-5-carboxylate

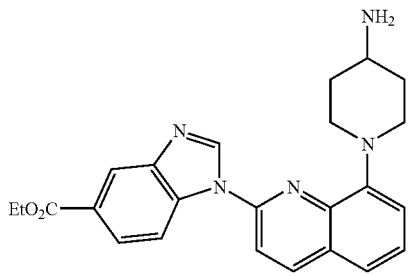

Example 141A,B

Ethyl 1-(8-chloroquinolin-2-yl)-benzimidazole-5-carboxylate and Ethyl 1-(8-chloroquinolin-2-yl)-benzimidazole-6-carboxylate 2,8-Dichloroquinoline (13.3 g, 67.2 mMol), sodium hydride (60% dispersion in mineral oil, 2.75 g, 68.8 mMol), 55 mL toluene and 109 mL of 1-methyl-2-pyrolidinone were combined under nitrogen. Ethyl benzimidazole-5-carboxylate (12.81 g, 67.4 mMol) was added portionwise over a 10 minute period, and the reaction mixture heated at reflux for 20 hr. The cooled mixture was diluted with EtOAc (~450 mL), and water (~600 mL) was added slowly to facilitate product crystallization. Filtration gave 25 g of light gray crystals, which were shown by $^1$H NMR analysis to contain both title regioisomers 141A,B in a ratio of about 3 to 2 in favor of the 5-carboxylate regioisomer 141A. Fractional crystallization from chloroform/ethanol allowed separation of the regioisomers.

5'-Ester regioisomer 141A: C.I. m/z 352 [M+1]; $^1$H NMR (CDCl$_3$) δ 8.91 (d, J=8.7 Hz, 1H), 8.75 (s, 1H), 8.58 (s, 1H), 8.40 (d, J=8.7 Hz, 1H), 8.22 (d, J=8.7 Hz, 1H), 7.92 (d, J=7.9 Hz, 1H), 7.80 (d, J=8.3 Hz, 1H), 7.78 (d, J=8.7 Hz, 1H), 7.51 (m, 1H), 4.43 (q, J=-7 Hz, 2H), 1.44 (t, J=7 Hz, 3H).

6'-Ester regioisome 141 Br: C.I. m/z 352 [M+1]; $^1$H NMR (CDCl$_3$) δ 9.70 (s, 1H), 8.82 (s, 1H), 8.40 (d, J=8.7 Hz, 1H), 8.15 (d, J=8.7 Hz, 1H), 7.93 (d, J=7.5 Hz, 1H), 7.89 (d, J=8.3 Hz, 1H), 7.80 (m, 2H), 7.51 (t, J=7.9 Hz, 1H), 4.44 (q, J=-7.2 Hz, 2H), 1.46 (t, J=7.1 Hz, 3H).

Example 141C

Ethyl-1-[8-(4-tert-butoxycarbonylaminopiperidin-1-yl)-quinolin-2-yl]-benzimidazole-5-carboxylate Ethyl 1-(8-chloroquinolin-2-yl)-benzimidazole-5-carboxylate 141A (3.00 g, 8.53 mMol), racemic-BINAP (806 mg, 1.29 mMol), $Cs_2CO_3$ (4.00 g, 12.3 mMol), piperidin-4-yl-carbamic acid tert-butyl ester (3.49 g, 17.4 mMol), xylenes (26 mL), and Pd(OAc)$_2$ (198 mg, 0.88 mMol) were combined under argon and heated at reflux for 3 days. After cooling, hexanes (25 mL) was added and the mixture stirred overnight. Solids were removed by filtration, and repeatedly washed with hexanes (5×30 mL). The solids were then extracted with EtOAc (3×500 mL), and the EtOAc solutions combined and evaporated, leaving 4.18 g of greenish-black foam.

The title product 141C (2.06 g) was isolated as pale-yellow crystals (mp=170–175° C.) after silica gel chromatography (hexanes/EtOAc) followed by brief ethyl ether trituration.

Example 141D

Ethyl 1-[8-(4-aminopiperidin-1-yl)-quinolin-2-yl]-benzimidazole-5-carboxylate

Ethyl-1-[8-(4-tert-butoxycarbonylaminopiperidin-1-yl)-quinolin-2-yl]-benzimidazole-5-carboxylate 141C (125 mg, 0.24 mMol) was stirred at ambient temperature with 4N HCl in dioxane (0.62 mL, 2;5 mMol). After 4 hr the mixture was evaporated under reduced pressure. The solid residue was slurried briefly in 0.5 mL ethyl ether, filtered and vacuum dried to give the title product 141 as a hydrochloride salt.

C.I. m/z 416 [M+1]; $^1$HNMR(DMSO) δ9.38 (s, 1H), 8.93 (d, J=8.7 Hz, 2H), 8.62 (d, J=9.1 Hz, 1H), 8.37 (s, 1H), 8.30 (d, J=8.7 Hz, 1H), 8.21 (d, J=8.7 Hz, 1H), 8.16 (brs, 3H), 7.68 (d, J=8.3 Hz, 1H), 7.54 (m, 1H), 7.37 (m, 1H), 4.36 (q, J=7 Hz, 2H), 3.88 (m, 2H), 3.22 (m, 1H), 2.84 (m, 2H), 2.08 (m, 2H), 1.97–2.00 (m, 2H), 1.36 (t, J=7 Hz, 3H).

Example 142

1-[8-(4-Aminopiperidin-1-yl]-quinolin-2-yl]-benzimidazole-5-carboxylic acid

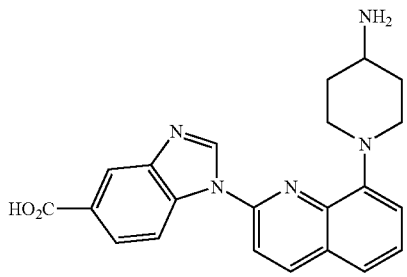

Example 142A

1-[8-(4-tert-Butoxycarbonylaminopiperidin-1-yl)-quinolin-2-yl]-benzimidazole-5-carboxylic acid Ethyl-1-[8-(4-tert-butoxycarbonylaminopiperidin-1-yl)-quinolin-2-yl]-benzimidazole-5-carboxylate 141C (1.300 g, 2.52 mMol), 1,4-dioxane (5.2 mL), MeOH (1.3 mL) and aqueous 1N NaOH (3.9 mL, 3.9 mMol) were combined and heated at 70° C. for 1 hr. After allowing the mixture to cool, aqueous 1 N HCl (3.9 mL, 3.9 mMol) was added slowly with stirring, followed by 120 mL of EtOAc. Precipitated solids were removed by filtration to give 0.916 mg of title product 142A. An additional 264 mg of compound 142A was recovered upon evaporation of the filtrate EtOAc layer.

Example 142B

1-[8-(4-Aminopiperidin-1-yl)-quinolin-2-yl]-benzimidazole-5-carboxylic acid

1-[8-(4-tert-Butoxycarbonylaminopiperidin-1-yl)-quinolin-2-yl]-benzimidazole-5-carboxylic acid 142A (51 mg, 0.105 mMol) was stirred at ambient temperature with 4N HCl in 1,4-dioxane (0.26 mL, 1.04 mMol). After 4 hr the mixture was evaporated under reduced pressure. The solid residue was slurried briefly in 1 mL Et$_2$O, filtered and vacuum dried to give the title product 142 as a hydrochloride salt.

C.I. m/z 388 [M+1]; $^1$H NMR (DMSO) δ 9.36 (s, 1H), 8.95 (d, J=8.3 Hz, 1H), 8.60 (d, J=9.1 Hz, 1H), 8.34 (s, 1H), 8.28 (d, J=9.1 Hz, 1H), 8.21 (d, J=8.7 Hz, 1H), 8.08 (br, 3H), 7.66 (d, J=8.3 Hz, 1H), 7.52 (m, 1H), 7.34 (d, J=7.1 Hz, 1H), 3.85–3.88 (m, 2H), 3.20 (m, 1H), 2.81 (m, 2H), 2.06 (m, 2H), 1.95–1.98 (m, 2H).

Example 143

N-(4-Morpholino)ethyl-1-[8-(4-aminopiperidin-1-yl)-quinolin-2-yl]-benzimidazole-5-carboxamide

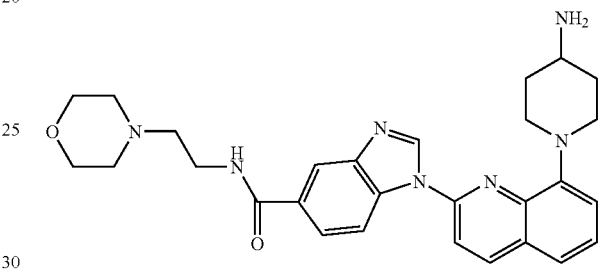

Example 143A

N-(4-Morpholino)ethyl-1-[8-(4-tert-butoxycarbonylaminopiperidin-1-yl)-quinolin-2-yl]benzimidazole-5-carboxamide 1-[8-(4-tert-Butoxycarbonylaminopiperidin-1-yl)-quinolin-2-yl]-benzimidazole-5-carboxylic acid 142A (146 mg, 0.30 mMol), DMF (1 mL) and 1,1'-carbonyldiimidazole were combined and stirred under nitrogen at ambient temperature for 2 hr. 4-(2-Aminoethyl)morpholine (0.050 mL, 0.38 mMol) was added and the mixture stirred at ambient temperature for 16 hr. EtOAc (10 mL) and saturated aqueous NaHCO$_3$ (5 mL) were added and stirred for 30 min. The white precipitate was removed by filtration and vacuum dried to give 158 mg of title compound 143A.

Example 143B

N-(4-Morpholino)ethyl-1-[8-(4-aminopiperidin-1-yl)-quinolin-2-yl]-benzimidazole-5-carboxamide N-(4-Morpholino)ethyl-1-[8-(4-tert-butoxycarbonylaminopiperidin-1-yl)-quinolin-2-yl]-benzimidazole-5-carboxamide 143A (133 mg, 0.22 mMol) was stirred at ambient temperature with 4N HCl in dioxane (2.0 mL, 8 mMol). After 4 hr the mixture was evaporated under reduced pressure, 2 mL 1,4-dioxane was added and evaporated, twice, leaving a solid residue, which was slurried briefly in 3 mL Et$_2$O, filtered and vacuum dried to give the title product 143 as its bis-HCl salt.

C.I. m/z 500 [M+1]; $^1$H NMR (DMSO) δ 9.43 (s, 1H), 9.07–9.12 (m, 2H), 8.61 (m, 2H), 8.46 (br, 3H), 8.38 (s, 1H), 8.23 (d, J=8.7 Hz, 1H), 7.68 (m, 1H), 7.54 (m, 1H), 7.39 (m, 1H), 3.95–3.98 (m, 2H), 3.78–3.84 (m, 4H), 3.70–3.74 (m,

2H), 3.57–3.68 (m, 2H), 3.36–3.38 (m, 2H), 3.11–3.23 (m, 3H), 2.85 (m, 2H), 2.11 (m, 4H).

Example 144

4-{1-[8-(4-Amino-piperidin-1-yl)-quinolin-2-yl]-1H-benzoimidazol-5-yl}-benzaldehyde

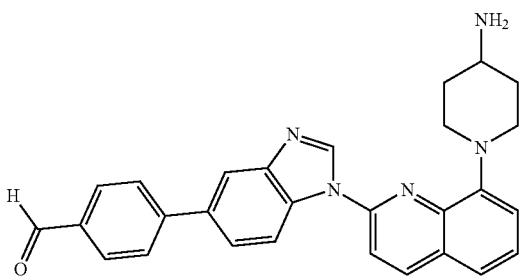

The same procedure that was used in example 118 was followed except that 4-formylbenzeneboronic acid was used in the place of phenylboronic acid in example 118B to give the title compound 144 as the bis-HCl salt.

C.I. m/z 448 [M+1]; $^1$H NMR (DMSO) δ 10.08 (s, 1H), 9.56 (s, 1H), 9.08 (d, J=8.7 Hz, 1H), 8.64 (d, J=8.7 Hz, 1H), 8.40 (brs, 4H), 8.33 (d, J=8.7 Hz, 1H), 8.25 (s, 1H), 8.13 (d, J=8.3 Hz, 2H), 8.02 (d, J=8.3 Hz, 1H), 7.73 (d, J=7.5 Hz, 1H), 7.58 (m, 2H), 7.44 (m, 1H), 3.91 (m, 2H), 3.26 (m, 1H), 2.92 (m, 2H), 2.14 (m, 4H).

Example 145

1-{2-[5-(4-Methylaminomethyl-phenyl]benzoimidazol-1-yl]-quinolin-8-yl}-piperidin-4-ylamine

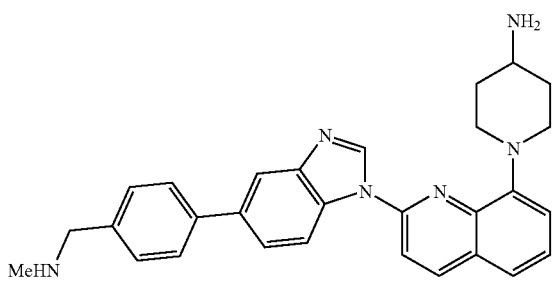

4-{1-[8-(4-amino-piperidin-1-yl)-quinolin-2-yl]-1H-benzoimidazol-5-yl}-benzaldehyde 144 (205 mg, 0.374 mMol) was dissolved in a solution of 3 mL of MeOH and 2 mL of DCE under an atmosphere of dry $N_2$. To this solution was added 935 µL of a solution of 2.0 M methylamine in MeOH and then AcOH was added dropwise until the pH of the solution was ~5. To this solution was added (47 mg, 0.75 mMol) NaCNBH$_3$ and the reaction mixture was stirred at ambient temperature for 4 hours. The reaction mixture was then concentrated under vacuum and subsequently partitioned between a solution of 2-propanol/DCM (18:82) and 0.1 N aqueous NaOH. The water layer was washed 2 more times with a solution of 2-propanol/DCM (18:82). The organic extracts were combined and concentrated under vacuum to give a yellow foam. The foam was chromatographed on flash silica gel eluting with a gradient DCM/MeOH/NH$_4$OH (297.80.2) to DCM/MeOH/NH$_4$OH (1089.80.2) to give 83 mg of a yellow foam. The foam was dissolved in 2 mL of EtOH in a pressure vial. To this solution was added 50 µL of concentrated HCl. The reaction mixture was heated to ~90° C. and reacted at this temperature for 2 hours. The reaction mixture was then cooled to ambient temperature and the resulting precipitate was collected via suction filtration. The solid was dried under vacuum to give 82 mg of the tri-HCl salt of the title compound 145 as a white solid.

C.I. m/z 463 [M+1]; $^1$H NMR (CD$_3$OD) δ 10.57 (s, 1H), 8.90 (d, J=8.7 Hz, 1H), 8.75 (d, J=9.5 Hz, 1H), 8.32 (d, J=9.1 Hz, 1H), 8.23 (m, 2H), 8.16 (d, J=8.3 Hz, 1H), 8.03 (d, J=8.3 Hz, 1H), 7.94 (d, J=8.3 Hz, 2H), 7.86 (m, 1H), 7.67 (d, J=8.3 Hz, 2H), 4.28 (s, 2H), 4.18 (m, 2H), 3.73 (m, 2H), 3.63 (m, 1H), 2.77 (s, 3H), 2.48 (m, 2H), 2.41 (m, 2H).

Example 146

1-(2-[5-(4-Dimethylaminomethyl-phenyl)-benzoimidazol-1-yl]-quinolin-8-yl}-piperidin-4-ylamine

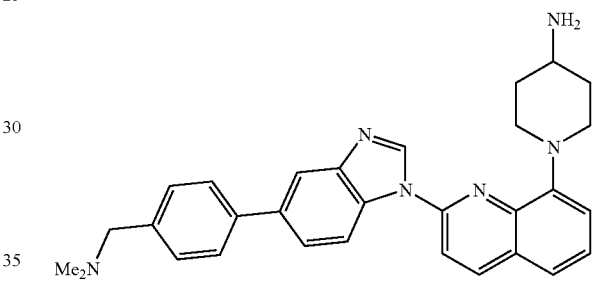

The same procedure that was used in example 145 was followed except that a solution of 2.0 M dimethylamine in MeOH was used in the place of a solution of 2.0 M methylamine in MeOH to give the tri-HCl salt of the title compound 146 as a white solid.

C.I. m/z 477 [M+1]; $^1$H NMR (CD$_3$OD) δ 10.74 (s, 1H), 8.97 (d, J=9.1 Hz, 1H), 8.70 (d, J=8.7 Hz, 1H), 8.39 (d, J=9.1 Hz, 1H), 8.28 (m, 4H), 7.97 (d, J=8.3 Hz, 2H), 7.93 (m, 1H), 7.72 (d, J=8.3 Hz, 2H), 4.43 (s, 2H), 4.22 (m, 2H), 3.97 (m, 2H), 3.73 (m, 1H), 2.91 (s, 6H), 2.61 (m, 2H), 2.49 (m, 2H).

Example 147

1-(2-{5-[2-(2-Methyl-imidazol-1-yl)-ethoxy]-benzoimidazol-1-yl}-quinolin-8-yl)-piperidin-4-ylamine

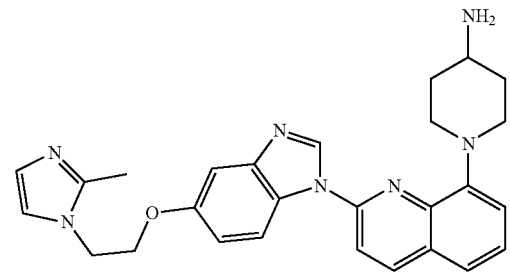

Example 147A

Methanesulfonic acid 2-{1-[8-(4-tert-butoxycarbonylamino-piperidin-1-yl)-quinolin-2-yl]-1H-benzoimidazol-5-yloxy)-ethyl ester 2-{1-[8-(4-Amino-piperidin-1-yl)-quinolin-2-yl]-1H-benzoimidazol-5-yloxy}-ethanol 83 (1.89 g 4.68 mMol) and di-tert-butyldicarbonate (1.02 g, 4.68 mMol) were added to a solution of 40 mL of anhydrous DCM and 20 mL of anhydrous THF under an atmosphere of dry $N_2$. The heterogeneous reaction mixture was stirred at ambient temperature for 3 hours after which time 1.2 mL of $NEt_3$ followed by 2.10 mL of methanesulphonyl chloride were added. The reaction mixture was stirred at ambient temperature for 48 hours and then partitioned between DCM and aqueous saturated $NaHCO_3$. The DCM layer was saved and washed 2 more times with aqueous saturated $NaHCO_3$, dried over $Na_2SO_4$, filtered and concentrated under vacuum to give a yellow foam as the title compound 147A and was used without further purification.

Example 147B 1-(2-{5-[2-(2-Methyl-imidazol-1-yl)-ethoxy]-benzoimidazol-1-yl}-quinolin-8-yl)-piperidin-4-ylamine Methanesulfonic acid 2-{1-[8-(4-tert-butoxycarbonylamino-piperidin-1-yl)-quinolin-2-yl]-1H-benzoimidazol-5-yloxy}-ethyl ester 147A (344 mg, 0.591 mMol) was slurried in 2.0 mL of anhydrous DMF under an atmosphere of dry $N_2$. To this heterogeneous solution was added 2-m thylimidazole (53 mg, 0.65 mMol) followed by sodium hydride (60% in oil) (16 mg, 0.65 mMol). The reaction mixture was then heated to 60° C. After 1 hour, the reaction mixture was cooled to ambient temperature and 26 mg more of sodium hydride (60% in oil) was added. The reaction mixture was reheated to 60° C. and reacted at this temperature overnight. The reaction mixture was cooled to ambient temperature and then quenched with water. The reaction mixture was concentrated under vacuum and the resulting brown oil was partitioned between DCM and aqueous 1.0 M NaOH. The DCM layer was saved and washed 2 more times with aqueous 1.0 M NaOH, dried over $Na_2SO_4$, filtered and concentrated under vacuum. The resulting residue was chromatographed on flash silica gel eluting with a gradient from DCM/MeOH/$NH_4OH$ (2/97.8/0.2) to DCM/MeOH/$NH_4OH$ (10/89.8/0.2) to give 158 mg of a yellow foam. The foam was dissolved in 1 mL of TFA under an atmosphere of dry $N_2$ and stirred at ambient temperature for 1 hour. The reaction mixture was concentrated under vacuum, and the resulting residue was partitioned between DCM and aqueous 0.1 M NaOH. The water layer was washed 2 more times with DCM. The DCM extracts were combined, dried over $Na_2SO_4$, filtered and concentrated under vacuum to give 128 mg of the title compound 147.

C.I. m/z 468 [M+1]; $^1$H NMR (CDCl$_3$) δ 8.63 (s, 1H), 8.37 (d, J=9.1 Hz, 1H), 8.28 (d, J=8.7 Hz, 1H), 7.64 (d, J=8. Hz, 1H), 7.46 (m, 2H), 7.26 (d, J=2.5 Hz, 1H), 7.22 (m, 1H), 6.97 (m, 2H), 6.91 (d, J=1.3 Hz, 1H), 4.28 (s, 4H), 3.88 (m, 2H), 2.88 (m, 3H), 2.46 (s, 3H), 2.05 (m, 2H), 1.86 (brs, 2H), 1.80 (m, 2H).

Example 148

1-{2-[5-(2-[1,2,4]Triazol-1-yl-ethoxy)-benzoimidazol-1-yl]-quinolin-8-yl}-piperidin-4-ylamine

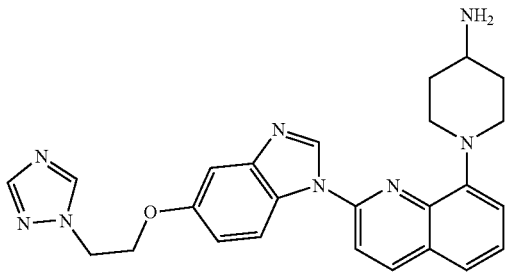

Methanesulfonic acid 2-{1-[8-(4-tert-butoxycarbonylamino-piperidin-1-yl)-quinolin-2-yl]-1H-benzoimidazol-5-yloxy}-ethyl, ester 147A (500 mg, 0.860 mMol) was slurried in 2.0 mL of anhydrous DMF under an atmosphere of dry $N_2$. To this heterogeneous solution was added 1,2,4-triazole (65 mg, 0.95 mMol) followed by sodium hydride (60% in oil) (23 mg, 095 mMol). The reaction mixture was then heated to 60° C. and reacted at this temperature for 3 hours. The reaction mixture was cooled to ambient temperature and then quenched with water. The reaction mixture was concentrated under vacuum and the resulting brown oil was partitioned between a solution of 2-propanol/DCM (18:82) and aqueous 0.1 M NaOH. The organic layer was saved and washed 2 more times with aqueous 0.1 M NaOH, dried over $Na_2SO_4$, filtered and concentrated under vacuum to a yellow oil. The yellow oil was chromatographed on flash silica gel eluting with DCM/MeOH/$NH_4OH$ (1.5/98.4/0.1) to give 126 mg of a yellow foam The foam was dissolved in 2 mL of EtOH in a pressure vial. To this solution was added 75 μL of concentrated HCl. The reaction mixture was heated to ~90° C. and reacted at this temperature for 2 hours. The reaction mixture was then cooled to ambient temperature and the resulting precipitate was collected via suction filtration. The solid was dried under vacuum to give 86 mg of the bis-HCl salt of the title compound 148 as a yellow solid.

C.I. m/z 455 [M+1]; $^1$H NMR (CD$_3$OD) δ 10.46 (s, 1H), 9.71 (s, 1H), 8.84 (d, J=9.7 Hz, 1H), 8.73 (s, 1H), 8.60 (d, J=9.1 Hz, 1H), 8.23 (d, J=8.7 Hz, 1H), 8.10 (d, J=8.3 Hz, 1H), 8.00 (d, J=7.5 Hz, 1H), 7.83 (m, 1H), 7.54 (dd, J=2.5, 9.1 Hz, 1H), 7.50 (d, J=2.1 Hz, 1H), 4.93 (m, 2H), 4.67 (m, 2H), 4.12 (m, 2H), 3.60 (m, 3H), 2.37 (m, 4H).

What is claimed is:
1. A compound of the formula

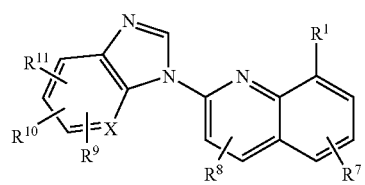

or a pharmaceutically acceptable salt, prodrug or solvate thereof, wherein:
X is CH;
$R^1$ is selected from —$(CR^4R^5)_tC(O)OR^3$, —$(CR^4R^5)_tC(O)NR^3R^4$, —$(CR^4R^5)_nOR^3$, —$(CR^4R^5)_nC(O)(C_3$–$C_{10}$ cycloalkyl), —$(CR^4R^5)_tC(O)(C_6$–$C_{10}$ aryl), —(CR$^4$R$^5$)$_n$C(O)(4 to 10 membered heterocyclic), —(CR$_4$R$^5$)$_t$(C$_3$–C$_{10}$ cycloalkyl), —(CR$^4$R$^5$)$_t$(C$_6$–C$_{10}$ aryl), and —(CR$^4$R$^5$)$_t$(4 to 10 membered heterocyclic), wherein each t is independently an integer from 0 to 5; said cycloalkyl, aryl and heterocyclic R$^1$ moieties are optionally fused to a benzene ring, a C$_5$–C$_8$ cycloalkyl group, or a 4 to 10 membered heterocyclic group; the —(CR$^4$R$^5$)$_t$-moities of the foregoing R$^1$ groups optionally include a carbon—carbon double or triple bond where t is an integer between 2 and 5; the foregoing R$^1$ groups are each optionally substituted by 1 or 2 groups independently selected from —NR$^3$R$^4$, —OR$^3$, C$_1$–C$_{10}$ alkyl, C$_2$–C$_{10}$ alkenyl, and C$_2$–C$_{10}$ alkynyl, wherein said alkyl, alkenyl and alkynyl groups are substituted by 1 or 2 groups independently selected from —NR$^3$R$^4$ and —OR$^3$; and the foregoing R$^1$ groups are optionally substituted by 1 to 3 R$^2$ groups;

each R$^2$ is independently selected from H, C$_1$–C$_{10}$ alkyl, C$_2$–C$_{10}$ alkenyl, C$_2$–C$_{10}$ alkynyl, C$_3$–C$_{10}$ cycloalkyl, oxo, halo, cyano, nitro, trifluoromethyl, difluoromethoxy, trifluoromethoxy, azido, —OR$^3$, —C(O)R$^3$, —C(O)OR$^3$, —NR$^4$C(O)OR$^6$, —OC(O)R$^3$, —NR$^4$SO$_2$R$^6$, —SO$_2$NR$^3$R$^4$, —NR$^4$C(O)R$^3$, —C(O)NR$^3$R$^4$, —NR$^5$C(O)NR$^3$R$^4$, —NR$^3$R$^4$, S(O)$_j$(CR$^4$R$^5$)$_m$(C$_6$–C$_{10}$ aryl), —S(O)$_j$(C$_1$–C$_6$ alkyl), wherein j is an integer from 0 to 2, —(CR$^4$R$^5$)$_m$(C$_6$–C$_{10}$ aryl), —O(CR$_4$R$^5$)$_m$(C$_6$–C$_{10}$ aryl), —NR$^4$(CR$^4$R$^5$)$_m$(C$_6$–C$_{10}$ aryl), —O(CR$^4$R$^5$)(4 to 10 membered heterocycle), —NR$^4$(CR$^4$R$^5$)$_m$(4 to 10 membered heterocycle), —(CR$^4$R$^5$)$_m$(4 to 10 membered heterocyclic), and —(CR$_4$R$^5$)$_m$(C$_3$–C$_{10}$ cycloalkyl) wherein each m is independently an integer from 0 to 4; said alkyl, alkenyl and alkynyl groups optionally contain 1 or 2 hetero moieties selected from O, —S(O)$_j$— wherein j is an integer from 0 to 2, and —N(R$^3$)— with the proviso that two O atoms, two S atoms, or an O and S atom are not attached directly to each other, and the proviso that an O atom, a S atom or a N atom are not attached directly to a triple bond or a non-aromatic double bond; said cycloalkyl, aryl and heterocyclic R$^2$ groups are optionally fused to a C$_6$–C$_{10}$ aryl group, a C$_5$–C$_8$ cycloalkyl group, or a 4 to 10 membered heterocyclic group; and said alkyl, cycloalkyl, aryl and heterocyclic R$^2$ groups are optionally substituted by 1 to 5 substituents independently selected from oxo (=O), halo, cyano, nitro, trifluoromethyl, difluoromethoxy, trifluoromethoxy, azido, —NR$^4$SO$_2$R$^6$, —SO$_2$NR$^3$R$^4$, —C(O)R$^3$, c(O)OR$^3$, —OC(O)R$^3$, —NR$^4$C(O)OR$^6$, —NR$^4$C(O)R$^3$, —C(O)NR$^3$R$^4$, —NR$^3$R$^4$, —OR$^3$, C$_1$–C$_{10}$ alkyl, —(CR$^4$R$^5$)$_m$(C$_6$–C$_{10}$ aryl), and —(CR$^4$R$^5$)$_m$(4 to 10 membered heterocyclic), wherein each m is independently an integer ranging from 0 to 4;

each R$^3$ is independently selected from H, C$_1$–C$_{10}$ alkyl, —(CR$^4$R$^5$)$_m$(C$_6$–C$_{10}$ aryl), and —(CR$^4$R$^5$)$_m$(4 to 10 membered heterocyclic), wherein each m is independently an integer from 0 to 4; said alkyl group optionally includes 1 or 2 hetero moieties selected from O, —S(O)$_j$— wherein j is an integer ranging from 0 to 2, and —N(R$^4$)— with the proviso that two O atoms, two S atoms, or an O and S atom are not attached directly to each other; said cycloalkyl, aryl and heterocyclic R$^3$ groups are optionally fused to a C$_6$–C$_{10}$ aryl group, a C$_5$–C$_8$ cycloalkyl group, or a 4 to 10 membered heterocyclic group; and the foregoing R$^3$ substituents, except H, are optionally substituted by 1 to 5 substituents independently selected from oxo, halo, cyano, nitro, trifluoromethyl, difluoromethoxy, trifluoromethoxy, azido, —C(O)R$^4$, —C(O)OR$^4$, —OC(O)R$^4$, —NR$^4$C(O)R$^5$, —C(O)NR$^4$R$^5$, —NR$^4$R$^5$, hydroxy, C$_1$–C$_6$ alkyl, and C$_1$–C$_6$ alkoxy;

each R$^4$ and R$^5$ is independently H or C$_1$–C$_6$ alkyl; or, where R$^4$ and R$^5$ are attached to the same carbon or nitrogen atom, R$^4$ and R$^5$ together with said carbon or nitrogen may be taken together to form a 4 to 10 membered ring which may be carbocyclic or heterocyclic;

each R$^6$ is selected from the substituents provided in the definition of R$^3$ except R$^6$ is not H;

each R$^7$, R$^8$, R$^9$, R$^{10}$ and R$^{11}$ is independently selected from the group of subsituents provided in the definition of R$^2$.

2. A compound according to claim 1 wherein R$^1$ is C$_6$–C$_{10}$ aryl or 4 to 10 membered heterocyclic wherein the foregoing R$^1$ groups are each substituted by 1 or 2 groups independently selected from —NR$^3$R$^4$, —OR$^3$ and C$_1$–C$_3$ alkyl, wherein said alkyl groups are substituted by 1 or 2 groups independently selected from —NR$^3$R$^4$ and —OR$^3$; and the foregoing R$^1$ groups are optionally substituted by 1 to 3 R$^2$ groups;

each R$^2$ is independently selected from H, C$_1$–C$_{10}$ alkyl, C$_3$–C$_{10}$ cycloalkyl, oxo(=O), —OR$^3$, —C(O)R$^3$, C(O)OR$^3$, —NR$^4$C(O)R$^3$, —C(O)NR$^3$R$^4$, —NR$^3$R$^4$, —NR$^4$SO$_2$R$^6$, —SO$_2$NR$^3$R$^4$, —(CR$^4$R$^5$)$_m$(4 to 10 membered heterocyclic), and (CR$^4$R$^5$)$_m$(C$_3$–C$_{10}$ cycloalkyl); and said alkyl groups optionally contain 1 or 2 hetero moieties selected from O, —S(O)$_j$— wherein j is an integer from 0 to 2, and —N(R$^3$)— with the proviso that two O atoms, two S atoms, or an O and atom are not attached directly to each other; and said alkyl and cycloalkyl R$^2$ groups are optionally substituted by 1 to 5 substituents independently selected from oxo, cyano, trifluoromethyl, trifluoromethoxy, —NR$^4$SO$_2$R$^6$, —SO$_2$NR$^3$R$^4$, —C(O)R$^3$, —C(O)OR$^3$, —NR$^4$C(O)OR$^6$, —NR$^4$C(O)R$^3$, —C(O)NR$^3$R$^4$, —NR$^3$R$^4$, —OR$^3$, and C$_1$–C$_{10}$ alkyl, wherein each m is independently an integer ranging from 0 to 4.

3. A compound according to claim 1 wherein R$^1$ is piperidinyl, piperzinyl, or phenyl, wherein said R$^1$ groups are substituted by —NR$^3$R$^4$, oxo (=O), —OR$^3$ and C$_1$–C$_3$ alkyl, wherein said alkyl group is optionally substituted by 1 or 2 groups independently selected from —NR$^3$R$^4$ and —OR$^3$; and the foregoing R$^1$ groups are optionally substituted by 1 to 3 R$^2$ groups.

4. A compound according to claim 2 wherein said R$^1$ groups are substituted by —NR$^3$R$^4$, oxo (=O), OR$^3$, or C$_1$–C$_3$ alkyl, wherein said alkyl group is optionally substituted by —NR$^3$R$^4$.

5. A compound according to claim 1 wherein R$^1$ is phenyl substituted by pyrrolidin-1-yl which pyrrolidin-1-yl is optionally substituted by 1 to 3 substituents independently selected from oxo, cyano, trifluoromethyl, trifluoromethoxy, —NR$^4$SO$_2$R$^6$, —SO$_2$NR$^3$R$^4$, —C(O)R$^3$, —C(O)OR$^3$, —NR$^4$C(O)OR$^6$, —NR$^4$C(O)R$^3$, —C(O)NR$^3$R$^4$, —NR$^3$R$^4$, OR$^3$, and C$_1$–C$_{10}$ alkyl; and R$^{11}$ is —OR$^3$.

6. A compound according to claim 5 wherein R$^1$ is 4-pyrrolidin-1-ylmethyl-phenyl optionally subtituted by 1 to 3 substituents independently selected from oxo, cyano, trifluoromethyl, trifluoromethoxy, —NR$^4$SO$_2$R$^6$, —SO$_2$NR$^3$R$^4$, —C(O)R$^3$, —C(O)OR$^3$, —NR$^4$C(O)OR$^6$, —NR$^4$C(O)R$^3$, —C(O)NR$^3$R$^4$, —NR$^3$R$^4$, —OR$^3$, and C$_1$–C$_{10}$ alkyl; and R$^{11}$ is —OR$^3$.

7. A compound according to claim 6 wherein R$^{11}$ is connected at the 5 position of the benzimidazole moiety of the compound of formula 1 and is —OR$^3$.

8. A compound according to claim 7 wherein $R^{11}$ is connected at the 5 position of the benzimidazole moiety of the compound of formula 1 and is 2-methoxyethoxy.

9. A compound according to claim 1 wherein $R^1$ is pyrrolidin-1-yl or piperidin-1-yl, said $R^1$ being optionally substituted by 1 to 3 substituents independently selected from oxo, cyano, trifluoromethyl, trifluoromethoxy, —$NR^4SO_2R^6$, —$SO_2NR^3R^4$, —$C(O)R^3$, —$C(O)OR^3$, —$NR^4C(O)OR^6$, —$NR^4C(O)R^3$, —$C(O)NR^3R^4$, —$NR^3R^4$, —$OR^3$, and $C_1$–$C_{10}$ alkyl.

10. A compound according to claim 9 wherein $R^1$ is pyrrolidin-1-yl or piperidin-1-yl substituted by —$NR^3R^4$ and optionally substituted by 1 or 2 substituents independently selected from oxo, cyano, trifluoromethyl, trifluoromethoxy, —$NR^4SO_2R^6$, —$SO_2NR^3R^4$, —$C(O)R^3$, —$C(O)OR^3$, —$NR^4C(O)OR^6$, —$NR^4C(O)R^3$, —$C(O)NR^3R^4$, —$NR^3R^4$, $OR^3$, and $C_1$–$C_{10}$ alkyl; and $R^{11}$ is —$OR^3$.

11. A compound according to claim 10 or claim 9 wherein $R^{11}$ is connected at the 5 position of the benzimidazole moiety of the compound of formula I and is —$OR^3$ and $R^9$ and $R^{10}$ are both H.

12. A compound according to claim 10 or claim 9 wherein $R^{11}$ is connected at the 5 position of the benzimidazole moiety of the compound of formula 1 and is 2-methoxyethoxy and $R^9$ and $R^{10}$ are both H.

13. A compound according to claim 1 wherein $R^9$ is —$C(O)R^3$ wherein $R^3$ is pyrrolidin-1-yl or azetidin-1-yl wherein said $R^3$ groups are optionally substituted by 1 to 3 substituents independently selected from oxo, halo, cyano, nitro, trifluoromethyl, difluoromethoxy, trifluoromethoxy, azido, —$C(O)R^4$, —$C(O)OR^4$, —$OC(O)R^4$, —$NR^4C(O)R^5$, —$C(O)NR^4R^5$, —$NR^4R^5$, hydroxy, $C_1$–$C_6$ alkyl, and $C_1$–$C_6$ alkoxy.

14. A compound according to claim 1 selected from the group consisting of:
[1-[2-(5-Methoxy-benzoimidazol-1-yl)-quinolin-8-yl]-piperidin-4-ylamine;
1-[8-(4-Amino-piperidin-1-yl)-quinolin-2-yl]-1H-benzoimidazol-5-ol;
1-{2-[5-(Pyridin-2-ylmethoxy)-benzoimidazol-1-yl]-quinolin-8-yl}-piperidin-4-ylamine;
{1-[2-(5-Methoxy-benzoimidazol-1-yl)-quinolin-8-yl]-piperidin-4-yl}-dimethyl-amine;
{4-[2-(5-Methoxy-benzoimidazol-1-yl)-quinolin-8-yl]-benzyl}-methyl-amine;
{4-[2-(5-Methoxy-benzoimidazol-1-yl)-quinolin-8-yl]-benzyl}-dimethyl-amine;
Cyclopropyl-{4-[2-(5-methoxy-benzoimidazol-1-yl)-quinolin-8-yl]-benzyl}-amine;
tert-Butyl-{4-[2-(5-methoxy-benzoimidazol-1-yl)-quinolin-8-yl]-benzyl}-amine;
4-[2-(5-Methoxy-benzoimidazol-1-yl)-quinolin-8-yl]-benzylamine;
1-[2-(5-Ethoxy-benzoimidazol-1-yl)-quinolin-8-yl]-piperidin-4-ylamine;
{1-[2-(5-Ethoxy-benzoimidazol-1-yl)-quinolin-8-yl]-piperidin-4-yl}-dimethylamine;
1-[2-(5-Trifluoromethoxy-benzoimidazol-1-yl)-quinolin-8-yl]-piperidin-4-ylamine;
{4-[2-(5-Ethoxy-benzoimidazol-1-yl)-quinolin-8-yl]-benzyl}-methyl-amine;
Cyclopropyl-{4-[2-(5-ethoxy-benzoimidazol-1-yl)-quinolin-8-yl]-benzyl}-amine;
tert-Butyl-{4-[2-(5-ethoxy-benzoimidazol-1-yl)-quinolin-8-yl]-benzyl}-amine;
{4-[2-(5-Ethoxy-benzoimidazol-1-yl)-quinolin-8-yl]-benzyl}-dimethyl-amine;
1-[2-(5-Methoxy-benzoimidazol-1-yl)-quinolin-8-yl]-piperidin-4-one;
1-[2-(5-Ethoxy-benzoimidazol-1-yl)-quinolin-8-yl]-piperidin-4-one;
1-[2-(5-Ethoxy-benzoimidazol-1-yl)-quinolin-8-yl]-piperidin-4-ol;
tert-Butyl-{1-[2-(5-ethoxy-benzoimidazol-1-yl)-quinolin-8-yl]-piperidin-4-yl}-amine;
{1-[2-(5-Methoxy-benzoimidazol-1-yl)-quinolin-8-yl]-piperidin-4-yl}-methylamine;
2-(5-Methoxy-benzoimidazol-1-yl)-8-(1-oxa-6-aza-spiro[2,5]oct-6-yl)-quinoline;
4-Dimethylaminomethyl-1-[2-(5-methoxy-benzoimidazol-1-yl)-quinolin-8-yl]-piperidin-4-ol;
1-[2-(5-Methoxy-benzoimidazol-1-yl)-quinolin-8-yl]-4-methylaminomethyl-piperidin-4-ol;
4-Aminomethyl-1-[2-(5-methoxy-benzoimidazol-1-yl)-quinolin-8-yl]-piperidin-4-ol;
1-[2-(5-Methoxy-benzoimidazol-1-yl)-quinolin-8-yl]-pyrrolidin-3-ylamine;
1-(2-Benzoimidazol-1-yl-quinolin-8-yl)-piperidin-4-ylamine;
1-(2-Imidazo[4,5-b]pyridin-3-yl-quinolin-8-yl)-piperidin-4-ylamine;
1-{2-[5-(4-Methoxy-phenyl)-benzoimidazol-1-yl]-quinolin-8-yl}-piperidin-4-ylamine;
1-[2-(5-Cyclopropylmethoxy-benzoimidazol-1-yl)-quinolin-8-yl]-piperidin-4-ylamine;
1-{2-[5-(3-Dimethylamino-propoxy)-benzoimidazol-1-yl]-quinolin-8-yl}-piperidin-4-ylamine;
1-{2-[5-(3-Amino-propoxy)-benzoimidazol-1-yl]-quinolin-8-yl}-piperidin-4-ylamine;
1-{2-[5-(2-Dimethylamino-ethoxy)-benzoimidazol-1-yl]-quinolin-8-yl}-piperidin-4-ylamine;
1-{2-[5-(Pyridin-4-ylmethoxy)-benzoimidazol-1-yl]-quinolin-8-yl}-piperidin-4-ylamine;
1-[2-(5-Benzyloxy-benzoimidazol-1-yl)-quinolin-8-yl]-piperidin-4-ylamine;
1-{2-[5-(Pyridin-3-ylmethoxy)-benzoimidazol-1-yl]-quinolin-8-yl}-piperidin-4-ylamine;
1-{2-[5-(2-Methoxy-ethoxy)-benzoimidazol-1-yl]-quinolin-8-yl}-piperidin-4-ylamine;
1-[2-(5-Methoxy-benzoimidazol-1-yl)-quinolin-8-yl]-piperidine-4-carboxylic acid ethyl ester;
1-[2-(5-Methoxy-benzoimidazol-1-yl)-quinolin-8-yl]-piperidine-4-carboxylic acid;
4-Dimethylaminomethyl-1-[2-(5-methoxy-benzoimidazol-1-yl)-quinolin-8-yl]-piperidin-4-ol;
N-{1-[2-(5-Methoxy-benzoimidazol-1-yl)-quinolin-8-yl]-piperidin-4-yl}-acetamide;
N-{1-[2-(5-Cyclopropylmethoxy-benzoimidazol-1-yl)-quinolin-8-yl]-piperidin-4-yl}-acetamide;
1-{2-[5-(2-Methoxy-ethoxy)-benzoimidazol-1-yl]-quinolin-8-yl}-piperidin-4-ol;
{1-[2-(5-Methoxy-benzoimidazol-1-yl)-quinolin-8-yl]-piperidin-4-yl}-urea;
4-Aminomethyl-1-{2-[5-(pyridin-2-ylmethoxy)-benzoimidazol-1-yl]-quinolin-8-yl}-piperidin-4-ol;
Cyclopropyl-(1-{2-[5-(2-methoxy-ethoxy)-benzoimidazol-1-yl]-quinolin-8-yl}-piperidin-4-yl)-amine;
(1-{2-[5-(2-Methoxy-ethoxy)-benzoimidazol-1-yl]-quinolin-8-yl}-piperidin-4-yl)-dimethyl-amine;
1-{2-[5-(2-Methoxy-ethoxy)-benzoimidazol-1-yl]-quinolin-8-yl}-piperidin-4-yl)-methyl-amine;

(1-{2-[5-(3-Dimethylamino-propoxy)-benzoimidazol-1-yl]-quinolin-8-yl}-piperidin-4-yl)-dimethyl-amine;
{1-[2-(5-Cyclopropylmethoxy-benzoimidazol-1-yl)-quinolin-8-yl]-piperidin-4-yl}-methyl-amine;
{1-[2-(5-Cyclopropylmethoxy-benzoimidazol-1-yl)-quinolin-8-yl]-piperidin-4-yl}-dimethyl-amine;
2-Amino-N-(1-{2-[5-(2-methoxy-ethoxy)-benzoimidazol-1-yl]-quinolin-8-yl}-piperidin-4-yl)-acetamide;
-(S)-2-Amino-N-(1-{2-[5-(2-methoxy-ethoxy)-benzoimidazol-1-yl]-quinolin-8-yl}-piperidin-4-yl)-propionamide;
-(R)-2-Amino-N-(1-{2-[5-(2-methoxy-ethoxy)-benzoimidazol-1-yl]-quinolin-8-yl}-piperidin-4-yl)-propionamide;
2-Amino-N-(1-{2-[5-(2-methoxy-ethoxy)-benzoimidazol-1-yl]-quinolin-8-yl}-piperidin-4-yl)-isobutyramide;
1-(1-{2-[5-(2-Methoxy-ethoxy)-benzoimidazol-1-yl]-quinolin-8-yl}-piperidin-4-ylamino)-2-methyl-propan-2-ol;
(1-{2-[5-(2-Methoxy-ethoxy)-benzoimidazol-1-yl]-quinolin-8-yl}-piperidin-4-yl)-pyridin-2-ylmethyl-amine;
(1-{2-[5-(2-Methoxy-ethoxy)-benzoimidazol-1-yl]-quinolin-8-yl}-piperidin-4-yl)pyridin-3-ylmethyl-amine;
4-{2-[5-(2-Methoxy-ethoxy)-benzoimidazol-1-yl]-quinolin-8-yl}-phenol;
[2-(4-{2-[5-(2-Methoxy-ethoxy)-benzoimidazol-1-yl]-quinolin-8-yl}-phenoxy)ethyl]-dimethyl-amine;
2-[5-(2-Methoxy-ethoxy)-benzoimidazol-1-yl]-8-piperazin-1-yl-quinoline;
[2-(4-{2-[5-(2-Methoxy-ethoxy)-benzoimidazol-1-yl]-quinolin-8-yl}-piperazin-1-yl)-ethyl]-dimethyl-amine;
2-[5-(2-Methoxy-ethoxy)-benzoimidazol-1-yl]-8-(4-pyridin-2-ylmethyl-piperazin-1-yl)-quinoline;
2-[5-(2-Methoxy-ethoxy)-benzoimidazol-1-yl]-8-(4-pyridin-3-ylmethyl-piperazin-1-yl)-quinoline;
2-Amino-1-(4-{2-[5-(2-methoxy-ethoxy)-benzoimidazol-1-yl]-quinolin-8-yl}-piperazin-1-yl)-2-methyl-propan-1-one;
(S)-2-Amino-1-(4-{2-[5-(2-methoxy-ethoxy)-benzoimidazol-1-yl]-quinolin-8-yl}-piperazin-1-yl)-propan-1-one;
(S)-2-Amino-1-(4-{2-[5-(2-methoxy-ethoxy)-benzoimidazol-1-yl]-quinolin-8-yl}-piperazin-1-yl)-propan-1-one;
2-Amino-1-(4-{2-[5-(2-methoxy-ethoxy)-benzoimidazol-1-yl]-quinolin-8-yl}-piperazin-1-yl)-ethanone;
(1-Amino-cyclopropyl)-(4-{2-[5-(2-methoxy-ethoxy)-benzoimidazol-1-yl]-quinolin-8-yl}-piperazin-1-yl)-methanone;
2-(4-{2-[5-(2-Methoxy-ethoxy)-benzoimidazol-1-yl]-quinolin-8-yl}-piperazin-1-yl)-ethylamine;
(R)-2-Amino-3-(4-{2-[5-(2-methoxy-ethoxy)-benzoimidazol-1-yl]-quinolin-8-yl}-piperazin-1-yl)-propan-1-ol;
3-{2-[5-(2-Methoxy-ethoxy)-benzoimidazol-1-yl]-quinolin-8-yl}-3-aza-bicyclo[3.1.0]hex-6-ylamine;
(S)-1-2-[5-(2-Methoxy-ethoxy)-benzoimidazol-1-yl]-quinolin-8-yl}-pyrrolidin-3-ylamine;
(R)-1-{2-[5-(2-Methoxy-ethoxy)-benzoimidazol-1-yl]-quinolin-8-yl}-pyrrolidin-3-ylamine;
2-[5-(2-Methoxy-ethoxy)-benzoimidazol-1-yl]-8-pyridin-3-yl-quinoline;
2-[5-(2-Methoxy-ethoxy)-benzoimidazol-1-yl]-8-(6-methoxy-pyridin-3-yl)-quinoline;
4-{2-[5-(2-Methoxy-ethoxy)-benzoimidazol-1-yl]-quinolin-8-yl}-benzoic acid methyl ester;
1-{2-[5-(2-Methoxy-ethoxy)-benzoimidazol-1-yl]-quinolin-8-yl}-4-methyl-piperidin-4-ylamine;
1-[2-(6,7-Dihydro-5,8-dioxa-1,3-diaza-cyclopenta[b]naphthalen-1-yl)-quinolin-8-yl]-piperidin-4-ylamine;
2-{1-[8-(4-Amino-piperidin-1-yl)-quinolin-2-yl]-1H-benzoimidazol-5-yloxy}-ethanol;
4-Cyclopropylaminomethyl-1-{2-[5-(2-methoxy-ethoxy)-benzoimidazol-1-yl]-quinolin-8-yl}-piperidin-4-ol;
1-[8-(4-Amino-piperidin-1-yl)-quinolin-2-yl]-1H-benzoimidazole-5-sulfonic acid dimethylamide;
1-[2-(6-Methoxy-benzoimidazol-1-yl)-quinolin-8-yl]-piperidin-4-ylamine;
1-[2-(5,6-Dimethoxy-benzoimidazol-1-yl)-quinolin-8-yl]-piperidin-4-ylamine;
2-Dimethylamino-1-(4-{2-[5-(2-methoxy-ethoxy)-benzoimidazol-1-yl]-quinolin-8-yl}-piperazin-1-yl)-ethanone;
1-[2-(5-Benzyloxy-benzoimidazol-1-yl)-quinolin-8-yl]-4-methyl-piperidin-4-ol;
(4-{2-[5-(2-Methoxy-ethoxy)-benzoimidazol-1-yl]-quinolin-8-yl}-benzyl)-dimethyl-amine;
(4-{2-[5-(2-Methoxy-ethoxy)-benzoimidazol-1-yl]-quinolin-8-yl}-benzyl)-methyl-amine;
2-[5-(2-Methoxy-ethoxy)-benzoimidazol-1-yl]-8-(4-morpholin-4-ylmethyl-phenyl)quinoline;
2-(4-{2-[5-(2-Methoxy-ethoxy)-benzoimidazol-1-yl]-quinolin-8-yl}-benzylamino)-ethanol;
4-{2-[5-(2-Methoxy-ethoxy)-benzoimidazol-1-yl]-quinolin-8-yl}-benzylamine;
2-[5-(2-Methoxy-ethoxy)-benzoimidazol-1-yl]-8-(4-pyrrolidin-1-ylmethyl-phenyl)quinoline;
2-[5-(2-Methoxy-ethoxy)-benzoimidazol-1-yl]-8-(4-pyrrolidin-1-ylmethyl-phenyl)quinoline;
2-[5-(2-Methoxy-ethoxy)-benzoimidazol-1-yl]-8-(4-pyrrolidin-1-ylmethyl-phenyl)quinoline;
1-(4-{2-[5-(2-Methoxy-ethoxy)-benzoimidazol-1-yl]-quinolin-8-yl}-benzyl)-cis-pyrrolidine-3,4-diol;
R,R-(1-(4-{2-[5-(2-Methoxy-ethoxy)-benzoimidazol-1-yl]-quinolin-8-yl}-benzyl)-trans-pyrrolidine-3,4-diol);
1-(4-{2-[5-(2-Methoxy-ethoxy)-benzoimidazol-1-yl]-quinolin-8-yl}-benzyl)-pyrrolidin-3-ol;
R-(1-(4-{2-[5-(2-Methoxy-ethoxy)-benzoimidazol-1-yl]-quinolin-8-yl}-benzyl)-pyrrolidin-3-ol);
S-(1-(4-{2-[5-(2-Methoxy-ethoxy)-benzoimidazol-1-yl]-quinolin-8-yl}-benzyl)-pyrrolidin-3-ol);
1-(4-{2-[5-(2-Methoxy-ethoxy)-benzoimidazol-1-yl]-quinolin-8-yl}-benzyl)-azetidin-3-ol;
2-[5-(2-Methoxy-ethoxy)-benzoimidazol-1-yl]-8-[4-(4-methyl-piperazin-1-ylmethyl)-phenyl]-quinoline;
4-(4-{2-[5-(2-Methoxy-ethoxy)-benzoimidazol-1-yl]-quinolin-8-yl}-benzyl)piperazine-1-carboxylic acid tert-butyl ester;
[1-(4-{2-[5-(2-Methoxy-ethoxy)-benzoimidazol-1-yl]-quinolin-8-yl}-benzyl)-piperidin-4-yl]-carbamic acid tert-butyl ester;
1-(4-{2-[5-(2-Methoxy-ethoxy)-benzoimidazol-1-yl]-quinolin-8-yl}-benzyl)-piperidin-4-ylamine;
(1-{2-[5-(2-Methoxy-ethoxy)-benzoimidazol-1-yl]-quinolin-8-yl}-piperidin-4-yl)-methanol;
(1-{2-[5-(2-Methoxy-ethoxy)-benzoimidazol-1-yl]-quinolin-8-yl}-piperidin-4-ylmethyl)-methyl-amine;
2-[5-(2-Methoxy-ethoxy)-benzoimidazol-1-yl]-8-[4-(4-methyl-piperazin-1-ylmethyl)-piperidin-1-yl]-quinoline;

(1-{2-[5-(2-Methoxy-ethoxy)-benzoimidazol-1-yl]-quinolin-8-yl}-piperidin-4-ylmethyl)-dimethyl-amine;
1-(1-{2-[5-(2-Methoxy-ethoxy)-benzoimidazol-1-yl]-quinolin-8-yl}-piperidin-4-ylmethyl)-pyrrolidin-3-ol;
C-(1-{2-[5-(2-Methoxy-ethoxy)-benzoimidazol-1-yl]-quinolin-8-yl}-piperidin-4-yl)-methylamine;
1-{2-[5-(2-Dimethylamino-ethoxy)-benzoimidazol-1-yl]-quinolin-8-yl}-4-methyl-piperidin-4-ol;
1-{2-[5-(2-Dimethylamino-ethoxy)-benzoimidazol-1-yl]-quinolin-8-yl}-piperidin-4-ol;
S,S-(1-(4-{2-[5-(2-Methoxy-ethoxy)-benzoimidazol-1-yl]-quinolin-8-yl}-benzyl)-trans-pyrrolidine-3,4-diol);
4-{2-[5-(3-Amino-propoxy)-benzoimidazol-1-yl]-quinolin-8-yl}-phenol;
4-{2-[5-(3-Dimethylamino-propoxy)-benzoimidazol-1-yl]-quinolin-8-yl}-phenol;
1-[2-(5-Phenyl-benzoimidazol-1-yl)-quinolin-8-yl]-piperidin-4-ylamine;
1-[2-(5-Pyridin-4-yl-benzoimidazol-1-yl)-quinolin-8-yl]-piperidin-4-ylamine;
1-{2-[5-(3-Methoxy-phenyl)-benzoimidazol-1-yl]-quinolin-8-yl}-piperidin-4-ylamine;
1-[2-(5-Pyridin-3-yl-benzoimidazol-1-yl)-quinolin-8-yl]-piperidin-4-ylamine;
1-{2-[5-(6-Methoxy-pyridin-3-yl)-benzoimidazol-1-yl]-quinolin-8-yl}-piperidin-4-ylamine;
1-{2-[5-(4-Aminomethyl-phenyl)-benzoimidazol-1-yl]-quinolin-8-yl}-piperidin-4-ylamine;
4-{1-[8-(4-Amino-piperidin-1-yl)-quinolin-2-yl]-1H-benzoimidazol-5-yl}-benzoic acid methyl ester;
4-{1-[8-(4-Amino-piperidin-1-yl)-quinolin-2-yl]-1H-benzoimidazol-5-yl}-phenol;
2-(5-Methoxy-benzoimidazol-1-yl)-quinoline-8-carboxylic acid methyl ester;
2-[5-(2-Methoxy-ethoxy)-benzoimidazol-1-yl]-quinoline-8-carboxylic acid methyl ester;
2-(5-Methoxy-benzoimidazol-1-yl)-quinoline-8-carboxylic acid (2-dimethylamino-ethyl)-amide;
2-(5-Cyclopropylmethoxy-benzoimidazol-1-yl)-quinoline-8-carboxylic acid methyl ester;
[2-(5-Cyclopropylmethoxy-benzoimidazol-1-yl)-quinolin-8-yl]-pyrrolidin-1-yl-methanone;
[2-(5-Cyclopropylmethoxy-benzoimidazol-1-yl)-quinolin-8-yl]-morpholin-4-yl-methanone;
[2-(5-Cyclopropylmethoxy-benzoimidazol-1-yl)-quinolin-8-yl]-piperidin-1-yl-methanone;
(3-Amino-pyrrolidin-1-yl)-[2-(5-cyclopropylmethoxy-benzoimidazol-1-yl)-quinolin-8-yl]-methanone;
8-Allyloxy-2-(5-methoxy-benzoimidazol-1-yl)-quinoline;
{2-[2-(5-Methoxy-benzoimidazol-1-yl)-quinolin-8-yloxy]-ethyl}-methyl-amine;
{2-[2-(5-Methoxy-benzoimidazol-1-yl)-quinolin-8-yloxy]-ethyl}-dimethyl-amine;
2-[2-(5-Methoxy-benzoimidazol-1-yl)-quinolin-8-yloxy]-ethylamine;
1-[[2-[5-(3-Morpholinoethoxy)-1H-benzimidazol-1-yl]-quinolin-8-yl]]-piperidin-4-ylamine trihydrochloride;
1-[[2-[5-(3-Morpholinoethoxy)-1H-benzimidazol-1-yl]-quinolin-8-yl]]-piperidin-4-ylamine trihydrochloride;
5-{2-[5-(2-Methoxy-ethoxy)-benzoimidazol-1-yl]-quinolin-8-yl}-[1,3,4]oxadiazol-2-ylamine;
Ethyl 1-[8-(4-aminopiperidin-1-yl)-quinolin-2-yl]-benzimidazole-5-carboxylate;
1-[8-(4-Aminopiperidin-1-yl)-quinolin-2-yl]-benzimidazole-5-carboxylic acid;
N-(4-Morpholino)ethyl-1-[8-(4-aminopiperidin-1-yl)-quinolin-2-yl]benzimidazole-5-carboxamide;
4-{1-[8-(4-Amino-piperidin-1-yl)-quinolin-2-yl]-1H-benzoimidazol-5-yl}-benzaldehyde;
1-{2-[5-(4-Methylaminomethyl-phenyl)-benzoimidazol-1-yl]-quinolin-8-yl}-piperidin-4-ylamine;
1-{2-[5-(4-Dimethylaminomethyl-phenyl)-benzoimidazol-1-yl]-quinolin-8-yl}-piperidin-4-ylamine;
1-(2-{5-[2-(2-Methyl-imidazol-1-yl)-ethoxy]-benzoimidazol-1-yl}-quinolin-8-yl)-piperidin-4-ylamine and
1-{2-[5-(2-[1,2,4]Triazol-1-yl-ethoxy)-benzoimidazol-1-yl]-quinolin-8-yl}-piperidin-4-ylamine,
and the pharmaceutically acceptable salts, prodrugs and solvates of the foregoing compounds.

15. A compound according to claim 1 selected from the group consisting of:
1-[2-(5-Methoxy-benzoimidazol-1-yl)-quinolin-8-yl]-piperidin-4-ylamine;
1-[8-(4-Amino-piperidin-1-yl)-quinolin-2-yl]-1H-benzoimidazol-5-ol;
1-{2-[5-(Pyridin-2-ylmethoxy)-benzoimidazol-1-yl]-quinolin-8-yl}-piperidin-4-ylamine;
{1-[2-(5-Methoxy-benzoimidazol-1-yl)-quinolin-8-yl]-piperidin-4-yl}-dimethyl-amine;
{4-[2-(5-Methoxy-benzoimidazol-1-yl)-quinolin-8-yl]-benzyl}-methyl-amine;
{4-[2-(5-Methoxy-benzoimidazol-1-yl)-quinolin-8-yl]-benzyl}-dimethyl-amine;
1-[2-(5-Ethoxy-benzoimidazol-1-yl)-quinolin-8-yl]-piperidin-4-ylamine;
{1-[2-(5-Ethoxy-benzoimidazol-1-yl)-quinolin-8-yl]-piperidin-4-yl}-dimethylamine;
{4-[2-(5-Ethoxy-benzoimidazol-1-yl)-quinolin-8-yl]-benzyl}-methyl-amine;
{4-[2-(5-Ethoxy-benzoimidazol-1-yl)-quinolin-8-yl]-benzyl}-dimethyl-amine;
{1-[2-(5-Methoxy-benzoimidazol-1-yl)-quinolin-8-yl]-piperidin-4-yl}-methyl-amine;
4-Dimethylaminomethyl-1-[2-(5-methoxy-benzoimidazol-1-yl)-quinolin-8-yl]-piperidin-4-ol;
1-[2-(5-Methoxy-benzoimidazol-1-yl)-quinolin-8-yl]-4-methylaminomethyl-piperidin-4-ol;
4-Aminomethyl-1-[2-(5-methoxy-benzoimidazol-1-yl)-quinolin-8-yl]-piperidin-4-ol;
1-{2-[5-(4-Methoxy-phenyl)-benzoimidazol-1-yl]-quinolin-8-yl}-piperidin-4 -ylamine;
1-[2-(5-Cyclopropylmethoxy-benzoimidazol-1-yl)-quinolin-8-yl]-piperidin-4-ylamine;
1-{2-[5-(3-Dimethylamino-propoxy)-benzoimidazol-1-yl]-quinolin-8-yl}-piperidin-4-ylamine;
1-{2-[5-(3-Amino-propoxy)-benzoimidazol-1-yl]-quinolin-8-yl}-piperidin-4-ylamine;
1-{2-[5-(2-Dimethylamino-ethoxy)-benzoimidazol-1-yl]-quinolin-8-yl}-piperidin-4-ylamine;
1-{2-[5-(Pyridin-4-ylmethoxy)-benzoimidazol-1-yl]-quinolin-8-yl}-piperidin-4-ylamine;
1-[2-(5-Benzyloxy-benzoimidazol-1-yl)-quinolin-8-yl]-piperidin-4-ylamine;
1-{2-[5-(Pyridin-3-ylmethoxy)-benzoimidazol-1-yl]-quinolin-8-yl}-piperidin-4-ylamine;
1-{2-[5-(2-Methoxy-ethoxy)-benzoimidazol-1-yl]-quinolin-8-yl}-piperidin-4-ylamine;
4-Dimethylaminomethyl-1-[2-(5-methoxy-benzoimidazol-1-yl)-quinolin-8-yl]-piperidin-4-ol;
4-Aminomethyl-1-{2-[5-(pyridin-2-ylmethoxy)-benzoimidazol-1-yl]-quinolin-8-yl}-piperidin-4-ol;

1-{2-[5-(2-Methoxy-ethoxy)-benzoimidazol-1-yl]-quinolin-8-yl}-piperidin-4-yl)-dimethyl-amine;
1-{2-[5-(2-Methoxy-ethoxy)-benzoimidazol-1-yl]-quinolin-8-yl}-piperidin-4-yl)-methyl-amine;
(1-{2-[5-(3-Dimethylamino-propoxy)-benzoimidazol-1-yl]-quinolin-8-yl}-piperidin-4-yl)-dimethyl-amine;
{1-[2-(5-Cyclopropylmethoxy-benzoimidazol-1-yl)-quinolin-8-yl]-piperidin-4-yl}-methyl-amine;
{1-[2-(5-Cyclopropylmethoxy-benzoimidazol-1-yl)-quinolin-8-yl]-piperidin-4-yl}-dimethyl-amine;
1-{2-[5-(2-Methoxy-ethoxy)-benzoimidazol-1-yl]-quinolin-8-yl}-piperidin-4-yl)-pyridin-2-ylmethyl-amine;
(1-{2-[5-(2-Methoxy-ethoxy)-benzoimidazol-1-yl]-quinolin-8-yl}-piperidin-4-yl)-pyridin-3-ylmethyl-amine;
4-{2-[5-(2-Methoxy-ethoxy)-benzoimidazol-1-yl]-quinolin-8-yl}-phenol;
[2-(4-{2-[5-(2-Methoxy-ethoxy)-benzoimidazol-1-yl]-quinolin-8-yl}-phenoxy)-ethyl]-dimethyl-amine;
2-[5-(2-Methoxy-ethoxy)-benzoimidazol-1-yl]-8-piperazin-1-yl-quinoline;
[2-(4-{2-[5-(2-Methoxy-ethoxy)-benzoimidazol-1-yl]-quinolin-8-yl}-piperazin-1-yl)-ethyl]-dimethyl-amine;
2-Amino-1-(4-{2-[5-(2-methoxy-ethoxy)-benzoimidazol-1-yl]-quinolin-8-yl}-piperazin-1-yl)-2-methyl-propan-1-one;
(S)-2-Amino-1-(4-{2-[5-(2-methoxy-ethoxy)-benzoimidazol-1-yl]-quinolin-8-yl}-piperazin-1-yl)-propan-1-one;
(S)-2-Amino-1-(4-{2-[5-(2-methoxy-ethoxy)-benzoimidazol-1-yl]-quinolin-8-yl}-piperazin-1-yl)-propan-1-one;
2-Amino-1-(4-{2-[5-(2-methoxy-ethoxy)-benzoimidazol-1-yl]-quinolin-8-yl}-piperazin-1-yl)-ethanone;
2-(4-{2-[5-(2-Methoxy-ethoxy)-benzoimidazol-1-yl]-quinolin-8-yl}-piperazin-1-yl)-ethylamine;
3-{2-[5-(2-Methoxy-ethoxy)-benzoimidazol-1-yl]-quinolin-8-yl}-3-aza-bicyclo[3.1.0]hex-6-ylamine;
1-{2-[5-(2-Methoxy-ethoxy)-benzoimidazol-1-yl]-quinolin-8-yl}-4-methyl-piperidin-4-ylamine;
2-{1-[8-(4-Amino-piperidin-1-yl)-quinolin-2-yl]-1H-benzoimidazol-5-yloxy}-ethanol;
1-[2-(5,6-Dimethoxy-benzoimidazol-1-yl)-quinolin-8-yl]-piperidin-4-ylamine;
1-[2-(6,7-Dihydro-5,8-dioxa-1,3-diaza-cyclopenta[b]naphthalen-1-yl)-quinolin-8-yl]-piperidin-4-ylamine;
(4-{2-[5-(2-Methoxy-ethoxy)-benzoimidazol-1-yl]-quinolin-8-yl}-benzyl)-dimethyl-amine;
(4-{2-[5-(2-Methoxy-ethoxy)-benzoimidazol-1-yl]-quinolin-8-yl}-benzyl)-methyl-amine;
2-(4-{2-[5-(2-Methoxy-ethoxy)-benzoimidazol-1-yl]-quinolin-8-yl}-benzylamino)-ethanol;
4-{2-[5-(2-Methoxy-ethoxy)-benzoimidazol-1-yl]-quinolin-8-yl}-benzylamine;
2-[5-(2-Methoxy-ethoxy)-benzoimidazol-1-yl]-8-(4-pyrrolidin-1-ylmethyl-phenyl)-quinoline;
2-[5-(2-Methoxy-ethoxy)-benzoimidazol-1-yl]-8-(4-pyrrolidin-1-ylmethyl-phenyl)-quinoline;
2-[5-(2-Methoxy-ethoxy)-benzoimidazol-1-yl]-8-(4-pyrrolidin-1-ylmethyl-phenyl)-quinoline;
1-(4-{2-[5-(2-Methoxy-ethoxy)-benzoimidazol-1-yl]-quinolin-8-yl}-benzyl)-cis-pyrrolidine-3,4-diol;
R,R-(1-(4-{2-[5-(2-Methoxy-ethoxy)-benzoimidazol-1-yl]-quinolin-8-yl}-benzyl)-trans-pyrrolidine-3,4-diol);
1-(4-{2-[5-(2-Methoxy-ethoxy)-benzoimidazol-1-yl]-quinolin-8-yl}-benzyl)-pyrrolidin-3-ol;
R-(1-(4-{2-[5-(2-Methoxy-ethoxy)-benzoimidazol-1-yl]-quinolin-8-yl}-benzyl)-pyrrolidin-3-ol);
S-(1-(4-{2-[5-(2-Methoxy-ethoxy)-benzoimidazol-1-yl]-quinolin-8-yl}-benzyl)-pyrrolidin-3-ol);
1-(4-{2-[5-(2-Methoxy-ethoxy)-benzoimidazol-1-yl]-quinolin-8-yl}-benzyl)-azetidin-3-ol
2-[5-(2-Methoxy-ethoxy)-benzoimidazol-1-yl]-8-[4-(4-methyl-piperazin-1-ylmethyl)-phenyl]-quinoline;
1-(4-{2-[5-(2-Methoxy-ethoxy)-benzoimidazol-1-yl]-quinolin-8-yl}-benzyl)-piperidin-4-ylamine;
(1-{2-[5-(2-Methoxy-ethoxy)-benzoimidazol-1-yl]-quinolin-8-yl}-piperidin-4-yl)-methanol;
(1-{2-[5-(2-Methoxy-ethoxy)-benzoimidazol-1-yl]-quinolin-8-yl}-piperidin-4-ylmethyl)-methyl-amine;
2-[5-(2-Methoxy-ethoxy)-benzoimidazol-1-yl]-8-[4-(4-methyl-piperazin-1-ylmethyl)-piperidin-1-yl]-quinoline;
(1-{2-[5-(2-Methoxy-ethoxy)-benzoimidazol-1-yl]-quinolin-8-yl}-piperidin-4-ylmethyl)-dimethyl-amine;
C-(1-{2-[5-(2-Methoxy-ethoxy)-benzoimidazol-1-yl]-quinolin-8-yl}-piperidin-4-yl)-methylamine;
S,S-(1-(4-{2-[5-(2-Methoxy-ethoxy)-benzoimidazol-1-yl]-quinolin-8-yl}-benzyl)-trans-pyrrolidine-3,4-diol);
4-{2-[5-(3-Dimethylamino-propoxy)-benzoimidazol-1-yl]-quinolin-8-yl}-phenol;
1-[2-(5-Phenyl-benzoimidazol-1-yl)-quinolin-8-yl]-piperidin-4-ylamine;
1-[2-(5-Pyridin-4-yl-benzoimidazol-1-yl)-quinolin-8-yl]-piperidin-4-ylamine;
1-{2-[5-(3-Methoxy-phenyl)-benzoimidazol-1-yl]-quinolin-8-yl}-piperidin-4-ylamine;
1-[2-(5-Pyridin-3-yl-benzoimidazol-1-yl)-quinolin-8-yl]-piperidin-4-ylamine;
1-{2-[5-(6-Methoxy-pyridin-3-yl)-benzoimidazol-1-yl]-quinolin-8-yl}-piperidin-4 -ylamine;
1-{2-[5-(4-Aminomethyl-phenyl)-benzoimidazol-1-yl]-quinolin-8-yl}-piperidin-4-ylamine;
4-{1-[8-(4-Amino-piperidin-1-yl)-quinolin-2-yl]-1H-benzoimidazol-5-yl}-benzoic acid methyl ester;
4-{1-[8-(4-Amino-piperidin-1-yl)-quinolin-2-yl]-1H-benzoimidazol-5-yl}-phenol;
1-[[2-[5-(3-Morpholinoethoxy)-1H-benzimidazol-1-yl]-quinolin-8-yl]]-piperidin-4-ylamine trihydrochloride;
Ethyl 1-[8-(4-aminopiperidin-1-yl)-quinolin-2-yl]-benzimidazole-5-carboxylate;
N-(4-Morpholino)ethyl-1-[8-(4-aminopiperidin-1-yl)-quinolin-2-yl]-benzimidazole-5-carboxamide;
1-{2-[5-(4-Methylaminomethyl-phenyl)-benzoimidazol-1-yl]-quinolin-8-yl}-piperidin-4-ylamine;
1-{2-[5-(4-Dimethylaminomethyl-phenyl)-benzoimidazol-1-yl]-quinolin-8-yl}-piperidin-4-ylamine;
1-(2-{5-[2-(2-Methyl-imidazol-1-yl)-ethoxy]-benzoimidazol-1-yl}-quinolin-8-yl)-piperidin-4-ylamine and
1-{2-[5-(2-[1,2,4]Triazol-1-yl-ethoxy)-benzoimidazol-1-yl]-quinolin-8-yl}-piperidin-4-ylamine,
and the pharmaceutically acceptable salts, prodrugs and solvates of the foregoing compounds.

16. A method for the treatment of abnormal cell growth in a mammal comprising administering to said mammal an amount of a compound of claim 1 that is effective in treating abnormal cell growth.

17. A method according to claim 16 wherein said abnormal cell growth is cancer.

18. A method according to claim 17 wherein said cancer is selected from lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers.

19. A pharmaceutical composition for the treatment of abnormal cell growth in a mammal comprising an amount of a compound of claim 1 that is effective in treating abnormal cell growth, and a pharmaceutically acceptable carrier.

20. The pharmaceutical composition of claim 19 wherein said abnormal cell growth is cancer.

* * * * *